(12) United States Patent
Lockhart et al.

(10) Patent No.: US 6,344,316 B1
(45) Date of Patent: *Feb. 5, 2002

(54) NUCLEIC ACID ANALYSIS TECHNIQUES

(75) Inventors: David J. Lockhart, Santa Clara; Mark Chee; Kevin Gunderson, both of Palo Alto; Lai Chaoqiang; Lisa Wodicka, both of Santa Clara; Maureen T. Cronin, Los Altos; Danny Lee; Huu M. Tran, both of San Jose; Hajime Matsuzaki, Palo Alto, all of CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 20 days.

(21) Appl. No.: 08/882,649

(22) Filed: Jun. 25, 1997

Related U.S. Application Data

(63) Continuation of application No. PCT/US97/01603, filed on Jan. 22, 1997.
(60) Provisional application No. 60/035,170, filed on Jan. 9, 1997, and provisional application No. 60/010,471, filed on Jan. 23, 1996.

(51) Int. Cl.$^7$ ................................................ C12Q 1/68
(52) U.S. Cl. ......................................... 435/6; 536/24.3
(58) Field of Search .............................. 435/6; 536/24.3

(56) References Cited

U.S. PATENT DOCUMENTS

| | | |
|---|---|---|
| 3,730,844 A | 5/1973 | Gilham et al. |
| 4,071,315 A | 1/1978 | Chateau |
| 4,327,073 A | 4/1982 | Huang |
| 4,373,071 A | 2/1983 | Itakura |
| 4,458,066 A | 7/1984 | Caruthers et al. |
| 4,483,920 A | 11/1984 | Gillespie et al. |
| 4,486,539 A | 12/1984 | Ranki et al. |
| 4,500,707 A | 2/1985 | Caruthers et al. |
| 4,542,102 A | 9/1985 | Dattagupta et al. |
| 4,556,643 A | 12/1985 | Paau et al. |
| 4,562,157 A | 12/1985 | Lowe et al. |
| 4,563,419 A | 1/1986 | Ranki et al. |
| 4,584,277 A | 4/1986 | Ullman et al. |
| 4,591,570 A | 5/1986 | Chang |
| 4,613,566 A | 9/1986 | Potter |
| 4,670,380 A | 6/1987 | Dattagupta |
| 4,677,054 A | 6/1987 | White et al. |
| 4,683,195 A | 7/1987 | Mullis et al. |
| 4,683,202 A | 7/1987 | Mullis |
| 4,689,405 A | 8/1987 | Frank |
| 4,704,353 A | 11/1987 | Humphries et al. |
| 4,711,955 A | 12/1987 | Ward et al. |
| 4,716,106 A | 12/1987 | Chiswell |
| 4,728,591 A | 3/1988 | Clark et al. |
| 4,731,325 A | 3/1988 | Palva et al. |
| 4,755,458 A | 7/1988 | Rabbani et al. |
| 4,767,700 A | 8/1988 | Wallace |
| 4,780,504 A | 10/1988 | Buendia et al. |
| 4,812,512 A | 3/1989 | Buendia et al. |
| 4,820,630 A | 4/1989 | Taub |
| 4,833,092 A | 5/1989 | Geysen |
| 4,849,513 A | 7/1989 | Smith et al. |
| 4,855,225 A | 8/1989 | Fung et al. |
| 4,868,103 A | 9/1989 | Stavrianopoulos et al. |
| 4,868,104 A | 9/1989 | Kurn et al. |
| 4,868,105 A | 9/1989 | Urdea et al. |
| 4,874,500 A | 10/1989 | Madou et al. |
| 4,921,805 A | 5/1990 | Gebeyehu et al. |
| 4,923,901 A | 5/1990 | Koester et al. |
| 4,925,785 A | 5/1990 | Wang et al. |

(List continued on next page.)

FOREIGN PATENT DOCUMENTS

| | | | |
|---|---|---|---|
| DE | 3505287 | 9/1985 | |
| EP | 063 810 | 11/1982 | |
| EP | 0 132 621 | 6/1984 | ............ C12Q/1/68 |
| EP | 0 159 719 | 10/1985 | ............ C12Q/1/68 |

(List continued on next page.)

OTHER PUBLICATIONS

Broude, Natalia E., et al., "Enhanced DNA Sequencing By Hybridization," *Proc. Natl. Acad. Sci. USA*, vol. 91, pp. 3072–3076, Apr. 1994.

Chee, Robert, et al., "Accessing Genetic Information with High–Density DNA Arrays," *Science*, vol. 274, Oct. 1996.

Eggers, M., et al., "A Microchip for Quantitative Detection of Molecules Utilizing Luminescent and Radioisotope Reporter Groups," *BioTechniques*, vol. 17, No. 3, 1994.

(List continued on next page.)

*Primary Examiner*—Scott W. Houtteman
(74) *Attorney, Agent, or Firm*—Townsend and Townsend and Crew LLP

(57) ABSTRACT

The present invention provides a simplified method for identifying differences in nucleic acid abundances (e.g., expression levels) between two or more samples. The methods involve providing an array containing a large number (e.g. greater than 1,000) of arbitrarily selected different oligonucleotide probes where the sequence and location of each different probe is known. Nucleic acid samples (e.g. mRNA) from two or more samples are hybridized to the probe arrays and the pattern of hybridization is detected. Differences in the hybridization patterns between the samples indicates differences in expression of various genes between those samples. This invention also provides a method of end-labeling a nucleic acid. In one embodiment, the method involves providing a nucleic acid, providing a labeled oligonucleotide and then enzymatically ligating the oligonucleotide to the nucleic acid. Thus, for example, where the nucleic acid is an RNA, a labeled oligoribonucleotide can be ligated using an RNA ligase. In another embodiment, the end labeling can be accomplished by providing a nucleic acid, providing labeled nucleoside triphosphates, and attaching the nucleoside triphosphates to the nucleic acid using a terminal transferase.

28 Claims, 47 Drawing Sheets

U.S. PATENT DOCUMENTS

| | | | |
|---|---|---|---|
| 4,981,783 A | 1/1991 | Augenlicht | 435/6 |
| 4,987,065 A | 1/1991 | Stavrianopoulos et al. | |
| 4,988,617 A | 1/1991 | Landegren et al. | |
| 4,992,383 A | 2/1991 | Farnsworth | |
| 4,994,373 A | 2/1991 | Stavrianopoulos et al. | |
| 5,002,867 A | 3/1991 | Macevicz | 435/6 |
| 5,013,669 A | 5/1991 | Peters, Jr. et al. | |
| 5,021,550 A | 6/1991 | Zeiger | |
| 5,026,840 A | 6/1991 | Dattagupta et al. | |
| 5,028,525 A | 7/1991 | Gray et al. | |
| 5,028,545 A | 7/1991 | Soini | |
| 5,043,265 A | 8/1991 | Tanke et al. | |
| 5,047,524 A | 9/1991 | Andrus et al. | |
| 5,064,754 A | 11/1991 | Mills | |
| 5,082,830 A | 1/1992 | Brakel et al. | |
| 5,091,652 A | 2/1992 | Mathies et al. | |
| 5,100,777 A | 3/1992 | Chang | |
| 5,141,813 A | 8/1992 | Nelson | |
| 5,143,854 A | 9/1992 | Pirrung et al. | 436/518 |
| 5,153,319 A | 10/1992 | Caruthers et al. | |
| 5,173,260 A | 12/1992 | Zander et al. | |
| 5,185,243 A | 2/1993 | Ullman et al. | |
| 5,188,963 A | 2/1993 | Stapleton | |
| 5,200,051 A | 4/1993 | Cozzette | |
| 5,200,312 A | 4/1993 | Oprandy | |
| 5,202,231 A | 4/1993 | Drmanac et al. | 435/6 |
| 5,204,268 A | 4/1993 | Matsumoto | |
| 5,215,882 A | 6/1993 | Bahl et al. | |
| 5,232,829 A | 8/1993 | Longiaru et al. | |
| 5,242,974 A | 9/1993 | Holmes | |
| 5,252,296 A | 10/1993 | Zuckerman et al. | |
| 5,252,743 A | 10/1993 | Barrett et al. | |
| 5,256,549 A | 10/1993 | Urdea | |
| 5,310,893 A | 5/1994 | Erlich et al. | |
| 5,324,633 A | 6/1994 | Fodor et al. | 435/6 |
| 5,328,824 A | 7/1994 | Ward et al. | |
| 5,338,688 A | 8/1994 | Deeg et al. | |
| 5,348,855 A | 9/1994 | Duttagupta et al. | |
| 5,389,512 A | 2/1995 | Sninsky et al. | |
| 5,412,087 A | 5/1995 | McGall et al. | |
| 5,422,241 A | 6/1995 | Goldrick et al. | 435/6 |
| 5,434,049 A | 7/1995 | Okano et al. | |
| 5,436,327 A | 7/1995 | Southern et al. | |
| 5,445,934 A | 8/1995 | Fodor et al. | 435/6 |
| 5,447,841 A | 9/1995 | Gray et al. | |
| 5,472,842 A | 12/1995 | Stokke et al. | |
| 5,474,796 A | 12/1995 | Brennan | |
| 5,474,895 A | 12/1995 | Ishii et al. | |
| 5,486,452 A | 1/1996 | Gordon et al. | |
| 5,489,507 A | 2/1996 | Chehab | |
| 5,489,678 A | 2/1996 | Fodor et al. | |
| 5,510,270 A | 4/1996 | Fodor et al. | |
| 5,512,430 A | 4/1996 | Gong | |
| 5,514,543 A | 5/1996 | Grossman et al. | |
| 5,514,785 A | 5/1996 | Van Ness et al. | |
| 5,516,641 A | 5/1996 | Ullman et al. | |
| 5,518,883 A | 5/1996 | Soini | |
| 5,543,292 A | 8/1996 | Imai et al. | 435/6 |
| 5,545,531 A | 8/1996 | Rava et al. | |
| 5,556,748 A | 9/1996 | Douglas | |
| 5,556,752 A | 9/1996 | Lockhart et al. | |
| 5,563,060 A | 10/1996 | Hozier | |
| 5,571,639 A | 11/1996 | Hubbell et al. | 430/5 |
| 5,578,832 A | 11/1996 | Trulson et al. | |
| 5,605,662 A | 2/1997 | Heller et al. | |
| 5,620,850 A * | 4/1997 | Bamdad et al. | 530/300 |
| 5,700,637 A | 12/1997 | Southern | |
| 5,744,305 A | 4/1998 | Fodor | |
| 5,795,714 A * | 8/1998 | Cantor et al. | 435/6 |
| 5,800,992 A | 9/1998 | Fodor et al. | |
| 5,807,522 A | 9/1998 | Brown et al. | |
| 5,830,645 A | 11/1998 | Pinkel et al. | |
| 5,972,619 A | 10/1999 | Drmanac et al. | |
| 6,018,041 A | 1/2000 | Drmanac et al. | |
| 6,025,136 A | 2/2000 | Drmanac et al. | |
| 6,030,788 A * | 2/2000 | Gerhold | 435/6 |
| 6,040,138 A | 3/2000 | Lockhart et al. | |
| 6,054,270 A | 4/2000 | Southern | |
| 6,110,426 A | 8/2000 | Shalon et al. | |

FOREIGN PATENT DOCUMENTS

| | | | |
|---|---|---|---|
| EP | 171 150 | 2/1986 | |
| EP | 173 339 | 3/1986 | |
| EP | 185 547 | 6/1986 | |
| EP | 225 807 | 6/1987 | |
| EP | 232 967 | 8/1987 | |
| EP | 235 726 | 9/1987 | |
| EP | 237 362 | 9/1987 | |
| EP | 281 927 | 9/1988 | |
| EP | 0 266 787 | 11/1988 | C12Q/1/68 |
| EP | 0 320 308 | 6/1989 | C12Q/1/68 |
| EP | 0 322 311 | 6/1989 | C12Q/1/68 |
| EP | 0 336 731 | 10/1989 | C12Q/1/68 |
| EP | 337 498 | 10/1989 | |
| EP | 392 546 | 10/1990 | |
| EP | 535 242 A1 | 4/1993 | C12Q/1/68 |
| EP | 0 717 113 A2 | 6/1996 | C12Q/1/68 |
| EP | 721 016 | 7/1996 | |
| EP | 0 721 016 A2 | 7/1996 | C12Q/1/68 |
| FR | 2559783 | 2/1985 | |
| GB | 2156074 | 10/1985 | |
| JP | 63-223557 | 9/1989 | |
| WO | WO84/03151 | 8/1984 | |
| WO | WO85/01051 | 3/1985 | |
| WO | WO89/10977 | 5/1989 | |
| WO | 89/10977 | 11/1989 | C12Q/1/68 |
| WO | WO89/11548 | 11/1989 | |
| WO | 90/00626 | 1/1990 | C12Q/1/68 |
| WO | WO90/03382 | 4/1990 | |
| WO | 90/04652 | 5/1990 | C12Q/1/68 |
| WO | 90/15070 | 12/1990 | C07K/1/04 |
| WO | 92/10092 | 6/1992 | A01N/1/02 |
| WO | WO92/10588 | 6/1992 | |
| WO | 92/10588 | 6/1992 | C12Q/1/68 |
| WO | WO93/11262 | 6/1993 | |
| WO | 93/17126 | 9/1993 | C12Q/1/68 |
| WO | WO93/22680 | 11/1993 | |
| WO | WO95/00530 | 1/1995 | |
| WO | 95/00530 | 1/1995 | C07H/21/04 |
| WO | 95/04594 | 2/1995 | |
| WO | 95/04833 | 2/1995 | |
| WO | 95/04834 | 2/1995 | C12Q/1/682 |
| WO | 95/11995 | 5/1995 | C12Q/1/68 |
| WO | WO95/15970 | 6/1995 | |
| WO | 95/20681 | 8/1995 | C12Q/1/68 |
| WO | WO95/21944 | 8/1995 | |
| WO | WO95/25116 | 9/1995 | |
| WO | 95/30774 | 11/1995 | C12Q/1/68 |
| WO | WO95/35505 | 12/1995 | |
| WO | 95/35505 | 12/1995 | |
| WO | WO96/17958 | 6/1996 | |
| WO | WO98/31836 | 7/1998 | |

OTHER PUBLICATIONS

Feldman, William, et al., "Gray Code Masks for Sequencing by Hybridization," *Genomics* 23, pp. 233–235, 1994.

Fodor et al., "Light–Directed, Spatially Addressable Parallel Chemical Synthesis", *Science*, vol. 221, pp. 767–773, Feb. 1991.

Hoheisel, Jorg D., "Application of Hybridization Techniques to Genome Mapping and Sequencing," *TIG*, vol. 10, No. 3, 1994.

Kallioniemi, Anne, et al., "Comparative Genomic Hybridization for Molecular Cytogenetic Analysis of Solid Tumors," *Science*, vol. 258, Oct. 30, 1992.

Khrapko, et al., "An oligonucleotide hybridization approach to DNA sequencing",*Elsevier Science Publishers B.V.*, vol. 256, Nos. 1,2 pp. 118–122, Oct., 1989.

Lennon, Gregory G., and Lehrach, Hans, "Hybridization Analyses of Arrayed cDNA Libraries," *TIG*, vol. 7, No. 10, Oct. 1991.

Lipshutz, R.J., et al., "Using Oligonucleotide Probe Arrays to Access Genetic Diversity," *BioTechniques*, vol. 19, No. 3, 1995.

Lockhart, David J., et al., "Expression Monitoring by Hybridization To High–Density Oligonucleotide Arrays," *Nature Biotechnology*, vol. 14, Dec. 1996.

Pevzner, P.A., "Improved Chips for Sequencing by Hybridization," *Journal of Biomolecular Structure & Dynamics*, ISSN 0739–1102, vol. 9, Issue 2, 1991.

Schena, Mark, et al., "Parallel Human Genome Analysis: Microarray–Based Expression Monitoring of 1000 Genes," *Proc. Natl. Acad. Sci. USA*, vol. 93, pp. 10614–10619.

Southern, et al. "Analyzing and Compairing Nucleic Acid Sequences by Hybridization to Arrays of Oligonucleotides: Evaluation Using Experimental Models" *Cenomics 13*, pp. 1008–1017, 1992.

Southern, E.M., et al. "Arrays of Complementary Oligonucleotides for Analysing the Hybridisation Behaviour of Nucleic Acids," *Nucleic Acids Research*, vol. 22, No. 8, 1994.

Stimpson, Don I., "Real–time Detection of DNA Hybridization and Melting on Oligonucleotide Arrays by Using Optical Wave Guides," *Proc. Natl. Acad. Sci. USA*, vol. 92, pp. 6379–6383, Jul. 1995.

Augenlicht, et al., "Cloning and Screening of Sequences Expressed in a Mouse Colon Tumor," Cancer Research, 42,1088–1093.

Augenlicht et al., " Expression of Cloned Sequences in Biopsies of Human Colonic Tissue and in Colonic Carcinoma Cells Induced to Differentiate in Vitro," Cancer Research, 47, 6017–6021 (1987).

Bains and Smith, A Novel Method for Nucleic Acid Sequence Determination. *Theor. Biol.* 135: 303–307 (1988).

Bartsh et al., "Cloning of mRNA sequences from the human colon: Preliminary characterization of defined mRNAs in normal neoplastic tissues," Br. J. Cancer, 54:791–798 (1986).

Billings et al., "New Techniques for Physical Mapping of the Human Genome," *FASEB*, 5:28–34 (1991).

Boyle et al, Differential distribution of long and short interspersed element sequences in the mouse genome: Chromosome karyotyping by fluorescence in situ hybridization, *J. Proc. Natl. Acad. Sci. USA* 87:7757–7761 (1990).

*Brock, et al., "Rapid fluorescence detection of in situ hybridization with biotinylated bovine herpesvirus–1 DNA probes," Journal of Veterinary Diagnostic Investigation, 1:34–38 (1989).

*Carrano et al, A High–Resolution. Fluorescence–Based. Semiautomated Method for DNA Fingerprinting, *Genomics* 4, 129–136 (1989).

Caruthers, Gene Synthesis Machines: DNA Chemistry and Its Uses, *Science* 230: 281 (1985).

Chee et al., "Accessing Genetic Information with High–Density DNA Arrays," *Science*, 274:610–614 (1996).

*Chehab et al., "Detecting of specific DNA sequences by fluorescence amplification: A color complementation assay," Proceedings of the national Academy of Sciences, 86:9178–9182 (1989).

*Chehab et al, Detection of sickle cell anemia mutation by colour DNA Amplification, The Lancet 335:15–17 (1990).

Craig et al, Ordering of Cosmid Clones Covering the Herpes Simplex Virus Type I (HSV–I) Genome, *Nuc. Acids. Res.* 18:2653–2660 (1990).

Drmanac et al., "DNA Sequence Determination by Hybridization: A Strategy for Efficeint Large–Scale Sequencing," *Science*, 260:1649–1652 (1993).

Drmanac et al., "Sequencing by Hybridization: Towards an Automated Sequencing of One Million M13 Clones Arrayed on Membranes," *Electrophoresis*, 13:566–573 (1992).

Drmanac et al, Laboratory Methods—Reliable Hybridization of Oligonucleotides as Short as Six Nucleotides, *DNA and Cell Biology*, 9:527–534 (1990).

Drmanac et al., "Partial Sequencing by Oligo–Hybridization: Concept and Applications in Genome Analysis," The First International Conference on Electrophoresis, Supercomputing and the Human Genome 60–74 (1990).

Drmanac et al. "Sequencing by Oligonucleotide Hybridization: A Promising Framework in Decoding of the Genome Program," The First International Conference on Electrophoresis, Supercomputing and the Human Genome 47–59 (1990).

Drmanac et al., "Sequencing of Megabase Plus DNA by Hybridization: Theory of the Method," Genomics, 4:114–128 (1989).

Eggers et al., "A microchip for quantitative detection of molecules utilizing luminiescent and radioisotope reporter groups," *Biotechniques*, 17(3):516–520, 522, 524–525 (1994).

*Ekins et al, Development of Microspot Multi–Analyte Ratiometric Immunoassay Using Dual Fluorescent–Labeled Antibodies, *Analytica Chimica Acta* 227: 73–96 (1989).

* Ekins et al., Fluorescence Spectroscopy and its Application to a New Generation of High Sensitivity, Multi–Microspot. Multianalyte, Immunoassay, *Clinica Chimica Acta* 194:91–114 (1990).

Ekins et al., "Multianalyte Immunoassay: the Immunological 'Compact disk' of the Future," *J. Clinical Immunoassay*, 13(4):169–181 (1990).

Evans et al., "Physical mapping of complex genomes by cosmid multiplex analysis," Proceedings of the national Academy of Sciences, 86:5030–5034 (1989).

Ezaki et al., "Small–Scale DNA Preparation for Rapid Genetic Identification of Campylobacter Species without Radioisotope," Microbiology Immunology, vol. 32 (2), 141–150 (1988).

*Fan et al. "Mapping small DNA sequences by fluorescene in situ hybridization directly on banded metaphase chromosomes," Proceedings of the national Academy of Sciences, 87:6223–6227 (1990).

Fodor et al., "Light–directed, Spatially Addressable Parrallel Chemical Synthesis," *Science*, 251:767–773 (1991).

Frank, et al., "Simultaneous Synthesis and Biological Applications of DNA Fragments: An Efficient and Complete Methodology," Methods in Enzymology, 154:221–251 (1987).

Gergen et al, Filter Replicas and Permanent Collections of Recombinant DNA Plasmids, *Nucleic Acids Res.* 7:2115–2135 (1979).

Gummerlock, et al., "RAS Enzyme–Linked Immunoblot Assay Discriminates p21 Species: A Technique to Dissect Gene Family Expression," Analytical Biochemistry, 180:158–168 (1989).

Guo et al., "Direct Fluorescence analysis of Genetic polymorphisms by Hybridization with oligonucleotide Arrays on Glass Supports," *Nuc. Acids Res.*, 22(24):5456–5465 (1994).

Haase et al "Detection of two Viral Genomes in Single Cells by Double–Label Hybridization in Situ and Color Microradioautography," Science 227, 189–192 (1985).

Hanahan et al., "Plasmid screening at high colony density", Gene 10:63–67 (1980).

Hanahan et al., "Plasmid screening at high density," Methods in Enzymology, 100:333–342 (1983).

*Hopman et al. "Bi–color detection of two target DNAs by non–radioactive in situ hybridization,"0 Histochemistry, 85:1–4 (1986).

J.A., "Putting Genes on a Chip," *Science*, 264: (1994).

Johnston et al., "Chemistry of High Density Arrays: Factors Impacting Issues of Complexity," (abstract) *Microbial & Comparative Genomics*, 1:235 (1996).

Kallioniemi et al., "Comparative Genomic Hybridization for Molecular Cytogenic Analysis of Solid Tumors," *Science*, 258:818–821 (1992).

Kallioniemi et al., "Optimizing Comparative Genomic Hybridization for Analysis of DNA Sequence Copy Number Changes in solid tumors," *Genes, Chromosomes & Cancer*, 10:231–243 (1994).

Kerkof & Kelly, A Procedure for Making Simultaneous Determinations of the Relative Levels of Gene transcripts in Tissues or Cells, *Anal. Biochem.*, 188: 349–355 (1990).

Khrapko et al., "A Method for DNA Sequencing by Hybridization with Oligonucleotide Matrix," *DNA Sequencing and Mapping*, 1:375–388 (1991).

*Kievits et al., "Rapid subchromosomal localization of cosmids by nonradioactive in situ hybridization," Cytogenetics and Cell Genetics, 53:134–136 (1990).

Kimura et al, An Immobilized Enzyme Membrane Fabrication Method Using an Ink Jet Nozzle, *Biosensors* 4:41–52 (1988).

*Kitazawa, et al., "In situ DNA–RNA hybridization using in vivo bromodeoxyuridine–labeled DNA probe," Histochemistry, 92:195–199 (1989).

Kleinfeld et al, Controlled Outgrowth of Dissociated Neurons on Patterned Substrates. *J. Neuroscience* 8:4098–4120 (1988).

Kohara et al, The Physical Map of the Whole E. coli Chromosome: Application of a New Strategy for Rapid Analysis and Sorting of a large Genomic Library, Cell 50: 495–508 (1987).

Kozal et al., "Extensive Ploymorphisms Observed in HIV–1 Clade B Protease Gene using High–Density Oligonucleotide Arrays," *Nature Medicine*, 2:753–759 (1996).

Kreiner, "Rapid Genetic Sequence Analysis Using a DNA Probe Array System," *American Laboratory*, (Mar. 1996).

Lanier, et al, "Human Lymphocyte Subpopulations Identified by Using Three–Color Immunofluorescence and Flow Cytometry Analysis", The Journal of Immunology, 132:151–156 (1984).

Laskey, et al., "Messenger RNA prevalence in sea urchin embryos measured with cloned cDNAs," Proc. Natl. Acad. Sci. USA, 77:5317–5321 (1986).

Lerach et al., "Labelling oligonucleotides to high specific activity (I)," *Nuc. Acids Res.*, 17(12):4605–4610 (1989).

Lerach et al., "λ Phage Vectors–EMBL Series," *Meth. in Enzymology*, 153:103–115 (1987).

Lehrach et al., "Hybridization Fingerprinting in Genome Mapping and Sequencing," *Vol. I: Genetic and Physical Mapping*, Davies et al., eds., Cold Spring Harbor Laboratory Press, pp. 39–81 (1990).

Lennon et al., "Hybridization Analyses of Arrayed cDNA Libraries," *Trends In Genetics*, 7:314–317 (1991).

Lichter, Ward, et al, Rapid detection of human chromosome 21 aberrations by in situ hybridization, *Proc. Natl. Acad. Sci. USA* 85:9664–9668 (1988).

Lichter et al, Fluorescence in situ hybridization with Alu and Ll polymerase chain reaction probes for rapid characterization of human chromosomes in hybrid cell lines, *Proc. Natl. Acad. Sci. USA* 87:6634–6638 (1990).

*Lichter et al, High–Resolution Mapping of Human Chromosome 11 by in Situ Hybridization with Cosmid Clones, *Science* 247:64–69 (1990).

*Lichter & Ward, Is non–isotopic in situ hybridization finally coming of age? *Nature*, 345: 93–94 (1990).

*Loken, et al, "Three–Color Immunofluorescence Analysis of Leu Antigens on Human Peripheral Blood Using Two Lasers on a Fluoroscence–Activated Cell Sorter," Cymoetry 5:151–158 (1984).

Love, et al., "Screening of Lambda Library for Differentially Expressed Genes Using in Vitro Transcripts," Anal Biochem, 150:429–41 (1985).

Lu et al., "Differential screening of murine ascites cDNA libraries by means of in vitro transcripts of cell–cylcle–phase–specific cDNA and digital image processing," Gene, 86:185–192 (1990).

Lysov, "DNA Sequencing By Oligonucleotide Hybridization," in *The First Intl. Conf. Electrophoresis. Supercomputing and the Human Genome.* Eds. Cantor and Lim, *World Scientific*, pp. 157–163. (4/90).

Lysov et al., "A New Method For Determining the DNA Nucleotide Sequence by Hybridization with Oligonucleotides," Doklady Biochemistry, 303:436–438 (1989).

Masiakowski, et al., "Cloning of cDNA sequences of hormone–regulated genes from the MCF–7 human breast cancer cell line," Nucleic Acids Research, 10:7895–7903 (1982).

Maskos et al., "A Study of Oligonucleotide Reassociation Using Large Arrays of Oligonucleotides Synthesized on a Glass Support," *Nuc. Acids Res.*, 21:4663–4669 (1993).

Medlin, "The Amazing Shrinking Laboratory," *Envr. Hlth. Persp.*, 103:244 (1991).

Meinkoth & Wahl, Hybridization of Nucleic Acids Immobilized on Solid Supports, , *Analytical Biochemistry* 138, 267–284 (1984).

Michiels et al., "Molecular approaches to genome analysis: a strategy for the construction of ordered overlapping clone libraries" CABIOS 3(3):203–210 (1987).

Monaco et al., "Human Genome Linking with Cosmids and Yeast Artificial Chromosomes," Abstract from CSHS p. 90 (1989).

Morrison et al., "Solution–Phase Detection of Polynucleotides Using Interacting Flourescent Labels and Competitive Hybridization" Analytical Biochemistry, 183:231–244 (1989).

Nakamori et al, A Simple and Useful Method for Simultaneous Screening of Elevated Levels of Expression of a Variety of Oncogenes in Malignant Cells, *Jpn. J. Cancer Res.* (Gann), 79:1311–1317 (1988).

Nederlof et al., "Multiple Fluorescence In Situ Hybridization," Cytometry, 11:126–131 (1990).

Nguyen et al., "Differential Gene Expression in the Murine Thymus Assayed by Quantitative Hybridization of Arrayed cDNA Clones," *Genomics*, 29:207–216 (1995).

NIH grant application of P.O. Brown submitted in 1992.

Nowak, "Entering the Postgenome Era," *Science*, 270:368–369 (1995).

Pease et al., "Light–generated oligonucleotide arrays for rapid DNA sequence analysis," *PNAS*, 91:5022–26 (1994).

Pietu et al., "Novel Gene Transcripts Preferentially Expressed in Human Muscles Revealed by Quantative Hybridization of a High Density cDNA Array," *Genome Research*, 6:492–503 (1996).

Poustka, et al., "Molecular Approaches to Mammalian Genetics", Cold Spring Harbor Symp. Quant. Biol., (1986).

Saiki et al., "Genetic analysis of amplified DNA with immobilized sequence–specific oligonucleotide probes," Proceedings of the national Academy of Sciences, 86:6230–6234 (1989).

Scharf et al., "HLA class II allelic variation adn susceptibility to pemphigus vulgaris," Proceedings of the National Academy of Sciences, 85:3504–3508 (1988).

Schena et al., "Structure of Homebox–Leucine Zipper Genes Suggests a Model for the Evolution of Gene Families," *PNAS*, 91:8393–8397 (1994).

Schena, "Genome Analysis with Gene Expression Microarrays," *BioEssays*, 18:427–431 (1996).

Schena et al., "Quantitative Monitoring of Gene Expression Patterns with a Complementary DNA Microarray," *Science*, 270:467–470 (1995).

Schena et al., "Parralel Human Genome Analysis: Microarray–based Expression Monitoring of 1000 Genes," *PNAS*, 93:10614–10619 (1996).

Schnea et al., "The HAT4 Gene of Arabidopsis Encodes a Developmental Regulator," *Genes and Development*, 7:367–379 (1993).

Schena et al., "HD–Zip Proteins: Members of an Arabidopsis Homeodomain Protein Superfamily," *PNAS*, 89:3894–3898 (1992).

Schober et al., "Accurate High–speed Liquid Handling of Very Small Biological Samples," *Biotechniques*, 15(2):324–329 (1993).

Shalon et al., "A DNA Microarray System for Analyzing Complex DNA Samples Using Two–Color Fluoroscent Probe Hybridization," *Genome Res.*, 6:639 (1996).

Shalon, "DNA Micro Arrays: A New Tool for Genetic Analysis," Ph.D. Thesis, Stanford University (1995).

Sim, et al., "Use of a cDNA Library for Studies on Evolution and Developmental Expression of the Chorion Multigene Families", Cell 18:1303–1316 (1979).

Southern et al., "Analyzing and Comparing Nucleic Acid Sequences by Hybridization to Arrays of Oligonucleotides: Evaluation using Experimental Models," *Genomics*, 13:1008–1017 (1992).

Titus, et al., "Texas Red, A Hydrophillic, Red–Emitting Fluorophore for use with Fluorescein in Dual Parameter Flow Microfluorometric and Fluorescence Microscopic Studies," Journal of Immunological Methods, 50:193–204. (1982).

Tkachuk et al., "Detection of bcr–abl Fusion in Chronic Myelogenous Leukemia by in situ Hybridization," Science, 250:559–562 (1990).

Tsusumi et al., "Expression of L– and M–Type Pyruvate Kinase in Human Tissues," Genomics, 2:86–89 (1988).

Turchinskii et al, Multiple Hybridization in Genome Analysis. The Reaction of Diamines and Bisulfite with Cytosine for Introduction of Nonradioactive Labels into DNA. *Molekulyarnaya Biologiya* (English Translation), 22: 1229–1235 (1988).

Urdea et al., "A comparison of non–radioisotopic hybridization assay methods using fluorescent, chemilunimescent and enzyme labeled synthetic oligodeoxyribonucleotide probes," Nucleic Acids Research, 16: 4937–4956 (1988).

Urdea et al., "A Novel Method For The Rapid Detection of Specific Nucleotide Sequences in Crude Biological Samples Without Blotting or Radioactivity; Application to the Analysis of Hepatitis B Virus In Human Serum," Gene 61,253–264 (1987).

Wallace et al., "Hybridization of synthetic oligodeoxyribonucleotides to *x 174 DNA: the effect of single base pair mismatch", Nucleic Acids Research, 11:3543–3557 (1979).

Widacki et al., "Biochemical Differences in Qa–2 Antigens Expressed By Qa–2+,6+ and Qa–2+,6– Strains. Evidence for Differential Expression of the Q7 and Q9 Genes," Molecular Immunology, 27:559–570 (1990).

Woolley et al., "Ultra–high–speed DNA Fragment Separations Using Microfabricated Capillary Array Electrophoresis Chips," *PNAS*, 91:11348 (1994).

Wu, et al., "Synthesis and Properties of Adnosine–5'–triphosphoro–y–1–(5– sulfonic acid) naphthyl Ethylamidate: A Fluorescent Nucleotide Substrate for DNA–Dependent RNA Polymerase from *Escherichia coli*" Arch Biochem Biophys, 246:564–71 (1989).

Wu et al, Direct Analysis of Single Nucleotide Variation in Human DNA and RNA Using In Situ Dot Hybridization, *DNA* 8:135–142 (1989).

Yarbrough, et al., "Synthesis and Properties of Fluorescent Nucleotide Substrates for DNA–dependent RNA Polymerases," J. Biol. Chem. 254:12069–73 (1979).

Young, "Simultaneous Use of Digoxigenin– and Raiolabeled Oligodeoxyribonucleotide Probes for Hybridization Histochemistry," Neuropeptides, 13:271–275 (1989).

Zhao et al., "High–Density cDNA Filter Analysis: A Novel Approach for Large Scale, Quantitative Analysis of Gene Expression," *Gene*, 156:207–213 (1995).

"Preparation of fluorescent–labeled DNA and its use as a probe in molecular hybridization," Bioorg Khim, 12:1508–13.

* cited by examiner

Monitoring mRNA expression from organisms with small genomes:

6 Mb genome or cDNA library

~ 1 kb genomic or cDNA fragments with 5' C

First strand cDNA synthesis

+ random primer set with restriction site restriction cut random primer PCR of cDNA Restriction digest PCR products Sort fragments by 5' ends on Generic Ligation GeneChip intensity differences

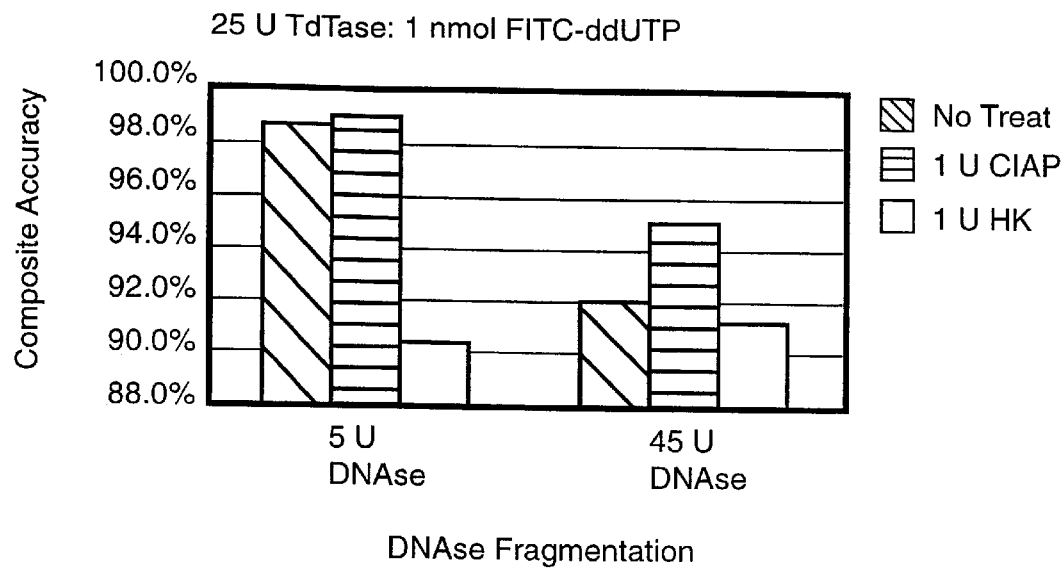
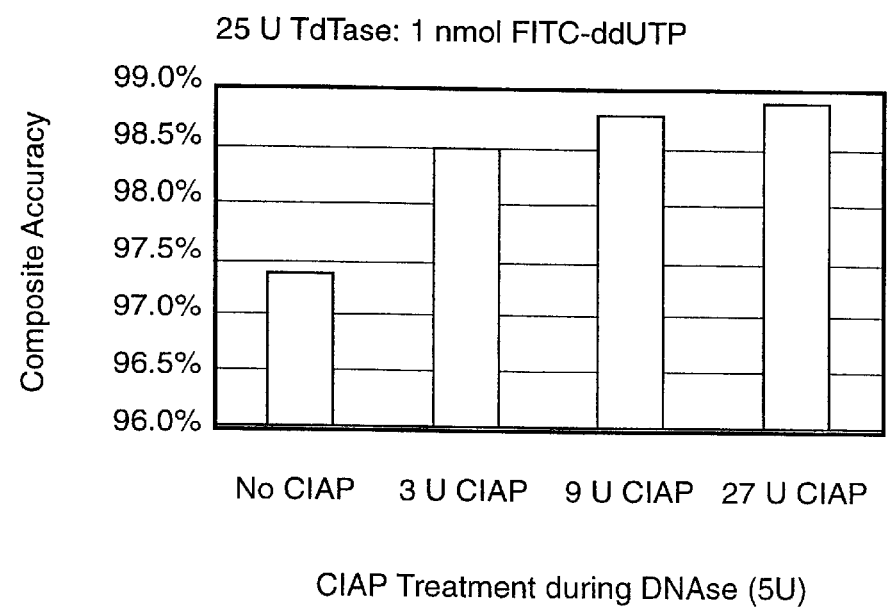
Figure 18

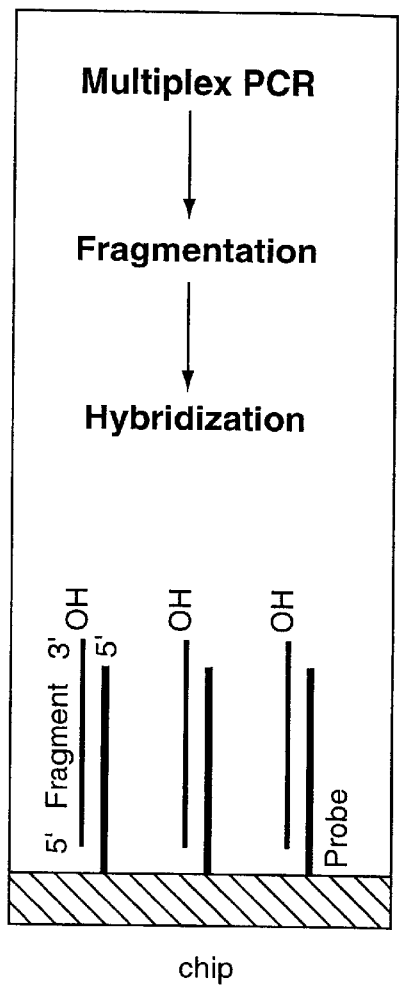
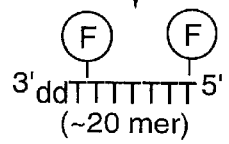
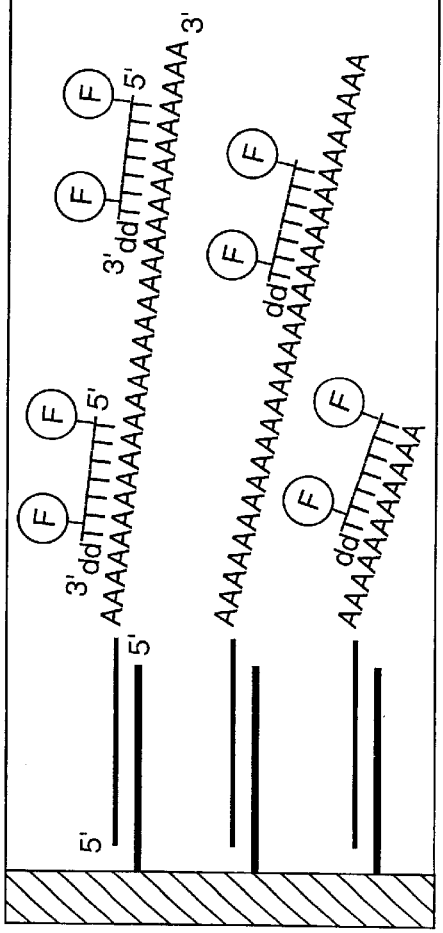
Figure 22 base = heterocycloc moiety (eg. analogs thereof)
∿∿∿ = linker;
LABEL = detectable signal-gene Resequencing a target DNA molecule with a set of generic n-mer tiling probes ie. 4-mer probes:

```
            5'                          3'
Target:     TGACATAGGACAGGCGAAGGGA...

Probe 1:  ACTG 5'
Probe 2:   CTGT
Probe 3:    TGTA
             GTAT
Probe 5:      TATC
               ATCC
                TCCT
                 CCTG
Probe 9:          CTGT...etc.
```

Figure 24

Four electronic tiling arrays are present on a 4-mer generic array:

(4 x 3 = 12 "nearest neighbors" for each probe)

| ie. Probe 5: | Pos. #1 | Pos. #2 | Pos. #3 | Pos. #4 |
|---|---|---|---|---|
| | 5' | | | |
| | TATA | TAAC | TATC | AATC |
| | TATG | TAGC | TGTC | GATC |
| | TATC | TACC | TCTC | CATC |
| | TATT | TATC | TTTC | TATC |
| | AGCT | AGCT | AGCT | AGCT |

Basecall: C T G T
Target Position: 8 7 6 5

Figure 25

Base Calling at the 8th position in the target

Target:     TGACATAGGACAGCGAAGGGA....
                         8th

|  |  | Base-Call |
|---|---|---|
| Probe 5, Pos. 1 | 3'TATC 5' | T |
| Probe 6, Pos. 2 | ATCC | G |
| Probe 7, Pos. 3 | TCCT | C |
| Probe 8, Pos. 4 | CCTG | C |

C is the winner

Figure 26

Mutation Detection by Intensity Comparisons

Algorithms:

$$I_{normalized} = I_{probe}/(\Sigma I_{NN})$$

$$I_{difference} = \frac{(I_{normalized, variant} - I_{normalized, control})}{(I_{normalized, variant} + I_{normalized, control})}$$

- Locally normalized intensities track well
- Local normalization is sensitive to mutations

Bubble Formation Detection of Mutation in HIV Genome
Normalized Intensity Comparison:
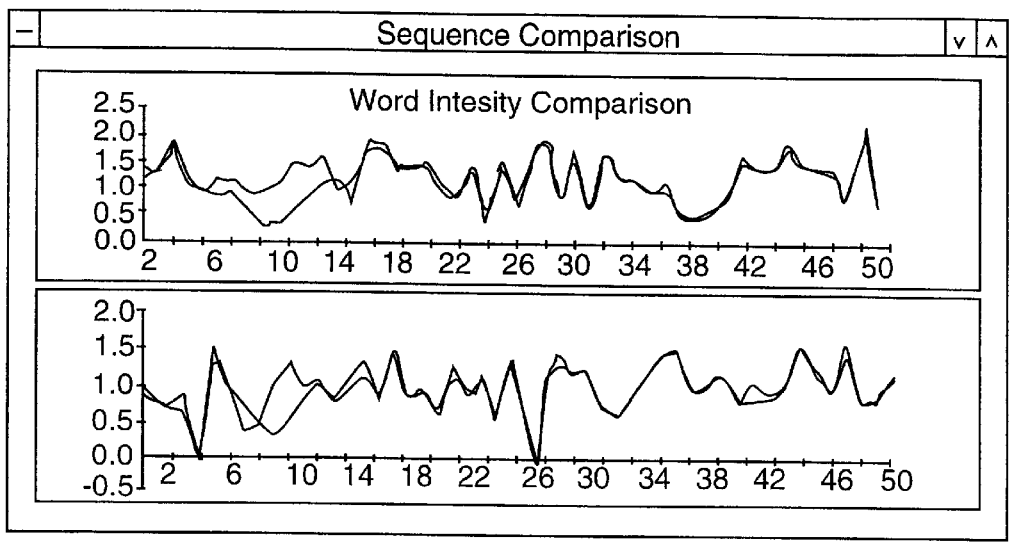
Normalized Difference:
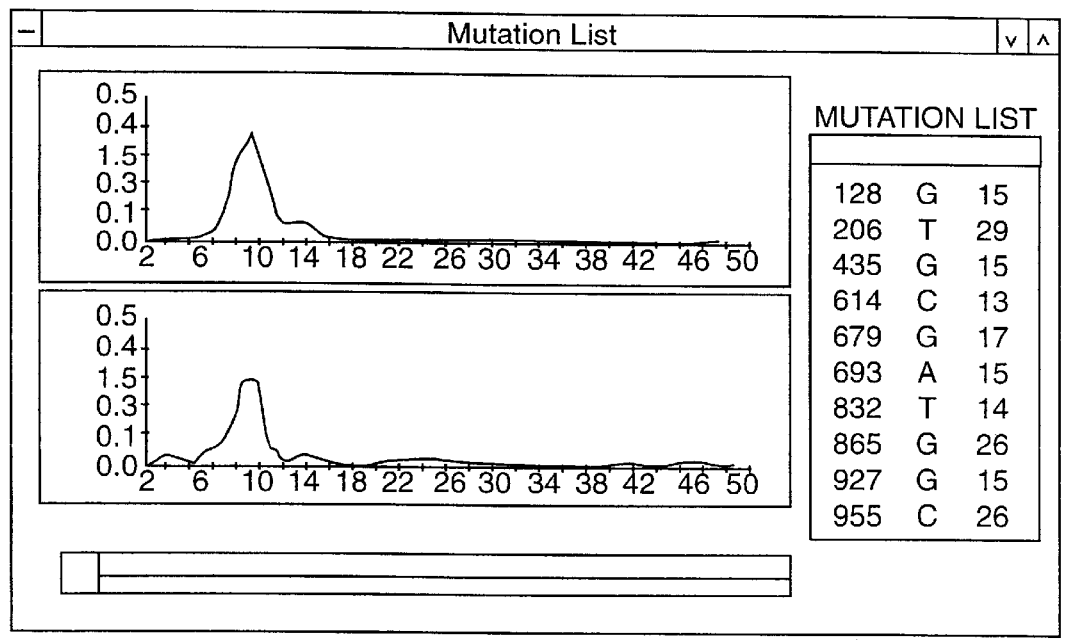
Figure 30

Induced Difference Nearest Neighbor Probe Scoring:

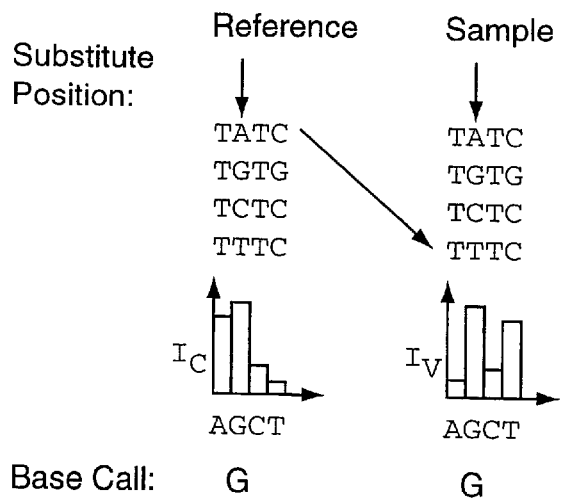

Induced Difference: $D_A = (I_{V,A} - I_{C,A}) / I_{C,A}$

- Average induced differences over all tilings and over both forward and reverse strands.

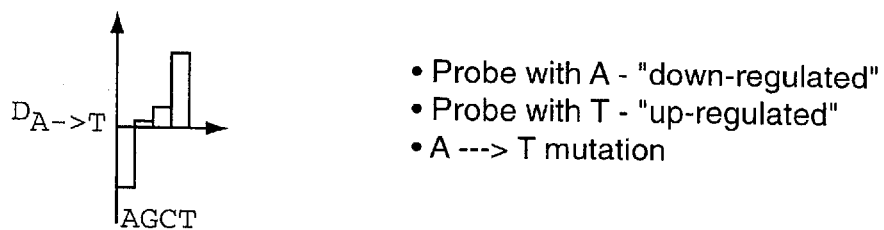

- Probe with A - "down-regulated"
- Probe with T - "up-regulated"
- A ---> T mutation

- Total Induced Difference > + Threshold:Mutation Exists
  Total Induced Difference < - Threshold:Mutation Exists

- Two criteria for mutations: Induced Difference Scores; Bubble Formation

Figure 31

Mutations found in an HIV PCR target (B) using a generic ligation GeneChip and induced difference analysis

```
     21        30        40        50
   actgtatcctttagcttccctcagatcact
   actgtatcctttaacttccctcagatcact
```

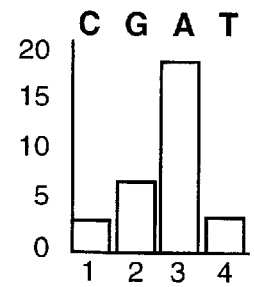

```
    134       140       150       160
   attagaagaaatgaatttgccaggaagatg
   attagaagaaatgagtttgccaggaagatg
```

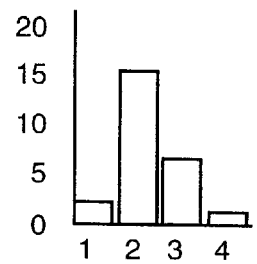

```
    211       220       230       240
   agtatgatcagatacccatagaaatctgtg
   agtatgatcagatactcatagaaatctgtg
```

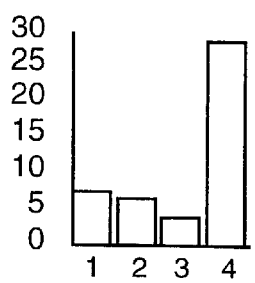

```
    440       420       430       440
   agaaatttgtacagaaatggaaaaggaagg
   agaaatttgtacagrgatggaaaaggaagg
```

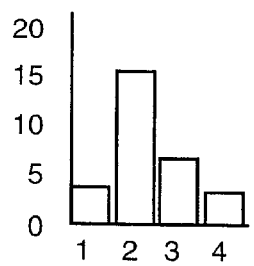

```
    621       630       640       650
   catcccgcagggttaaaaagaaaaaatca
   catcccgcagggtcmaaaaagaaaaaatca
```

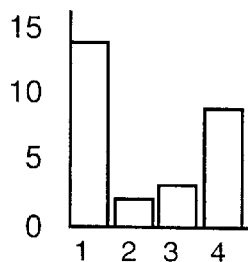

Figure 32a

```
693       700         710        720
ttagataaagacttcaggaagtatactgca
ttagatgaagacttcaggaaatatactgca
```

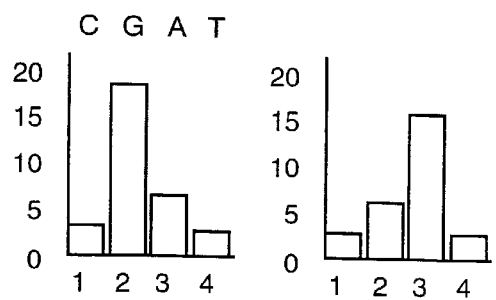

```
840       850        860    867
tagagccttttagaaaacaaaatccagaca
tagagccttttagataacaaaatccagaca
```

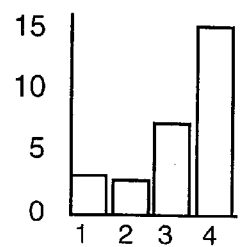

```
872       880        890        900
tatctatcaatacatggatgatttgtatgt
tatctatcaatacgtggatgatttgtatgt
```

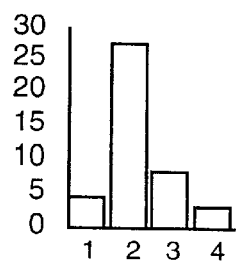

```
934   940       950        960
caaaaatagaggaactgagacaacatctgt
caaaaatagaggagctgagacaacatctgt
```

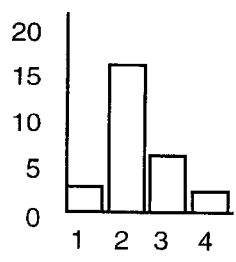

```
960       970        980    989
ctgttgaggtggggatttaccacaccagac
ctgttgaggtggggacttaccacaccagac
```

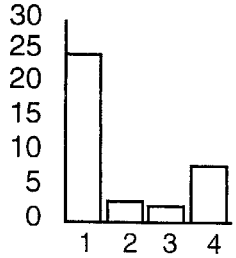

Figure 32b

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 1:

AGCTTTTTTCATGCATCTAT      20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 2:

AAGCGCGATC GATTATGCTC      20

(2) INFORMATION FOR SEQ ID NO: 3:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 3:

ATCTCGGATC GATCGGATAA GCGCGATCGA TTATGCTCGG CGA      43

(2) INFORMATION FOR SEQ ID NO: 4:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (ix) Features:

```
        (xi) SEQUENCE DESCRIPTION: SEQ ID NO: 4:

NVANVGNVCN VT                                                    12

(2) INFORMATION FOR SEQ ID NO: 5:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 5:

GAATTGTAAT ACGACTCACT ATAGGGAGG                                  29

(2) INFORMATION FOR SEQ ID NO: 6:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 6:

AGATGCAATT AACCCTCACT AAAGGGAGA                                  29

(2) INFORMATION FOR SEQ ID NO: 7:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 7:

CVAAAAAAAA AAAAA                                                 15

(2) INFORMATION FOR SEQ ID NO: 8:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 8:

GVTTTTTTTT TTTTTT                                                16
```

(2) INFORMATION FOR SEQ ID NO: 9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 9:

AAAATAAAAT AAAA                                                      14

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 10:

AAAAAAAAAA AAAAAAAAAA AAAAAAAAAA                                     30

(2) INFORMATION FOR SEQ ID NO: 11:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 11:

AAAAAAAAAA A                                                         11

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 12:

TGACATAGGA CAGCGAAGGG A                                              21

(2) INFORMATION FOR SEQ ID NO: 13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 13:

ACTGTATCCT TTAGCTTCCC TCAGATCACT                                               30

(2) INFORMATION FOR SEQ ID NO: 14:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 14:

ACTGTATCCT TTAACTTCCC TCAGATCACT                                               30

(2) INFORMATION FOR SEQ ID NO: 15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 15:

ATTAGAAGAA ATGAATTTGC CAGGAAGATG                                               30

(2) INFORMATION FOR SEQ ID NO: 16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 16:

ATTAGAAGAA ATGAGTTTGC CAGGAAGATG                                               30

(2) INFORMATION FOR SEQ ID NO: 17:

(i) SEQUENCE CHARACTERISTICS:
            (A) LENGTH: 30 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 17:

AGTATGATCA GATACCCATA GAAATCTGTG                    30

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 18:

AGTATGATCA GATACTCATA GAAATCTGTG                    30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 19:

AGAAATTTGTA CAGAAATGGA AAAGGAAGG                    30

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 20:

AGAAATTTGTA CAGRGATGGA AAAGGAAGG                    30

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: YES (ix) Features:

(xi) SEQUENCE DESCRIPTION: SEQ ID NO: 21

CATCCCGCAG   GGTTAAAAAA GAAAAAATCA                                         30

(2) INFORMATION FOR SEQ ID NO: 22:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 22

CATCCCGCAG   GGTCMAAAAA GAAAAAATCA                                         30

(2) INFORMATION FOR SEQ ID NO: 23:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 23

TTAGATAAAG ACTTCAGGAA GTATACTGCA                                           30

(2) INFORMATION FOR SEQ ID NO: 24:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 24

TTAGATGAAG ACTTCAGGAA ATATACTGCA                                           30

(2) INFORMATION FOR SEQ ID NO: 25:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)
```

(iii) HYPOTHETICAL: YES (ix) Features:

(xi) SEQUENCE DESCRIPTION: SEQ ID NO: 25

TAGAGCCTTT TAGAAAACAA AATCCAGACA                                                    30

(2) INFORMATION FOR SEQ ID NO: 26:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 26

TAGAGCCTTT TAGATAACAA AATCCAGACA                                                    30

(2) INFORMATION FOR SEQ ID NO: 27:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 27

TATCTATCAA TACATGGATG ATTTGTATGT                                                    30

(2) INFORMATION FOR SEQ ID NO: 28:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 28

TATCTATCAA TACGTGGATG ATTTGTATGT                                                    30

(2) INFORMATION FOR SEQ ID NO: 29:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) Features:

-continued

```
    (xi) SEQUENCE DESCRIPTION: SEQ ID NO: 29

CAAAAATAGA GGAACTGAGA CAACATCTGT                                              30

(2) INFORMATION FOR SEQ ID NO: 30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 30

CAAAAATAGA GGAGCTGAGA CAACATCTGT                                              30

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 31

CTGTTGAGGT GGGGATTTAC CACACCAGAC                                              30

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) Features:

(xi) SEQUENCE DESCRIPTION: SEQ ID NO: 32

CTGTTGAGGT GGGGACTTAC CACACCAGAC                                              30
```

NUCLEIC ACID ANALYSIS TECHNIQUES

CROSS REFERENCE TO RELATED APPLICATIONS

This is a continuation of PCT/US97/01603, filed on Jan. 22, 1997, designating the United States of America, which derives priority from USSN 60/010,471 filed Jan. 23, 1996 and USSN 60/035,170, filed Jan. 9, 1997, all of which are herein incorporated by reference for all purposes.

BACKGROUND OF THE INVENTION

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

Many disease states are characterized by differences in the expression levels of various genes either through changes in the copy number of the genetic DNA or through changes in levels of transcription (e.g. through control of initiation, provision of RNA precursors, RNA processing, etc.) of particular genes. For example, losses and gains of genetic material play an important role in malignant transformation and progression. These gains and losses are thought to be "driven" by at least two kinds of genes. Oncogenes are positive regulators of tumorigenesis, while tumor suppressor genes are negative regulators of tumorigenesis (Marshall, Cell, 64: 313–326 (1991); Weinberg, Science, 254: 1138–1146 (1991)). Therefore, one mechanism of activating unregulated growth is to increase the number of genes coding for oncogene proteins or to increase the level of expression of these oncogenes (e.g. in response to cellular or environmental changes), and another is to lose genetic material or to decrease the level of expression of genes that code for tumor suppressors. This model is supported by the losses and gains of genetic material associated with glioma progression (Mikkelson et al. J. Cell. Biochem. 46: 3–8 (1991)). Thus, changes in the expression (transcription) levels of particular genes (e.g. oncogenes or tumor suppressors), serve as signposts for the presence and progression of various cancers.

Similarly, control of the cell cycle and cell development, as well as diseases are characterized by the variations in the transcription levels of particular genes. Thus, for example, a viral infection is often characterized by the elevated expression of genes of the particular virus. For example, outbreaks of Herpes simplex, Epstein-Barr virus infections (e.g. infectious mononucleosis), cytomegalovirus, Varicella-zoster virus infections, parvovirus infections, human papillomavirus infections, etc. are all characterized by elevated expression of various genes present in the respective virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states.

The use of "traditional" hybridization protocols for monitoring or quantifying gene expression is problematic. For example two or more gene products of approximately the same molecular weight will prove difficult or impossible to distinguish in a Northern blot because they are not readily separated by electrophoretic methods. Similarly, as hybridization efficiency and cross-reactivity varies with the particular subsequence (region) of a gene being probed it is difficult to obtain an accurate and reliable measure of gene expression with one, or even a few, probes to the target gene.

The development of VLSIPS™ technology provided methods for synthesizing arrays of many different oligonucleotide probes that occupy a very small surface area. See U.S. Pat. No. 5,143,854 and PCT patent publication No. WO 90/15070. U.S. patent application Ser. No. 082,937, filed Jun. 25, 1993, describes methods for making arrays of oligonucleotide probes that can be used to provide the complete sequence of a target nucleic acid and to detect the presence of a nucleic acid containing a specific nucleotide sequence.

Previous methods of measuring nucleic acid abundance differences or changes in the expression of various genes (e.g., differential diaplay, SAGE, cDNA sequencing, clone spotting, etc.) require assumptions about, or prior knowledge regarding the target sequences in order to design appropriate sequence-specific probes. Other methods, such as subtractive hybridization, do not require prior sequence knowledge, but also do not directly provide sequence information regarding differentially expressed nucleic acids.

SUMMARY OF THE INVENTION

The present invention, in one embodiment, provides methods of monitoring the expression of a multiplicity of preselected genes (referred to herein as "expression monitoring"). In another embodiment this invention provides a way of identifying differences in the compositions of two or more nucleic acid (e.g., RNA or DNA) samples. Where the nucleic acid abundances reflect expression levels in biological samples from which the samples are derived, the invention provides a method for identifying differences in expression profiles between two or more samples. These "generic difference screening methods" are rapid, simple to apply, require no a priori assumptions regarding the particular sequences whose expression may differ between the two samples, and provide direct sequence information regarding the nucleic acids whose abundances differ between the samples.

In one embodiment, this invention provides a method of identifying differences in nucleic acid levels between two or more nucleic acid samples. The method involves the steps of: (a) providing one or more oligonucleotide arrays said arrays comprising probe oligonucleotides attached to a surface; (b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; (c) contacting said one or more arrays with a nucleic acid ligase; and (d) determining differences in hybridization between said nucleic acid samples wherein said differences in hybridization indicate differences in said nucleic acid levels.

In another embodiment, the method of identifying differences in nucleic acid levels between two or more nucleic acid samples involves the steps of: (a) providing one or more oligonucleotide arrays comprising probe oligonucleotides wherein said probe oligonucleotides comprise a constant region and a variable region; (b) hybridizing said nucleic acid samples to said one or more arrays to form hybrid duplexes between nucleic acids in said nucleic acid samples and said variable regions that are complementary to said nucleic acids or subsequences thereof; and (c) determining differences in hybridization between said nucleic acid samples wherein said differences in hybridization indicate differences in said nucleic acid levels.

In yet another embodiment, the method of identifying differences in nucleic acid levels between two or more nucleic acid samples involves the steps of: (a) providing one or more high density oligonucleotide arrays; (b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; and (c) determining the differences in hybridization between said nucleic acid samples wherein said differences in hybridization indicate differences in said nucleic acid levels.

In still yet another embodiment, the method of identifying differences in nucleic acid levels between two or more nucleic acid samples involves the steps of: (a) providing one or more oligonucleotide arrays each comprising probe oligonucleotides wherein said probe oligonucleotides are not chosen to hybridize to nucleic acids derived from particular preselected genes or mRNAs; (b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; and (d) determining differences in hybridization between said nucleic acid samples wherein said differences in hybridization indicate differences in said nucleic acid levels.

In another embodiment, the methods of identifying differences in nucleic acid levels between two or more nucleic acid samples involves the steps of: (a) providing one or more oligonucleotide arrays each comprising probe oligonucleotides wherein said probe oligonucleotides comprise a nucleotide sequences or subsequences selected according to a process selected from the group consisting of a random selection, a haphazard selection, a nucleotide composition biased selection, and all possible oligonucleotides of a preselected length; (b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; and (c) determining differences in hybridization between said nucleic acid samples wherein said differences in hybridization indicate differences in said nucleic acid levels.

In another embodiment, the methods of identifying differences in nucleic acid levels between two or more nucleic acid samples involve the steps of: (a) providing one or more oligonucleotide arrays each comprising probe oligonucleotides wherein said probe oligonucleotides comprise a nucleotide sequence or subsequences selected according to a process selected from the group consisting of a random selection, a haphazard selection, a nucleotide composition biased selection, and all possible oligonucleotides of a preselected length; (b) providing software describing the location and sequence of probe oligonucleotides on said array; (c) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; and (d) operating said software such that said hybridizing indicates differences in said nucleic acid levels.

This invention also provides methods of simultaneously monitoring the expression of a multiplicity of genes. In one embodiment these methods involve (a) providing a pool of target nucleic acids comprising RNA transcripts of one or more of said genes, or nucleic acids derived from said RNA transcripts; (b) hybridizing said pool of nucleic acids to an oligonucleotide array comprising probe oligonucleotides immobilized on a surface; (c) contacting said oligonucleotide array with a ligase; and (d) quantifying the hybridization of said nucleic acids to said array wherein said quantifying provides a measure of the levels of transcription of said genes.

Still yet another method of identifying differences in nucleic acid levels between two or more nucleic acid samples involves the steps of: (a) providing one or more arrays of oligonucleotides each array comprising pairs of probe oligonucleotides where the members of each pair of probe oligonucleotides differ from each other in preselected nucleotides; (b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; (c) determining the differences in hybridization between said nucleic acid samples wherein said differences in hybridization indicate differences in said nucleic acid levels.

Another method of simultaneously monitoring the expression of a multiplicity of genes, involves the steps of: (a) providing one or more oligonucleotide arrays comprising probe oligonucleotides wherein said probe oligonucleotides comprise a constant region and a variable region; (b) providing a pool of target nucleic acids comprising RNA transcripts of one or more of said genes, or nucleic acids derived from said RNA transcripts; (c) hybridizing said pool of nucleic acids to an array of oligonucleotide probes immobilized on a surface; and (d) quantifying the hybridization of said nucleic acids to said array wherein said quantifying provides a measure of the levels of transcription of said genes.

This invention additionally provides methods of making a nucleic acid array for identifying differences in nucleic acid levels between two or more nucleic acid samples. In one embodiment the method involves the steps of: (a) providing an oligonucleotide array comprising probe oligonucleotides wherein said probe oligonucleotides comprise a constant region and a variable region; (b) hybridizing one or more of said nucleic acid samples to said arrays to form hybrid duplexes of said variable region and nucleic acids in said nucleic acid samples comprising subsequences complementary to said variable region; (c) attaching the sample nucleic acids comprising said hybrid duplexes to said array of probe oligonucleotides; and (d) removing unattached nucleic acids to provide a high density oligonucleotide array bearing sample nucleic acids attached to said array.

In another embodiment the method of making a nucleic acid array for identifying differences in nucleic acid levels between two or more nucleic acid samples, involves the steps of: (a) providing a high density array; (b) contacting said array one or more of said two or more nucleic acid samples whereby nucleic acids of said one of said two or more nucleic acid samples form hybrid duplexes with probe oligonucleotides in said arrays; (c) attaching the sample nucleic acids comprising said hybrid duplexes to said array of probe oligonucleotides; and (d) removing unattached nucleic acids to provide a high density oligonucleotide array bearing sample nucleic acids attached to said array.

This invention additionally provides kits for practice of the methods described herein. One kit comprises a container containing one or more oligonucleotide arrays said arrays comprising probe oligonucleotides attached to a surface; and a container containing a ligase. Another kit comprises a container containing one or more oligonucleotide arrays said arrays comprising probe oligonucleotides wherein said probe oligonucleotides comprise a constant region and a variable region. This kit optionally includes a constant oligonucletide complementary to said constant region or a subsequence thereof.

Preferred high density oligonucleotide arrays of this invention comprise more than 100 different probe oligonucleotides wherein: each different probe oligonucleotide is localized in a predetermined region of the array; each different probe oligonucleotide is attached to a surface through a terminal covalent bond; and the density of said probe different oligonucleotides is greater than about 60 different oligonucleotides per 1 $cm^2$. The high density arrays can be used in all of the array-based methods discussed herein. High density arrays used for expression monitoring will typically include oligonucleotide probes selected to be complementary to a nucleic acid derived from one or more preselected genes. In contrast, generic difference screening arrays may contain probe oligonucleotides selected randomly, haphazardly, arbitrarily, or including sequences or subsequences comprising all possible nucleic acid sequences of a particular (preselected) length.

In a preferred embodiment, pools of oligonucleotides or oligonucleotide subsequences comprising all possible nucleic acids of a particular length are selected from the group consisting of all possible 6 mers, all possible 7 mers, all possible 8 mers, all possible 9 mers, all possible 10 mers, all possible 11 mers, and all possible 12 mers.

This invention also provides methods of labeling a nucleic acid. In one embodiment, this method involves the steps of: (a) providing a nucleic acid; (b) amplifying said nucleic acid to form amplicons; (c) fragmenting said amplicons to form fragments of said amplicons; and (d) coupling a labeled moiety to at least one of said fragments.

In another embodiment, the methods involve the steps of: (a) providing a nucleic acid; (b) transcribing said nucleic acid to formed a transcribed nucleic acid; (c) fragmenting said transcribed nucleic acid to form fragments of said transcribed nucleic acid; and (d) coupling a labeled moiety to at least one of said fragments.

In yet another embodiment the methods involve the steps of: (a) providing at least one nucleic acid coupled to a support; (b) providing a labeled moiety capable of being coupled with a terminal transferase to said nucleic acid; (c) providing said terminal transferase; and (d) coupling said labeled moiety to said nucleic acid using said terminal transferase.

In still another embodiment, the methods involve the steps of: (a) providing at least two nucleic acids coupled to a support; (b) increasing the number of monomer units of said nucleic acids to form a common nucleic acid tail on said at least two nucleic acids; (c) providing a labeled moiety capable of recognizing said common nucleic acid tails; and (d) contacting said common nucleic acid tails and said labeled moiety.

In still yet another embodiment, the methods involve the steps of: (a) providing at least one nucleic acid coupled to a support; (b) providing a labeled moiety capable of being coupled with a ligase to said nucleic acid; (c) providing said ligase; and (d) coupling said labeled moiety to said nucleic acid using said ligase.

This invention also provides compounds of the formulas described herein.

Definitions

An array of oligonucleotides as used herein refers to a multiplicity of different (sequence) oligonucleotides attached (preferably through a single terminal covalent bond) to one or more solid supports where, when there is a multiplicity of supports, each support bears a multiplicity of oligonucleotides. The term "array" can refer to the entire collection of oligonucleotides on the support(s) or to a subset thereof. The term "same array" when used to refer to two or more arrays is used to mean arrays that have substantially the same oligonucleotide species thereon in substantially the same abundances. The spatial distribution of the oligonucleotide species may differ between the two arrays, but, in a preferred embodiment, it is substantially the same. It is recognized that even where two arrays are designed and synthesized to be identical there are variations in the abundance, composition, and distribution of oligonucleotide probes. These variations are preferably insubstantial and/or compensated for by the use of controls as described herein.

The phrase "massively parallel screening" refers to the simultaneous screening of at least about 100, preferably about 1000, more preferably about 10,000 and most preferably about 1,000,000 different nucleic acid hybridizations.

The terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides.

An oligonucleotide is a single-stranded nucleic acid ranging in length from 2 to about 1000 nucleotides, more typically from 2 to about 500 nucleotides in length.

As used herein a "probe" is defined as an oligonucleotide capable of binding to a target nucleic acid of complementary sequence through one or more types of chemical bonds, usually through complementary base pairing, usually through hydrogen bond formation. As used herein, an oligonucleotide probe may include natural (i.e. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

The term "target nucleic acid" refers to a nucleic acid (often derived from a biological sample and hence referred to also as a sample nucleic acid), to which the oligonucleotide probe specifically hybridizes. It is recognized that the target nucleic acids can be derived from essentially any source of nucleic acids (e.g., including, but not limited to chemical syntheses, amplification reactions, forensic samples, etc.). It is either the presence or absence of one or more target nucleic acids that is to be detected, or the amount of one or more target nucleic acids that is to be quantified. The target nucleic acid(s) that are detected preferentially have nucleotide sequences that are complementary to the nucleic acid sequences of the corresponding probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. The difference in usage will be apparent from context.

A "ligatable oligonucleotide" or "ligatable probe" or "ligatable oligonucleotide probe" refers to an oligonucleotide that is capable of being ligated to another oligonucleotide by the use of a ligase (e.g., T4 DNA ligase). The ligatable oligonucleotide is preferably a deoxyribonucleotide. The nucleotides comprising the ligatable oligonucleotide are preferably the "standard" nucleotides; A, G, C, and T or U. However derivatized, modified, or alternative nucleotides (e.g., inosine) can be present as long as their presence does not interfere with the ligation reaction. The ligatable probe may be labeled or otherwise modified as long as the label does not interfere with the ligation reaction. Similarly the internucleotide linkages can be modified as long as the modification does not interfere with ligation. Thus, in some instances, the ligatable oligonucleotide can be a peptide nucleic acid.

"Subsequence" refers to a sequence of nucleic acids that comprises a part of a longer sequence of nucleic acids.

A "wobble" refers to a degeneracy at a particular position in an oligonucleotide. A fully degenerate or "4 way" wobble refers to a collection of nucleic acids (e.g., oligonucleotide probes having A, G, C, or T for DNA or A, G, C, or U for RNA at the wobble position.). A wobble may be approximated by the replacement of the nucleotide with inosine which will base pair with A, G, C, or T or U. Typically oligonucleotides containing a fully degenerate wobble produced during chemical synthesis of an oligonucleotide is prepared by using a mixture of four different nucleotide monomers at the particular coupling step in which the wobble is to be introduced.

The term "cross-linking" when used in reference to cross-linking nucleic acids refers to attaching nucleic acids such that they are not separated under typical conditions that are used to denature complementary nucleic acid sequences. Crosslinking preferably involves the formation of covalent linkages between the nucleic acids. Methods of cross-linking nucleic acids are described herein.

The phrase "coupled to a support" means bound directly or indirectly thereto including attachment by covalent binding, hydrogen bonding, ionic interaction, hydrophobic interaction, or otherwise.

"Amplicons" are the products of the amplification of nucleic acids by PCR or otherwise.

"Transcribing a nucleic acid" means the formation of a ribonucleic acid from a deoxyribonucleic acid and the converse (the formation of a deoxyribonucleic acid from a ribonucleic acid). A nucleic acid can be transcribed by DNA-dependent RNA polymerase, reverse transcriptase, or otherwise.

A labeled moiety means a moiety capable of being detected by the various methods discussed herein or known in the art.

The term "complexity" is used here according to standard meaning of this term as established by Britten et al. *Methods of Enzymol.* 29:363 (1974). See, also *Cantor and Schimmel Biophysical Chemistry: Part III* at 1228–1230 for further explanation of nucleic acid complexity.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe." In the case of expression monitoring arrays, perfect match probes are typically preselected (designed) to be complementary to particular sequences or subsequences of target nucleic acids (e.g., particular genes). In contrast, in generic difference screening arrays, the particular target sequences are typically unknown. In the latter case, prefect match probes cannot be preselected. The term perfect match probe in this context is to distinguish that probe from a corresponding "mismatch control" that differs from the perfect match in one or more particular preselected nucleotides as described below.

The term "mismatch control" or "mismatch probe", in expression monitoring arrays, refers to probes whose sequence is deliberately selected not to be perfectly complementary to a particular target sequence. For each mismatch (MM) control in a high-density array there preferably exists a corresponding perfect match (PM) probe that is perfectly complementary to the same particular target sequence. In "generic" (e.g., random, arbitrary, haphazard, etc.) arrays, since the target nucleic acid(s) are unknown perfect match and mismatch probes cannot be a priori determined, designed, or selected. In this instance, the probes are preferably provided as pairs where each pair of probes differ in one or more preselected nucleotides. Thus, while it is not known a priori which of the probes in the pair is the perfect match, it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3, 4, 5, or more) of probes that differ from each other in particular preselected nucleotides. While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each region of the array. In a preferred embodiment, background is calculated as the average hybridization signal intensity for the lowest 1% to 10% of the probes in the array, or region of the array. In expression monitoring arrays (i.e., where probes are preselected to hybridize to specific nucleic acids (genes)), a different background signal may be calculated for each target nucleic acid. Where a different background signal is calculated for each target gene, the background signal is calculated for the lowest 1% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is of mammalian origin). Background can also be calculated as the average signal intensity produced by regions of the array that lack any probes at all.

The term "quantifying" when used in the context of quantifying nucleic acid abundances or concentrations (e.g., transcription levels of a gene) can refer to absolute or to relative quantification. Absolute quantification may be accomplished by inclusion of known concentration(s) of one or more target nucleic acids (e.g. control nucleic acids such as BioB or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes or between two or more treatments to quantify the changes in hybridization intensity and, by implication, transcription level.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, Adv. Appl. Math. 2: 482 (1981), by the homology alignment algorithm of Needleman and Wunsch J. Mol. Biol. 48: 443 (1970), by the search for similarity method of Pearson and Lipman, Proc. Natl. Acad. Sci. USA 85: 2444 (1988), by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in Gene, 73: 237–244 (1988) and in CABIOS 5: 151–153 (1989)).

BRIEF DESCRIPTION OF THE DRAWINGS

FIG. 12 generally illustrates the various components of the probe oligonucleotide/ligation reaction system. FIG. 12b illustrates discrimination of non-perfectly complementary target:oligonucleotide hybrids using the probe oligonucleotide/ligation reaction system.

FIG. 13a illustrates various components of the ligation/hybridization reaction some of which are optional in various embodiments. FIG. 13b illustrates a ligation strateby that discriminates mismatches at the terminus of the probe oligonucleotide. FIG. 13c illustrates a ligation strategy that discriminates mismatches at the terminus of the sample oligonucleotide. FIG. 13d illustrates a method for improving the discrimination at both the probe terminus and the sample terminus.

FIG. 14a shows the recognition site and cleavage pattern of SacI (a 6 cutter) and Hsp92II (4 cutter). FIG. 14b illustrates the effect of SacI cleavage on a (target) nucleic acid sample. FIG. 14c illustrates a 6 Mb genome (i.e., E. coli) digested with SacI and SphI generating ~1 kb genomic fragments with a 5' C. FIG. 14d illustrates the hybridization/ligation of these fragments to a generic difference screening chip and their subsequent use as probes to hybridize to the appropriate nucleic acid (Format I) or the fragments are labeled, hybridized/ligated to the oligonucleotide aray and directly analyzed (Format II).

FIG. 15a shows first strand cDNA synthesis (SEQ ID NO:7) by reverse transcription of poly(a) mRNA using an anchored poly(T) primer (SEQ ID NO:8). FIG. 15b illustrates upstream primers for PCR reaction containing an engineered restriction site and degenerate bases (N=A,G,C,T) at the 3' end. FIG. 15c shows randomly primed PCR of the first strand cDNA. FIG. 15d shows restriction digest of PCR products, and 15e shows sorting of PCR products on a generic ligation array by ther 5' end.

FIG. 16a shows the differences between replicate 1 and replicate 2 for sample 1, the normal cell line. FIG. 16b shows the differences between replicate 1 and replicate 2 for sample 2, the tumor cell line). FIG. 16c plots the differences between sample 1 and 2 averaged over the two replicates.

FIG. 17a shows the relative change in hybridization intensities of replicate 1 and 2 of sample 1 for the difference of each oligonucleotide pair. FIG. 17b shows the ratio of replicate 1 and 2 of sample 2 for the difference of each oligoncleotide pair, normalized, filtered, and plotted the same way as in FIG. 17A. FIG. 17c shows the ratio of sample 1 and sample 2 averaged over two replicates for the difference of each oligonucleotide pair. The ratio is calculated as in FIG. 17A, but based on the absolute value of $[(X_{21k1}+X_{22k2})/2]/[(X_{11k1}+X_{12k2})/2]$ and $[(X_{11k1}+X_{12k2})/2]/[(X_{21k1}+X_{22k2})/2]$ after normalization as in FIG. 16c.

FIG. 18 illustrates post-fragmentation labeling using a CIAP treatment.

FIG. 22 illustrates oligo dT labeling on a high density oligonucleotide array (SEQ ID NOS:10 and 11).

FIG. 23 illustrates various labeling reagents suitable for use in the methods disclosed herein.

FIG. 24 illustrates resequencing of a target DNA molecule with a set of generic n-mer tiling probes (target sequence is SEQ ID NO:12).

FIG. 25 illustrates four tiling arrrays present on a 4-mer generic array.

FIG. 26 illustrates base calling at the 8th position in the target.

FIG. 30 illustrates bubble formation detection of mutation in the HIV genome.

FIG. 31 illustrates induced difference nearest neighbor probe scoring.

FIG. 32 illustrates mutations found in an HIV PCR target (B) using a generic ligation GeneChip™ and induced difference analysis (SEQ ID NOS:13–32 respectively).

DETAILED DESCRIPTION

Expression Monitoring and Generic Difference Screening

Figure 1:
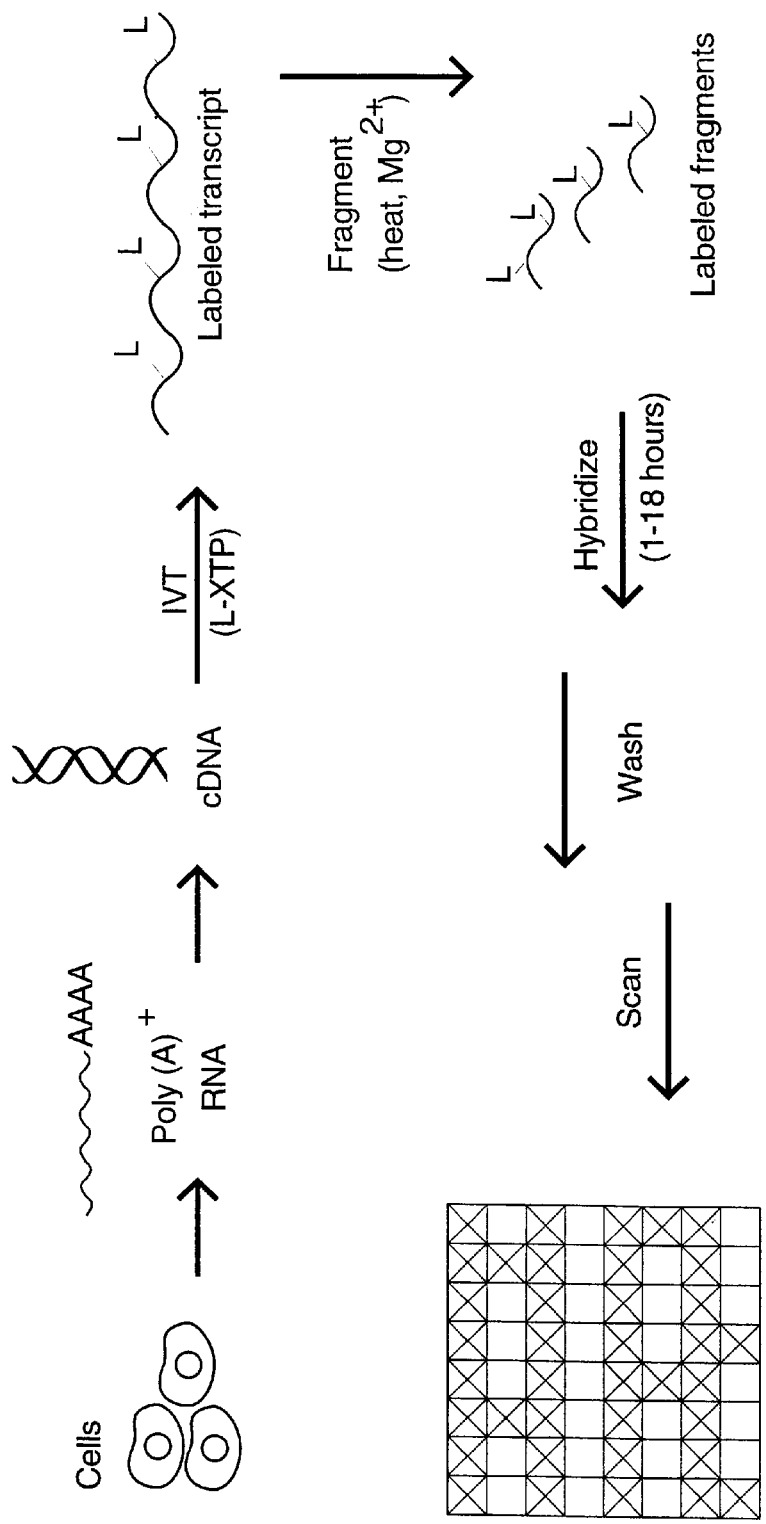
FIG. 1 shows a schematic of expression monitoring using oligonucleotide arrays. Extracted poly $(A)^+$ RNA is converted to cDNA, which is then transcribed in the presence of labeled ribonucleotide triphosphates. L is either biotin or a dye such as fluorescein. RNA is fragmented with heat in the presence of magnesium ions. Hybridizations are carried out in a flow cell that contains the two-dimensional DNA probe arrays. Following a brief washing step to remove unhybridized RNA, the arrays are scanned using a scanning confocal microscope. Alternatives in which cellular mRNA is directly labeled without a cDNA intermediate are described in the Examples. Image analysis software converts the scanned array images into text files in which the observed intensities at specific physical locations are associated with particular probe sequences.

This invention provides methods of expression monitoring and generic difference screening. The term expression monitoring is used to refer to the determination of levels of expression of particular, typically preselected, genes. In a preferred embodiment, the expression monitoring methods of this invention utilize high density arrays of oligonucleotides selected to be complementary to predetermined subsequences of the gene or genes whose expression levels are to be detected. Nucleic acid samples are hybridized to the arrays and the resulting hybridization signal provides an indication of the level of expression of each gene of interest. Because of the high degree of probe redundancy (typically there are multiple probes per gene) the expression monitoring methods provide an essentially accurate absolute measurement and do not require comparison to a reference nucleic acid.

In another embodiment, this invention provides generic difference screening methods, that identify differences in the abundance (concentration) of particular nucleic acids in two or more nucleic acid samples. The generic difference screening methods involve hybridizing two or more nucleic acid samples to the same array high density oligonucleotide array, or to different high density oligonucleotide arrays having the same oligonucleotide probe composition, and optionally the same oligonucleotide spatial distribution. The resulting hybridizations are then compared allowing determination which nucleic acids differ in abundance (concentration) between the two or more samples.

Where the concentrations of the nucleic acids comprising the samples reflects transcription levels genes in a sample from which the nucleic acids are derived, the generic difference screening methods permit identification of differences in transcription (and by implication in expression) of the nucleic acids comprising the two or more samples. The differentially (e.g., over- or under) expressed nucleic acids thus identified can be used (e.g., as probes) to determine and/or isolate those genes whose expression levels differs between the two or more samples.

The generic difference screening methods are advantageous in that, in contrast to the expression monitoring methods, they require no a priori assumptions about the probe oligonucleotide composition of the array. To the contrary, the sequences of the probe oligonucleotides may be random, haphazard, or any arbitrary subset of oligonucleotide probes. Where the oligonucleotide probes are short enough (e.g., less than or equal to a 12 mer) the array may contain every possible nucleic acid of that length. Despite the fact that the generic difference screening arrays might be arbitrary or random, since the sequence of each probe in the array is known the generic difference screening methods still provide direct sequence information regarding the differentially expressed nucleic acids in the samples.

The expression monitoring and generic difference screening methods of this invention involve providing an array containing a large number (e.g. greater than 1,000) of arbitrarily selected different oligonucleotide probes (probe oligonucleotides) where the sequence and location in the array of each different probe is known. Nucleic acid samples (e.g. mRNA) are hybridized to the probe arrays and the pattern of hybridization is detected.

It is demonstrated herein and in copending applications U.S. patent Ser. No. 08/529,115 filed on Sep. 15, 1995 and PCT/US96/14839 that hybridization with high density oligonucleotide probe arrays provides an effective means of detecting and/or quantifying the expression of particular nucleic acids in complex nucleic acid populations. The expression monitoring and difference screening methods of this invention may be used in a wide variety of circumstances including detection of disease, identification of differential gene expression between two samples (e.g., a pathological as compared to a healthy sample), screening for compositions that upregulate or downregulate the expression of particular genes, and so forth.

In one preferred embodiment, the methods of this invention are used to monitor the expression (transcription) levels of nucleic acids whose expression is altered in a disease state. For example, a cancer may be characterized by the overexpression of a particular marker such as the HER2 (c-erbB-2/neu) proto-oncogene in the case of breast cancer. Similarly, overexpression of receptor tyrosine kinases (RTKs) is associated with the etiology of a number of tumors including carcinomas of the breast, liver, bladder, pancreas, as well as glioblastomas, sarcomas and squamous carcinomas (see Carpenter, *Ann. Rev. Biochem.*, 56: 881–914 (1987)). Conversely, a cancer (e.g., colerectal, lung and breast) may be characterized by the mutation of or underexpression of a tumor suppressor gene such as P53 (see, e.g., Tominaga et al. *Critical Rev. in Oncogenesis*, 3: 257–282 (1992)).

Where the particular genes of interest are known. The high density arrays will preferably contain probe oligonucleotides selected to be complementary to the sequences or subsequences of those genes of interest. High probe redundancy for each gene of interest can be achieved and absolute expression levels of each gene can be determined.

Conversely, where it is unknown which genes differ in expression between the healthy and disease state the generic difference screening methods of this invention are particularly appropriate. Hybridization of the healthy and pathological nucleic acids to the generic difference screening arrays disclosed herein and comparison of the hybridization patterns identifies those genes whose regulation is altered in the pathological state.

Similarly, the expression monitoring and generic difference screening methods of this invention can be used to monitor expression of various genes in response to defined stimuli, such as a drug, cell activation, etc. The methods are particularly advantageous because they permit simultaneous monitoring of the expression of large numbers of genes. This is especially useful in drug research if the end point description is a complex one, not simply asking if one particular gene is overexpressed or underexpressed. Thus, where a disease state or the mode of action of a drug is not well characterized, the methods of this invention allow rapid determination of the particularly relevant genes. Again, where the gene of interest is known or suspected, expression monitoring methods will preferably be used, while generic screening methods will be used when the particular genes of interest are unknown.

Using the generic difference screening methods disclosed herein, lack of knowledge regarding the particular genes does not prevent identification of useful therapeutics. For example, if the hybridization pattern on a particular high density array for a healthy cell is known and significantly different from the pattern for a diseased cell, then libraries of compounds can be screened for those that cause the pattern for a diseased cell to become like that for the healthy cell. This provides a very detailed measure of the cellular response to a drug.

Generic difference screening methods thus provide a powerful tool for gene discovery and for elucidating mechanisms underlying complex cellular responses to various stimuli. For example, in one embodiment, generic difference screening can be used for "expression fingerprinting". Suppose it is found that the mRNA from a certain cell type displays a distinct overall hybridization pattern that is different under different conditions (e.g. when harboring mutations in particular genes, in a disease state). Then this pattern of expression (an expression fingerprint), if reproducible and clearly differentiable in the different cases can be used as a very detailed diagnostic. It is not even required that the pattern be fully interpretable, but just that it is specific for a particular cell state (and preferably of diagnostic and/or prognostic relevance).

Both expression monitoring methods and generic difference screening may also be used in drug safety studies. For example, if one is making a new antibiotic, then it should not significantly affect the expression profile for mammalian cells. The hybridization pattern could be used as a detailed measure of the effect of a drug on cells. In other words, as a toxicological screen.

The expression monitoring and generic difference screening methods of this invention are particularly well suited for gene discovery. For example, as explained above, the generic difference screening methods identify differences in abundances of nucleic acids in two or more samples. These differences may indicate changes in the expression levels of previously unknown genes. The sequence information provided by a difference screening array can be utilized, as described herein, to identify the unknown gene.

The expression monitoring methods can be used in gene discovery by exploiting the fact that many genes that have been discovered to date have been classified into families based on commonality of the sequences. Because of the extremely large number of probes it is possible to place in the high density array, it is possible to include oligonucleotide probes representing known or parts of known members from every gene class. In utilizing such a "chip" (high density array) genes that are already known would give a positive signal at loci containing both variable and common regions. For unknown genes, only the common regions of the gene family would give a positive signal. The result would indicate the possibility of a newly discovered gene.

The expression monitoring and generic difference screening methods of this invention thus also allow the development of "dynamic" gene databases. The Human Genome Project and commercial sequencing projects have generated large static databases which list thousands of sequences without regard to function or genetic interaction. Analyses using the methods of this invention produces "dynamic" databases that define a gene's function and its interactions with other genes. Without the ability to monitor the expression of large numbers of genes simultaneously, or the ability to detect differences in abundances of large numbers of "unknown" nucleic acids simultaneously, the work of creating such a database is enormous.

The tedious nature of using DNA sequence analysis for determining an expression pattern involves preparing a cDNA library from the RNA isolated from the cells of interest and then sequencing the library. As the DNA is sequenced, the operator lists the sequences that are obtained and counts them. Thousands of sequences would have to be determined and then the frequency of those gene sequences would define the expression pattern of genes for the cells being studied.

By contrast, using an expression monitoring, or generic difference screening, array to obtain the data according to the methods of this invention is relatively fast and easy. For example to in one embodiment, cells may be stimulated to induce expression. The RNA is obtained from the cells and then either labeled directly or a cDNA copy is created. Fluorescent molecules may be incorporated during the DNA polymerization. Either the labeled RNA or the labeled cDNA is then hybridized to a high density array in one overnight experiment. The hybridization provides a quantitative assessment of the levels of every single one of the hybridized nucleic acids with no additional sequencing. In addition the methods of this invention are much more sensitive allowing a few copies of expressed genes per cell to be detected. This procedure is demonstrated in the examples provided herein. These uses of the methods of this invention are intended to be illustrative and in no manner limiting.

II. High Density Arrays for Generic Difference Screening and Expression Monitoring As indicated above, this invention provides methods of monitoring (detecting and/or quantifying) the expression levels of a large number of nucleic acids and/or determining differences in nucleic acid concentrations (abundances) between two or more samples. The methods involve hybridization of one or more a nucleic acid samples (target nucleic acids) to one or more high density arrays of nucleic acid probes and then quantifying the amount of target nucleic acids hybridized to each probe in the array.

While nucleic acid hybridization has been used for some time to determine the expression levels of various genes (e.g., Northern Blot), it was a surprising discovery of this invention that high density arrays are suitable for the quantification of the small variations in abundance (e.g, transcription and, by implication, expression) of a nucleic acid (e.g., gene) in the presence of a large population of heterogenous nucleic acids. The signal (e.g, particular gene or gene product, or differentially abundant nucleic acid) may be present at a concentration of less than about 1 in 1,000, and is often present at a concentration less than 1 in 10,000 more preferably less than about 1 in 50,000 and most preferably less than about 1 in 100,000, 1 in 300,000, or even 1 in 1,000,000.

The oligonucleotide arrays can have oligonucleotides as short as 10 nucleotides, more preferably 15 oligonucleotides and most preferably 20 or 25 oligonucleotides are used to specifically detect and quantify nucleic acid expression levels. Where ligation discrimination methods are used, the oligonculeotide arrays can contain shorter oligonucleotides. In this instance, oligonucleotide arrays comprising oligonucleotides ranging in length from 6 to 15 nucleotides, more preferably from about 8 to about 12 nucleotides in length are preferred. Of course arrays containing longer oligonucleotides, as described herein, are also suitable.

The expression monitoring arrays, which are designed to detect particular preselected genes, provide for simultaneous monitoring of at least about 10, preferably at least about 100, more preferably at least about 1000, still more preferably at least about 10,000, and most preferably at least about 100,000 different genes.

A) Advantages of Oligonucleotide Arrays

In one preferred embodiment, the high density arrays used in the methods of this invention comprise chemically synthesized oligonucleotides. The use of chemically synthesized oligonucleotide arrays, as opposed to, for example, blotted arrays of genomic clones, restriction fragments, oligonucleotides, and the like, offers numerous advantages. These advantages generally fall into four categories:

1) Efficiency of production;
2) Reduced intra- and inter-array variability;
3) Increased information content; and
4) Improved signal to noise ratio.

1) Efficiency of Production

In a preferred embodiment, the arrays are synthesized using methods of spatially addressed parallel synthesis (see, e.g., Section V, below). The oligonucleotides are synthesized chemically in a highly parallel fashion covalently attached to the array surface. This allows extremely efficient array production. For example, arrays containing any collection of tens (or even hundreds) of thousands of specifically selected 20 mer oligonucleotides are synthesized in fewer than 80 synthesis cycles. The arrays are designed and synthesized based on sequence information alone. Thus, unlike blotting methods, the array preparation requires no handling of biological materials. There is no need for cloning steps, nucleic acid purifications or amplifications, cataloging of clones or amplification products, and the like. The preferred chemical synthesis of high density oligonucleotide arrays in this invention is thus more efficient than blotting methods and permits the production of highly reproducible high-density arrays.

2) Reduced Intra- and Inter-array Variability

The use of chemically synthesized high-density oligonucleotide arrays in the methods of this invention improves intra- and inter-array variability. The oligonucleotide arrays preferred for this invention are made in large batches (presently 49 arrays per wafer with multiple wafers synthesized in parallel) in a highly controlled reproducible manner. This makes them suitable as general diagnostic and research tools permitting direct comparisons of assays performed at different times and locations.

Because of the precise control obtainable during the chemical synthesis the arrays of this invention show less than about 25%, preferably less than about 20%, more preferably less than about 15%, still more preferably less than about 10%, even more preferably less than about 5%, and most preferably less than about 2% variation between high density arrays (within or between production batches) having the same probe composition. Array variation is assayed as the variation in hybridization intensity (against a labeled control target nucleic acid mixture) in one or more oligonucleotide probes between two or more arrays. More preferably, array variation is assayed as the variation in hybridization intensity (against a labeled control target nucleic acid mixture) measured for one or more target genes between two or more arrays.

In addition to reducing inter- and intra-array variability, chemically synthesized arrays also reduce variations in relative probe frequency inherent in spotting methods, particularly spotting methods that use cell-derived nucleic acids (e.g., cDNAs). Many genes are expressed at the level of thousands of copies per cell, while others are expressed at only a single copy per cell. A cDNA library will reflect this very large bias as will a cDNA library made from this material. While normalization (adjustment of the amount of each different probe e.g., by comparison to a reference cDNA) of the library will reduce the representation of over-expressed sequences to some extent, normalization has been shown to lessen the odds of selecting highly expressed cDNAs by only about a factor of 2 or 3. In contrast, chemical synthesis methods can insure that all oligonucleotide probes are represented in approximately equal concentrations. This decreases the inter-gene (intra-array) variability and permits direct comparison between hybridization signals for different oligonoucleotide probes.

3) Increased Information Content i) Advantages for Expression Monitoring

The use of high density oligonucleotide arrays for expression monitoring provides a number of advantages not found with other methods. For example, the use of large numbers of different probes that specifically bind to the transcription product of a particular target gene provides a high degree of redundancy and internal control that permits optimization of probe sets for effective detection of particular target genes and minimizes the possibility of errors due to cross-reactivity with other nucleic acid species.

Apparently suitable probes often prove ineffective for expression monitoring by hybridization. For example, certain subsequences of a particular target gene may be found in other regions of the genome and probes directed to these subsequences will cross-hybridize with the other regions and not provide a signal that is a meaningful measure of the expression level of the target gene. Even probes that show little cross reactivity may be unsuitable because they generally show poor hybridization due to the formation of structures that prevent effective hybridization. Finally, in sets with large numbers of probes, it is difficult to identify hybridization conditions that are optimal for all the probes in a set. Because of the high degree of redundancy provided by the large number of probes for each target gene, it is possible to eliminate those probes that function poorly under a given set of hybridization conditions and still retain enough probes to a particular target gene to provide an extremely sensitive and reliable measure of the expression level (transcription level) of that gene.

In addition, the use of large numbers of different probes to each target gene makes it possible to monitor expression of families of closely-related nucleic acids. The probes may be selected to hybridize both with subsequences that are conserved across the family and with subsequences that differ in the different nucleic acids in the family. Thus, hybridization with such arrays permits simultaneous monitoring of the various members of a gene family even where the various genes are approximately the same size and have high levels of homology. Such measurements are difficult or impossible with traditional hybridization methods.

ii) General Advantages

Because the high density arrays contain such a large number of probes it is possible to provide numerous controls including, for example, controls for variations or mutations in a particular gene, controls for overall hybridization conditions, controls for sample preparation conditions, controls for metabolic activity of the cell from which the nucleic acids are derived and mismatch controls for non-specific binding or cross hybridization.

Effective detection and quantitation of gene transcription in complex mammalian cell message populations can be determined with relatively short oligonucleotides and with relative few (e.g., fewer than 40, preferably fewer than 30, more preferably fewer than 25, and most preferably fewer than 20, 15, or even 10) oligonucleotide probes per gene. There are a large number of probes which hybridize both strongly and specifically for each gene. This does not mean that a large number of probes is required for detection, but rather that there are many from which to choose and that choices can be based on other considerations such as sequence uniqueness (gene families), checking for splice variants, or genotyping hot spots (things not easily done with CDNA spotting methods).

In use, sets of four arrays for expression monitoring are made that contain approximately 400,000 probes each. Sets of about 40 probes (20 probe pairs) are chosen that are complementary to each of about 40,000 genes for which there are ESTs in the public database. This set of ESTs covers roughly one-third to one-half of all human genes and these arrays will allow the levels of all of them to be monitored in a parallel set of overnight hybridizations.

4) Improved Signal to Noise Ratio

Blotted nucleic acids sometimes rely on ionic, electrostatic, and hydrophobic interactions to attach the blotted nucleic acids to the substrate. Bonds are formed at multiple points along the nucleic acid restricting degrees of freedom and interfering with the ability of the nucleic acid to hybridize to its complementary target. In contrast, the preferred arrays of this invention are chemically synthesized. The oligonucleotide probes are attached to the substrate by a single terminal covalent bond. The probes have more degrees of freedom and are capable of participating in complex interactions with their complementary targets. Consequently, the probe arrays of this invention show significantly higher hybridization efficiencies (10 times, 100 times, and even 1000 times more efficient) than blotted arrays. Less target oligonucleotide is used to produce a given signal thereby dramatically improving the signal to noise ratio. Consequently the methods of this invention permit detection of only a few copies of a nucleic acid in extremely complex nucleic acid mixtures.

B) Preferred High Density Arrays

Preferred high density arrays of this invention comprise greater than about 100, preferably greater than about 1000, more preferably greater than about 16,000 and most preferably greater than about 65,000 or 250,000 or even greater than about 1,000,000 different oligonucleotide probes. The oligonucleotide probes range from about 5 to about 50 or about 5 to about 45 nucleotides, more preferably from about 10 to about 40 nucleotides and most preferably from about 15 to about 40 nucleotides in length. In particular preferred embodiments, the oligonucleotide probes are 20 or 25 nucleotides in length, while in other preferred embodiments (particularly where ligation discrimination reactions are used) the oligonucleotide probes are preferably shorter (e.g., 6 to 20 more preferably 8 to 15 nucleotides in length). It was a discovery of this invention that relatively short oligonucleotide probes sufficient to specifically hybridize to and distinguish target sequences. Thus in one preferred embodiment, the oligonucleotide probes are less than 50 nucleotides in length, generally less than 46 nucleotides, more generally less than 41 nucleotides, most generally less than 36 nucleotides, preferably less than 31 nucleotides, more preferably less than 26 nucleotides, and most preferably less than 21 nucleotides in length. The probes can also be less than 16 nucleotides, less than 13 nucleotides in length, less than 9 nucleotides in length and less than 7 nucleotides in length. It is also recognized that the oligonucleotide probes can be relatively long, ranging in length up to about 1000 nucleotides, more typically up to about 500 nucleotides in length.

The location and, in some embodiments, sequence of each different oligonucleotide probe in the array is known. Moreover, the large number of different probes occupies a relatively small area providing a high density array having a probe density of generally greater than about 60, more generally greater than about 100, most generally greater than about 600, often greater than about 1000, more often greater than about 5,000, most often greater than about 10,000, preferably greater than about 40,000 more preferably greater than about 100,000, and most preferably greater than about 400,000 different oligonucleotide probes per $cm^2$. The small surface area of the array (often less than about 10 $cm^2$, preferably less than about 5 $cm^2$ more preferably less than about 2 $cm^2$, and most preferably less than about 1.6 $cm^2$) permits the use of small sample volumes and extremely uniform hybridization conditions (temperature regulation, salt content, etc.) while the extremely large number of probes allows massively parallel processing of hybridizations.

Finally, because of the small area occupied by the high density arrays, hybridization may be carried out in extremely small fluid volumes (e.g., 250 $\mu l$ or less, more preferably 100 $\mu l$ or less, and most preferably 10 $\mu l$ or less). In addition, hybridization conditions are extremely uniform throughout the sample, and the hybridization format is amenable to automated processing.

III. Monitoring Gene Expression and Generic Difference Screening

As explained above, this invention provides methods for monitoring gene expression (expression monitoring) and for identifying differences in abundance (concentration) of nucleic acids in two or more nucleic acid samples (generic difference screening). Generally the methods of monitoring gene expression of this invention involve (1) providing a pool of target nucleic acids comprising RNA transcript(s) of one or more target gene(s), or nucleic acids derived from the RNA transcript(s); (2) hybridizing the nucleic acid sample to a high density array of probes (including control probes); and (3) detecting the hybridized nucleic acids and calculating a relative expression (transcription) level. These methods preferably involve the use of high density oligonucleotide arrays containing probes to specifically preselected genes.

In contrast, the arrays used in the generic difference screening methods of this invention do not require that specific target genes be identified. To the contrary, the methods are designed to detect changes or differences in expression of various genes where the particular gene to be identified is unknown prior to performing the difference screening.

The methods of generic difference screening typically involve the steps of: 1) providing one or more high density oligonucleotide arrays (preferably including probes pairs differing in one or more nucleotides); 2) providing two or more nucleic acid samples; 3) hybridizing the nucleic acid samples to one or more arrays to form hybrid duplexes between nucleic acids in the nucleic acid samples and probe oligonucleotides in the array(s); 3) detecting the hybridization of the nucleic acids to the arrays; and 4) determining the differences in hybridization between the nucleic acid samples.

The provision of a nucleic acid sample, the hybridization of the sample to the arrays, and detection of the hybridized nucleic acid(s) is performed in essentially the same manner in expression monitoring and in generic difference screening methods. As disclosed herein, in preferred embodiments, the methods are distinguished, in part, by oligonucleotide probe selection, in the use of at least two nucleic acid samples in generic difference screening, and in subsequent analysis.

A) Providing a Nucleic Acid Sample

In order to measure the nucleic acid concentration in a sample, it is desirable to provide a nucleic acid sample for such analysis. Where it is desired that the nucleic acid concentration, or differences in nucleic acid concentration between different samples, reflect transcription levels or differences in transcription levels of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, such a nucleic acid sample is the total mRNA or a total cDNA isolated and/or otherwise derived from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

In a preferred embodiment, the total nucleic acid is isolated from a given sample using, for example, an acid guanidinium-phenol-chloroform extraction method and polyA$^+$ mRNA is isolated by oligo dT column chromatography or by using (dT)n magnetic beads (see, e.g, Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications,* Innis et al., Academic Press, Inc. N.Y., (1990).

Other suitable amplification methods include, but are not limited to polymerase chain reaction (PCR) (Innis, et al., *PCR Protocols. A guide to Methods and Application.* Academic Press, Inc. San Diego, (1990)), ligase chain reaction (LCR) (see Wu and Wallace, *Genomics,* 4: 560 (1989), Landegren, et al., *Science,* 241: 1077 (1988) and Barringer, et al., *Gene,* 89: 117 (1990), transcription amplification (Kwoh, et al., *Proc. Natl. Acad. Sci. USA,* 86: 1173 (1989)), and self-sustained sequence replication (Guatelli, et al., *Proc. Nat. Acad. Sci. USA,* 87: 1874 (1990)).

In a particularly preferred embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the CDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA,* 87: 1663–1667 (1990) who demonstrate that in vitro amplification according to this method preserves the relative frequencies of the various RNA transcripts. Moreover, Eberwine et al. *Proc. Natl. Acad. Sci. USA,* 89: 3010–3014 provide a protocol that uses two rounds of amplification via in vitro transcription to achieve greater than $10^6$ fold amplification of the original starting material thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene,* 88: 25–36 (1990)).

In a particularly preferred embodiment, a high activity RNA polymerase (e.g. about 2500 units/$\mu$L for T7, available from Epicentre Technologies) is used.

B) Labeling Nucleic Acids i) Labeling Methods/Strategies

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. For example, polymerase chain reaction (PCR) with labeled primers or labeled nucleotides will provide a labeled amplification product. The nucleic acid (e.g., DNA) is be amplified in the presence of labeled deoxynucleotide triphosphates (dNTPs). The amplified nucleic acid can be fragmented, exposed to an oligonucleotide array, and the extent of hybridization determined by the amount of label now associated with the array. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Such labeling can result in the increased yield of amplification products and reduce the time required for the amplification reaction. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). End labeling is discussed in more detail below in Section III(B)(iii).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

A wide variety of suitable dyes are available, being primary chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers can be employed either by alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes. oxacarbocyanine, marocyanine, 3-aminoequilenin, perylene, bisbenzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4(3'pyrenyl) butyrate; d-3-aminodesoxy-equilenin; 12-(9'anthroyl) stearate; 2-methylanthracene; 9-vinylanthracene; 2,2' (vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N(7-dimethylamino-4-methyl-2-oxo-3-chromenyl)maleimide; N-[p-(2-benzimidazolyl)-phenyl] maleimide; N-(4-fluoranthyl)maleimide; bis(homovanillic acid); resazarin; 4-chloro-7-nitro-2,1,3benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectible signal or donates energy to a fluorescent acceptor. A diverse number of families of compounds have been found to provide chemiluminescence under a variety or conditions. One family of compounds is 2,3-dihydro-1,-4-phthalazinedione. The must popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence can also be obtained with oxalates, usually oxalyl active esters, e.g., p-nitrophenyl and a peroxide, e.g., hydrogen peroxide, under basic conditions. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology,* Vol. 24: *Hybridization With Nucleic Acid Probes,* P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base mioeties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

ii. End-labeling Nucleic Acids

In many applications it is useful to directly label nucleic acid samples without having to go through an amplification, transcription or other nucleic acid conversion step. This is especially true for monitoring of mRNA levels where one would like to extract total cytoplasmic RNA or poly A+RNA (mRNA) from cells and hybridize this material without any intermediate steps that could skew the original distribution of mRNA concentrations.

In general, end-labeling methods permit the optimization of the size of the nucleic acid to be labeled. End-labeling methods also decrease the sequence bias sometimes associated with polymerase-facilitated labeling methods. End labeling can be performed using terminal transferase (TdT).

End labeling can also be accomplished by ligating a labeled oligonucleotide or analog thereof to the end of a target nucleic acid or probe. Other end-labeling methods include the creation of a labeled or unlabeled "tail" for the nucleic acid using ligase or terminal transferase, for example. The tailed nucleic acid is then exposed to a labeled moiety that will preferentially associate with the tail. The tail and the moiety that preferentially associates with the tail can be a polymer such as a nucleic acid, peptide, or carbohydrate. The tail and its recognition moiety can be anything that permits recognition between the two, and includes molecules having ligand-substrate relationships such as haptens, epitopes, antibodies, enzymes and their substrates, and complementary nucleic acids and analogs thereof.

The labels associated with the tail or the tail recognition moiety include detectable moieties. When the tail and its recognition moiety are both labeled, the respective labels associated with each can themselves have a ligand-substrate relationship. The respective labels can also comprise energy transfer reagents such as dyes having different spectroscopic characteristics. The energy transfer pair can be chosen to obtain the desired combined spectral characteristics. For example, a first dye that absorbs at a wavelength shorter than that absorbed by the second dye can, upon absorption at that shorter wavelength, transfer energy to the second dye. The second dye then emits electromagnetic radiation at a wavelength longer than would have been emitted by the first dye alone. Energy transfer reagents can be particularly useful in two-color labeling schemes such as those set forth in a copending U.S. patent application, filed Dec. 23, 1996, and which is a continuation-in-part of U.S. Ser. No. 08/529,115, filed Sep. 15, 1995, and Int'l Appln. No. WO 96/14839, filed Sep. 13, 1996, which is also a continuation-in-part of U.S. Ser. No. 08/670,118, filed on Jun. 25, 1996, which is a division of U.S. Ser. No. 08/168,904, filed Dec. 15, 1993, which is a continuation of U.S. Ser. No. 07/624,114, filed Dec. 6, 1990. U.S. Ser. No. 07/624,114 is a CIP of U.S. Ser. No. 07/362,901, filed Jun. 7, 1990, incorporated herein by reference.

This invention thus provides methods of labeling a nucleic acid and reagents useful therefor. Many of the methods disclosed herein involve end-labeling. Those skilled in the art will appreciate that the invention as disclosed is generally applicable in the chemical and molecular-biological arts.

In one embodiment, the method involves providing a nucleic acid. providing a labeled oligonucleotide and enzymatically ligating the oligonucleotide to the nucleic acid. Thus, for example, where the nucleic acid is an RNA, a labeled riboligonucleotide can be ligated using an RNA ligase. RNA ligase catalyzes the covalent joining of single-stranded RNA (or DNA, but the reaction with RNA is more efficient) with a 5' phosphate group to the 3'-OH end of another piece of RNA (or DNA). The specific requirements for the use of this enzyme are provided in *The Enzymes, Volume XV, Part B, T4 RNA Ligase,* Uhlenbeck and Greensport, pages 31–58; and 5.66–5.69 in Sambrook et al., *Molecular Cloning, A Laboratory Manual,* Cold Spring Harbor Press, Cold Spring Harbor, New York (1982)

This invention thus provides a method to add a label to the nucleic acid (e.g extracted RNA) directly rather than incorporating labeled nucleotides in a nucleic acid polymerization step. This can be accomplished by adding a short labeled oligonucleotide to the ends of a single stranded nucleic acid. The method more fully labels a sample; a higher percentage of available molecules will be labeled than by conventional techniques.

RNA can be randomly fragmented with heat in the presence of $Mg^{2+}$. This generally produces RNA fragments with 5' OH groups and phosphorylated 3' ends. A phosphate group is added to the 5' ends of the fragments using standard protocols with T4 Polynucleotide Kinase, or similar enzyme. To the pool of 5'-phosphorylated RNA fragments is added RNA ligase plus a short RNA oligonucleotide with a 3' OH group and a label, either at the 5' end (such as fluorescein or other dye, or biotin for later labeling with a streptavidin conjugate, or with dioxigenin for later labeling with a labeled antibody) or with one or more labeled bases. A $riboA_6$ (deoxyribonucleic acid 6 mer poly A) labeled with either fluorescein or biotin at the 5' end provides a particularly preferred label. In another embodiment, the ligated RNA oligonucleotide can have rioibnucleotides near the ligation end, but deoxyrigonucleotides further away. Of course, the RNA oligonucleotide can be longer or shorter and can have a virtually any sequence. However, the ligation reaction is most efficient with A and least efficient with U at the 3' end of the acceptor. The reaction is allowed to proceed under standard conditions. Unincorporated RNA 6 -mers can be removed by a simple size selection step (e.g. electrophoresis. NAP column, etc.) if necessary following the ligation reaction.

An advantage of this procedure is that extracted mRNA can be used directly and that each fragment should be labeled once, not any number of times depending on the sequence as is the case when labeled bases are incorporated during polymerization reactions.

In another embodiment, fragmented DNA can also be end-labeled using a different procedure with a different enzyme. Terminal transferase will add deoxynucleoside triphosphates (dNTPs), which can be labeled, to the 3' OH ends of single stranded DNA. Single dNTPs can be added if modified nucleotides are used (for example, dideoxynucleotide triphosphates), or multiple bases can be added if desired. DNA can be fragmented either physically (shearing) or enzymatically (nucleases), or chemically (e.g. acid hydrolysis). Following fragmentation, depending on the method, 3' OH ends may need to be produced. The DNA fragments are then labeled using labeled dNTPs or ddNTPs in the presence of terminal transferase.

Various other embodiments are illustrated by the Examples provided herein and their associated figures.

C) Modifying Sample to Improve Signal to Noise Ratio

The nucleic acid sample may be modified prior to hybridization to the high density probe array in order to reduce sample complexity thereby decreasing background signal and improving sensitivity of the measurement. In one embodiment, complexity reduction for expression monitoring methods is achieved by selective degradation of background mRNA. This is accomplished by hybridizing the sample mRNA (e.g., polyA$^+$ RNA) with a pool of DNA oligonucleotides that hybridize specifically with the regions to which the probes in the expression monitoring array specifically hybridize. In a preferred embodiment, the pool of oligonucleotides consists of the same probe oligonucleotides as found on the high density array.

The pool of oligonucleotides hybridizes to the sample mRNA forming a number of double stranded (hybrid duplex) nucleic acids. The hybridized sample is then treated with RNase A, a nuclease that specifically digests single stranded RNA. The RNase A is then inhibited, using a protease and/or commercially available RNase inhibitors, and the double stranded nucleic acids are then separated from the digested single stranded RNA. This separation may be accomplished in a number of ways well known to those of skill in the art including, but not limited to, electrophoresis, and gradient centrifugation. However, in a preferred embodiment, the pool of DNA oligonucleotides is provided attached to beads forming thereby a nucleic acid affinity column. After digestion with the RNase A, the hybridized DNA is removed simply by denaturing (e.g., by adding heat or increasing salt) the hybrid duplexes and washing the previously hybridized mRNA off in an elution buffer.

The undigested mRNA fragments which will be hybridized to the probes in the high density array or other solid support are then preferably end-labeled with a fluorophore attached to an RNA linker using an RNA ligase. This procedure produces a labeled sample RNA pool in which the nucleic acids that do not correspond to probes in the array are eliminated and thus unavailable to contribute to a background signal.

Another method of reducing sample complexity involves hybridizing the mRNA with deoxyoligonucleotides that hybridize to regions that border on either side the regions to which the high density array probes are directed. Treatment with RNAse H selectively digests the double stranded (hybrid duplexes) leaving a pool of single-stranded mRNA corresponding to the short regions (e.g., 20 mer) that were formerly bounded by the deoxyoligonucleotide probes and which correspond to the targets of the high density array probes and longer mRNA sequences that correspond to regions between the targets of the probes of the high density array. The short RNA fragments are then separated from the long fragments (e.g., by electrophoresis), labeled if necessary as described above, and then are ready for hybridization with the high density probe array.

In a third approach, sample complexity reduction involves the selective removal of particular (preselected) mRNA messages. In particular, highly expressed mRNA messages that are not specifically probed by the probes in the high density array are preferably removed. This approach involves hybridizing the polyA$^+$ mRNA with an oligonucleotide probe that specifically hybridizes to the preselected message close to the 3' (poly A) end. The probe may be selected to provide high specificity and low cross reactivity. Treatment of the hybridized message/probe complex with RNase H digests the double stranded region effectively removing the polyA$^+$ tail from the rest of the message. The sample is then treated with methods that specifically retain or amplify polyA$^+$ RNA (e.g., an oligo dT column or (dT)n magnetic beads). Such methods will not retain or amplify the selected message(s) as they are no longer associated with a polyA$^+$ tail. These highly expressed messages are effectively removed from the sample providing a sample that has reduced background mRNA.

IV. Hybridization Array Design

A) Probe Composition

One of skill in the art will appreciate that an enormous number of array designs are suitable for the practice of this invention. Generic difference screening arrays, for example may include random, haphazardly selected, or arbitrary probe sets. Alternatively, the generic difference screening arrays may include all possible oligonucleotides of a particular pre-selected length. Conversely, other expression monitoring arrays typically include a number of probes that specifically hybridize to the nucleic acid(s) expression of which is to be detected. In a preferred embodiment, the array will include one or more control probes.

I) Test Probes

In its simplest embodiment, the high density array includes "test probes" (also referred to as probe oligonucleotides) more than 5 bases long, preferably more than 10 bases long, and some more than 40 baes long. In some embodiments, the probes are less than 50 bases long. In some cases, these oligonucleotides range from about 5 to about 45 or 5 to about 50 nucleotides long, more preferably from about 10 to about 40 nucleotides long, and most preferably from about 15 to about 40 nucleotides in length. In other particularly preferred embodiments the probes are 20 or 25 nucleotides in length. In preselected expression monitoring arrays, these probe oligonucleotides have sequences complementary to particular subsequences of the genes whose expression they are designed to detect. Thus, the test probes are capable of specifically hybridizing to the target nucleic acid they are to detect.

In high density oligonucleotide arrays, designed for generic difference screening, the probe oligonucleotides need not be selected to hybridize to particular preselected subsequences of genes. To the contrary, preferred generic difference screening arrays comprise probe oligonucleotides whose sequences are random, arbitrary, or haphazard. Alternatively, the probe oligonucleotides may include all possible nucleotides of a given length (e.g., all possible 4 mers, all possible 5 mers, all possible 6 mers, all possible 7 mers, all possible 8 mers, all possible 9 mers, all possible 10 mers, all possible 11 mers, all possible 12 mers, etc.)

A random oligonucleotide array is an array in which the pool of nucleotide sequences of a particular length does not significantly deviate from a pool of nucleotide sequences selected in a random manner (i.e., blind, unbiased selection) from a collection of all possible sequences of that length.

Arbitrary or haphazard nucleotide arrays of probe oligonucleotides are arrays in which the probe oligonucleotide selection is selected without identifying and/or preselecting target nucleic acids. Arbitrary or haphazard nucleotide arrays may approximate or even be random, however there in no assurance that they meet a statistical definition of randomness.

The arrays may reflect some nucleotide selection based on probe composition, and/or non-redundancy of probes, and/ or coding sequence bias as described herein. In a preferred embodiment, however such "biased" probe sets are still not chosen to be specific for any particular genes.

An array comprising all possible oligonucleotides of a particular length refers to an array that contains oligonucleotides having sequences corresponding to substantially every permutation of a sequence. Thus since the probe oligonucleotides of this invention preferably include up to 4 bases (A, G, C, T) or (A, G, C, U) or derivatives of these bases, an array having all possible nucleotides of length X contains substantially $4^x$ different nucleic acids (e.g., 16 different nucleic acids for a 2 mer, 64 different nucleic acids for a 3 mer, 65536 different nucleic acids for an 8 mer, etc.). It will be appreciated that some small number of sequences may be inadvertently absent from a pool of all possible nucleotides of a particular length due to synthesis problems, inadvertent cleavage, etc.). Thus, it will be appreciated that an array comprising all possible nucleotides of length X refers to an array having substantially all possible nucleotides of length X. Substantially all possible nucleotides of length X includes more than 90%, typically more than 95%, preferably more than 98%, more preferably more than 99% and most preferably more than 99.9% of the possible number of different nucleotides.

The probe oligonucleotides described above can additionally include a constant domain. A constant domain being a nucleotide subsequence that is common to substantially all of the probe oligonculeotides. Particularly preferred constant domains are located at the terminus of the oligonucleotide probe closest to the substrate (i.e., attached to the linker/anchor molecule). The constant regions may comprise virtually any sequence. However, in one embodiment, the constant regions comprise a sequence or subsequence complementary to the sense or antisense strand of a restriction site (a nucleic acid sequence recognized by a restriction endonuclease).

The constant domain can be synthesized de novo on the array. Alternatively, the constant region may be prepared in a separate procedure and then coupled intact to the array. Since the constant domain can be synthesized separately and then the intact constant subsequences coupled to the high density array, the constant domain can be virtually any length. Some constant domains range from 3 nucleotides to about 500 nucleotides in length, more typically from about 3 nucleotides in length to about 100 nucleotides in length, most typically from 3 nucleotides in length to about 50 nucleotides in length. In particular embodiments, constant domains range from 3 nucleotides to about 45 nucleotides in length, more preferably from 3 nucleotides in length to about 25 nucleotides in length and most preferably from 3 to about 15 or even 10 nucleotides in length. In other embodiments, preferred constant regions range from about 5 nucleotides to about 15 nucleotides in length.

In addition to test probes that bind the target nucleic acid(s) of interest, the high density array can contain a number of control probes. The control probes fall into three categories referred to herein as 1) Normalization controls; 2) Expression level controls; and 3) Mismatch controls.

2) Normalization Controls

Normalization controls are oligonucleotide probes that are perfectly complementary to labeled reference oligonucleotides that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Normalization probes can be localized at any position in the array or at multiple positions throughout the array to control for spatial variation in hybridization efficiently. In a preferred embodiment, the normalization controls are located at the corners or edges of the array as well as in the middle.

3) Expression Level Controls

Expression level controls are probes that hybridize specifically with constitutively expressed genes in the biological sample. Expression level controls are designed to control for the overall health and metabolic activity of a cell. Examination of the covariance of an expression level control with the expression level of the target nucleic acid indicates whether measured changes or variations in expression level of a gene is due to changes in transcription rate of that gene or to general variations in health of the cell. Thus, for example, when a cell is in poor health or lacking a critical metabolite the expression levels of both an active target gene and a constitutively expressed gene are expected to decrease. The converse is also true. Thus where the expression levels of both an expression level control and the target gene appear to both decrease or to both increase, the change may be attributed to changes in the metabolic activity of the cell as a whole, not to differential expression of the target gene in question. Conversely, where the expression levels of the target gene and the expression level control do not covary, the variation in the expression level of the target gene is attributed to differences in regulation of that gene and not to overall variations in the metabolic activity of the cell.

Virtually any constitutively expressed gene provides a suitable target for expression level controls. Typically expression level control probes have sequences complementary to subsequences of constitutively expressed "housekeeping genes" including, but not limited to the β-actin gene, the transferring receptor gene, the GAPDH gene, and the like.

4) Mismatch Controls

Mismatch controls may also be provided for the probes to the target genes, for expression level controls or for normalization controls. Mismatch controls are oligonucleotide probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

In "generic" (e.g., random, arbitrary, haphazard, etc.) arrays, since the target nucleic acid(s) are unknown perfect match and mismatch probes cannot be a priori determined, designed, or selected. In this instance, the probes are preferably provided as pairs where each pair of probes differ in one or more preselected nucleotides. Thus, while it is not known a priori which of the probes in the pair is the perfect match. it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3. 4, 5, or more) of probes that differ from each other in particular preselected nucleotides.

In both expression monitoring and generic difference screening arrays, mismatch probes provide a control for non-specific binding or cross-hybridization to a nucleic acid in the sample other than the target to which the probe is complementary. Mismatch probes thus indicate whether a hybridization is specific or not. For example, if the complementary target is present the perfect match probes should be consistently brighter than the mismatch probes. In addition, if all central mismatches are present, the mismatch probes can be used to detect a mutation. Finally, it was also a discovery of the present invention that the difference in intensity between the perfect match and the mismatch probe (I(PM)−I(MM)) provides a good measure of the concentration of the hybridized material.

5) Sample Preparation/Amplification/Quantitation Controls

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

Quantitation controls are similar. Typically they are combined with the sample nucleic acid(s) in known amounts prior to hybridization. They are useful to provide a quantitation reference and permit determination of a standard curve for quantifing hybridization amounts (concentrations).

B) Probe Selection and Optimization
  i) Generic Difference Screening Arrays
  a) Assumption-free Probe Selection As explained above, probe oligonculetide selection for generic difference screening arrays can be random, arbitrary haphazard, composition biased, or include all possible oligonculeotides of a particular length. Probe choice is thus essentially assumption free. In some embodiments, however, particular oligonucleotides may be excluded from the array or from analysis. For example, probes that contain palindormic sequences or probes that contain long stretches of all As, Cs, Gs, Ts, etc, may be excluded. Probes for exclusion may be identified by hybridizing a single array to the same sample multiple times and/or hybridizing different copies of the array to the same sample. Probes that show that show an unacceptable variation (variation above a particular threshold value) in hybridization intensity against the same sample may be excluded (either in array construction or in signal analysis). The variation level at which a probe may be excluded is a function of the sensitivity desired of the assay. The more sensitive an assay is desired, the lower the exclusion threshold is set. In a preferred embodiment, the probe is excluded when the variation in hybridization intensity exceeds 2 times the background signal and has a relative variation of more than 50%.

Alternatively such exclusion may be inherent in the selective identification of differentially hybridizing sequences where the difference between a test nucleic acid sample and a reference nucleic acid sample is compared to the difference between the reference nucleic acid sample and itself. This is described more fully below in Section IX(B).

b) Exploitation of Codon Degeneracy

In another embodiment, species-specific codon usage can be exploited to utilize a longer (and hence more specific and stable) probe without increasing the number of probe oligonucleotides necessary to hybridize to all possible sequences. Amino acid codons are conserved in the first and second position of their codons, while the third position is highly redundant. Moreover each species or organism favors particular codons to encode any particular amino acid. The preferred codon for a particular amino acid in a particular species being the codon that is used at the highest frequency for that species. Codon preferences are well known to those of skill in the art. They can also be readily determined by a simple frequency analysis of the nucleotide sequences of a particular organism or species.

Similarly, the di, tri-, tetra-nucleotide frequency biases of an particular organism or species can be used to weight the selection of oligonucleotide probes used in "composition biased" generic difference screening array.

In one preferred embodiment, the probe oligonucleotides are prepared having the first two nucleotides in each codon being fixed but allowing the third nucleotide to vary (either by use of a 4 way wobble or by the use of inosine or other non-specifically hybridizing base). In a preferred embodiment, each codon of the probe will have the general formula $$3'\text{-}X^1\text{-}X^2\text{-}I\text{-}5'$$

where I is inosine or a 4-way wobble and $X^1$ and $X^2$ are A, G, C, T/U selected according to the preferred codon usage for a particular species. Thus, for example, an array of 16 mers that will hybridize to substantially all nucleic acids of a particular species can be prepared where the probes have the formula:

$$\text{Support-}I^1\text{-}X^2X^3I^4\text{-}X^5X^6I^7\text{-}X^8X^9I^{10}\text{-}X^{11}X^{12}I^{13}\text{-}X^{14}X^{15}\ I^{16}\text{-}3'$$

with only $4^{10}$ different probe oligonucleotides. Suitable codons for this probe are illustrated in Table 1.

TABLE 1

Preferred sequences for generic coding sequence 16 mer probe oligonucleotides.
(Derived from standard tabel of amino acid codons (the genetic code).)

| | | | | Codon 5 | | | Codon 4 | | | Codon 3 | | | Codon 2 | | | Codon 1 | |
|---|---|---|---|---|---|---|---|---|---|---|---|---|---|---|---|---|---|
| $I^1$ | $X^2$ | $X^3$ | $I^4$ | $X^5$ | $X^6$ | $I^7$ | $X^8$ | $X^9$ | $I^{10}$ | $X^{11}$ | $X^{12}$ | $I^{13}$ | $X^{14}$ | $X^{15}$ | $I^{16}$ | | |
| I | G | A | I | G | A | I | G | A | I | G | A | I | G | A | I | | |
| I | A | A | I | A | A | I | A | A | I | A | A | I | A | A | I | | |
| I | C | T | I | C | T | I | C | T | I | C | T | I | C | T | I | | |
| I | G | C | I | G | C | I | G | C | I | G | C | I | G | C | I | | |
| I | C | A | I | C | A | I | C | A | I | C | A | I | C | A | I | | |
| I | A | T | I | A | T | I | A | T | I | A | T | I | A | T | I | | |
| I | G | G | I | G | G | I | G | G | I | G | G | I | G | G | I | | |
| I | G | T | I | G | T | I | G | T | I | G | T | I | G | T | I | | |
| I | C | C | I | C | C | I | C | C | I | C | C | I | C | C | I | | |
| I | T | T | I | T | T | I | T | T | I | T | T | I | T | T | I | | |
| I | A | C | I | A | C | I | A | C | I | A | C | I | A | C | I | | |
| I | A | T | I | A | T | I | A | T | I | A | T | I | A | T | I | | |
| I | T | C | I | T | C | I | T | C | I | T | C | I | T | C | I | | |
| I | T | G | I | T | G | I | T | G | I | T | G | I | T | G | I | | |
| I | C | G | I | C | G | I | C | G | I | C | G | I | C | G | I | | |
| I | T | A | I | T | A | I | T | A | I | T | A | I | T | A | I | | |

The affinity of the probes may be further enhanced by the includsion of additional intosines, (or 4,-way, 3-way, or 2-way wobbles, or other generic bases) to the 3' and 5' ends of the oligonucleotide probes. These codon usage biased probes can be used in conjunction with a ligase discrimination to further increase obtainable sequence information. Thus, for example, where the hybridization to an array comprising the above-described 16 mers also includes a ligation with one or more ligatable oligonucleotides of fixed length N, whose sequence is known, each successful ligation provides 16+N nucleotides of sequence information.

ii) Expression Monitoring Arrays

In a preferred embodiment, oligonucleotide probes in the expression monitoring high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA.

There, may exist, however, 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long or longer. For most applications it would be useful to identify the presence, absence, or expression level of several thousand to one hundred thousand genes. Because the number of oligonucleotides per array is limited, in a preferred embodiment, it is desired to include only a limited set of probes specific to each gene whose expression is to be detected.

a) Hybridization and Cross-hybridization Data

Thus, in one embodiment, this invention provides for a method of optimizing a probe set for detection of a particular gene. Generally, this method involves providing a high density array containing a multiplicity of probes of one or more particular length(s) that are complementary to subsequences of the mRNA transcribed by the target gene. In one embodiment the high density array may contain every probe of a particular length that is complementary to a particular mRNA. The probes of the high density array are then hybridized with their target nucleic acid alone and then hybridized with a high complexity, high concentration nucleic acid sample that does not contain the targets complementary to the probes. Thus, for example, where the target nucleic acid is an RNA, the probes are first hybridized with their target nucleic acid alone and then hybridized with RNA made from a cDNA library (e.g., reverse transcribed poly $A^+$ mRNA) where the sense of the hybridized RNA is opposite that of the target nucleic acid (to insure that the high complexity sample does not contain targets for the probes). Those probes that show a strong hybridization signal with their target and little or no cross-hybridization with the high complexity sample are preferred probes for use in the high density arrays of this invention.

The high density array may additionally contain mismatch controls for each of the probes to be tested. In a preferred embodiment, the mismatch controls contain a central mismatch. Where both the mismatch control and the target probe show high levels of hybridization (e.g., the hybridization to the mismatch is nearly equal to or greater than the hybridization to the corresponding test probe), the test probe is preferably not used in the high density array.

In a particularly preferred embodiment, optimal probes are selected according to the following method: First, as indicated above, an array is provided containing a multiplicity of oligonucleotide probes complementary to subsequences of the target nucleic acid. The oligonucleotide probes may be of a single length or may span a variety of lengths. The high density array may contain every probe of a particular length that is complementary to a particular mRNA or may contain probes selected from various regions of particular mRNAs. For each target-specific probe the array also contains a mismatch control probe; preferably a central mismatch control probe.

The oligonucleotide array is hybridized to a sample containing target nucleic acids having subsequences complementary to the oligonucleotide probes and the difference in hybridization intensity between each probe and its mismatch control is determined. Only those probes where the difference between the probe and its mismatch control exceeds a threshold hybridization intensity (e.g preferably greater than 10% of the background signal intensity, more preferably greater than 20% of the background signal intensity and most preferably greater than 50% of the background signal intensity) are selected. Thus, only probes that show a strong signal compared to their mismatch control are selected.

The probe optimization procedure can optionally include a second round of selection. In this selection, the oligonucleotide probe array is hybridized with a nucleic acid sample that is not expected to contain sequences complementary to the probes. Thus, for example, where the probes are complementary to the RNA sense strand a sample of antisense RNA is provided. Of course, other samples could be provided such as samples from organisms or cell lines known to be lacking a particular gene, or known for not expressing a particular gene.

Only those probes where both the probe and its mismatch control show hybridization intensities below a threshold value (e.g. less than about 5 times the background signal intensity, preferably equal to or less than about 2 times the background signal intensity, more preferably equal to or less than about 1 times the background signal intensity, and most preferably equal or less than about half background signal intensity) are selected. In this way probes that show minimal non-specific binding are selected. Finally, in a preferred embodiment, the n probes (where n is the number of probes desired for each target gene) that pass both selection criteria and have the highest hybridization intensity for each target gene are selected for incorporation into the array, or where already present in the array, for subsequent data analysis. Of course, one of skill in the art, will appreciate that either selection criterion could be used alone for selection of probes.

b) Heuristic Rules

Using the hybridization and cross-hybridization data obtained as described above, graphs can be made of hybridization and cross-hybridization intensities versus various probe properties e.g., number of As, number of Cs in a window of 8 bases, palindomic strength, etc. The graphs can then be examined for correlations between those properties and the hybridization or cross-hybridization intensities. Thresholds can be set beyond which it looks like hybridization is always poor or cross hybridization is always very strong. If any probe fails one of the criteria, it is rejected from the set of probes and therefore, not placed on the chip. This will be called the heuristic rules method.

One set of rules developed for 20 mer probes in this manner is the following:

Hybridization rules:
1) Number of As is less than 9.
2) Number of Ts is less than 10 and greater than 0.
3) Maximum run of As, Gs, or Ts is less than 4 bases in a row.
4) Maximum run of any 2 bases is less than 11 bases.
5) Palindrome score is less than 6.
6) Clumping score is less than 6.
7) Number of As+Number of Ts is less than 14
8) Number of As+number of Gs is less than 15

With respect to rule number 4, requiring the maximum run of any two bases to be less than 11 bases guarantees that at least three different bases occur within any 12 consecutive nucleotides. A palindrome score is the maximum number of complementary bases if the oligonucleotide is folded over at a point that maximizes self complementarity. Thus, for example a 20 mer that is perfectly self-complementary would have a palindrome score of 10. A clumping score is the maximum number of three-mers of identical bases in a given sequence. Thus, for example, a run of 5 identical bases will produce a clumping score of 3 (bases 1–3, bases 2–4, and bases 3–5).

If any probe failed one of these criteria (1–8), the probe was not a member of the subset of probes placed on the chip. For example, if a hypothetical probe was 5'-AGCTTTTTTCATGCATCTAT-3+ (SEQ ID NO:1) the probe would not be synthesized on the chip because it has a run of four or more bases (i.e., run of six).

The cross hybridization rules developed for 20 mers were as follows:
1) Number of Cs is less than 8;
2) Number of Cs in any window of 8 bases is less than 4.

Thus, if any probe failed any of either the hybridization ruses (1–8) or the cross-hybridization rules (1–2), the probe was not a member of the subset of probes placed on the chip. These rules eliminated many of the probes that cross hybridized strongly or exhibited low hybridization, and performed moderate job of eliminating weakly hybridizing probes.

These heuristic rules may be implemented by hand calculations, or alternatively, they may be implemented in software as is discussed below in Section XII.

c) Neural Net

In another embodiment, a neural net can be trained to predict the hybridization and cross-hybridization intensities based on the sequence of the probe or on other probe properties. The neural net can then be used to pick an arbitrary number of the "best" probes. One such neural net was developed for selecting 20-mer probes. This neural net was produced a moderate (0.7) correlation between predicted intensity and measured intensity, with a better model for cross hybridization than hybridization. Details of this neural net are provided in Example 6.

d) ANOVA Model

An analysis of variance (ANOVA) model may be built to model the intensities based on positions of consecutive base pairs. This is based on the theory that the melting energy is based on stacking energies of consecutive bases. The annova model was used to find correlation between the a probe sequence and the hybridization and cross-hybridization intensities. The inputs were probe sequences broken down into consecutive base pairs. One model was made to predict hybridization, another was made to predict cross hybridization. The output was the hybridization or cross-hybridization intensity.

There were 304 (19*16) possible inputs, consisting of the 14 possible two base combinations, and the 19 positions that those combinations could be found in. For example, the sequence aggctga . . . has "ag" in the first position, "gg" in the second position, "gc" in the third, "ct" in the fourth and so on.

The resulting model assigned a component of the output intensity to each of the possible inputs, so to estimate the intensity for a given sequence one simply adds the intensities for each of it's 19 components.

e) Pruning (Removal) of Similar Probes

One of the causes of poor signals in expression chips is that genes other than the ones being monitored have sequences which are very similar to parts of the sequences which are being monitored. The easiest way to solve this is to remove probes which are similar to more than one gene. Thus, in a preferred embodiment, it is desirable to remove (prune) probes that hybridize to transcription products of more than one gene.

The simplest pruning method is to line up a proposed probe with all known genes for the organism being monitored, then count the number of matchingbases. For example, given a probe (SEQ ID NO:2)to gene 1 of an organism and gene 2 (SEQ ID NO:3) of an organism as follows:

```
probe from gene 1: aagcgcgatcgattatgctc
                   |      |||||||
gene 2:            atctcggatcgatcggataagcgcgatcgattatgctcggcga
``` has 8 matching bases in this alignment, but 20 matching bases in the following alignment:

```
probe from gene 1:            aagcgcgatcgattatgctc
                              ||||||||||||||||||||
gene 2:            atctcggatcgatcggataagcgcgatcgattatgctcggcga
```

More complicated algorithms also exist, which allow the detection of insertion or deletion mismatches. Such sequence alignment algorithms are well known to those of skill in the art and include, but are not limited to BLAST, or FASTA, or other gene matching programs such as those described above in the definitions section.

In another variant, where an organism has many different genes which are very similar, it is difficult to make a probe set that measures the concentration only one of those very similar genes. One can then prune out any probes which are dissimilar, and make the probe set a probe set for that family of genes.

Synthesis Cycle Pruning

The cost of producing masks for a chip is approximately linearly related to the number of synthesis cycles. In a normal set of genes the distribution of the number of cycles any probe takes to build approximates a Gausian distribution. Because of this the mask cost can normally be reduced by 15% by throwing out about 3 percent of the probes. In a preferred embodiment, synthesis cycle pruning simply involves eliminating (not including) those probes those probes that require a greater number of synthesis cycles than the maximum number of synthesis cycles selected for prepaation of the particular subject high density oligonucleotide array. Since the typical synthesis of probes follows a regular pattern of bases put down (acgtacgtacgt . . . ) counting the number of synthesis steps needed to build a probe is easy. The listing shown in Table 1 provides typical code for counting the number of synthesis cycles a probe will need.

TABLE 1

Typical code for counting synthesis cycles required for the chemical synthesis of a probe.

```
static char base[] = "acgt";
//      a b c d e f g h i j k l m n o p q r s t u v w x y z
static short index [] = {0, 0, 1, 0, 0, 0, 2, 0, 0, 0, 0, 0, 0, 0, 0, 0, 0, 0, 0, 3, 0, 0, 0, 0, 0, 0};
short lookupIndex( char aBase ){
        if( isupper( aBase ) || !isalpha( aBase) ){
                errorHwnd( "illegal base");
                return −1;
        }
        if( strchr( base, aBase ) == NULL ){
                errorHwnd( "non-dna base");
                return 0;
        }
        return index[aBase - 'a'];
}
static short calculateMinNumberOfSynthesisStepsForComplement( char local * buffer ){
        short i, last, current, cycles = 1;
        char buffer1[40];
        for( i = 3D 0; buffer[i] != 0; i++ ){
                switch( tolower(buffer[i]) ) {
                    case 'a': buffer1 [i] = 't';break;
                    case 'c': buffer1 [i] = 'g';break;
                    case 'g': buffer1 [i] = 'c';break;
                    case 't': buffer1 [i] = 'a';break;
                }
        }
        buffer1[i] = 0;
```

TABLE 1-continued

Typical code for counting synthesis cycles required for the chemical synthesis of a probe.

```
    if( buffer1[0] == 0 ) return 0;
    last = lookupIndex( buffer1 [0]);
    for(i= 1;buffer1[i] != 0; i++ ){
        current = lookupIndex( buffer1 [i]);
        if( current <= last) cycles++;
        last = current;
    }
    return (short)((cycles -1) * 4 + current +1);
}
``` g) Combination of Selection Methods

The heuristic rules, neural net and annova model provide ways of pruning or reducing the number of probes for monitoring the expression of genes. As these methods do not necessarily produce the same results, or produce entirely independent results, it may be advantageous to combine the methods. For example, probes may be pruned or reduced if more than one method (e.g., two out of three) indicate the probe will not likely produce good results. Then, synthesis cycle pruning may be performed to reduce costs.

Figure 11:
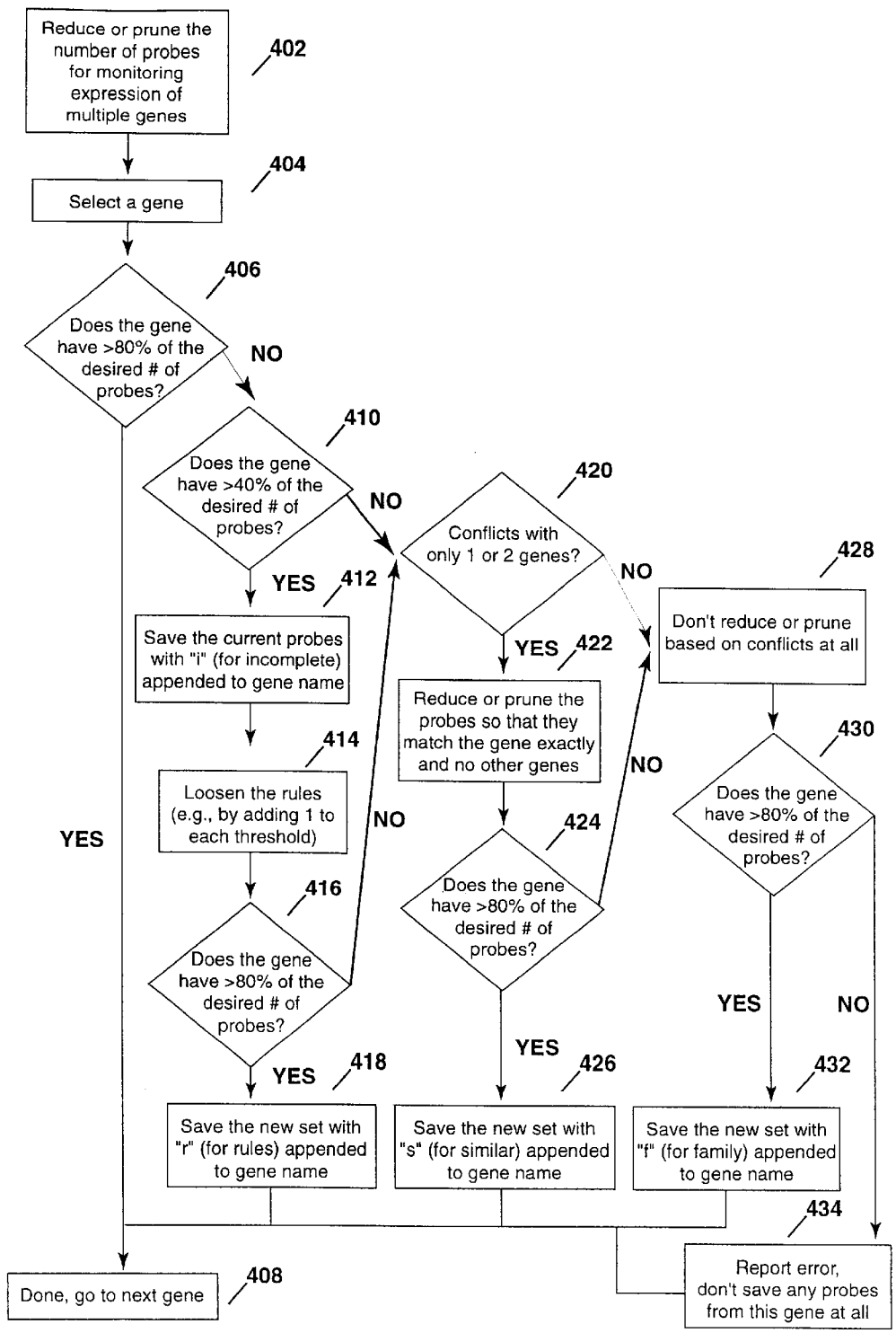
FIG. 11 shows the flow of a process of increasing the number of probes for monitoring the expression of genes after the number of probes has been reduced or pruned.

FIG. 11 shows the flow of a process of increasing the number of probes for monitoring the expression of genes after the number of probes has been reduced or pruned. In one embodiment, a user is able to specify the number of nucleic acid probes that should be placed on the chip to monitor the expression of each gene. As discussed above, it is advantageous to reduce probes that will not likely produce good results; however, the number of probes may be reduced to substantially less than the desired number of probes.

At step 402, the number of probes for monitoring multiple genes is reduced by the heuristic rules method, neural net, annova model, synthesis cycle pruning, or any other method, or combination of methods. A gene is selected at step 404.

A determination is made whether the remaining probes for monitoring the selected gene number greater than 80% (which may be varied or user defined) of the desired number of probes. If yes, the computer system proceeds to the next gene at step 408 which will generally return to step 404.

If the remaining probes for monitoring the selected gene do not number greater than 80% of the desired number of probes, a determination is made whether the remaining probes for monitoring the selected gene number greater than 40% (which may be varied or user defined) of the desired number of probes. If yes, an "i" is appended to the end of the gene name to indicate that after pruning, the probes were incomplete at step 412.

At step 414, the number of probes is increased by loosening the constraints that rejected probes. For example, the thresholds in the heuristic rules may be increased by 1. Therefore, if previously probes were rejected if they had four As in a row, the rule may be loosened to five As in a row.

A determination is then made whether the remaining probes for monitoring the selected gene number greater than 80% of the desired number of probes at step 416. If yes, an "r" is appended to the end of the gene name at step 412 to indicate that the rules were loosened to generate the number of synthesized probes for that gene.

At step 420, a check is made to see if the probes for monitoring the selected gene only conflict with one or two other genes. If yes, the full set of probes complementary to the gene (or target sequence) are taken and pruned so that the probes remaining are exactly complementary to the selected gene exclusively at step 422.

A determination is then made whether the remaining probes for monitoring the selected gene number greater than 80% of the desired number of probes at step 424. If yes, an "s" is appended to the end of the gene name at step 426 to indicate that the only a few genes were similar to the selected gene.

At step 428, the probes for monitoring the selected gene are not reduced by conflicts at all. A determination is then made whether the remaining probes for monitoring the selected gene number greater than 80% of the desired number of probes at step 430. If yes, an "f" is appended to the end of the gene name at step 432 to indicate that the probes include the whole family of probes perfectly complementary to the gene.

If there are still not 80% of the desired number of probes, an error is reported at step 434. Any number of error handling procedures may be undertaken. For example, an error message may be generated for the user and the probes for the gene may not be stored. Alternatively, the user may be prompted to enter a new desired number of probes.

V. Synthesis of High Density Arrays

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., *Science,* 251, 767–77 (1991). These procedures for synthesis of polymer arrays are now referred to as VLSIPS™ procedures. Using the VLSIPS™ approach, one heterogenous array of polymers is converted, through simultaneous coupling at a number of reaction sites, into a different heterogenous array. See, U.S. application Ser. Nos. 07/796.243 and 07/980,523.

The development of VLSIPS™ technology as described in the above-noted U.S. Patent No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993 describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

According to other embodiments the channels will be formed by depositing an electron or photoresist such as those used extensively in the semiconductor industry. Such materials include polymethyl methacrylate (PMMA) and its derivatives, and electron beam resists such as poly(olefin sulfones) and the like (more fully described in Chapter 10 of Ghandi, *VLSI Fabrication Principles,* Wiley (1983)). According to these embodiments, a resist is deposited, selectively exposed, and etched, leaving a portion of the substrate exposed for coupling. These steps of depositing resist, selectively removing resist and monomer coupling are repeated to form polymers of desired sequence at desired locations.

The "spotting" methods of preparing compounds and libraries of the present invention can be implemented in much -the same manner as the flow channel methods. For example, a monomer A, or a coupled, or dimer, or trimer, or tetramer, etc, or a fully synthesized material, can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

VI. Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the rasuing of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at about 40° C. to about 50° C. (0.005% Triton X-100) to ensure hybridization and then subsequent washes are performed at higher stringency (e.g, 1×SSPE-T at 37° C.) to eliminate mismatched hybrid duplexes. Successive washes may be performed at increasingly higher stringency (e.g., down to as low as 0.25×SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished. e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl or other alhylated ammonium salts) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol.* 24: *Hybridization With Nucleic Acid Probes,* P. Tijssen, ed. Elsevier, N.Y., (1993)).

VII. Detection Methods

Methods for detection depend upon the label selected and are known to those of skill in the art. Thus, for example, where a calorimetric label is used, simple visualization of the label is sufficient. Where a radioactive labeled probe is used, detection of the radiation (e.g with photographic film or a solid state detector) is sufficient.

As explained above, the use of a fluorescent label is preferred because of its extreme sensitivity and simplicity. Standard procedures are used to determine the positions where interactions between a target sequence and a reagent take place. For example, if a target sequence is labeled and exposed to an array of different oligonucleotide probes, only those locations where the oligonucleotides interact with the target (sample nucleic acid(s)) will exhibit significant signal. In addition to using a label, other methods may be used to scan the matrix to determine where interaction takes place. The spectrum of interactions can, of course, be determined in a temporal manner by repeated scans of interactions which occur at each of a multiplicity of conditions. However, instead of testing each individual interaction separately, a multiplicity of sequence interactions may be simultaneously determined on a matrix.

B. Scanning System

In a preferred embodiment, the hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

Detection of the fluorescence signal preferably utilizes a confocal microscope, more preferably a confocal microscope automated with a computer-controlled stage to automatically scan the entire high density array. The microscope may be equipped with a phototransducer (e.g., a. photomultiplier, a solid state array, a ccd camera, etc.) attached to an automated data acquisition system to automatically record the fluorescence signal produced by hybridization to each oligonucleotide probe on the array. Such automated systems are described at length in U.S. Pat. No: 5,143,854, PCT Application No. 20 92/10092, and copending U.S. Ser. No. 08/195,889 filed on Feb. 10, 1994. Use of laser illumination in conjunction with automated confocal microscopy for signal detection permits detection at a resolution of better than about 100 µm, more preferably better than about 50 µm, and most preferably better than about 25 µm.

With the automated detection apparatus, the correlation of specific positional labeling is converted to the presence on the target of sequences for which the oligonucelotides have specificity of interaction. Thus, the positional information is directly converted to a database indicating what sequence interactions have occurred. For example, in a nucleic acid hybridization application, the sequences which have interacted between the substrate matrix and the target molecule can be directly listed from the positional information. A preferred detection system is described in PCT publication no. WO90/15070; and U.S. Ser. No. 0 7/624,120. Although the detection described therein is a fluorescence detector the detector can be replaced by a spectroscopic or other detector. The scanning system can make use of a moving detector relative to a fixed substrate, a fixed detector with a moving substrate, or a combination. Alternatively, mirrors or other apparatus can be used to transfer the signal directly to the detector. See, e.g., U.S. Ser. No. 07/624,120.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

More sophisticated signal processing techniques can be applied to the initial determination of whether a positive signal exists or not. See, e.g., U.S. Ser. No. 07/624,120 and discussion below in Section XII.

VIII. Ligation-Enhanced Signal Detection

A) General Ligation Reaction

Ligation reactions can be used to discriminate between fully complementary hybrids and those that differ by one or more base pairs, particularly in cases where the mismatch is near the 5' terminus of the probe oligonucleotide. Use of a ligation reaction in signal detection increases the stability of the hybrid duplex, improves hybridization specificity (particularly for shorter probe oligonucleotides e.g., 5 to 12 mers), and optionally, provides additional sequence information.

Figure 13A:
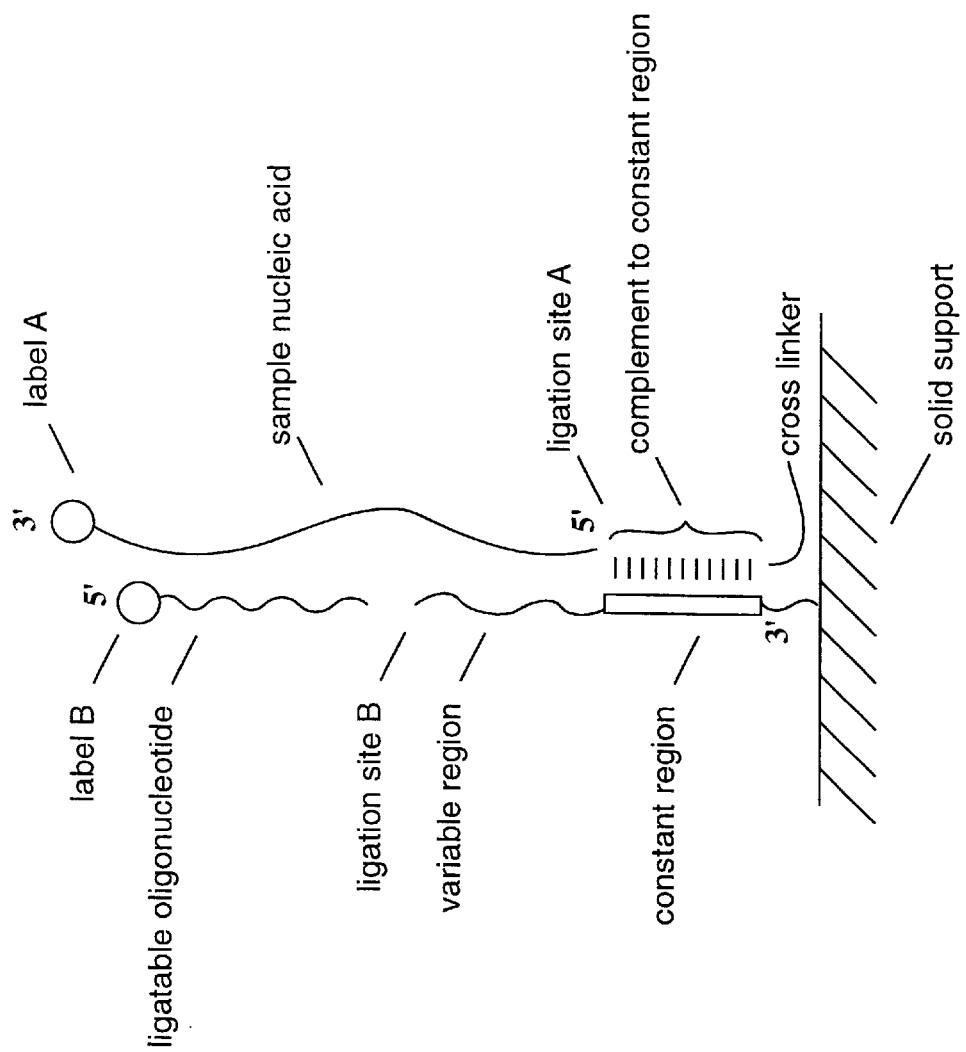
FIGS. 13a, 13b, 13c, and 13d illustrate the various components of ligation/hybridization reactions and illustrates various ligation strategies.

Various components for use of ligation reaction(s) in combination with generic difference arrays are illustrated in FIG. 13a. In its simplest embodiment, the probe oligonucleotide/ligation reaction system includes an array of olignucleotide probes. As discussed above, the oligonculcleotide probes can be randomly selected. haphazardly selected, composition biased, inclusive of all possible oligonucleotides of a particular length, and so forth. The oligonucleotide probes can optionally include a predetermined "constant" region (see FIG. 13a) which has substantially the same sequence for substantially all of the probe oligonucleotides on the array.

Where the probe comprises a constant region it also preferably comprises a "variable region" (see FIG. 13a) which can be randomly selected, haphazardly selected, composition biased, inclusive of all possible oligonucleotides of a particular length, and so forth. When constant and variable regions are present, a sample nucleic acid that hybridizes to the oligonucleotide probe typically hybridizes to at least the variable region and optionally to the constant region as well.

The probe oligonucleotide/ligation reaction system also optionally includes a nucleic acid that is complementary to the constant region. This complement may be a subsequence of a sample nucleic acid or a separate oligonucleotide. When the complement to the constant region is a separate oligonucleotide, hybridization to the constant region provides a ligation site (see FIG. 13a, ligation site A). The hybridized complement to the constant region can optionally be permanently crosslinked to the constant region by the use of cross-linking reagents (e.g., psoralens). The sample nucleic acid, and/or the ligatable oligonucleotide can optionally be labeled. Where both are labeled, the labels can be the same or distinguishable.

The probe oligonucleotide/ligation reaction system optionally includes a ligatable oligonucleotide that can be ligated to free terminus of the variable region (see FIG. 13a, ligation site B). The ligatable oligonucleotide can be a single oligonucleotide of known nucleotide sequence, a collection of nucleic acids of known sequence, or a pool of all possible oligonculeotides of a particular length.

These various components of the probe oligonucleotide/ ligation reaction system can be combined in a variety of ways to increases the stability of the hybrid duplex, and/or improve hybridization specificity (particularly for shorter probe oligonucleotides e.g., 5 to 12 mers), and/or provides sequence information. Various uses of the probe oligonucleotide/ligation reaction system are described in detail below.

While FIG. 13a illustrates ligation components in solid phase, similar approaches and components can be used in solution phase. It will be appreciated that the order of the constant region and variable region can be altered. In addition, a probe oligonucleotide may comprise multiple constant regions and/or multiple variable regions. In addition, while FIG. 13a illustrates the probe oligonucleotide attached to a solid support by a 3' terminus, the probe can also be reversed and attached via the 5' terminus.

It will be appreciated that sequences or subsequences of the probe oligonucleotide where variable regions are present or absent can act as a primer site for initiation of polymerization using the remainder of the probe oligonucleotide and/or the ligation oligonucleotide and/or the sample nucleic acid as a polymerization template.

Figure 13C:
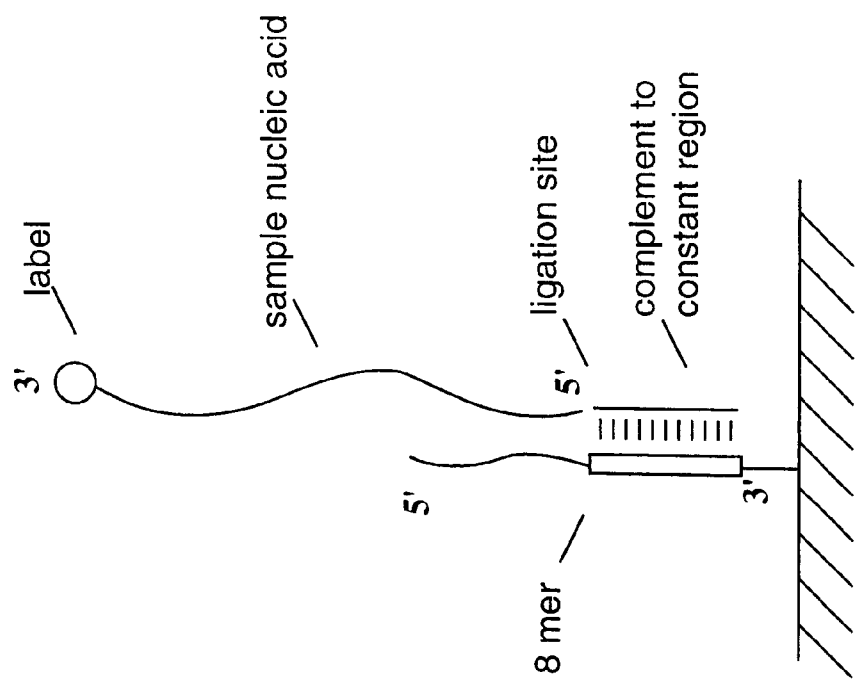
Figure 13B:
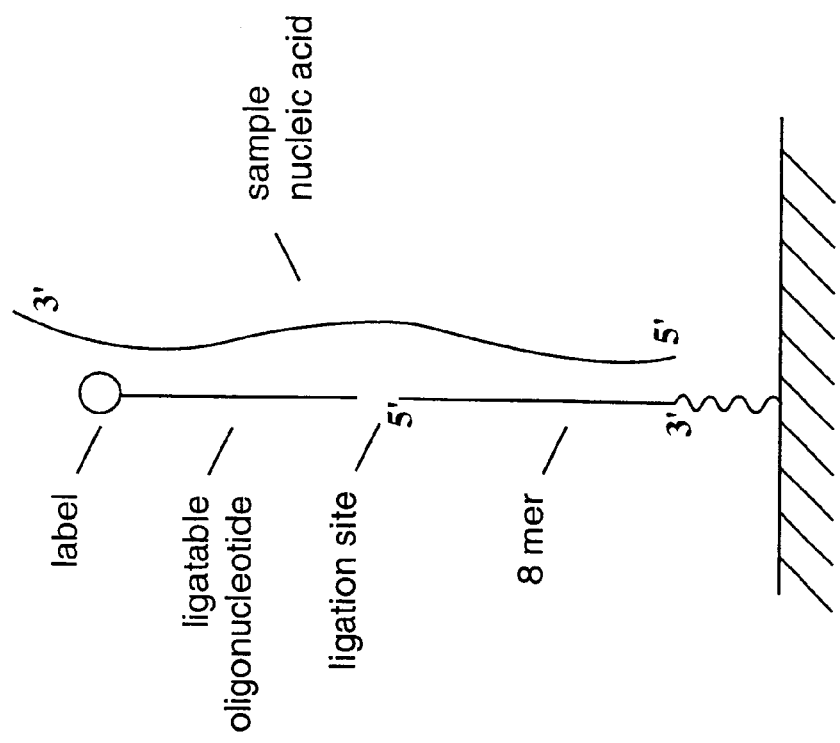

B) Ligation Reactions to Discriminate Mismatches at Probe Termini, Target Termini, or Both Termini In one embodiment, a simple ligation reaction discriminated mismatches at or near the terminus of the probe oligonucleotide (see FIG. 13b). Typically, the nucleic acid fragments comprising the sample nucleic acid are longer than the probe oligonucleotides in the array. So that, when hybridized, the target nucleic acid typically has an overhang. When the array comprises probe oligonucleotides attached through their 3' termini, the hybridized target (sample) nucleic acid provides a 3' overhang. In this embodiment, the target nucleic acid is not necessarily labelled (see, e.g., FIG. 13b).

When the array of oligonucleotides is combined with the target nucleic acid to form target-oligonucleotide hybrid complexes, the target-oligonucleotide hybrid complexes are contacted with a ligase and a labelled, ligatable oligonucleotide or, alternatively, with a pool of labelled, ligatable probes. While the hybridization of the sample nucleic acids and the ligatable probes can be performed sequentially, in a preferred embodiment both hybridization and ligation are performed simultaneously (i.e., the target, ligatable oligonucleotide, and ligate are all added together). The pool may comprise particular preselected probes or may be a collection of all possible probes of a particular length (e.g., 3 mer up to 12 irLer) (see, e.g., FIG. 13b).

Figure 12A:
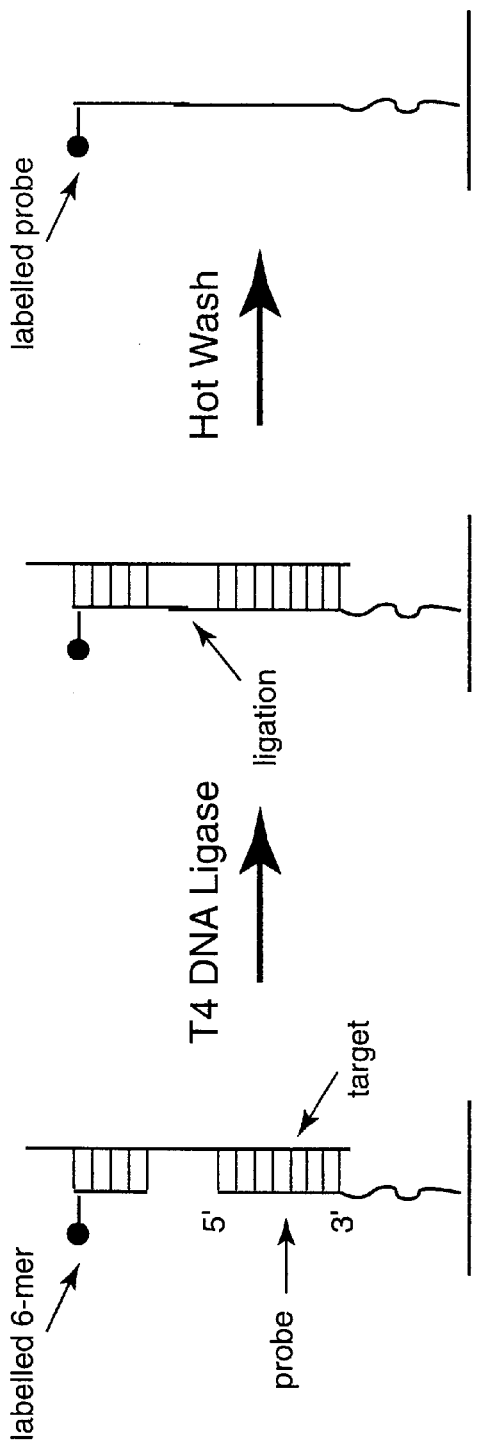
FIGS. 12a and 12b illustrate the probe oligonucleotide/ligation reaction system.
Figure 12B:
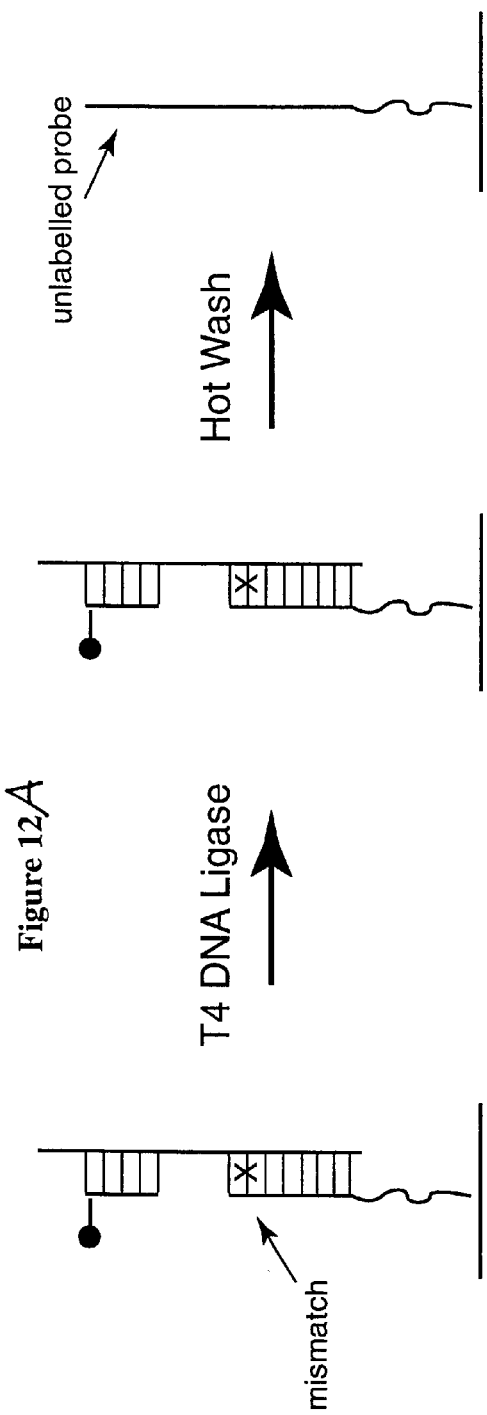

The ligation reaction of the labelled ligatable probes to the phosphorylated 5' end of the oligonucleotide probes on the substrate will occur, in the presence of the ligase, predominantly when the target:oligonucleotide hybrid has formed with correct base-pairing near the 5' end of the oligonucleotide probe and where there is a suitable 3' overhang of the target nucleic acid to serve as a template for hybridization and ligation (see FIG. 12). After the ligation reaction, the substrate is washed (multiple times if necessary) under conditions suitable to remove the target nucleic acid and the labeled, unligated probes (e.g., above 40° C. to 50° C., or under otherwise highly stringent conditions).

Thereafter, a fluorescence image (e.g., a quantitative fluorescent image) of the hybridization pattern is obtained as described above in Section VII(B). Labeled oligonucleotide probes, i.e., the oligonucleotide probes which are complementary to the target nucleic acid, are identified. The presence, absence, and/or intensity of the hybridization signal provides information regarding the presence and level of the nucleic acid sequence or subsequence in the nucleic acid sample as described above.

Any enzyme that catalyzes the formation of a phosphodiester bond at the site of a single-stranded break in duplex DNA can be used to enhance discrimination between fully complementary hybrids and those that differ by one or more base pairs. Such ligases include, but are not limited to, T4 DNA ligase, ligases isolated from E. coli and ligases isolated from other bacteria and bacteriophages. The concentration of the ligase will vary depending on- the particular ligase used, the concentration of target and buffer conditions, but will typically range from about 50 units/ml to about 5,000 units/ml. Moreover, the time in which the array of target:oligonucleotide hybridization complexes is in contact with the ligase will vary. Typically, the ligase treatment is carried out for a period of time ranging from minutes to hours. Methods of performing ligase discrimination can be found in copending U.S. Ser. No. 08/533,582, filed on Oct. 18, 1995 and in Jackson et al. (1996) *Nature Biotechnology,* 14: 1685–1691.

It will be appreciated that the method described above primarily discriminates mismatches at or near the 5' terminus of the surface bound probe oligonucleotide and does little to discriminate mismatches at, or near, the 5' terminus of the target (sample) nucleic acid (see FIG. 13b).

In another embodiment, a ligation can be used to discriminate mismatches at, or near, the end of the sample nucleic acid (FIG. 13c). In this instance, the probe oligonucleotides comprise a constant region and a variable region (e.g., the variable regions can include all possible 8 mers as illustrated in FIG. 13c). A constant oligonucleotide (complementary to the constant region or a subsequence thereof) is hybridized to the constant region and cross-linked (e.g., covalently bound) at that location. The remainder of the probe oligonucleotide (e.g., the variable region or subsequences thereof and optionally a subsequence of the constant region) forms a 5' overhang to which the nucleic acid sample can hybridize. Where there are no mismatches at or near the terminus of the sample oligonucleotide, a ligation event then joins the sample oligonucleotide to the constant oligonucleotide. Free nucleic acids are washed away leaving bound hybridized sample oligonucleotides which can then be detected.

Figure 13D:
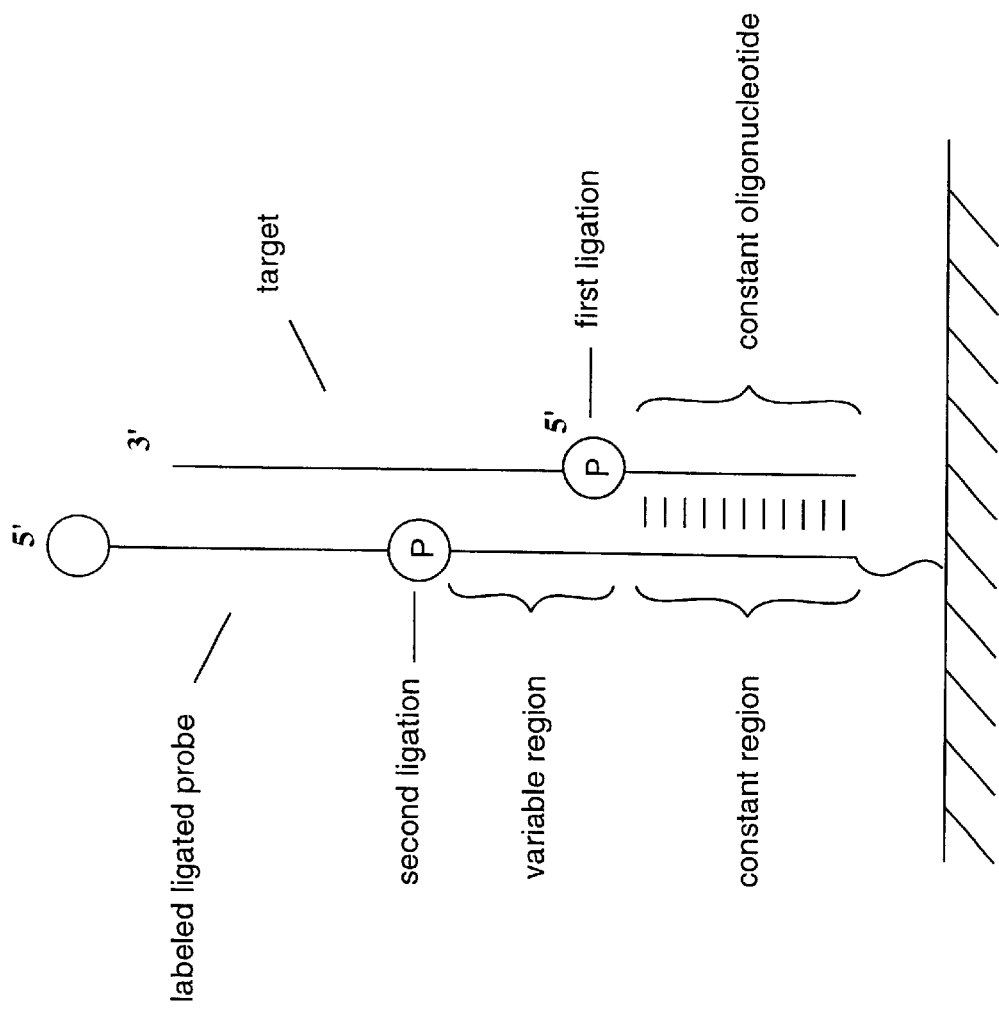

In still another embodiment, a double ligation (illustrated in FIG. 13d) can be used to discriminate mismatches at or near the ends of both the probe oligonucleotide and the target nucleic acid. In this approach, the probe oligonucleotides each comprise a constant region and a variable region as described above in VIII(A). The surface bound oligonucleotide probes are hybridized to a constant oligonucleotide having a sequence which is complementary to the constant region of the oligonucleotide probes. The sample (target) nucleic acids are contacted to the hybrid duplex in the presence of a ligase. Where there is no terminal mismatch between the sample nucleic acid and the variable region, the ligation is successful resulting in the ligation of the constant oligonucleotide to the sample nucleic acid (see "first ligation" in FIG. 13d). This ligation thus discriminates mismatches at the terminus of the sample nucleic acid.

The hybridized duplex is contacted with a pool of labeled ligatable oligonucleotides. Where a ligatable probe is complementary to the overhang produced by the hybridized sample nucleic acid and there are no mismatches at or near the free terminus of the variable region of the probe oligonucleotide a second ligation will attach the labeled ligatable probe (see FIG. 13d). The second ligation thus discriminates against mismatches near the free terminus of the probe oligonucleotide. It will be appreciated that the various hybridization and ligation reactions may be carried out sequentially or simultaneously, and in a preferred embodiment are carried out simultaneously.

As with the previously described method, any enzyme that catalyzes the formation of a phosphodiester bond at the site of a single-strand break in duplex DNA can be used to enhance discrimination between fully complementary hybrids and those that differ by one or more base pairs. Such ligases include, but are not limited to, T4 DNA ligase, ligases isolated from E. coli and ligases isolated from other bacteria or bacteriophages. The concentration of the ligase will vary depending on the particular ligase used, the concentration of target and buffer conditions, but will typically range from about 50 units/ml to about 5,000 units/ml. Moreover, the time in which the array of target oligonucleotide:oligonucleotide probe hybrid complexes is in contact with the ligase will vary. Typically, the ligase treatment is carried out for a period of time ranging from minutes to hours. In addition, it will be readily apparent to those of skill that the two ligation reactions can either be done sequentially or, alternatively, simultaneously in a single reaction mix that contains: target oligonucleotides; constant oligonucleotides; a pool of labeled, ligatable probes; and a ligase.

In this dual ligation method, the first ligation reaction generally occurs only if the 5' end of the target oligonucleotide (i.e., the last 3–4 bases) matches the variable region of the oligonucleotide probe. Similarly, the second ligation reaction, which adds a label to the probe, generally occurs efficiently only if the first ligation reaction was successful and if the ligated target is complementary to the 5' end of the probe. Thus, this method provides for specificity at both ends of the variable region. Moreover, this method is advantageous in that it allows a shorter variable probe region to be used; increases probe:target specificity and removes the necessity of labeling the target. Dual ligation methods of this sort are described in detail in copending U.S. Ser. No. 08/533,582, filed on Oct. 18, 1995.

In another embodiment, after hybridization of the nucleotide complementary to the constant region of the probe oligonculeotides, the hybrid duplex formed thereby can be permanently cross-linked so as to prevent subsequent denaturation of the hybrid duplex. When the sample nucleic acid is ligated to the overhang thus formed it is also permanently attached to the solid support. In this embodiment, the use of a ligatable oligonucleotide is optional. The sample nucleic acid may itself be labeled thereby permitting detection of the ligated sample nucleic acids.

Methods for cross-linking nucleic acids are well known to those of skill in the art. Such methods include, but are not limited to, baking, exposure to UV, exposure to ionizing radiation, and contact with chemical cross-linking reagents. In a particularly preferred embodiment, cross-linking is accomplished by the formation of covalent bonds with chemical cross-linking reagents. Preferred cross-linking reagents include bifunctional cross-linking reagents and cross-linking is accomplished by chemical or photoactivation of the cross-linking reagent with the nucleic acids. The reagents may be applied after formation hybrid duplexes, but in a preferred embodiment, the cross-linker is initially attached to either the probe or complementary (to the constant region) nucleic acids before hybridization.

The cross-linking reagent can be any bifunctional molecule which covalently cross-links the tester nucleic acid to a hybridized driver nucleic acid. Generally the cross-linking agent will be a bifunctional photoreagent which will be monoadducted to the tester or driver nucleic acids leaving a second photochemically reactive residue which can bind covalently to the corresponding hybridized nucleic acid upon photoexcitation. The cross-linking molecule may also be a mixed chemical and photochemical bifunctional reagent which will be non-photochemically bound to the probe or tester nucleic acids via a chemical reaction such as alkylation, condensation, or addition, followed by photochemical binding to the corresponding hybridized nucleic acid. Bifunctional chemical cross-linking molecules activated either catalytically or by high temperature following hybridization may also be employed.

Examples of bifunctional photoreagents include furocoumarins, benzodipyrones, and bis azides such as bis-azido ethidium bromide. Examples of mixed bifunctional reagents with both chemical and photochemical binding moieties include haloalkyl-furocoumarins, haloalkyl benzodipyrones, haloalkyl-coumarine and various azido nucleoside triphosphates.

Particularly preferred cross-linkers include linear furocoumarins (psoralens) such as 8-methoxypsoralin, 5-methoxypsoralin and 4, 5',8-trimethylpsoralin, and the like. Other suitable cross-linkers include cis-benzodipyrone and trans-benzodipyrone. The cross-linker known commercially as Sorlon is also suitable. For a detailed description of the cross-linking of hybridized nucleic acids see WO 85/02628.

The foregoing enhancement discrimination methods involving the use of ligation reactions can be used in all instances where improved discrimination between fully complementary hybrids and those that differ by one or more base pairs would be helpful. More particularly, such methods can be used to more accurately determine the sequence (e.g., de novo sequencing), monitor expression, monitor mutations, or resequence the target nucleic acid (i.e., such methods can be used in conjunction with a second sequencing procedure to provide independent verification). The foregoing is intended to illustrate, and not restrict, the way in which an array of target:oligonucleotide hybrid complexes can be treated with a ligase and a pool of labeled, ligatable probes to improve hybridization signals on high density oligonucleotide arrays.

B) Ligation Reaction to Add Sequence Information i) Extended Sequence Information From Simple Ligation The ligation reactions described above can also be used to increase the sequence information obtained regarding the hybridized nucleic acid. It will be appreciated that the nucleotide sequence of each probe oligonucleotide on the high density oligonucleotide array is known. Specific hybridization to a sample nucleic acid indicates that the hybridized sample nucleic acid has a sequence or subsequence complementary to the hybridized probe oligonucleotide. Thus a hybridization event provides sequence information that can be used to identify the nucleic acids (e.g., gene transcripts) present in the hybridized sample. Generally speaking, the sequence information obtained is governed by the length of the probe oligonucleotide. Thus, where the probe oligonucleotide is an 8 mer, 8 nucleotides of sequence information is obtained.

However, the ligation discrimination reactions described above can be used to provide additional sequence information. In this embodiment, rather than every possible ligatable oligonucleotide of a given length, the array and sample nucleic acids are hybridized to predetermined ligatable oligonucleotides in which the nucleotides at one or more positions are known. Successful hybridization and ligation of the label oligonucleotide thus indicates that the hybridized sample nucleic acid has nucleotides complementary to the ligatable oligonucleotide in addition to the probe oligonucleotide.

Thus, for example, where the probe oligonucleotide is an 8 mer and specific 6 mer ligatable probes are used, the resulting hybridization will provide 14 nucleotides worth of sequence information.

Where different ligatable oligonucleotides are used in this context, it is desirable to distinguish between the various ligated oligonucleotides. This can be accomplished by sequential ligations with each different species of ligatable probe followed by reading of the array. Alternatively, each species of ligatable oligonucleotide can be labeled with a different detection label allowing simultaneous ligation and subsequent detection of the various different labels.

ii) Use of a Generic Ligation GeneChip for Interrogating Sequences Adjacent to Restriction Sites in a Complex (Target) Sample Nucleic Acid The generic difference arrays can be used to fingerprint complex DNA clones or to monitor the complex pattern of gene expression from a given source. In fingerprinting a nucleic acid sequence (e.g., an 8 bp sequence) adjacent to a given restriction enzyme site is sequenced.

Figure 14A:
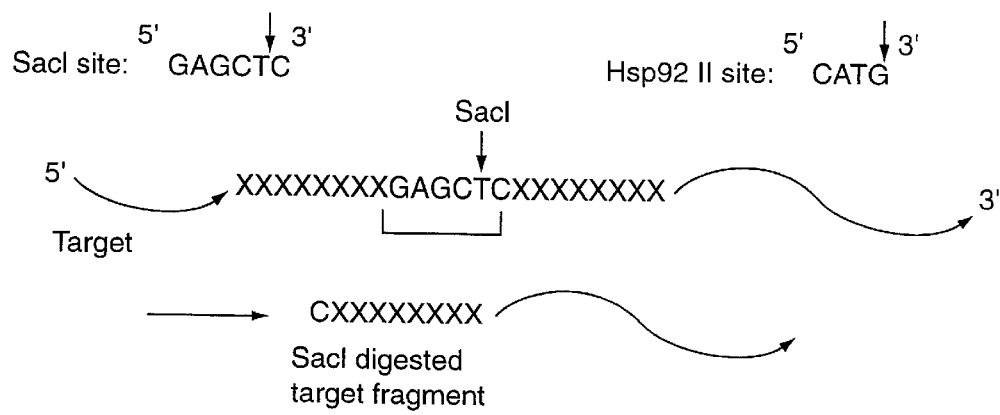
FIGS. 14a, 14b, 14c, and 14d illustrates a ligation discrimination used in conjunction with a restriction digest of the sample nucleic acid.
Figure 14B:
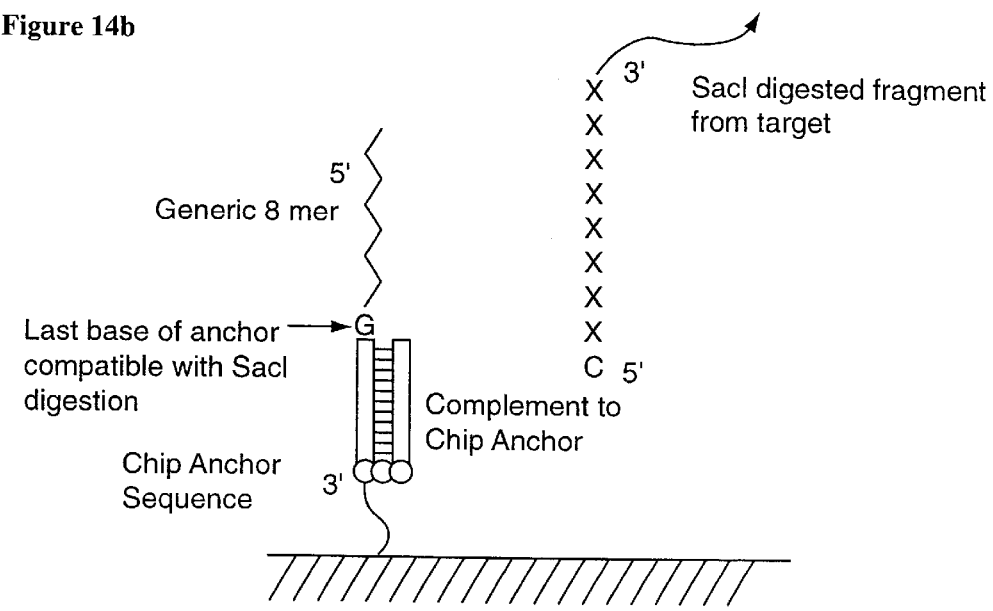
Figure 14C:
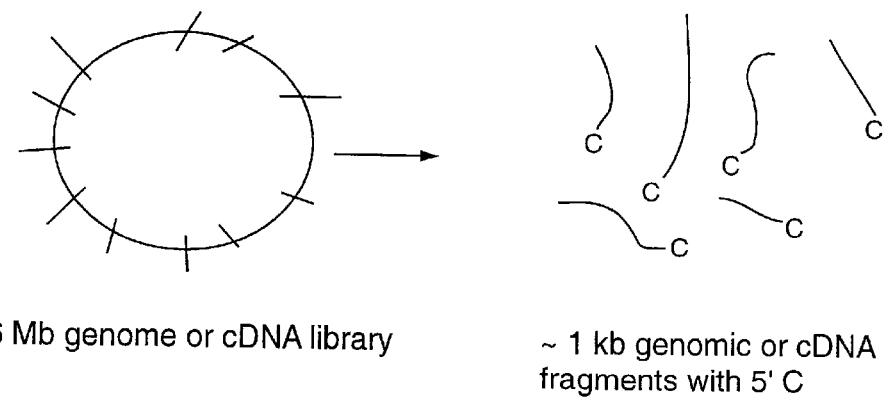

In fingerprinting, a restriction enzyme is used which cleaves the target at a frequency dependent on the length of the recognition sequence. The restriction digest thus generate nucleic acid fragments approximately uniformly distributed along the genomic DNA. For instance, a 4-cutter like Hsp92 II would cut a target about once every several hundred basepairs, whereas a 6-cutter, like SacI would cut a target about once every several thousand (4,000) basepairs. With restriction enzyme fragments, the individual fragments are typically non-overlapping and average several thousand basepairs in length. For the purposes of fingerprinting, with a 6-cutter restriction enzyme it is possible to examine (2000–3000 fragments×4000 bases/fragment=8–12 million basepairs per target. This indicates that it is possible to routinely sort an 8–12 million basepair target in a high density array to measure expression differences or to monitor gene expression (see, e.g., FIG. 14c) thereby providing a characteristic expression "fingerprint" or abundance difference fingerprint for each restriction digest of the sample nucleic acid. The fingerprinting methods thus provide means to subsample a nucleic acid population in a roughly uniform and reproducible manner and determine expression profiles and/or abundance differences for target nucleic acid thus subsampled.

In general, the method involves providing a high density generic difference screening array where the probe oligonucleotides comprise a constant region and a variable region as described above. In this instance, however, the last few bases of the constant region (anchor sequence) are selected to complement the 5' end of the restriction recognition site (see, e.g., FIGS. 14a and 14b) and the complementary anchor sequence is shortened by the appropriate number of bases. The variable region can be randomly selected, haphazardly selected, composition biased as described above. However, in a preferred embodiment, the variable region include all possible nucleic acids of a particular length (e.g., all possible 3 mers, all possible 4 mers . . . all possible 12 mers), more preferably all possible 8 mers.

The sample nucleic acids are prepared by fragmentation using a restriction enzyme. Preferred restriction enzymes leaving only 0, 1, or 2 bases at the 5' end provide a greater specificity of ligation (i.e., SacI leaves just a 5'° C. and Hsp92 II leaves no recognition site bases at the 5' end). However, restriction enzymes leaving more bases at the 5' end can be used. Several restriction enzymes can be used simultaneously if they all leave the same recognition base at the 5' end. For instance, Aat II, Sacd, SphI, HhaI Bsp1286I, ApaI, Kpn I, Ban II, all leave just a C at the 5' end making these compatible enzymes. Restriction enzymes and their characteristic recognition/cleavage sites are well known to those of skill in the art (see, e.g., CloneTech catalogue, Clonetech Laboratories Inc. Palo Alto, Calif.).

The digested target is then hybridized and ligated to the high density array, preferably in the presence of a complement to the constant region, using standard conditions (e.g., 30° C., o/n, 800 U T4 ligase, T4 ligase buffer). The hybridization in effect sorts (locates and/or localizes) the sample nucleic acids the position of the sample nuclei acids being determined by the sequence of the bases adjacent to the restriction site at the 5' end. The hybridization data can be used directly in an expression monitoring method as described above, or the same procedure can be performed on two or more sample nucleic acids for generic difference screening.

In a preferred embodiment, one of two formats are used. In Format I, the ligated fragment (e.g, the sample nucleic acid and, optionally, the complement to the constant region) is locked into place in the high density array by its attachment (e.g., by cross-linking) to the complement (e.g., by the use of a psoralen). The complementary strand to the fragment can be denatured and washed off of the array with a dilute base (e.g., 1 N NaOH). These cross-linked fragments can then be used as probes in a second round of hybridization to one or more nucleic acid samples. Differential nucleic acid abundances (e.g., differential gene expression) can then be monitored by comparing the hybridization pattern between different nucleic acids hybridized simultaneously or sequentially to the same array or separate arrays.

In a second format (format II), particularly where the sample nucleic acid is a deoxynucleic acid sample, the DNA is restriction digested as described above, and then directly hybridized/ligated to the generic difference array. Sites where intensity differences occur indicate a difference in nucleic acid abundance. The differentially abundant (e.g., differentially expressed) nucleic acid can be cloned by designing primers specific to that nucleic acid based upon the sequence information derived from the location of the probe in the array and the sequence of the recognition site. For an 8 mer (variable region) and a 6 base restriction enzyme, this gives a 14 mer primer sequence. For short genomes, a 14 mer primer may be used to isolate the clone. Longer genomes become more tractable as the length of the primary probes (variable region) increases beyond 8 mers.

Figure 14D:
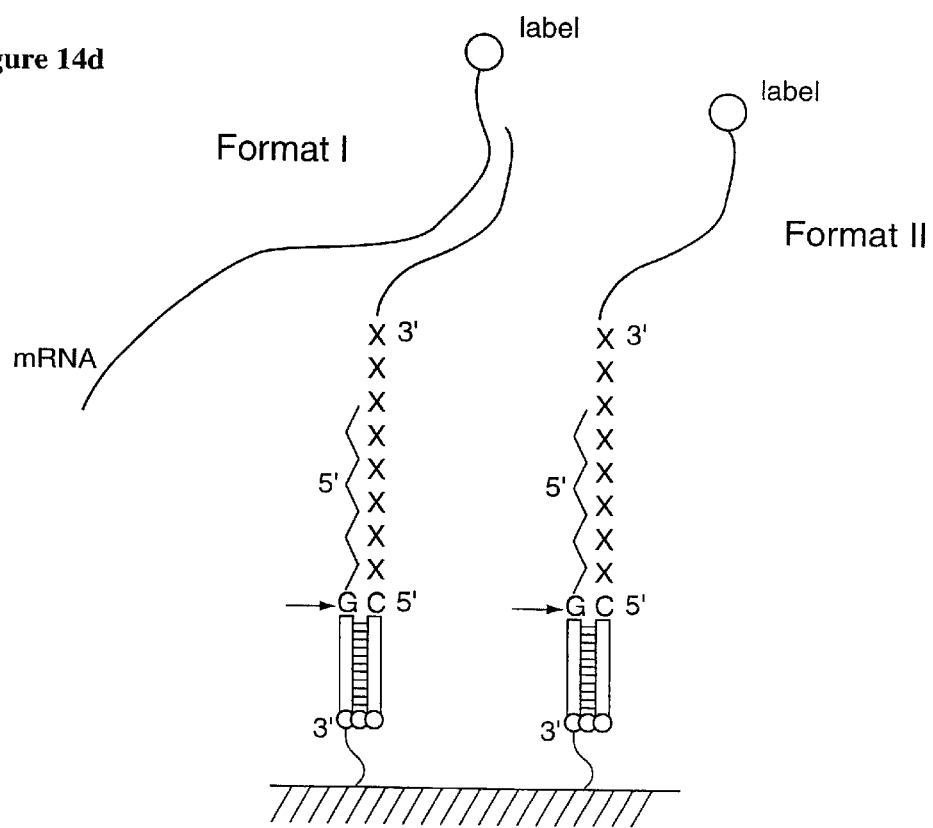

The restriction enzyme digested sample nucleic acid is preferably labeled and ligated to the high density array in fingerprinting method and in format II (see discussion above and FIG. 14d). In the case of format I assays the ligated target sequence is preferably not labeled and instead, serves as a hybridization probe in a second round of hybridization of labeled sample nucleic acids to the high density array.

To insure that sites which have not been cleaved by the given restriction enzymes do not ligate to the high density array, alkaline phosphatase can be used to treat the sample nucleic acids before restriction enzyme digestion.

iii) Analysis of Differential Display Fragments on a Generic Difference Array

The princinple behind differential display is to generate a set of randomly primed amplification (e.g., PCR) fragments from a first strand cDNA population transcribed from RNA using anchor primers of the form:

$(T)_nVA$, $(T)_nVG$, $(T)_nVC$, and $(T)_nVT$ (SEQ ID NO:4)

in which V is A, G, or C, and n ranges from about 6 to about 30, preferably from about 8 to about 20 and more preferably about 10 to about 16 with n=14 being most preferred. Depending on what random primer and anchoring primer and anchoring proimer is chosen, different sets of cDNA transcripts are represented in a particular nucleic acid fragment set. These amplification fragments are analyzed by sorting the fragments on a generic screening oligonucleotide array where they hybridize based on the sequence at the 5' end of the fragment.

Figure 16A:
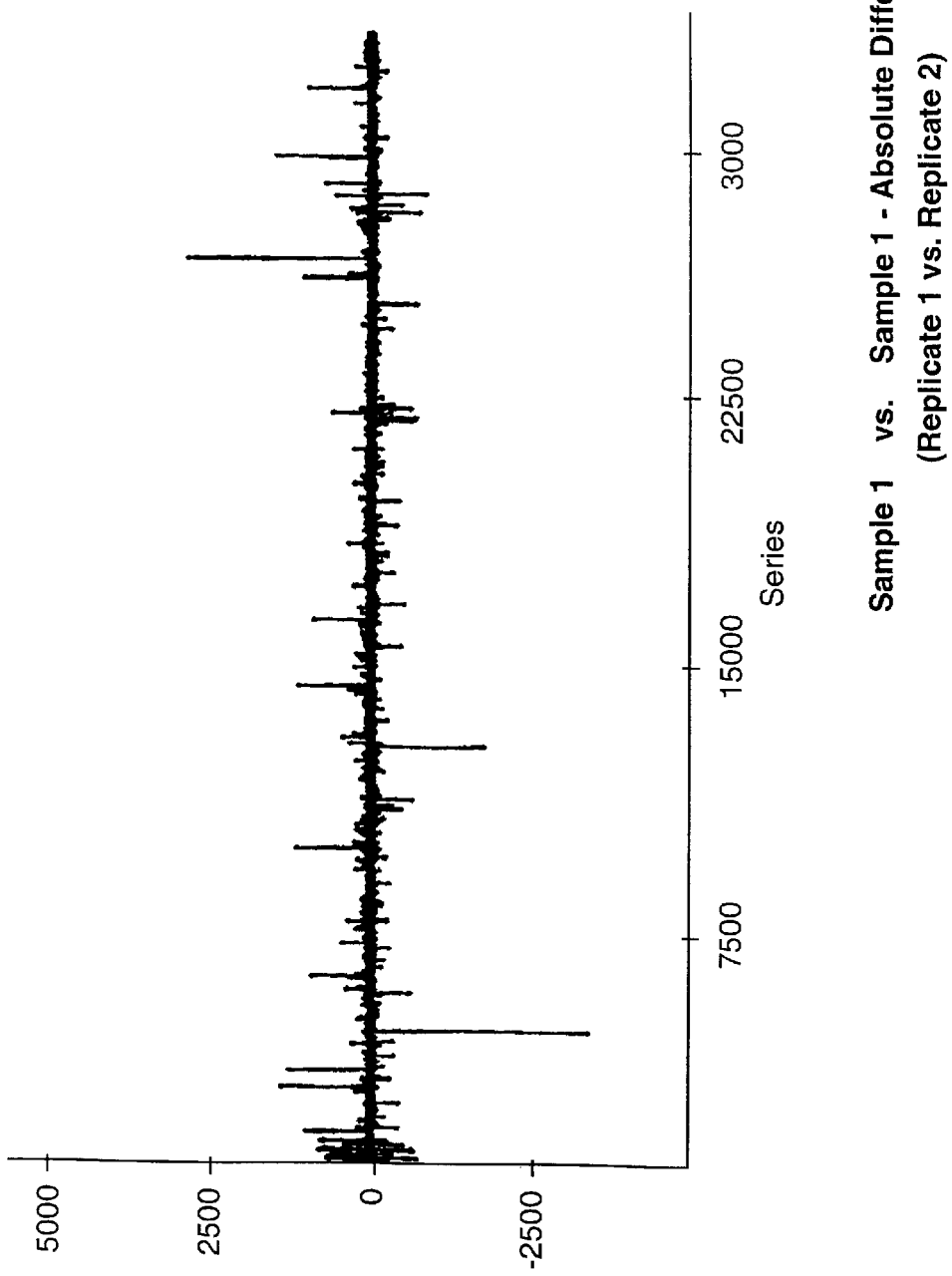
FIGS. 16a, 16b, and 16c illustrate the differences between replicate 1 and replicate 2 for sample 1 and sample 2 nucleic acids.

The method is illustrated in FIGS. 16a through 16e. First strand cDNA is synthesized by reverse transcription of poly(A) mRNA using an anchored poly(t) primer according to standard methods (FIG. 16a). The first strand DNA acts as a template for amplification (e.g., via PCR) using upstream primers comprising an engineered restriction site and one or more degenerate bases (N=A,C,G,T) at the 3' end. Randomly primed PCR is then performed using the upstream primers the anchor primers and a random primer (e.g., anchor primers $(T)_{14}VA$, $(T)_{14}VG$, $(T)_{14}VC$, $(T)_{14}VT$ and random primer e.g., SacI site: 5'-CATGAGCTCNN). The resulting amplification fragments are then digested with a restriction endonuclease corresponding to the engineered restriction sites. The resulting sample nucleic acids are then hybridized to a generic difference screening array as described above.

The method is preferably performed to two or more nucleic acid samples thereby allowing use of the generic difference screening methods of this invention. In one embodiment, the probe oligonucleotides comprise a constant region complementary to the remaining restriction site on the sample nucleic acids if present. The remaining analysis proceeds as described above.

The method allows analysis of several thousand or even more "bands" (nucleic acids) simultaneously, furthermore, sequence information is also provided on the differentially abundant nucleic acid. For example where the cleavage is with Sac I, providing a 9 base tail (CATGAGCTC) the array can comprise probe oligonucleotides having a complementary 9 base constant region and variable regions comprising all possible 9 mers. This provides 17 nucleotides of sequence information for each hybridization (9 mer constant+8 mer variable).

iv) Use of Ligation to Extract Additional Sequence Information from Restriction Selected Nucleic Acid Hybridizations Ligation reactions can also be used in combination with restriction digests to subsample the sample nucleic acids at approximately uniform intervals and simultaneously provide additional sequence information using a ligation reaction. In this embodiment, a high density array is provided in which the probe oligonucleotides comprise a nucleic acid sequence complementary to the sense or antisense strand of a restriction site (see, e.g., FIG. 14). The sample nucleic acids are digested randomly with a DNAse or specifically with a restriction endonuclease (e.g., Sau 3A). The digested oligonucleotides are then hybridized to the high density array. Only those nucleic acids having termini complementary to the constant regions will bind to the probe oligonucleotides. Thus, the restriction fragments will be preferentially selected.

The array is also hybridized with a pool of ligatable oligonucleotides comprising all possible oligonucleotides of a particular length (e.g., a 6 mer) in the presence of a ligase thereby ligating the complementary ligatable oligonucleotides to the terminus of the probe oligonucleotide. This produces probe oligonucleotides increased in length by the length of the ligatable oligonucleotide and complementary to nucleic acids known to be present in the nucleic acid sample.

The DNA is then stripped off of the array and the elongated probes are used to perform generic difference screening of the nucleic acid samples as described above. When probes corresponding to nucleic acid differentially expressed in the various samples are identified, the known probe sequence can be used to identify the nucleic acids that are differentially expressed in the samples.

In one embodiment, this is accomplished by producing 4 primer oligonucleotides comprising the constant region plus the known variable region and an additional nucleotide (A, G, C, or T) on one end. The genomic clone is then digested with a second restriction enzyme and ligated to an adaptor sequence. Using the 4 primer oligonucleotides and the adapter sequence as primers the genomic sequence of interest can be amplified (e.g., using PCR) from the genomic clones. The PCR amplified sequence can then be used to probe (e.g., in a Southern blot) the cDNA library to obtain the whole cDNA of interest.

For example, in one embodiment, a 10 mer high density array is designed so that it comprises all possible combination of 10 mer oligonucleotides (i.e., $4^{10}=1048576$ nucleic acids) and, at the beginning of each oligonucleotide, a constant sequence (e.g, 3'-TAGT-5'), the first 4 bases of which are complementary to the recognition sequence of a restriction enzyme (e.g., Sau 3A plus one base T).

Complete digestion of a large genomic clone or a simplified cDNA library (e.g., a cDNA library that only includes parts of the 5' end or 3' end of whole mRNA) with, for example, a 4 cutter enzyme (illustrated herein by Sau 3A) generates DNA fragments with a 5' overhang sequence (for Sau 3A, the overhangs is GATC). The recognition site exists at approximately every 500 bp.

When the DNA, fragments are hybridized with the 10 mer chip in the presence of all possible combinations of a ligatable oligonucleotide of a particular length (e.g., a 6 mer) and a T4 DNA ligase ,the ligatable oligonucleotide is ligated onto the probe oligonucleotide.

The DNA is then stripped off the chip and generic difference screening is performed as described above. This permits identification of probe oligonculeotides that hyridize to nucleic acids that are present at different levels in the tested samples.

Based on the 14 bp sequence in this example (5 mer constant region bases plus 10 mers) from the probes of interest in the array, four 16 base primers are produced by adding one base (A, G, C, or T) at the end. Using these primers and adaptor sequences as primers, the genomic sequence of interest can be amplified. The amplified sequence can then be used to probe a cDNA library to obtain the whole cDNA of interest as described above.

IX. Signal Evaluation

A) Signal Evaluation for Expression Monitoring

One of skill in the art will appreciate that methods for evaluating the hybridization results vary with the nature of the specific probe nucleic acids used as well as the controls provided. In the simplest embodiment simple quantification of the fluorescence intensity for each probe is determined. This is accomplished simply by measuring probe signal strength at each location (representing a different probe) on the high density array (e.g., where the label is a fluorescent label, detection of the amount of fluorescence (intensity) produced by a fixed excitation illumination at each location on the array). Comparison of the absolute intensities of an array hybridized to nucleic acids from a "test" sample with intensities produced by a "control" sample provides a measure of the relative abundance of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls as described above in Section IV(A)(2). These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in array synthesis or in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the BioB probes). The resulting values may be multiplied by a constant value to scale the results.

As indicated alcove, the high density array can include mismatch controls or, in the case of generic difference screening arrays, pairs of related oligonucleotie probes differing in one or more preselected nucleotides. In preferred expression monitoring arrays, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should primarily reflect non-specific binding or the presence in the sample of a nucleic acid that hybridizes with the mismatch. In expression monitoring analyses, where both the probe in question and its corresponding mismatch control both show high signals, or the mismatch shows a higher signal than its corresponding test probe, the signal from those probes is preferably ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe. Similar, as discussed below, in generic difference screening, the difference between probe pairs is calculated.

The concentration of a particular sequence can then be determined by measuring the signal intensity of each of the probes that bind specifically to that nucleic acid and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

It is a surprising discovery of this invention, that normalization controls are often unnecessary for useful quantification of a hybridization signal. Thus, where optimal probes have been identified in the two step selection process as described above, in Section IV(B)(ii)(a), the average hybridization signal produced by the selected optimal probes provides a good quantified measure of the concentration of hybridized nucleic acid.

B) Signal Evaluation for Generic Difference Screening

Signal evaluation for generic difference screening is performed in essentially the same manner as expression monitoring described above. However, data is evaluated on a probe-by-probe basis rather than a gene by gene basis.

In a preferred embodiment, for each probe oligonucleotide the signal intensity difference between the members of each probe pair (K) is calculated as:

$$X_{ijk1} - X_{ijk2}$$

where X is the hybridization intensity of the probe, i indicates which sample (in this case sample 1 or 2), and j indicates which replicate for each sample (in the case of Example 7 where there were two replicates for each nucleic acid sample, j is 1 or 2), K is the probe pair ID number (in the case of Example 7, 1 . . . 34,320), and 1 indicates one member of the probe pair, while 2 indicates the other member of the probe pair.

The differences between the signal intensity difference for each probe pair between the replicates for each sample is then calculated. Thus, for example, the differences between replicate 1 and 2 of sample 1 (e.g, a normal the normal cell line) and between replicate 1 and replicate 2 of sample 2 (e.g., a the tumor cell line) for each probe is calculated as $$(x_{11k1} - X_{11k2}) - (X_{12k1} - X_{12k2})$$

for k–1 to the total number of probes.

The replicates can be normalized to each other as:

$$(X_{11k1} - X_{11k2})/(X_{12k1} - X_{12k2}) \quad \text{for sample 1}$$

or $$(X_{21k1} - X_{21k2}) - (X_{22k1} - X_{22k2}) \quad \text{for sample 2}$$

for all probe pairs (i.e., after normalization, the average ratio should approximate 1).

Finally, the the differences between sample 1 and 2 averaged over the two replicates is calculated. This value is calculated as $$((X_{21k1} + X_{22k2})/2) - ((X_{11k1} + X_{12k2})/2)$$

after normalization between the two samples based on the average ratio of $$[(X_{21k1} + X_{22k2})/2]/[(X_{11k1} + X_{12k2})/2].$$

Figure 16B:
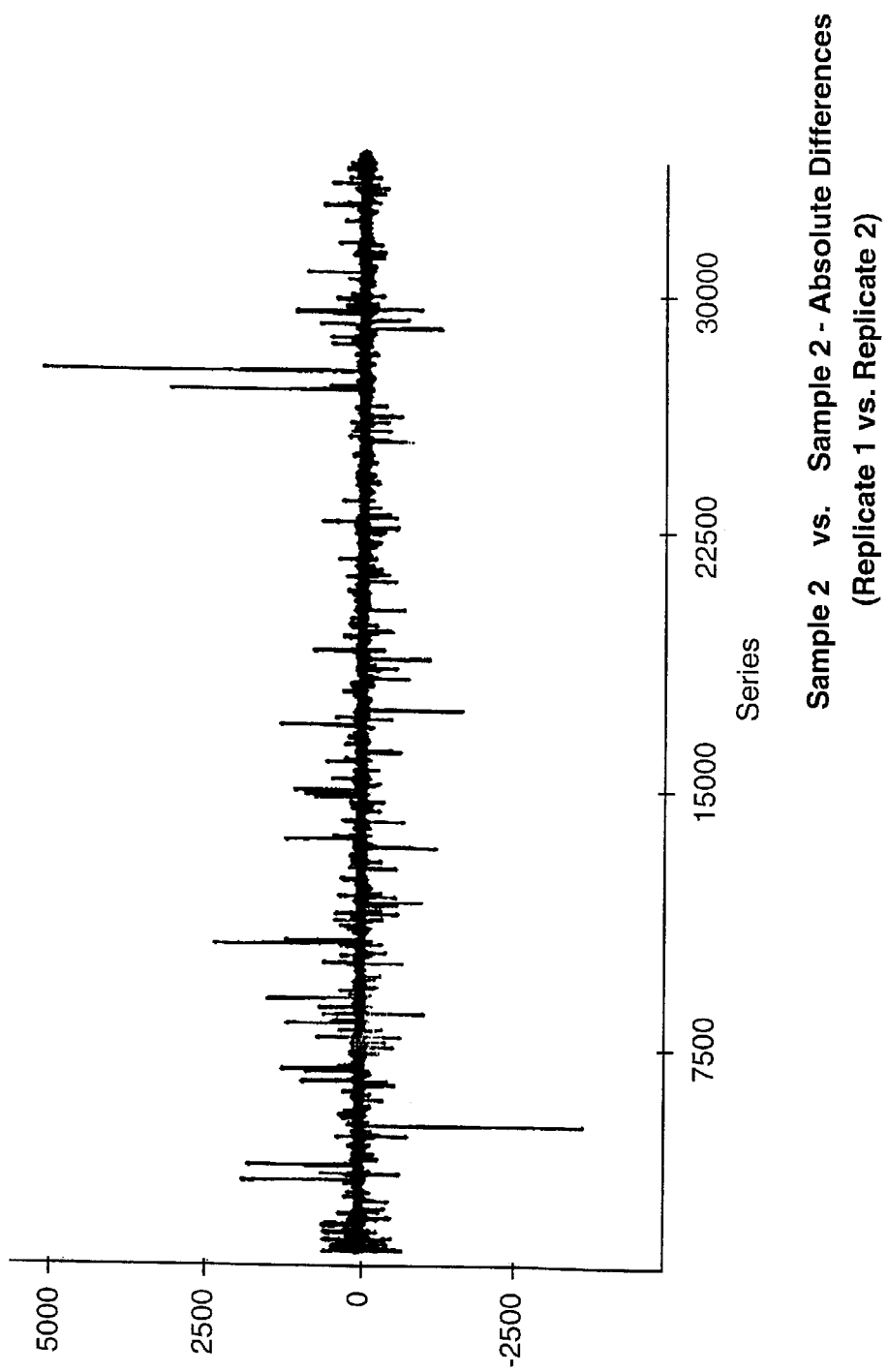
Figure 16C:
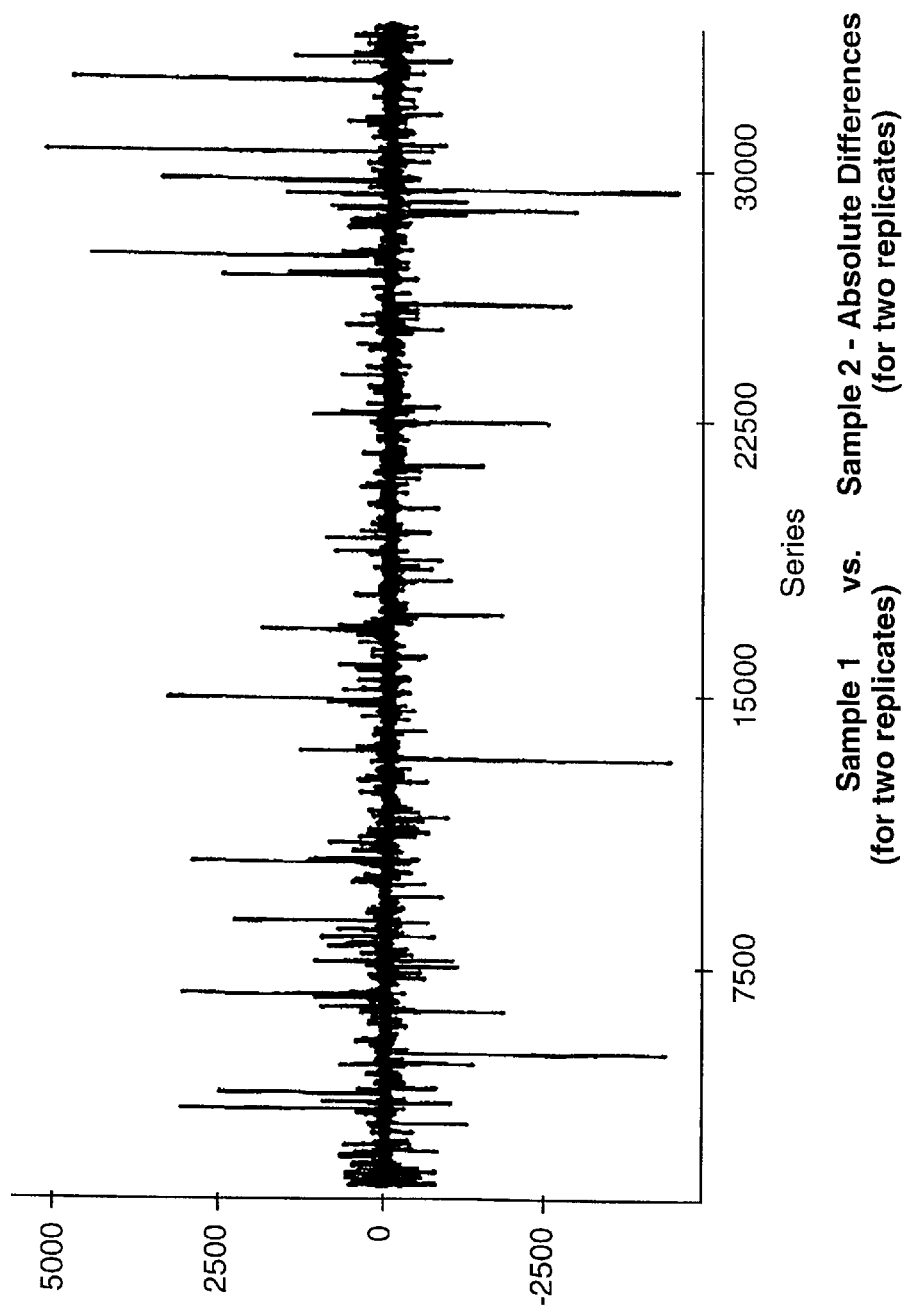

This data is plotted as a function of probe number (ID) and probes having differentially hybridized nucleic acids are readily discernable (see, e.g., FIG. 16c).

However, the data may also be filtered to reduce background signal. In this instance, after normalization between replicates (see above), the ratio is calculated as follows: If the absolute value of $(X_{11k1} - X_{11k2})/(X_{12k1} - X_{12k2}) > 1$, then the ratio=$(X_{11k1} - X_{11k2})/(X_{12k1} - X_{12k2})$ else the ratio=$(X_{12k} - X_{12k2})/(X_{11k1} - X_{11k2})$ (the inverse).

The ratio of replicate 1 and 2 of sample 2 for the difference of each oligonucleotide pair, is calculated in the same way, but based on the absolute value of $$(X_{21k1}-X_{21k2})/(X_{22k1}-X_{22k2})$$

and $$(X_{22k1}-X_{22k2})/(X_{21k1}-X_{21k2}).$$

Figure 17A:
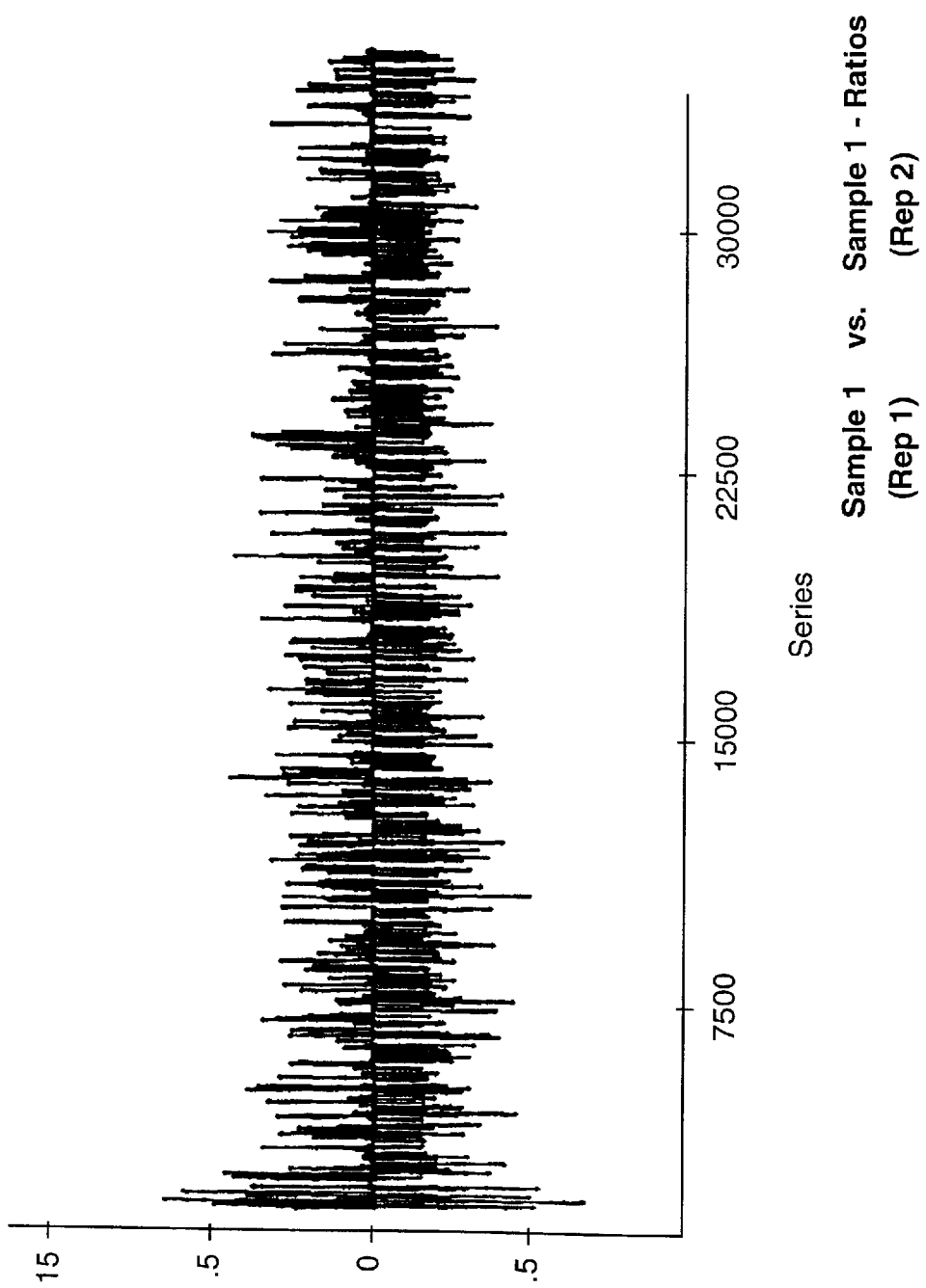
FIGS. 17a, 17b, and 17c illustrates the data of FIGS. 16A, 16b, and 16c filtered.

Finally, as above, the ratio of sample 1 and sample 2 averaged over two replicates for the difference of each oligonucleotide pair is calculated as in FIG. 17a, but based on the absolute value of $$[(X_{21k1}+X_{22k2})/2]/[(X_{11k1}+X_{12k2})/2]$$

and $$[(X_{11k1}+X_{12k2})/2]/[(X_{21k1}+X_{22k2})/2]$$

after normalization as described above.

The oligonucleotide pairs that show the greatest differential hybridization between the two samples can be identified by sorting the observed hybridization ratio and difference values. The oligonucleotides that show the largest change (increase or decrease) can be readily seen from the ratio plot (see, e.g. FIG. 17c).

X. Identification of Gene Whose Expression is Altered

As indicated above, the nucleic acid sequences of the probe oligonucleotides comprising the high density arrays are known. The sequences of the probes showing the largest hybridization differences (and families of such differences) can be used to identify the differentially expressed genes in the compared samples by any of a number of means.

Thus, for example, sequences of the differentially hybridizing probes may be used to search a nucleic acid database (e.g., by a BLAST, or related search of the fragments against all known sequences). Alternatively, some sequence reconstruction using the families of probes that change by similar amounts can also be done. The database search for known genes that include sequences complementary (or nearly complementary ) to the probes that change the most is not difficult and because it is generally easier than sequence reconstruction is the preferred method for identifying the differentially expressed sequences.

In another embodiment, the differential hybridization pattern indicates that there are significant differences in the overall expression profile(s) between the tested samples, and identifies probes that are specific for the differences. These probes can be used as specific affinity reagents to extract from the samples the parts that differ. This can be accomplished in several ways:

In one approach, the material hybridized to the probes that show the greatest differences between samples can be microextracted from the high density array. For example, the hybridized nucleic acids can be removed using small capillaries. Alternatively probes that are anchored to the chip with a photolabile linker can be released by selective irradiation at the desired parts of the high-density array.

In another approach, because the sequence of all the probes on the high-density array is known, and the probes that hybridize differentially have been identified, the latter can be used as affinity reagents to extract the nucleic acids that differentially hybridize in the test samples. Once the differentially hybridizing probes are identified in the array, the probe (or probes) can be synthesized on beads (or other solid support) and hybridized to the samples (not necessarily fragmented for this step—full length clones may be desirable). The material that is extracted can be cloned and/or sequenced, according to standard methods known to those of skill in the art, to obtain the desired information about the differentially expressed species (e.g. clones can be screened with labeled oligonucleotides to determine ones with appropriate inserts, and/or randomly chosen and sequenced).

In still another approach the sequence of the hybridized probes of interest can be used to generate amplification primers (e.g., reverse transcription and/or PCR primers). The differentially expressed sequence can then be amplified and used as a probe to probe a genomic or cDNA library using sequence specific primers determined from the array in combination with specific sequences added during a reverse transcriptase cDNA step as described above (e.g., primer based on poly A or added 3' sequence). Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif.; Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In short, using the above-described method, differentially expressed genes can be identified without prior assumptions about which genes to monitor and without prior knowledge of sequence. Once identified (and sequenced if not a previously sequenced gene), the new sequences can be included in a high density array designed to detect and quantify specific genes in the same way as described in copending applications Ser. No. 08/529,115 filed on Sep. 15, 1995 and PCT/US96/14839. Thus, the two approaches are complementary in that one can be used to broadly search for expression differences of perhaps unknown genes,, while the other is used to more specifically monitor those genes that have been chosen as important or those genes that have been previously at least partially sequenced.

XI. Kits for Expression Monitoring and Generic Difference Screening

In another embodiment, this invention provides kits for expression monitoring and/or generic difference screening. The kits include, but are not limited to a a container or containers containing one or more high density oligonucleotide arrays of this invention. Preferred kits for generic difference screening include at least two high density arrays. The kits can also include a label or labels for labeling one or more nucleic acid samples. In addition, the kits can include one or more ligatable oligonucleotides. In certain embodiments, the kit contains pools of different ligatable oligonucleotides, preferably pools of every possible oligonucleotide of a particular length (e.g., all possible 6 mers) or sets of specific ligatable oligonucleotides. One of skill in the art will appreciate that the kits may include any other of the various blocking reagents, labels, devices (e.g, trays, microscope filters, syringes, etc.) buffers, and the like useful for performing the hybridizations and ligation reactions described herein. In addition, the kits may include software provided on a storage medium (e.g., optical or magnetic disk) for the selection of probes and/or the analysis of hybridization data as described herein. In addition, the kits may contain instructional materials teaching the use of the kit in the various methods of this invention (e.g., in practice of various expression monitoring methods or generic difference screening methods described herein).

XII. Computer-Implemented Expression Monitoring

The methods of monitoring gene expression of this invention may be performed utilizing a computer. The computer typically runs a software program that includes computer code incorporating the invention for analyzing hybridization intensities measured from a substrate or chip and thus, monitoring the expression of one or more genes or screening for differences in nucleic acid abundances. Although the following will describe specific embodiments of the invention, the invention is not limited to any one embodiment so the following is for purposes of illustration and not limitation.

Figure 6:
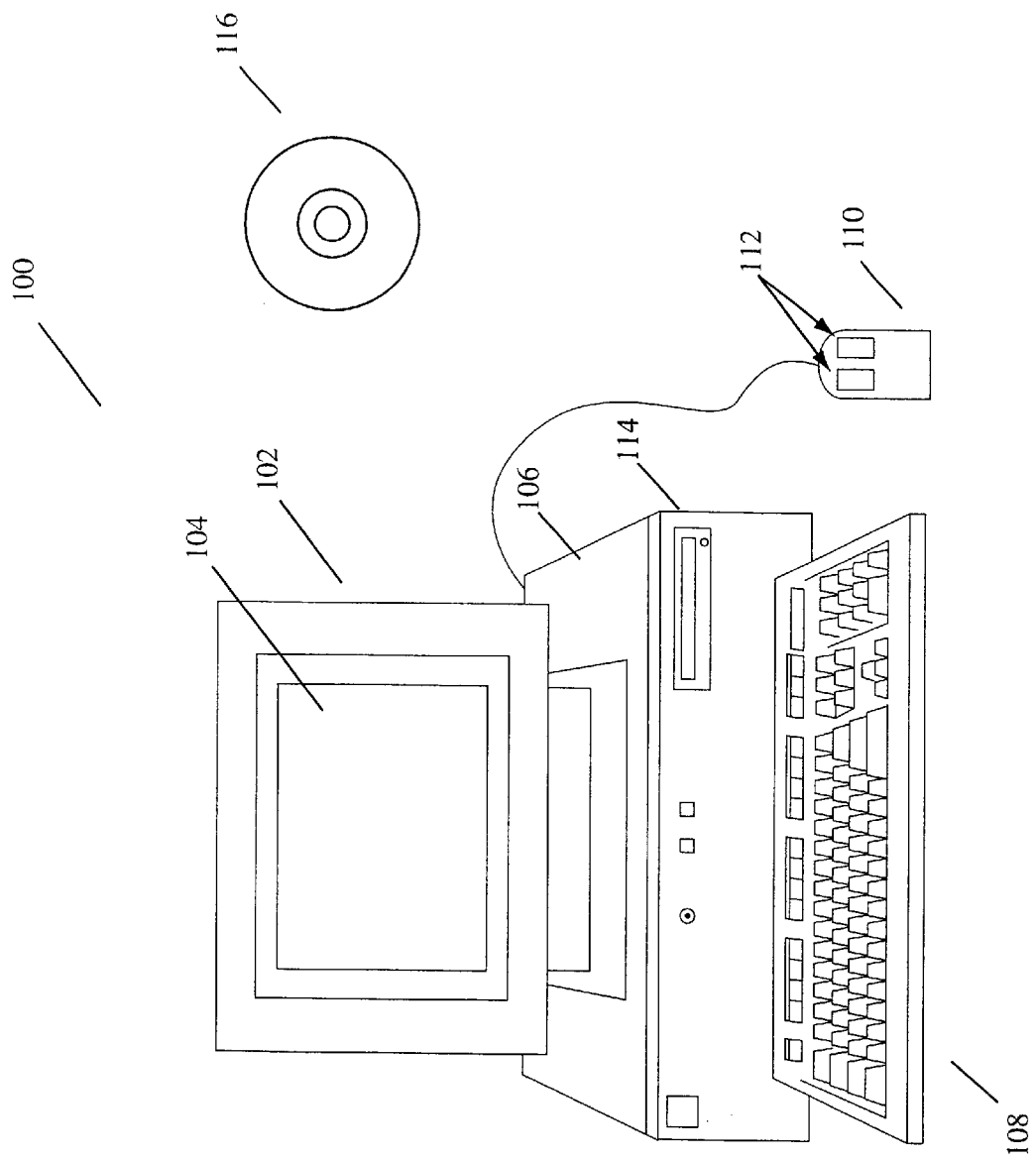
FIG. 6 shows an example of a computer system used to execute the software of an embodiment of the present invention.

FIG. 6 illustrates an example of a computer system used to execute the software of an embodiment of the present invention. As shown, shows a computer system 100 includes a monitor 102, screen 104, cabinet 106, keyboard 108, and mouse 110. Mouse 110 may have one or more buttons such as mouse buttons 112. Cabinet 106 houses a CD-ROM drive 114, a system memory and a hard drive (both shown in FIG. 7) which may be utilized to store and retrieve software programs incorporating computer code that implements the invention, data for use with the invention, and the like. Although a CD-ROM 116 is shown as an exemplary computer readable storage medium, other computer readable storage media including floppy disks, tape, flash memory, system memory, and hard drives may be utilized. Cabinet 106 also houses familiar computer components (not shown) such as a central processor, system memory, hard disk, and the like.

Figure 7:
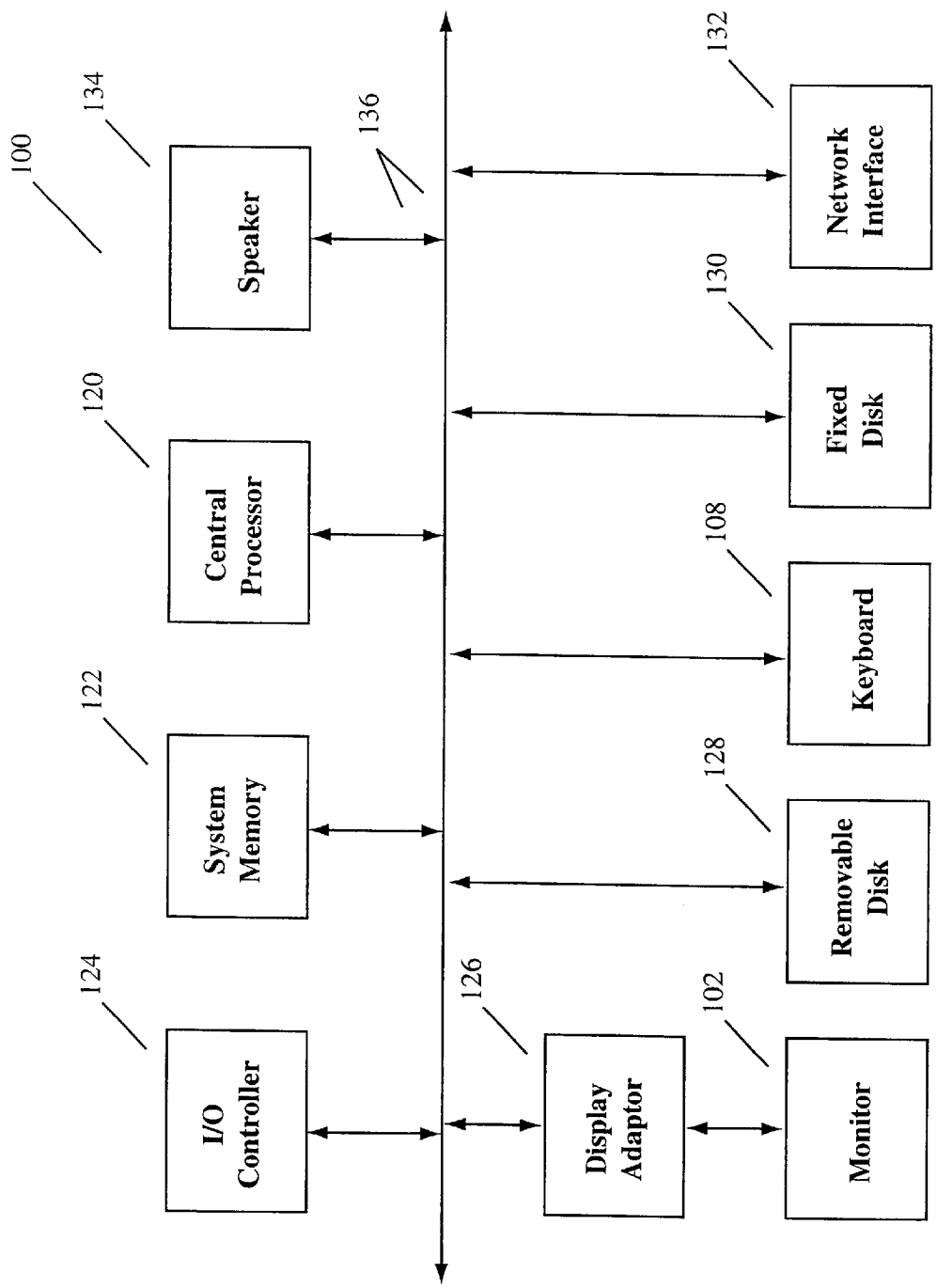
FIG. 7 shows a system block diagram of a typical computer system used to execute the software of an embodiment of the present invention.

FIG. 7 shows a system block diagram of computer system 100 used to execute the software of an embodiment of the present invention. As in FIG. 6, computer system 100 includes monitor 102 and keyboard 108. Computer system 100 further includes subsystems such as a central processor 120, system memory 122, I/O controller 124, display adapter 126, removable disk 128 (e.g., CD-ROM drive), fixed disk 130 (e.g., hard drive), network interface 132, and speaker 134. Other computer systems suitable for use with the present invention may include additional or fewer subsystems. For example, another computer system could include more than one processor 120 (i.e., a multi-processor system) or a cache memory.

Arrows such as 136 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 7 is but an example of a computer system suitable for use with the present invention. Other configurations of subsystems suitable for use with the present invention will be readily apparent to one of ordinary skill in the art.

Figure 8:
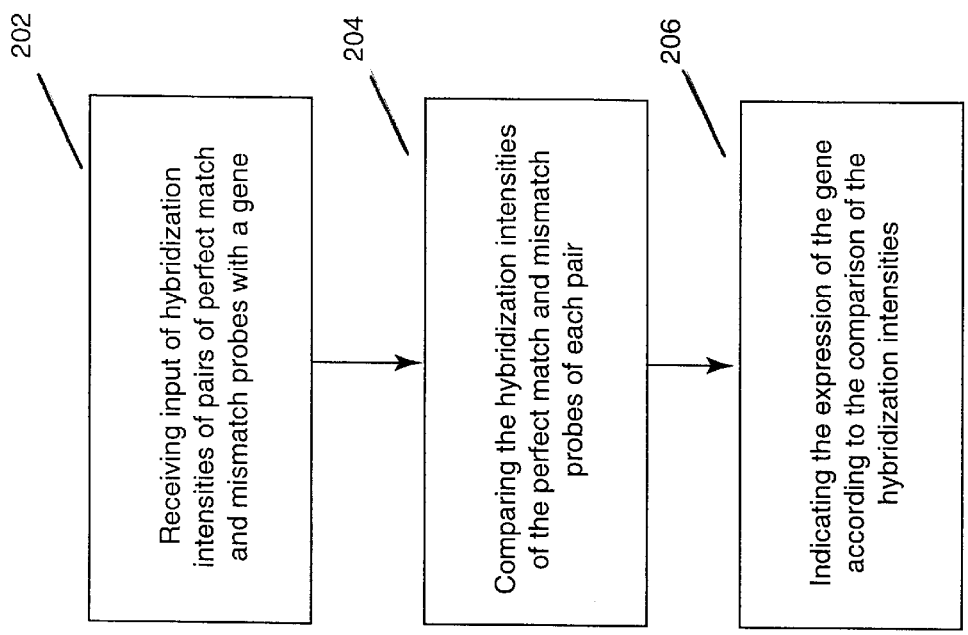
FIG. 8 shows the high level flow of a process of monitoring the expression of a gene by comparing hybridization intensities of pairs of perfect match and mismatch probes.

FIG. 8 shows a flowchart of a process of monitoring the expression of a gene. The process compares hybridization intensities of pairs of perfect match and mismatch probes that are preferably covalently attached to the surface of a substrate or chip. Most preferably, the nucleic acid probes have a density greater than about 60 different nucleic acid probes per 1 $cm^2$ of the substrate. Although the flowcharts show a sequence of steps for clarity, this is not an indication that the steps must be performed in this specific order. One of ordinary skill in the art would readily recognize that many of the steps may be reordered, combined, and deleted without departing from the invention.

Initially, nucleic, acid probes are selected that are complementary to the target sequence (or gene). These probes are the perfect match probes. Another set of probes is specified that are intended to be not perfectly complementary to the target sequence. These probes are the mismatch probes and each mismatch probe includes at least one nucleotide mismatch from a perfect match probe. Accordingly, a mismatch probe and the perfect match probe from which it was derived make up a pair of probes. As mentioned earlier, the nucleotide mismatch is preferably near the center of the mismatch probe.

The probe lengths of the perfect match probes are typically chosen to exhibit high hybridization affinity with the target sequence. For example, the nucleic acid probes may be all 20-mers. However, probes of varying lengths may also be synthesized on the substrate for any number of reasons including resolving ambiguities.

The target sequence is typically fragmented, labeled and exposed to a substrate including the nucleic acid probes as described earlier. The hybridization intensities of the nucleic acid probes is then measured and input into a computer system. The computer system may be the same system that directs the substrate hybridization or it may be a different system altogether. Of course, any computer system for use with the invention should have available other details of the experiment including possibly the gene name, gene sequence, probe sequences, probe locations on the substrate, and the like.

Referring to FIG. 8, after hybridization, the computer system receives input of hybridization intensities of the multiple pairs of perfect match and mismatch probes at step 202. The hybridization intensities indicate hybridization affinity between the nucleic acid probes and the target nucleic acid (which corresponds to a gene). Each pair includes a perfect match probe that is perfectly complementary to a portion of the target nucleic acid and a mismatch probe that differs from the perfect match probe by at least one nucleotide.

At step 204, the computer system compares the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes. An exemplary process of comparing the hybridization intensities of the pairs of probes will be described in more detail in reference to FIG. 9.

After the system compares the hybridization intensity of the perfect match and mismatch probes, the system indicates expression of the gene at step 206. As an 1o example, the system may indicate to a user that the gene is either present (expressed), marginal or absent (unexpressed).

Figure 9:
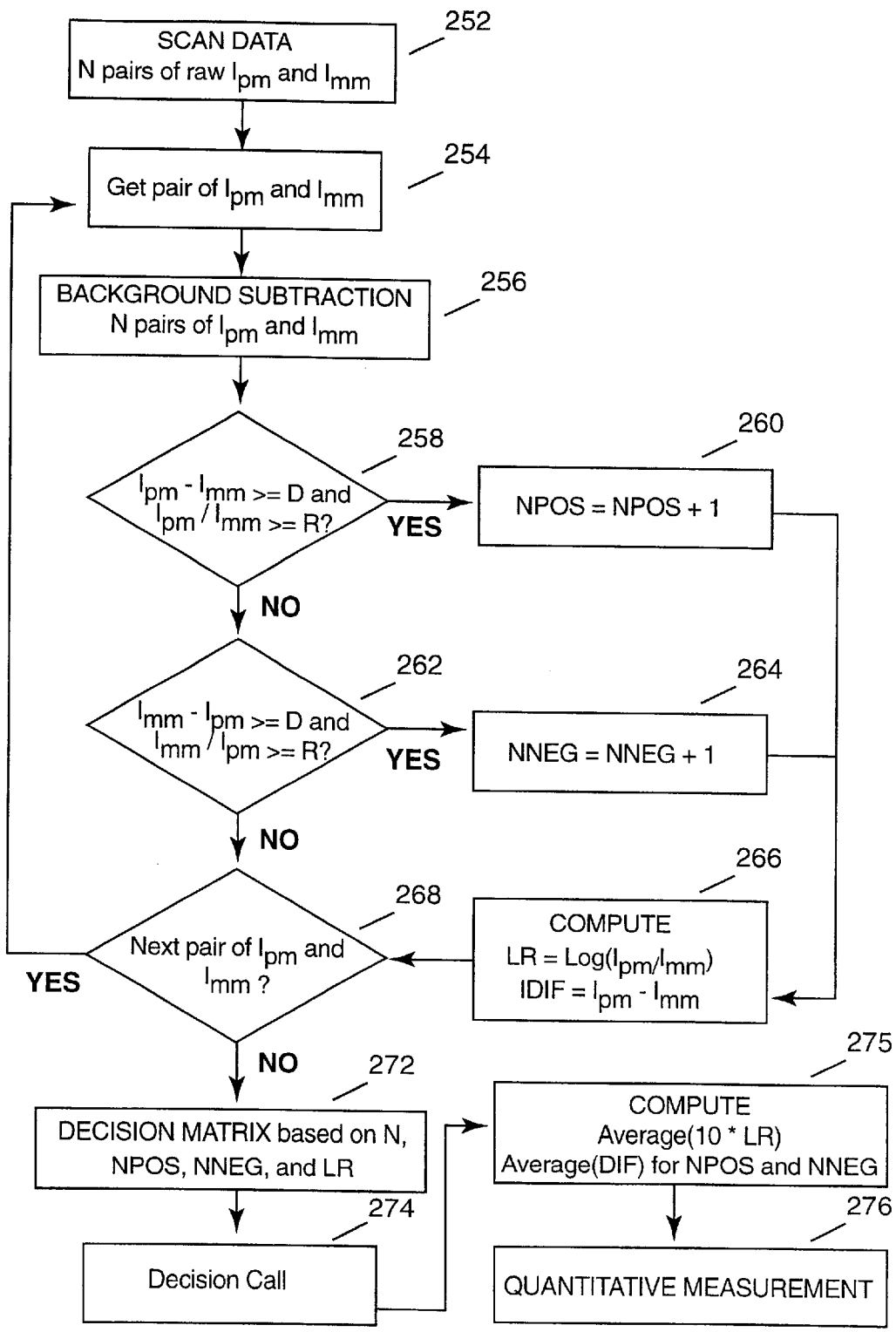
FIG. 9 shows the flow of a process of determining if a gene is expressed utilizing a decision matrix.

FIG. 9 shows a flowchart of a process of determining if a gene is expressed utilizing a decision matrix. At step 252, the computer system receives raw scan data of N pairs of perfect match and mismatch probes. In a preferred embodiment, the hybridization intensities are photon counts from a fluorescein labeled target that has hybridized to the probes on the substrate. For simplicity, the hybridization intensity of a perfect match probe will be designed "$I_{pm}$" and the hybridization intensity of a mismatch probe will be designed "$I_{mm}$."

Hybridization intensities for a pair of probes is retrieved at step 254. The background signal intensity is subtracted from each of the hybridization intensities of the pair at step 256. Background subtraction may also be performed on all the raw scan data at the same time.

At step 258, the hybridization intensities of the pair of probes are compared to a difference threshold (D), and a ratio threshold (R). It is determined if the difference between the hybridization intensities of the pair ($I_{pm}-I_{mm}$) is greater than or equal to the difference threshold AND the quotient of the hybridization intensities of the pair ($I_{pm}/I_{mm}$) is greater than or equal to the ratio threshold. The difference thresholds are typically user defined values that have been determined to produce accurate expression monitoring of a gene or genes. In one embodiment, the difference threshold is 20 and the ratio threshold is 1.2.

If $I_{pm}-I_{mm}>=D$ and $I_{pm}/I_{mm}>=R$, and $I_{pm}/Imm >=R$, the value NPOS is incremented at step 260. In general, NPOS is a value that indicates the number of pairs of probes which have hybridization intensities indicating that the gene is likely expressed. NPOS is utilized in a determination of the expression of the gene.

At step 262, it is determined if $I_{mm}-I_{pm}>=D$ and $I_{mm}/I_{pm}>=R$. If this expression is true, the value INNEG is incremented at step 264. In general, NNEG is a value that indicates the number of pairs of probes which have hybridization intensities indicating that the gene is likely not expressed. NNEG, like NPOS, is utilized in a determination of the expression of the gene.

For each pair that exhibits hybridization intensities either indicating the gene is expressed or not expressed, a log ratio value (LR) and intensity difference value (IDIF) are calculated at step 266. LR is calculated by the log of the quotient of the hybridization intensities of the pair ($I_{pm}/I_{mm}$). The IDIF is calculated by the difference between the hybridization intensities of the pair ($I_{pm}-I_{mm}$). If there is a next pair of hybridization intensities at step 268, they are retrieved at step 254.

At step 272, a decision matrix is utilized to indicate if the gene is expressed. The decision matrix utilizes the values N, NPOS, NNEG, and LR (multiple LRs). The following four assignments are performed:

P1=NPOS/NNEG

P2=NPOS/N

P3=(10*SUM(LR))/(NPOS+NNEG)

These P values are then utilized to determine if the gene is expressed.

For purposes of illustration, the P values are broken down into ranges. If P1 is greater than or equal to 2. 1, then A is true. If P1 is less than 2.1 and greater than or equal to 1.8, then B is true. Otherwise, C is true. Thus, P1 is broken down into three ranges A, B and C. This is done to aid the readers understanding of the invention.

Thus, all of the P values are broken down into ranges according to the following:

A=(P1>=2.1)
B=(2.1>P1>=1.8)
C=(P1<1.8)
X=(P2>=0.35)
Y=(0.35>P2>=0.20)
Z=(P2<0.20)
Q=(P3>=1.5)
R=(1.5>P3>=1.1)
S=(P3<1.1)

Once the P values are broken down into ranges according to the above boolean values, the gene expression is determined.

The gene expression is indicated as present (expressed), marginal or absent (not expressed). The gene is indicated as expressed if the following expression is true: A and (X or Y) and (Q or R). In other words, the gene is indicated as expressed if P1>=2.1, P2>=0.20 and P3>=1.1. Additionally, the gene is indicated as expressed if the following expression is true: B and X and Q.

With the forgoing explanation, the following is a summary of the gene expression indications:

| | |
|---|---|
| Present | A and (X or Y) and (Q or R) |
| | B and X and I |
| Marginal | A and X and S |
| | B and X and R |
| | B and Y and (Q or R) |
| Absent | All others cases (e.g., any C combination) |

In the output to the user, present may be indicated as "P," marginal as "M" and absent as "A" at step 274.

Once all the pairs of probes have been processed and the expression of the gene indicated, an average of ten times the LRs is computed at step 275. Additionally, an average of the IDIF values For the probes that incremented NPOS and NNEG is calculated. These values may be utilized for quantitative comparisons of this experiments with other experiments.

Quantitative measurements may be performed at step 276. For example, the current experiment may be compared to a previous experiment (e.g., utilizing values calculated at step 270). Additionally, the experiment may be compared to hybridization intensities of RNA (such as from bacteria) present in the biological sample in a known quantity. In this manner, one may verify the correctness of the gene expression indication or call, modify threshold values, or perform any number of modifications of the preceding.

For simplicity, FIG. 9 was described in reference to a single gene. However, the process may be utilized on multiple genes in a biological sample. Therefore, any discussion of the analysis of a single gene is not an indication that the process may not be extended to processing multiple genes.

Figure 10A:
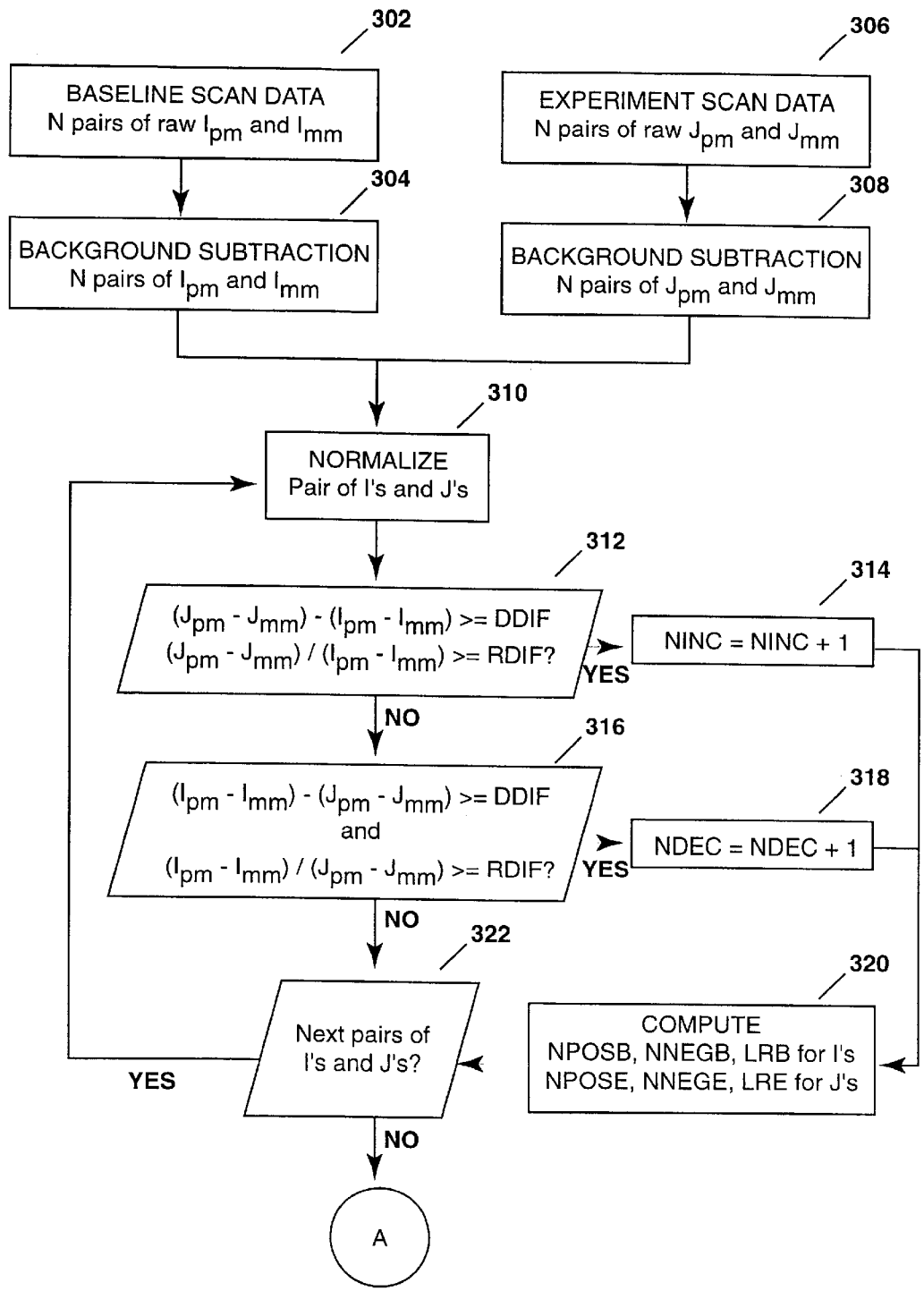
FIGS. 10A and 10B show the flow of a process of determining the expression of a gene by comparing baseline scan data and experimental scan data.
Figure 10B:
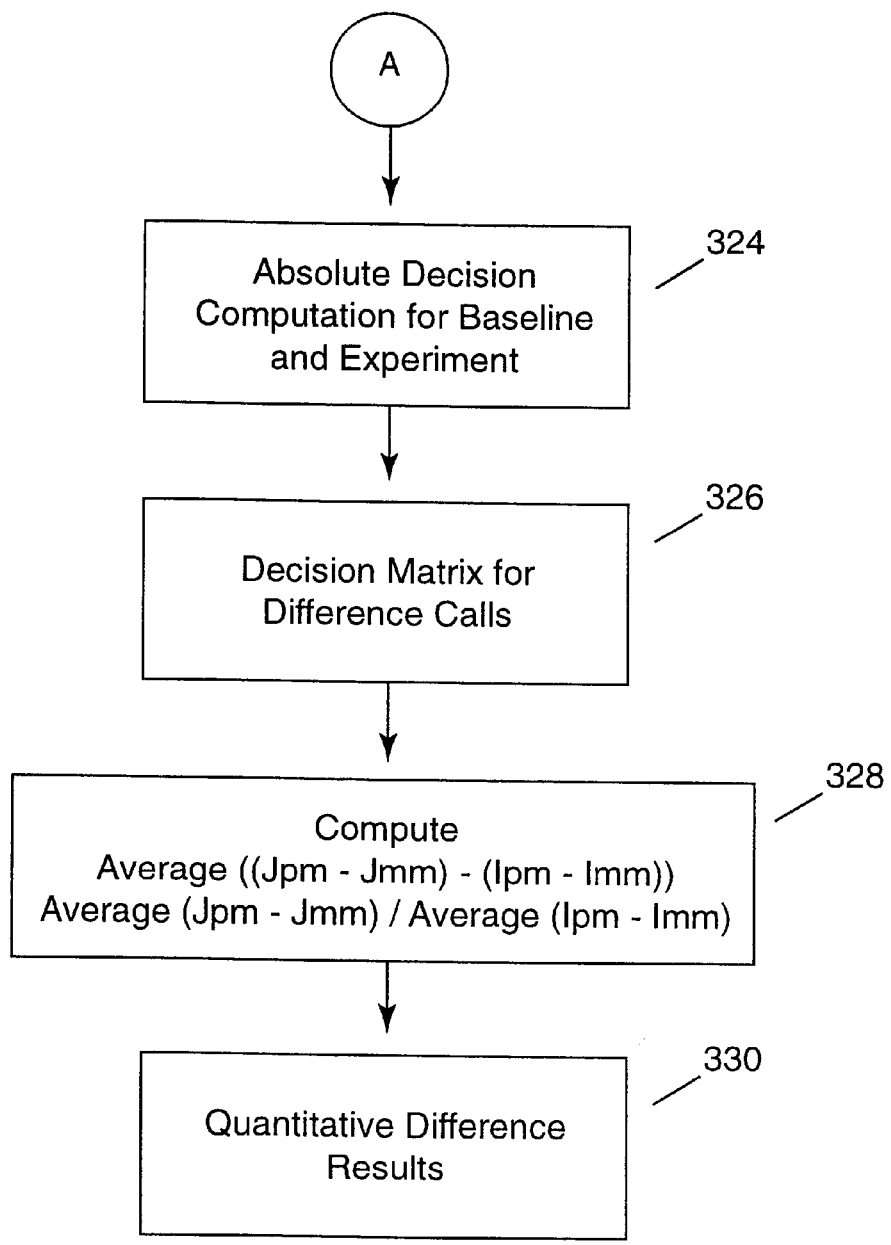

FIGS. 10A and 10B show the flow of a process of determining the expression of a gene by comparing baseline scan data and experimental scan data. For example, the baseline scan data may be from a biological sample where it is known the gene is expressed. Thus, this scan data may be compared to a different biological sample to determine if the gene is expressed. Additionally, it may be determined how the expression of a gene or genes changes over time in a biological organism.

At step 302, the computer system receives raw scan data of N pairs of perfect match and mismatch probes from the baseline. The hybridization intensity of a perfect match probe from the baseline will be designed "$I_{pm}$" and the hybridization intensity of a mismatch probe from the baseline will be designed "$I_{mm}$." The background signal intensity is subtracted from each of the hybridization intensities of the pairs of baseline scan data at step 304.

At step 306, the computer system receives raw scan data of N pairs of perfect match and mismatch probes from the experimental biological sample. The hybridization intensity of a perfect match probes from the experiment will be designed "$J_{pm}$" and the hybridization intensity of a mismatch probe from the experiment will be designed "$J_{mm}$." The background signal intensity is subtracted from each of the hybridization intensities of the pairs of experimental scan data at step 308.

The hybridization intensities of an I and J pair may be normalized at step 310. For example, the hybridization intensities of the I and J pairs may be divided by the hybridization intensity of control probes as discussed above in Section IV(A).

At step 312, the hybridization intensities of the I and J pair of probes are compared to a difference threshold (DDIF) and a ratio threshold (RDIF). It is determined if the difference between the hybridization intensities of the one pair ($J_{pm}$-$J_{mm}$) and the other pair ($I_{pm}$-$I_{mm}$) are greater than or equal to the difference threshold AND the quotient of the hybridization intensities of one pair ($J_{pm}$-$J_{mm}$) and the other pair ($I_{pm}$-$I_{mm}$) are greater than or equal to the ratio threshold. The difference thresholds are typically user defined values that have been determined to produce accurate expression monitoring of a gene or genes.

If ($J_{pm}$-$J_{mm}$)-($I_{pm}$-$I_{mm}$)>=DDIF and ($J_{pm}$-$J_{mm}$)/($I_{pm}$-$I_{mm}$) >=RDIF, the value NINC is incremented at step 314. In general, NINC is a value that indicates the experimental pair of probes indicates that the gene expression is likely greater (or increased) than the baseline sample. NINC is utilized in a determination of whether the expression of the gene is greater (or increased), less (or decreased) or did not change in the experimental sample compared to the baseline sample.

At step 316, it is determined if ($J_{pm}$-$J_{mm}$)-($I_{pm}$-$I_{mm}$)>= DDIF and ($J_{pm}$-$J_{mm}$)/($I_{pm}$/$I_{mm}$)>=RDIF. If- this expression is true, NDEC is incremented. In general, NDEC is a value that indicates the experimental pair of probes indicates that the gene expression is likely less (or decreased) than the baseline sample. NDEC is utilized in a determination of whether the expression of the gene is greater (or increased), less (or decreased) or did not change in the experimental sample compared to the baseline sample.

For each of the pairs that exhibits hybridization intensities either indicating the gene is expressed more or less in the experimental sample, the values NPOS, NNEG and LR are calculated for each pair of probes. These values are calculated as discussed above in reference to FIG. 9. A suffix of either "B" or "E" has been added to each value in order to indicate if the value denotes the baseline sample or the experimental sample, respectively. If there are next pairs of hybridization intensities at step 322, they are processed in a similar manner as shown.

Referring now to FIG. 10B, an absolute decision computation is performed for both the baseline and experimental samples at step 324. The absolute decision computation is an indication of whether the gene is expressed, marginal or absent in each of the baseline and experimental samples. Accordingly, in a preferred embodiment, this step entails performing steps 272 and 274 from FIG. 9 for each of the samples. This being done, there is an indication of gene expression for each of the samples taken alone.

At step 326, a decision matrix is utilized to determine the difference in gene expression between the two samples. This decision matrix utilizes the values, N, NPOSB, NPOSE, NNEGB, NNEGE, NINC, NDEC, LRB, and LRE as they were calculated above. The decision matrix performs different calculations depending on whether NINC is greater than or equal to NDEC. The calculations are as follows.

If NINC>=NDEC, the following four P values are determined:
P1=NINC/NDEC
P2=NINC/N
P3=((NPOSE−NPOSB)−(NNEGE−NNEGB))/N
P4=10*SUM(LRE−LRB)/N These P values are then utilized to determine the difference in gene expression between the two samples.

For purposes of illustration, the P values are broken down into ranges as was done previously. Thus, all of the P values are broken down into ranges according to the following:
A=(P1>=2.7)
B=(2.7>P1>=1.8)
C=(P1<1.8)
X=(P2>=0.24)
Y=(0.24>P2>=0.16)
Z=(P2<0.160)
M=(P3>=0.17)
N=(0.17>P3>=0.10)
O=(P3<0.10)
Q=(P4>=1.3)
R=(1.3>P4>=0.9)
S=(P4<0.9)

Once the P values are broken down into ranges according to the above boolean values, the difference in gene expression between the two samples is determined.

In this case where NINC>=NDEC, the gene expression change is indicated as increased, marginal increase or no change. The following is a summary of the gene expression indications:

| | |
|---|---|
| Increased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal Increase | A or Y or S or O |
| | B and (X or Y) and (Q or R) and O |
| | B and (X or Y) and S and (M or N) |
| | C and (X or Y) and (Q or R) and (M or N) |
| No Change | All others cases (e. g., any Z combination) |

In the output to the user, increased may be indicated as "I," marginal increase as "MI" and no change as "NC."

If NINC<NDEC, the following four P values are determined:
P1=NDEC/NINC
P2=NDEC/N
P3=((NNEGE−NNEGB)−(NPOSE−NPOSB))/N
P4=10*SUM(LRE−LRB)/N These P values are then utilized to determine the difference in gene expression between the two samples.

The P values are broken down into the same ranges as for the other case where NINC>=NDEC. Thus, P values in this case indicate the same ranges and will not be repeated for the sake of brevity. However, the ranges generally indicate different changes in the gene expression between the two samples as shown below.

In this case where NINC<NDEC, the gene expression change is indicated as decreased, marginal decrease or no change. The following is a summary of the gene expression indications:

| | |
|---|---|
| Decreased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal | A or Y or S or O |
| Decrease | B and (X or Y) and (Q or R) and O |
| | B and (X or Y) and S and (M or N) |
| | C and (X or Y) and (Q or R) and (M or N) |
| No Change | All others cases (e.g., any Z combination) |

In the output to the user, decreased may be indicated as "D," marginal decrease as "MD" and no change as "NC."

The above has shown that the relative difference between the gene expression between a baseline sample and an experimental sample may be determined. An additional test may be performed that would change an I, MI, D, or MD (i.e., not NC) call to NC if the gene is indicated as expressed in both samples (e.g., from step 324) and the following expressions are all true:

Average(IDIFB)>=200

Average(IDIFE)>=200

1.4>=Average(IDIFE)/Average(IDIFB)>=0.7

Thus, when a gene is expressed in both samples a call of increased or decreased (whether marginal or not) will be changed to a no change call if the average intensity difference for each sample is relatively large or substantially the same for both samples. The IDIFB and IDIFE are calculated as the sum of all the IDIFs for each sample divided by N.

At step 328, values for quantitative difference evaluation are calculated. An average of $((J_{pm}-J_{mm})-(I_{pm}-I_{mm}))$ for each of the pairs is calculated. Additionally, a quotient of the average of $J_{pm}-J_{mm}$ and the average of $I_{pm}-I_{mm}$ is calculated. These values may be utilized to compare the results with other experiments in step 330.

EXAMPLES

The following examples are offered to illustrate, but not to limit the present invention.

Example 1

First Generation Oligonucleotide Arrays Designed to Measure mRNA Levels for at Small Number of Murine Cytokines A) Preparation of Labeled RNA 1) From Each of the Preselected Genes Fourteen genes (IL-2, IL-3, Il–4, IL-6, Il–10, IL-12p40, GM-CSF, IFN-γ, TNF-α, CTLA8, β-actin, GAPDH, IL-11 receptor, and Bio B) were each cloned into the p Bluescript II KS (+) phagemid (Stratagene, La Jolla, Calif., USA). The orientation of the insert was such that T3 IRNA polymerase gave sense transcripts and T7 polymerase gave antisense RNA.

Labeled ribonucleotides in an in vitro transcription (IVT) reaction. Either biotin- or fluorescein-labeled UTP and CTP (1:3 labeled to unlabeled) plus unlabeled ATP and GTP were used for the reaction with 2500 units of T7 RNA polymerase (Epicentre Technologies, Madison, Wis., USA). In vitro transcription was done with cut templates in a manner like that described by Melton et al., *Nucleic Acids Research*, 12: 7035–7056 (1984). A typical in vitro transcription reaction used 5 μg DNA template, a buffer such as that included in Ambion's Maxiscript in vitro Transcription Kit (Ambion Inc., Houston, Tex., USA) and GTP (3 mM), ATP (1.5 mM), and CTP and fluoresceinated UTP (3 mM total, UTP: Fl-UTP 3:1) or UTP and fluoresceinated CTP (2 mM total, CTP: Fl-CTP, 1). Reactions done in the Ambion buffer had 20 mM DTT and RNase inhibitor. The reaction was run from 1.5 t o about 8 hours.

Following the reaction, unincorporated nucleotide triphosphates were removed using a size-selecting membrane (microcon-100) or Pharmacia microspin S-200 column. The total molar concentration of RNA was based on a measurement of the absorbance at 260 nm. Following quantitation of RNA amounts, RNA was fragmented randomly to an average length of approximately 50–100 bases by heating at 94° C. in 40 mM Tris-acetate pH 8. 1, 100 mM potassium acetate, 30 mM magnesium acetate for 30–40 minutes. Fragmentation reduces possible interference from RNA secondary structure, and minimizes the effects of multiple interactions with closely spaced probe molecules.

2) From cDNA Libraries

Labeled RNA was produced from one of two murine cell lines; T10, a B cell plasmacytoma which was known not to express the genes (except IL- 10, actin and GAPDH) used as target genes in this study, and 2D6, an IL- 12 growth dependent T cell line ($Ih_1$ subtype) that is known to express most of the genes used as target genes in this study. Thus, RNA derived from the T 10 cell line provided a good total RNA baseline mixture suitable for spiking with known quantities of RNA from the particular target genes. In contrast, mRNA derived from the 2D6 cell line provided a good positive control providing typical endogenously transcribed amounts of the RNA from the target genes.

i) The T10 Murine B Cell Line

The T10 cell line (B cells) was derived from the IL-6 dependent murine plasmacytoma line T1165 Nordan et al (1986) *Science* 233: 566–569) by selection in the presence of IL-11. To prepare the directional cDNA library, total cellular RNA was isolated from T10 cells using RNAStat60 (Tel-Test B), and poly $(A)^+$ RNA was selected using the PolyAtract kit (Promega, Madison, Wis., USA). First and second strand cDNA was synthesized according to Toole et al., (1984) *Nature*, 312:342–347, except that 5-methyldeoxycytidine 5'triphosphate (Pharmacia LKB, Piscataway, N.J., USA) was substituted for DCTP in both reactions.

To determine cDNA frequencies T10 libraries were plated, and DNA was transferred to nitrocellulose filters and probed with $^{32}$P-labeled β-actin, GAPDH and IL-10 probes. Actin was represented at a frequency of 1:3000, GAPDH at 1:1000, and IL-10 at 1:35.000. Labeled sense and antisense T10 RNA samples were synthesized from NotI and SfiI cut CDNA libraries in in vitro transcription reactions as described above.

ii) The 2D6 Murine Helper T Cells Line

The 2D6 cell line is a murine IL-12 dependent T cell line developed by Fujiwara et al. Cells were cultured in RPMI 1640 medium with 10% heat inactivated fetal calf serum (JRH Biosciences), 0.05 mM P-mercaptoethanol and recombinant murine IL-12 (100 units/mL, Genetics Institute, Cambridge, Mass., USA). For cytokine induction, cells were preincubated overnight in IL-12 free medium and then resuspended ($10^6$ cells/ml). After incubation for 0, 2, 6 and 24 hours in media containing 5 nM calcium ionophore A23187 (Sigma Chemical Co., St. Louis Mo., USA) and 100 nM 4-phorbol-12-myristate 13-acetate (Sigma), cells were collected by centrifugation and washed once with phosphate buffered saline prior to isolation of RNA.

Labeled 2D6 mRNA was produced by directionally cloning the 2D6 cDNA with αZipLox, NotI-SalI arms available from GibcoBRL in a manner similar to T10. The linearized pZ11 library was transcribed with T7 to generate sense RNA as described above.

iii) RNA Preparation

For material made directly from cellular RNA, cytoplasmic RNA was extracted from cells by the method of Favaloro et al., (1980) Meth. Enzym., 65: 718–749, and poly (A)$^+$ RNA was isolated with an oligo dT selection step (PolyAtract, Promega,). RNA was amplified using a modification of the procedure described by Eberwine et al. (1992) Proc. Natl. Acad. Sci. USA, 89: 3010–3014 (see also Van Gelder et al. (1990) Science 87: 1663–1667). One microgram of poly (A)+ RNA was converted into double-stranded cDNA using a cDNA synthesis kit (Life Technologies) with an oligo dT prime incorporating a T7 RNA polymerase promoter site. After second strand synthesis, the reaction mixture was extracted with phenol/chloroform and the double-stranded DNA isolated using a membrane filtration step (Mircocon-100, Amicon, Inc. Beverly, Mass., USA). Labeled cRNA was made directly from the cDNA pool with an IVT step as described above. The total molar concentration of labeled CRNA was determined from the absorbance at 260 and assuming an average RNA size of 1000 ribonucleotides. RNA concentration was calculated using the conventional conversion that 1 OD is equivalent to 40 $\mu$g of RNA, and that 1 $\mu$g of cellular mRNA consists of 3 pmoles of RNA molecules.

Cellular mRNA was also labeled directly without any intermediate cDNA or RNA synthesis steps. Poly (A)$^+$ RNA was fragmented as described above, and the 5' ends of the fragments were kinased and then incubated overnight with a biotinylated oligoribonucleotide (5'-biotin-AAAAAA-3') in the presence of T4 RNA ligase (Epicentre Technologies). Alternatively, mRNA was labeled directly by UV-induced crosslinking to a psoralen derivative linked to biotin (Schleicher & Schuell).

B) High Density Array Preparation

A high density array of 20 mer oligonucleotide probes was produced using VLSIPS technology. The high density array included the oligonucleotide probes as listed in Table 2. A central mismatch control probe was provided for each gene-specific probe resulting in a high density array containing over 16,000 different oligonucleotide probes.

TABLE 2

High density array design. For every probe there was also a mismatch control having a central 1 base mismatch.

| Probe Type | Target Nucleic Acid | Number of Probes |
| --- | --- | --- |
| Test Probes: | IL-2 | 691 |
|  | IL-3 | 751 |
|  | IL-4 | 361 |
|  | IL-6 | 691 |
|  | IL-10 | 481 |
|  | IL-12p40 | 911 |
|  | GM-CSF | 661 |
|  | IFN-γ | 991 |
|  | TNF-α | 641 |
|  | mCTLA8 | 391 |
|  | IL-11 receptor | 158 |
| House Keeping Genes: | GAPDH | 388 |
|  | β-actin | 669 |
| Bacterial gene (sample preparation/amplification control) | Bio B | 286 |

The high density array was synthesized on a planar glass slide.

C) Array Hybridization and Scanning

The RNA transcribed from cDNA was hybridized to the high density oligonucleotide probe array(s) at low stringency and then washed under more stringent conditions. The hybridization solutions contained 0.9 M NaCl, 60 mM NaH$_2$PO$_4$, 6 mM EDTA and 0.005% Triton X-100, adjusted to pH 7.6 (referred to as 6×SSPE-T). In addition, the solutions contained 0.5 mg/ml unlabeled, degraded herring sperm DNA (Sigma Chemical Co., St. Louis, Mo., USA). Prior to hybridization, RNA samples were heated in the hybridization solution to 9° C. for 10 minutes, placed on ice for 5 minutes, and allowed to equilibrate at room temperature before being placed in the hybridization flow cell, Following hybridization, the solution was removed, the arrays were washed with 6×SSPE-T at 22° C. for 7 minutes, and then washed with 0.5×SSPE-T at 40° C. for 15 minutes. When biotin-labeled RNA was used, the hybridized RNA was stained with a streptavidin-phycoerythrin conjugate (Molecular Probes,. Inc., Eugene, Oreg., USA) prior to reading. Hybridized arrays were stained with 2$\mu$g/ml streptavidin-phycoerythrin in 6×SSPE-T at 40° C. for 5 minutes.

The arrays were read using scanning confocal microscope (Molecular Dynamics, Sunnyvale, Calif., USA) modified for the purpose. The scanner uses an argon ion laser as the excitation source, and the emission was detected with a photomultiplier tube through either a 530 nm bandpass filter (fluorescein) or a 560 nm longpass filter (phycoerythrin).

Nucleic acids of either sense or antisense orientations were used in hybridization experiments. Arrays with for either orientation (reverse complements of each other) were made using the same set of photolithographic masks by reversing the order of the photochemical steps and incorporating the complementary nucleotide.

D) Quantitative Analysis of Hybridization Patterns and Intensities

The quantitative analysis of the hybridization results involved counting the instances in which the perfect match probe (PM) was brighter than the corresponding mismatch probe (MM), averaging the differences (PM minus MM) for each probe family (i.e., probe collection for each gene), and comparing the values to those obtained in a side-by-side experiment on an identically synthesized array with an unspiked sample (if applicable). The advantage of the difference method is that signals from random cross hybridization contribute equally, on average, to the PM and MM probes while specific hybridization contributes more to the PM probes. By averaging the pairwise differences, the real signals add constructively while the contributions from cross hybridization tend to cancel.

The magnitude of the changes in the average of the difference (PM-MM) values was interpreted by comparison with the results of spiking experiments as well as the signal observed for the internal standard bacterial RNA spiked into each sample at a known amount. Analysis was performed using algorithms and software described herein.

E) Optimization of Probe Selection

In order to optimize probe selection for each of the target genes, the high density array of oligonucleotide probes was hybridized with the mixture of labeled RNAs transcribed from each of the target genes. Fluorescence intensity at each location on the high density array was determined by scanning the high density array with a laser illuminated scanning confocal fluorescence microscope connected to a data acquisition system.

Probes were then selected for further data analysis in a two-step procedure. First, in order to be counted, the difference in intensity between a probe and its corresponding mismatch probe had to exceed a threshold limit (50 counts, or about half background, in this case). This eliminated from consideration probes that did not hybridize well and probes for which the mismatch control hybridizes at an intensity comparable to the perfect match.

The high density array was hybridized to a labeled RNA sample which, in principle, contains none of the sequences on the high density array. In this case, the oligonucleotide probes were chosen to be complementary to the sense RNA. Thus, an anti-sense RNA population should have been incapable of hybridizing to any of the probes on the array. Where either a probe or its mismatch showed a signal above a threshold value (100 counts above background) it was not included in subsequent analysis.

Then, the signal for a particular gene was counted as the average difference (perfect match—mismatch control) for the selected probes for each gene.

E) Results: The High Density Arrays Provide Specific and Sensitive Detection of Target Nucleic Acids As explained above, the initial arrays contained more than 16,000 probes that were complementary to 12 murine mRNAs—9 cytokines, 1 cytokine receptor, 2 constitutively expressed genes (5-actin and glyceraldehyde 3-phosphate dehydrogenase)—1 rat cytokine and 1 bacterial gene (*E.coli* biotin synthetase, bioB) which serves as a quantitation reference. The initial experiments with these relatively simple arrays were designed to determine whether short in situ synthesized oligonucleotides can be made to hybridize with sufficient sensitivity and specificity to quantitatively detect RNAs in a complex cellular RNA population. These arrays were intentionally highly redundant, containing hundreds of oligonucleotide probes per RNA, many more than necessary for the determination of expression levels. This was done to investigate the hybridization behavior of a large number of probes and develop general sequence rules for a priori selection of minimal probe sets for arrays covering substantially larger numbers of genes.

The oligonucleotide arrays contained collections of pairs of probes for each of the RNAs being monitored. Each probe pair consisted of a 20-mer that was perfectly complementary (referred to as a perfect match, or PM probe) to a subsequence of a particular message, and a companion that was identical except for a single base difference in a central position. The mismatch (MM) probe of each pair served as an internal control for hybridization specificity. The analysis of PM/MM pairs allowed low intensity hybridization patterns from rare RNAs to be sensitively and accurately recognized in the presence of crosshybridization signals.

For array hybridization experiments, labeled RNA target samples were prepared from individual clones, cloned CDNA libraries, or directly from cellular mRNA as described above. Target RNA for array hybridization was prepared by incorporating fluorescently labeled ribonucleotides in an in vitro transcription (IVT) reaction and then randomly fragmenting the RNA to an average size of 30–100 bases. Samples were hybridized to arrays in a self-contained flow cell (volume ~200 $\mu$L) for times ranging from 30 minutes to 22 hours. Fluorescence imaging of the arrays was accomplished with a scanning confocal microscope (Molecular Dynamics). The entire array was read at a resolution of 11.25 $\mu$m (~80-fold oversampling in each of the 100×100 $\mu$m synthesis regions) in less than 15 minutes, yielding a rapid and quantitative measure of each of the individual hybridization reactions.

1) Specificity of Hybridization

In order to evaluate the specificity of hybridization, the high density array described above was hybridized with 50 pM of the RNA sense strand of IL-2, IL-3, IL-4, IL-6, Actin, GAPDH and Bio B or IL-10, IL-12p40, GM-CSF, IFN-$\gamma$, TNF-$\alpha$, mCTLA8 and Bio B. The hybridized array showed strong specific signals for each of the test target nucleic acids with minimal cross hybridization.

2) Detection of Gene Expression Levels in a Complex Target Sample

To determine how well individual RNA targets could be detected in the presence of total mammalian cell message populations, spiking experiments were carried out. Known amounts of individual RNA targets were spiked into labeled RNA derived from a representative cDNA library made from the murine B cell line T10. The T10 cell line was chosen because of the cytokines being monitored, only IL-10 is expressed at a detectable level.

Because simply spiking the RNA mixture with the selected target genes and then immediately hybridizing might provide an artificially elevated reading relative to the rest of the mixture, the spiked sample was treated to a series of procedures to mitigate differences between the library RNA and the added RNA. Thus the "spike" was added to the sample which was then heated to 37° C. and annealed. The sample was then frozen, thawed, boiled for 5 minutes, cooled on ice and allowed to return to room temperature before performing the hybridization.

Figure 2A:
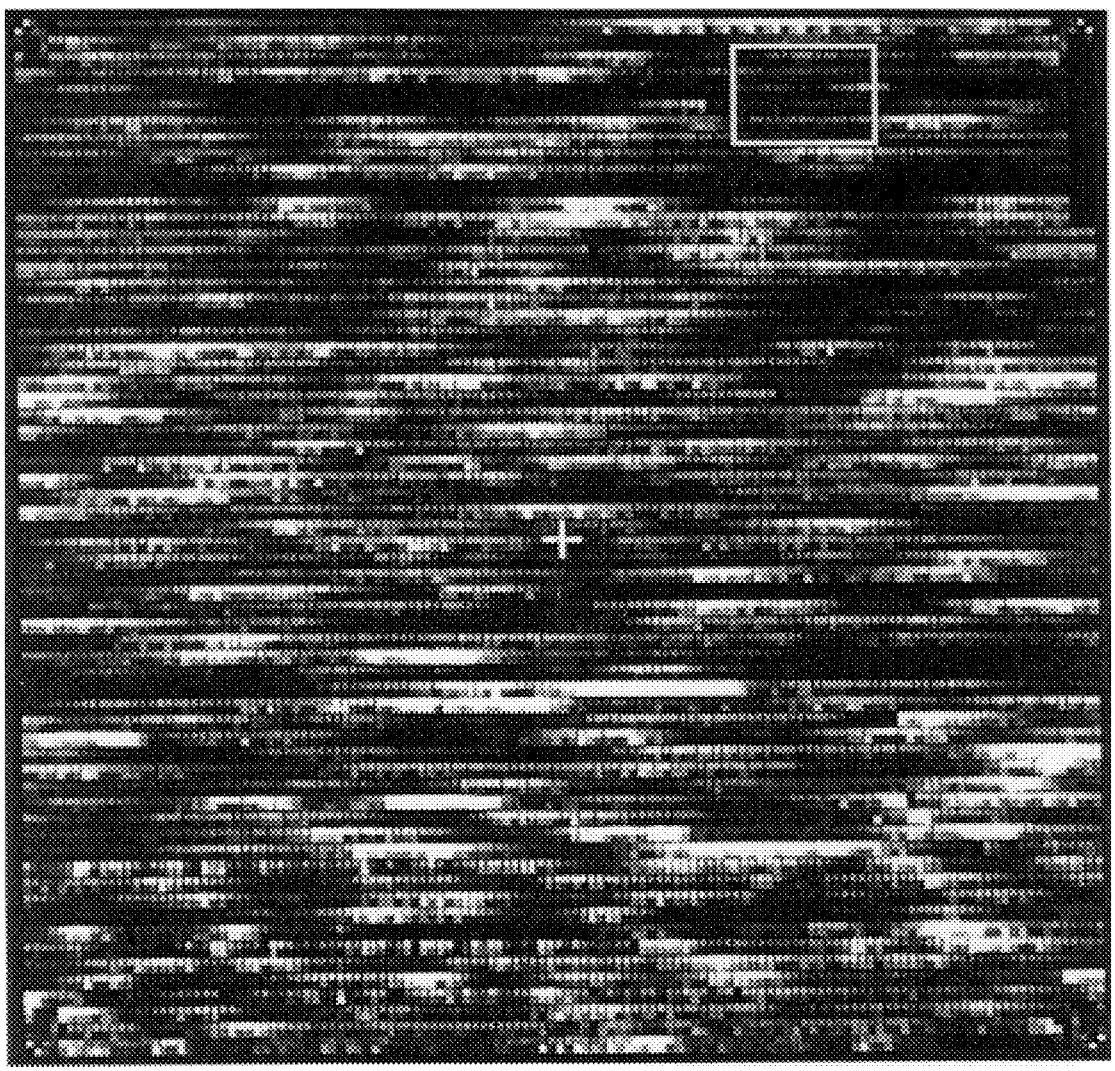
FIG. 2A shows a fluorescent image of a high density array containing over 16,000 different oligonucleotide probes. The image was obtained following hybridization (15 hours at 40° C.) of biotin-labeled randomly fragmented sense RNA transcribed from the murine B cell (T10) cDNA library, and spiked at the level of 1:3,000 (50 pM equivalent to about 100 copies per cell) with 13 specific RNA targets. The brightness at any location is indicative of the amount of labeled RNA hybridized to the particular oligonucleotide probe.
Figure 2B:
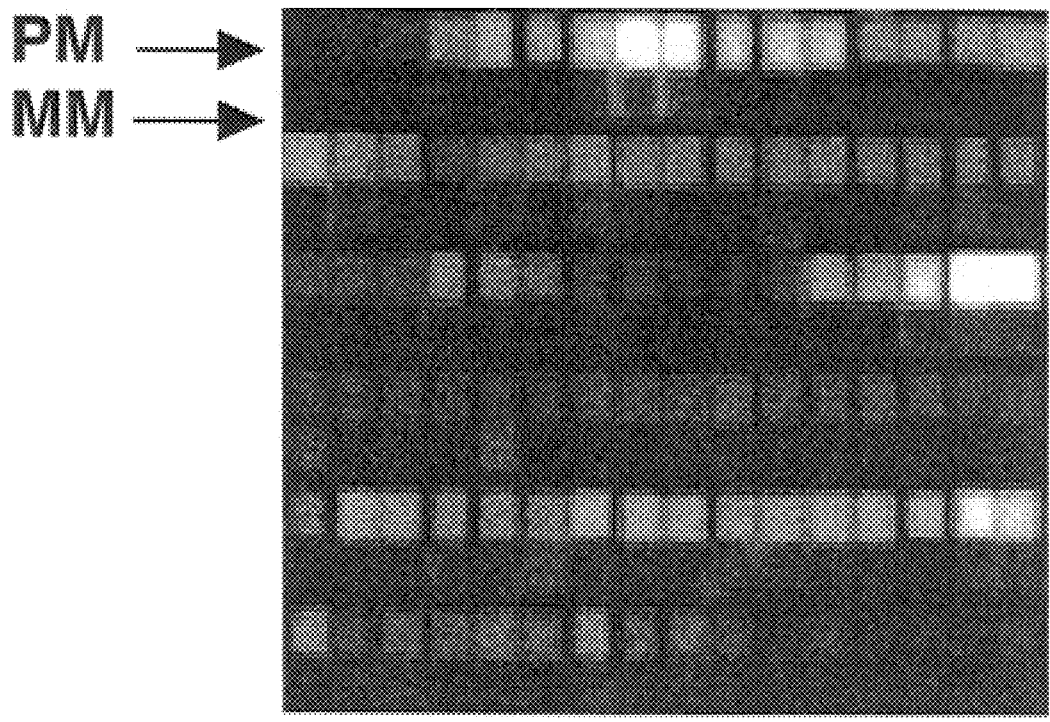
FIG. 2B shows a small portion of the array (the boxed region of FIG. 2A) containing probes for IL-2 and IL-3 RNAs. For comparison.
Figure 2C:
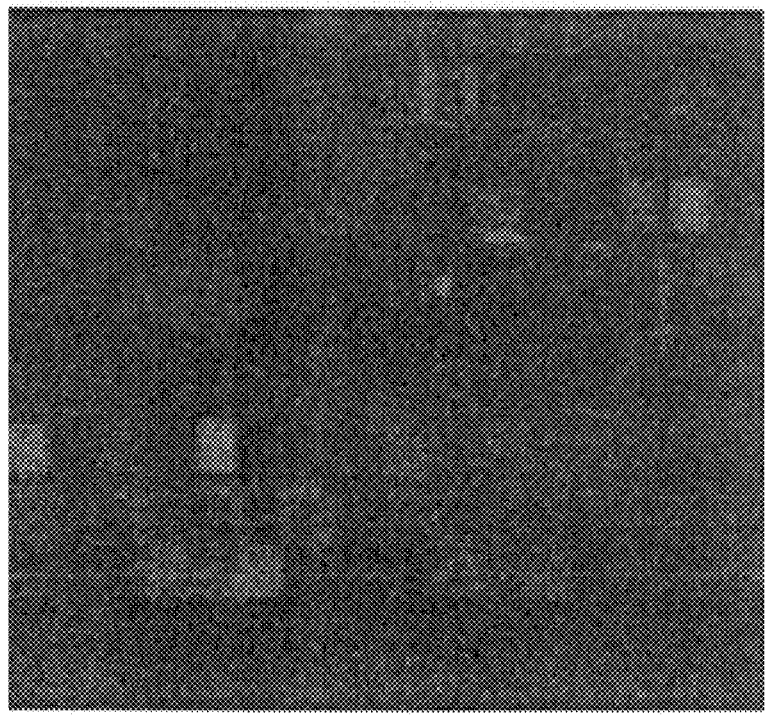
FIG. 2C shows shown the same region of the array following hybridization with an unspiked T10 RNA samples (T10 cells do not express IL-2 and IL-3). The variation in the signal intensity was highly reproducible and reflected the sequence dependence of the hybridization efficiencies. The central cross and the four corners of the array contain a control sequence that is complementary to a biotin-labeled oligonucleotide that was added to the hybridization solution at a constant concentration (50 pM). The sharpness of the images near the boundaries of the features was limited by the resolution of the reading device (11.25 $\mu$m) and not by the spatial resolution of the array synthesis. The pixels in the border regions of each synthesis feature were systematically ignored in the quantitative analysis of the images.

FIG. 2A shows the results of an experiment in which 13 target RNAS were spiked into the total RNA pool at a level of 1:3000 (equivalent to a few hundred copies per cell). RNA frequencies are given as the molar amount of an individual RNA per mole of total RNA. FIG. 2B shows a small portion of the array (the boxed region of 2A) containing probes specific for interleukin-2 and interleukin-3 (IL-2 and IL-3,) RNA, and FIG. 2C shows the same region in the absence of the spiked targets. The hybridization signals are specific as indicated by the comparison between the spiked and unspiked images, and perfect match (PM) hybridizations are well discriminated from missmatches (MM) as shown by the pattern of alternating brighter rows (corresponding to PM probes) and darker rows (corresponding to MM probes). The observed variation among the different perfect match hybridization signals was highly reproducible and reflects the sequence dependence of the hybridizations. In a few instances, the perfect match (PM) probe was not significantly brighter than its mismatch (MM) partner because of cross-hybridization with other members of the complex RNA population. Because the patterns are highly reproducible and because detection does not depend on only a single probe per RNA, infrequent cross hybridization of this type did not preclude sensitive and accurate detection of even low level RNAS.

Similarly, infrequent poor hybridization due to for example, RNA or probe secondary structure, the presence of polymorphism or database sequence errors does not preclude detection. An analysis of the observed patterns of hybridization and cross hybridization led to the formulation of general rules for the selection of oligonucleotide probes with the best sensitivity and specificity described herein.

3) Relationship Between Target Concentration and Hybridization Signal

Figure 3:
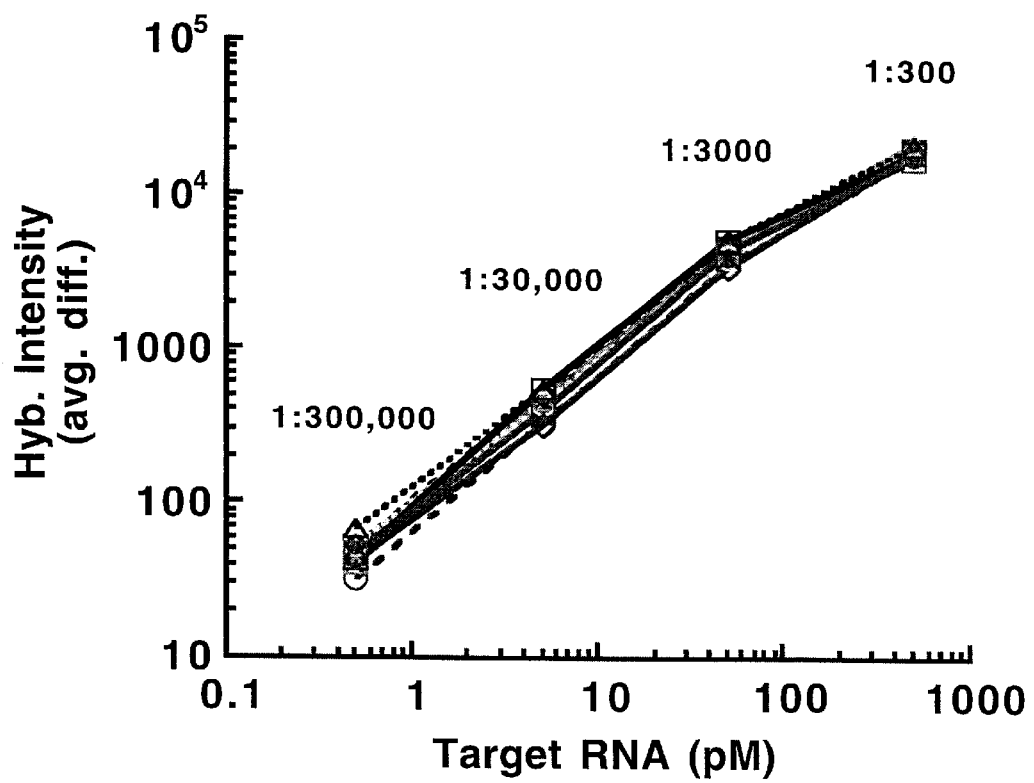
FIG. 3 provides a log/log plot of the hybridization intensity (average of the PM-MM intensity differences for each gene) versus concentration for 11 different RNA targets. The hybridization signals were quantitatively related to target concentration. The experiments were performed as described in the Examples herein and in FIG. 2. The ten 10 cytokine RNAs (plus bioB) were spiked into labeled T10 RNA at levels ranging from 1:300,000 to 1:3,000. The signals continued to increase with increased concentration up to frequencies of 1:300, but the response became sublinear at the high levels due to saturation of the probe sites, The linear range can be extended to higher concentrations by using shorter hybridization times. RNAs from genes expressed in T10 cells (IL-10, β-actin and GAPDH) were also detected at levels consistent with results obtained by probing cDNA libraries.

A second set of spiking experiments was carried out to determine the range of concentrations over which hybridization signals could be used for direct quantitation of RNA levels. FIG. 3 shows the results of experiments in which the ten cytokine RNAs were spiked together into 0.05 mg/ml of labeled RNA from the B cell (T10) cDNA library at levels ranging from 1:300 to 1:300,000. A frequency of 1:300,000 is that of an mRNA present at less than a few copies per cell.

In 10 μg of total RNA and a volume of 200 μl, a frequency of 1:300,000 corresponds to a concentration of approximately 0.5 picomolar and 0.1 femptomole (~6×10$^7$ molecules or about 30 picograms) of specific RNA.

Hybridizations were carried out in parallel at 40° C. for 15 to 16 hours. The presence of each of the 10 cytokine RNAs was reproducibly detected above the background even at the lowest frequencies. Furthermore, the hybridization intensity was linearly related to RNA target concentration between 1:300,000 and 1:3000 (FIG. 3). Between 1:3000 and 1:300, the signals increased by a factor of 4–5 rather than 10 because the probe sites were beginning to saturate at the higher concentrations in the course of a 15 hour hybridization. The linear response range can be extended to higher concentrations by reducing the hybridization time. Short and long hybridizations can be combined to quantitatively cover more than a 10$^4$-fold range in RNA concentration.

Blind spiking experiments were performed to test the ability to simultaneously detect and quantitate multiple related RNAs present at a wide range of concentrations in a complex RNA population. A set of four samples was prepared that contained 0.05 mg/ml of sense RNA transcribed from the murine B cell CDNA library, plus combinations of the 10 cytokine RNAs each at a different concentration. Individual cytokine RNAs were spiked at one of the following levels: 0, 1:300,000, 1:30,000, 1:3000, or 1:300. The four samples plus an unspiked reference were hybridized to separate arrays for 15 hours at 40° C. The presence or absence of an RNA target was determined by the pattern of hybridization and how it differed from that of the unspiked reference, and the concentrations were detected by the intensities. The concentrations of each of the ten cytokines in the four blind samples were correctly determined, with no false positives or false negatives.

One case is especially noteworthy: IL-10 is expressed in the mouse B cells used to make the CDNA library, and was known to be present in the library at a frequency of 1:60,000 to 1:30,000. In one of the unknowns, an additional amount of IL-10 RNA (corresponding to a frequency of 1:300,000) was spiked into the sample. The amount of the spiked IL-10 RNA was correctly determined, even though it represented an increase of only 10–20% above the intrinsic level. These results indicate that subtle changes in expression are sensitively determined by performing side-by-side experiments with identically prepared samples on identically synthesized arrays.

Example 2

T Cell Induction Experiments Measuring Cytokine mRNAs as a Function of Time Following Stimulation The high density arrays of this invention were next used to monitor cytokine mRNA levels in murine T cells at different times following a biochemical stimulus. Cells from the murine T helper cell line (2D6) were treated with the phorbol ester 4-phorbol-12-myristate 13-acetate (PMA) and a calcium ionophore. Poly (A)$^+$ mRNA was then isolated at 0, 2, 6 and 24 hours after stimulation. Isolated mRNA (approximately 1 μg) was converted to labeled antisense RNA using a procedure that combines a double-stranded cDNA synthesis step with a subsequent in vitro transcription reaction. This RNA synthesis and labeling procedure amplifies the entire mRNA population by 20 to 50-fold in an apparently unbiased and reproducible fashion (Table 2).

Figure 4:
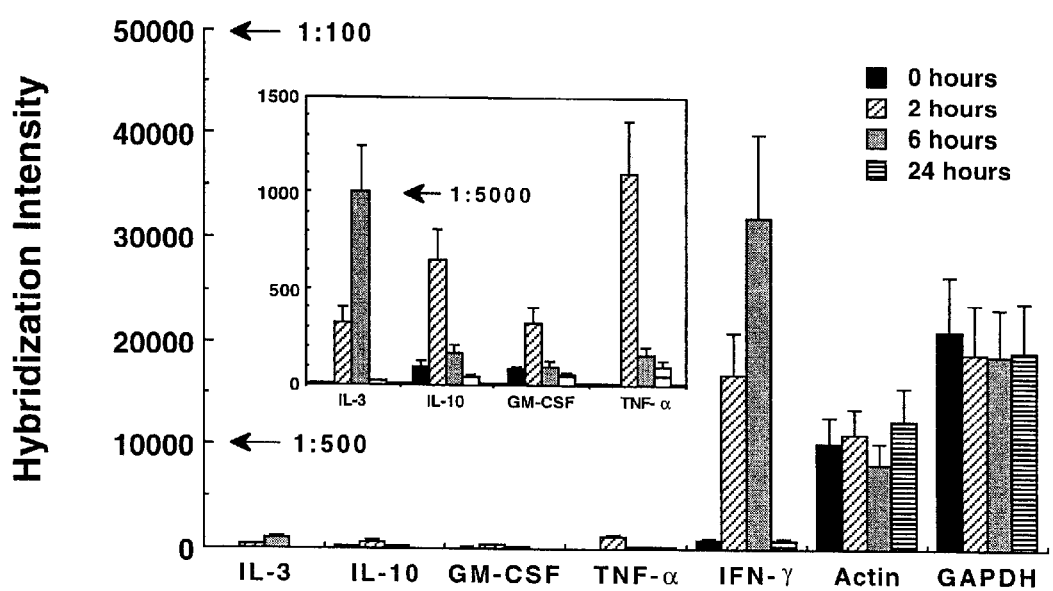
FIG. 4 shows cytokine mRNA levels in the murine 2D6 T helper cell line at different times following stimulation with PMA and a calcium ionophore. Poly (A)$^+$ RNA was extracted at 0, 2, 6, and 24 hours following stimulation and converted to double stranded cDNA containing an RNA polymerase promoter. The cDNA pool was then transcribed in the presence of biotin labeled ribonucleotide triphosphates, fragmented, and hybridized to the oligonucleotide probe arrays for 2 and 22 hours. The fluorescence intensities were converted to RNA frequencies by comparison with the signals obtained for a bacterial RNA (biotin synthetase) spiked into the samples at known amounts prior to hybridization. A signal of 50,000 corresponds to a frequency of approximately 1:100,000 to a frequency of 1:5, 000, and a signal of 100 to a frequency of 1:50,000. RNAs for IL-2, IL-4, IL-6, and IL-12p40 were not detected above the level of approximately 1:200,000 in these experiments. The error bars reflect the estimated uncertainty (25 percent) in the level for a given RNA relative to the level for the same RNA at a different time point. The relative uncertainty estimate was based on the results of repeated spiking experiments, and on repeated measurements of IL-10, β-actin and GAPDH RNAs in preparations from both T10 and 2D6 cells (unstimulated). The uncertainty in the absolute frequencies includes message-to-message differences in the hybridization efficiency as well as differences in the mRNA isolation, cDNA synthesis, and RNA synthesis and labeling steps. The uncertainty in the absolute frequencies is estimated to be a factor of three.

The labeled antisense T-cell RNA from the four time points was then hybridized to DNA probe arrays for 2 and 22 hours. A large increase in the γ-interferon mRNA level was observed, along with significant changes in four other cytokine mRNAs (IL-3, IL-10, GM-CSF and TNFα). As shown in FIG. 4, the cytokine messages were not induced with identical kinetics. Changes in cytokine mRNA levels of less than 1:130,000 were unambiguously detected along with the very large changes observed for γ-interferon.

These results highlight the value of the large experimental dynamic range inherent in the method. The quantitative assessment of RNA levels from the hybridization results is direct, with no additional control hybridizations, sample manipulation, amplification, cloning or sequencing. The method is also efficient. Using current protocols, instrumentation and analysis software, a single user with a single scanner can read and analyze as many as 30 arrays in a day.

Example 3

Higher-Density Arrays Containing 65,000 Probes for Over 100 Murine Genes

Figure 5:
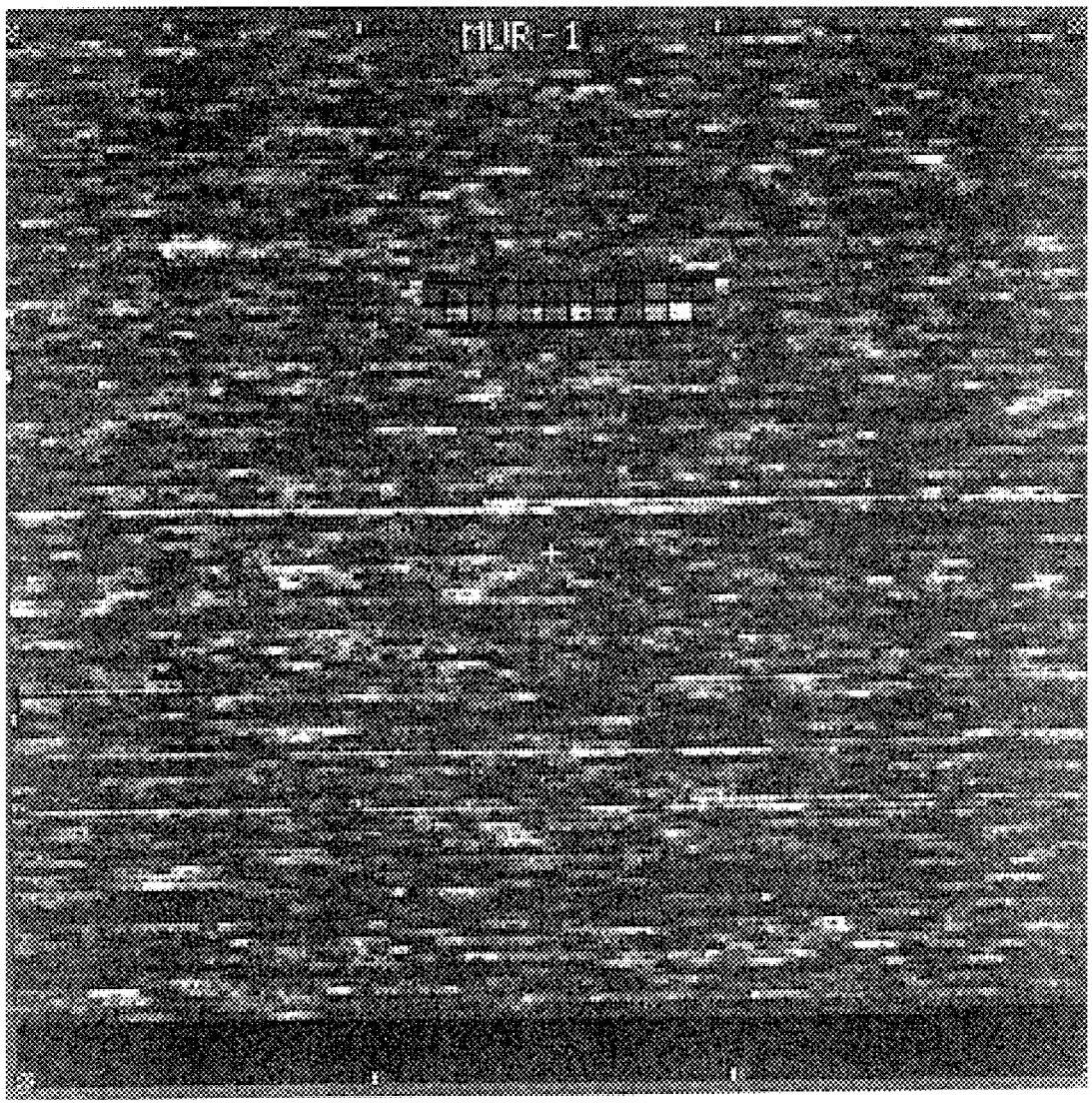
FIG. 5 shows a fluorescence image of an array containing over 63,000 different oligonucleotide probes for 118 genes. The image was obtained following overnight hybridization of a labeled murine B cell RNA sample. Each square synthesis region is 50×50 μm and contains 107 to 108 copies of a specific oligonucleotide. The array was scanned at a resolution of 7.5 μm in approximately 15 minutes. The bright rows indicate RNAs present at high levels. Lower level RNAs were unambiguously detected based on quantitative evaluation of the hybridization patterns. A total of 21 murine RNAs were detected at levels ranging from approximately 1:300,000 to 1:100. The cross in the center, the checkerboard in the corners, and the MUR-1 region at the top contain probes complementary to a labeled control oligonucleotide that was added to all samples.

FIG. 5 shows an array that contains over 65,000 different oligonucleotide probes (50 μm feature size) following hybridization with an entire murine B cell RNA population. Arrays of this complexity were read at a resolution of 7.5 lim in less than fifteen minutes. The array contains probes for 118 genes including 12 murine genes represented on the simpler array described above, 35 U.S.C. §102( ) additional murine genes, three bacterial genes and one phage gene. There are approximately 300 probe pairs per gene, with the probes chosen using the selection rules described herein. The probes were chosen from the 600 bases of sequence at the 3' end of the translated region of each gene. A total of 21 murine RNAs were unambiguously detected in the B cell RNA population, at levels ranging from approximately 1:300,000 to 1:100.

Labeled RNA samples from the T cell induction experiments (FIG. 4) were hybridized to these more complex 118-gene arrays, and similar results were obtained for the set of genes in common to both chip types. Expression changes were unambiguously observed for more than 20 other genes in addition to those shown in FIG. 4.

To determine whether much smaller sets of probes per gene are sufficient for reliable detection of RNAs, hybridization results from the 118 gene chip were analyzed using ten different subsets of 20 probe pairs per gene. That is to say, the data were analyzed as if the arrays contained only 20 probe pairs per gene. The ten subsets of 20 pairs were chosen from the approximately 300 probe pairs per gene on the arrays. The initial probe selection was made utilizing the probe selection and pruning algorithms described above. The ten subjects of 20 pairs were then randomly chosen from those probes that survived selection and pruning. Labeled RNAs were spiked into the murine B cell RNA population at levels of 1:25,000, 1:50,000 and 1:100,000. Changes in hybridization signals for the spiked RNAs were consistently detected at all three levels with the smaller probe sets. As expected, the hybridization intensities do not cluster as tightly as when averaging over larger numbers of probes. This analysis indicates that sets of 20 probe pairs per gene are sufficient for the measurement of expression changes at low levels, but that improvements in probe selection and experimental procedures will are preferred to routinely detect RNAs at the very lowest levels with such small probe sets. Such improvements include, but are not limited to higher stringency hybridizations coupled with use of slightly longer oligonucleotide probes (e.g., 25 mer probes)) are in progress.

Example 4

Scale Up to Thousands of Genes

A set of four high density arrays each containing 25-mer oligonucleotide probes approximately 1650 different human genes provided probes to a total of 6620 genes. There were about 20 probes for each gene. The feature size on arrays was 50 microns. This high density array was successfully hybridized to a cDNA library using essentially the protocols described above. Similar sets of high density arrays containing oligonucleotide probes to every known expressed sequence tag (EST) are in preparation.

Example 5

Direct Scale up for the Simultaneous Monitoring of Tens of Thousands of RNAs In addition to being sensitive, specific and quantitative, the approach described here is intrinsically parallel and readily scalable to the monitoring of very large numbers of mRNAs. The number of RNAs monitored can be increased greatly by decreasing the number of probes per RNA and increasing the number of probes per array.

For example, using the above-described technology, arrays containing as many as 400,000 probes in an area of 1.6 cm$^2$ (20×20 $\mu$m synthesis features) are currently synthesized and read. Using 20 probe pairs per gene allows 10,000 genes to be monitored on a single array while maintaining the important advantages of probe redundancy. A set of four such arrays could cover the more than 40,000 human genes for which there are expressed sequence tags (ESTS) in the public data bases, and new ESTs can be incorporated as they become available. Because of the combinatorial nature of the chemical synthesis, arrays of this complexity are made in the same amount of time with the same number of steps as the simpler ones used here. The use of even fewer probes per gene and arrays of higher density makes possible the simultaneous monitoring of all sequenced human genes on a single, or small number of small chips.

The quantitative monitoring of expression levels for large numbers of genes will prove valuable in elucidating gene function, exploring the causes and mechanisms of disease, and for the discovery of potential therapeutic and diagnostic targets. As the body of genomic information grows, highly parallel methods of the type described here provide an efficient and direct way to use sequence information to help elucidate the underlying physiology of the cell.

Example 6

Probe Selection Using a Neural Net

A neural net can be trained to predict the hybridization and cross hybridization intensities of a probe based on the sequence of bases in the probe, or on other probe properties. The neural net can then be used to pick an arbitrary number of the "best" probes. When a neural net was trained to do this it produced a moderate (0.7) correlation between predicted intensity and measured intensity, with a better model for cross hybridization than hybridization.

A) Input/Output Mapping

The neural net was trained to identify the hybridization properties of 20-mer probes. The 20-mer probes were mapped to an eighty bit long input vector, with the first four bits representing the base in the first position of the probe, the next four bits representing the base in the second position, etc. Thus, the four bases were encoded as follows:

A: 1000

C: 0100

G: 0010

T: 0001

The neural network produced two outputs; hybridization intensity, and crosshybridization intensity. The output was scaled linearly so that 95% of the outputs from the actual experiments fell in the range 0. to 1.

B) Neural Net Architecture

The neural net was a backpropagation network with 80 input neurons, one hidden layer of 20 neurons, and an output layer of two neurons. A sigmoid transfer function was used: $(s(x)=1/(1+\exp(-1*x)))$ that scales the input values from 0 to 1 in a non-linear (sigmoid) manner.

C) Neural Net Training

The network was trained using the default parameters from Neural Works Professional 2.5 for a backprop network. (Neural Works Professional is a product of NeuralWare, Pittsburgh Pa., USA). The training set consisted of approximately 8000 examples of probes, and the associated hybridization and crosshybridization intensities.

D) Neural Net Weights

Neural net weights are provided in two matrices; an 81×20 matrix (Table 3) (weights_1) and a 2×20 matrix Table 4 (weights_2).

TABLE 3

| Neural net weights (81 × 20 matrix) (weights_1). | | | | | |
|---|---|---|---|---|---|
| −0.0316746 | −0.0263491 | 0.15907079 | −0.0353881 | −0.0529314 | 0.09014647 |
| 0.19370709 | −0.0515666 | 0.06444275 | −0.0480836 | 0.29237783 | −0.034054 |
| 0.02240546 | 0.08460676 | 0.14313674 | 0.06798329 | 0.06746746 | 0.033717 |
| 0.16692482 | −0.0913482 | 0.05571244 | 0.22345543 | 0.04707823 | −0.0035547 |
| 0.02129388 | 0.12105247 | 0.1405973 | −0.0066357 | −0.0760119 | 0.11165894 |
| 0.03684745 | −0.0714359 | 0.02903421 | 0.09420238 | 0.12839544 | 0.08542864 |
| 0.00603615 | 0.04986377 | 0.02134438 | 0.0852259 | 0.13453935 | 0.03089394 |
| 0.11111762 | 0.12571541 | 0.09278143 | 0.11373715 | 0.03250757 | −0.0460193 |
| 0.01354388 | 0.1131407 | 0.06123798 | 0.14818664 | 0.07090721 | 0.05089445 |
| −0.0635492 | −0.0227965 | 0.1081195 | 0.13419148 | 0.08916269 | −0.010634 |
| 0.18790121 | 0.09624594 | −0.0865264 | −0.0126238 | 0.11497019 | −0.0057307 |
| 0.02378313 | 0.10295142 | 0.05553147 | −0.0193289 | −0.0627925 | −0.024633 |
| −0.0403537 | 0.23566079 | 0.10335726 | 0.07325625 | 0.11329328 | 0.2555581 |
| −0.0694051 | −0.0637478 | 0.2687766= | | | |
| −0.0731941 | 0.08858298 | 0.39719725 | −0.0709359 | 0.14039235 | 0.23244983 |
| 0.06500423 | 0.11003297 | 0.0403917 | 0.02953459 | 0.26901209 | −0.0605089 |
| 0.03036973 | 0.06836637 | 0.02345118 | 0.0206452 | −0.0079707 | 0.20967795 |

TABLE 3-continued

Neural net weights (81 × 20 matrix) (weights_1).

| | | | | | |
|---|---|---|---|---|---|
| 0.17097448 | −0.007098 | −0.0348659 | 0.09989586 | 0.07417496 | −0.1236805 |
| 0.05442215 | 0.23686385 | 0.01979881 | −9.80E-06 | −0.0549301 | 0.08891765 |
| 0.08683836 | 0.14047802 | 0.00982503 | 0.11756061 | 0.09054346 | −0.028868 |
| 0.08829379 | 0.17881326 | 0.12465772 | 0.13134554 | 0.09500015 | 0.04572553 |
| 0.0749867 | 0.08564588 | 0.05334799 | 0.14341639 | 0.11468539 | 0.14277624 |
| 0.05022619 | 0.14544216 | 0.03519877 | 0.12799838 | 0.01427337 | 0.16172577 |
| 0.08078995 | −0.0022168 | 0.05439407 | −0.0789278 | 0.07312368 | 0.11417327 |
| 0.03405219 | 0.06140256 | 0.01802093 | 0.0954654 | 0.00130152 | −0.035995 |
| 0.11517255 | 0.17431773 | 0.09664405 | 0.01782892 | 0.03840308 | 0.05180788 |
| 0.14236264 | 0.17182963 | 0.02306779 | −0.0489743 | −0.0006051 | 0.19077648 |
| −0.0866363 | 0.11008894 | 0.40543473= | | | |
| −0.0163019 | 0.06256609 | 0.16058824 | 0.14149499 | 0.15698175 | −0.1197781 |
| 0.38030735 | 0.28241798 | 0.2882407 | −0.2227429 | 0.34799534 | 0.38490915 |
| 0.23144296 | −0.3207987 | 0.56366867 | 0.35976714 | 0.20325871 | −0.343972 |
| 0.46158856 | 0.20649959 | 0.35099933 | −0.5071837 | 0.56459975 | 0.21605791 |
| 0.45084599 | −0.5829023 | 0.51297456 | 0.33494622 | 0.43086055 | −0.5538613 |
| 0.55080342 | 0.30968052 | 0.54485208 | −0.7155912 | 0.30799151 | 0.29871368 |
| 0.36848074 | −0.5196409 | 0.33829662 | 0.21612473 | 0.41646513 | −0.5573701 |
| 0.47133151 | 0.30909833 | 0.37790757 | −0.464661 | 0.50172138 | 0.21158406 |
| 0.46017882 | −0.5331213 | 0.60684419 | 0.47586009 | 0.28597337 | −0.3345993 |
| 0.33042327 | 0.4072904 | 0.24270254 | −0.3750777 | 0.14083703 | 0.30998308 |
| 0.19591335 | −0.4028497 | 0.30585453 | 0.35896543 | 0.24851802 | −0.2937264 |
| 0.19672842 | 0.16133355 | 0.21780767 | −0.2419563 | 0.17847325 | 0.07593013 |
| 0.1710967 | −0.2708708 | 0.1234024 | 0.06987085 | 0.1741322 | 0.05922241 |
| 0.03326527 | 0.22045346 | 0.98782647= | | | |
| −0.0752053 | −0.0571054 | −0.1834571 | 0.14263187 | −0.0715346 | −0.0524248 |
| −0.0838031 | 0.01667063 | −0.0945634 | −0.1137057 | −0.1040308 | 0.04263301 |
| −0.2039919 | −0.0532526 | −0.0828366 | 0.1373803 | −0.0562212 | −0.2127942 |
| −0.0482095 | 0.04316666 | −0.1732933 | 0.0550463 | −0.0526818 | 0.06739104 |
| −0.0065265 | −0.2011867 | −0.0434558 | −0.0369132 | −0.0196296 | −0.1314755 |
| 0.09420983 | −0.0010159 | −0.1768979 | −0.2365085 | −0.0150508 | 0.14120786 |
| 0.00565713 | −0.1990354 | 0.11568499 | −0.0690084 | −0.1509431 | −0.0575663 |
| 0.11275655 | 0.01772332 | −0.0016695 | −0.249011 | 0.09066539 | 0.05357879 |
| −0.0850152 | −0.1931012 | 0.08498721 | 0.03673514 | −0.1446398 | −0.199778 |
| 0.1065109 | 0.07205399 | −0.1304159 | −0.1723315 | 0.09151162 | 0.05596334 |
| −0.0922655 | −0.1478272 | 0.08858409 | 0.14206541 | −0.0314846 | −0.1985286 |
| 0.19862956 | −0.0502828 | −0.11447 | −0.1440073 | 0.01366408 | 0.11101657 |
| −0.0721622 | −0.1506944 | 0.14910588 | 0.03297219 | −0.0266356 | −0.2501774 |
| 0.20344114 | −0.061502 | −0.1647823= | | | |
| 0.02848385 | 0.00254791 | −0.0646306 | 0.02634032 | −0.0654473 | 0.04731949 |
| −0.0742345 | −0.0545447 | −0.1119258 | 0.10765317 | −0.0606677 | 0.05693235 |
| −0.0747124 | 0.13325705 | −0.0508435 | −0.1761459 | −0.0883804 | −0.0777852 |
| −0.1090026 | −0.0988943 | −0.0445145 | 0.03802977 | −0.0484086 | −0.0337959 |
| 0.07326921 | 0.02654305 | −0.1239398 | 0.03043288 | 0.09781751 | 0.02590732 |
| −0.0586419 | −0.08015 | −0.0073617 | −0.1682889 | 0.00400978 | 0.01282504 |
| 0.05150735 | −0.1449667 | 0.06144469 | 0.1005446 | 0.22570252 | −0.3763809 |
| −0.0001517 | −0.0521925 | 0.21106339 | −0.4393073 | 0.0053312 | 0.13283829 |
| 0.12470152 | −0.3589714 | −0.0061972 | 0.07370338 | 0.25447422 | −0.3289591 |
| −0.049451 | 0.05717351 | 0.14784867 | −0.3082401 | 0.01207511 | −0.1141143 |
| 0.18880892 | −0.3259364 | 0.04754021 | −0.0576587 | 0.02376083 | −0.2828108 |
| 0.0234996 | −0.1177034 | 0.02549919 | −0.1671077 | 0.00582423 | −0.0715723 |
| 0.16712189 | −0.0122822 | −0.109654 | −0.0327367 | 0.01481733 | −0.0636454 |
| −0.0487184 | 0.01467591 | −0.0759871= | | | |
| 0.146753 | −0.0931665 | −0.1475015 | 0.07284982 | −0.0609536 | −0.0945313 |
| −0.0739603 | 0.17018235 | −0.0636651 | 0.04693379 | −0.2586751 | 0.15556844 |
| −0.1548294 | −0.0908961 | −0.0415557 | 0.04915113 | −0.0436857 | −0.031472 |
| −0.1728483 | 0.12621336 | −0.1321529 | −0.1091831 | −0.0989133 | 0.0294641 |
| −0.0950026 | −0.1562225 | −0.0917397 | 0.18711324 | 0.04599057 | −0.2039073 |
| 0.07691807 | 0.13016214 | 0.10801306 | −0.3151104 | 0.0105284 | 0.10938062 |
| −0.035349 | −0.302975 | 0.03706082 | 0.12322487 | 0.07198878 | −0.2535323 |
| 0.04664604 | 0.08887579 | −0.0210248 | −0.1427284 | 0.09078772 | 0.08646259 |
| 0.00194441 | −0.1631221 | 0.11259725 | −0.0984519 | −0.0939511 | −0.218395 |
| 0.13777457 | 0.00339417 | −0.2007502 | −0.0703103 | 0.1548807 | 0.13540466 |
| −0.0514387 | −0.0722146 | 0.07706029 | 0.04593663 | −0.2334163 | −0.0250262 |
| 0.0994828 | −0.035077 | −0.106266 | −0.059766 | 0.13616422 | 0.22308858 |
| −0.1571046 | −0.1713289 | 0.14155054 | 0.00283311 | 0.01067419 | −0.360891 |
| 0.13411179 | −0.0159559 | −0.1296399= | | | |
| −0.0304715 | −0.0845574 | 0.17682472 | −0.0552084 | 0.07044557 | −0.1482136 |
| 0.13328855 | −0.1492282 | 0.11350834 | −0.1121938 | 0.02089526 | 0.00104415 |
| 0.0217719 | −0.3102229 | 0.18922243 | −0.0940011 | 0.08787836 | −0.1835242 |
| 0.04117605 | 0.03997391 | 0.06022124 | −0.1808036 | 0.04742034 | −0.0744867 |
| 0.08965616 | −0.1572192 | 0.00942572 | 0.07957069 | 0.12980177 | −0.2440033 |
| 0.08670026 | 0.03785197 | 0.21052985 | −0.3564453 | 0.01492627 | 0.04286519 |
| 0.00865917 | −0.2995701 | −0.0835971 | 0.14536868 | 0.08446889 | −0.1689682 |
| −0.1322389 | 0.21433547 | 0.08046963 | −0.1548838 | −0.021533 | 0.0558197 |
| 0.1623435 | −0.3362183 | −0.1335399 | 0.10284293 | 0.16658102 | −0.3004514 |
| −0.0887844 | 0.07691832 | 0.11459036 | −0.056257 | 0.01970494 | 0.08940192 |

TABLE 3-continued

Neural net weights (81 × 20 matrix) (weights__1).

| | | | | | |
|---|---|---|---|---|---|
| 0.08622501 | −0.2421202 | 0.00845924 | −0.0151014 | 0.19088623 | −0.1967196 |
| −0.0290916 | −0.0839412 | 0.10590381 | −0.1593935 | −0.0399097 | −0.0861852 |
| 0.17453311 | −0.1529943 | 0.02726452 | 0.06178628 | 0.06624542 | 0.01004315 |
| −0.158326 | −0.0149114 | −0.1479269= | | | |
| 0.11429903 | −0.0432327 | 0.14520219 | 0.51860482 | 0.19151463 | −0.1127352 |
| 0.33529782 | 0.24581231 | 0.07311282 | −0.2268714 | 0.31717882 | 0.35736522 |
| 0.09062219 | −0.2974442 | 0.46336258 | 0.17145836 | 0.32802406 | −0.3898261 |
| 0.49959001 | 0.22195752 | 0.32254469 | −0.4994924 | 0.75497276 | 0.35112098 |
| 0.52447188 | −0.5555881 | 0.68481833 | 0.20251468 | 0.39860719 | −0.7198414 |
| 0.78773916 | 0.45518181 | 0.71273196 | −0.7655811 | 0.7155844 | 0.39701831 |
| 0.47296903 | −0.672706 | 0.69020337 | 0.37193877 | 0.47959387 | −0.9032337 |
| 0.80210346 | 0.40167108 | 0.50383294 | −0.6195157 | 0.80366057 | 0.3884458 |
| 0.45408139 | −0.7316507 | 0.48975253 | 0.47984859 | 0.33738744 | −0.5510914 |
| 0.56882453 | 0.29653791 | 0.4472059 | −0.5177853 | 0.36228263 | 0.40129057 |
| 0.4490836 | −0.4754149 | 0.46366793 | 0.31378582 | 0.48470935 | −0.2453159 |
| 0.39600489 | 0.24787127 | 0.20359448 | −0.203447 | 0.25734761 | 0.17168433 |
| 0.35209069 | −0.203685 | 0.25115264 | 0.21313109 | 0.12461348 | 0.10632347 |
| 0.13266218 | 0.20236486 | 1.1078833= | | | |
| −0.0112394 | 0.01601524 | 0.11363719 | −0.1440069 | 0.05522444 | −0.0711868 |
| 0.09505147 | −0.0220034 | 0.0714381 | −0.1994763 | 0.12304886 | −0.1611445 |
| 0.16811867 | −0.4498019 | 0.10313182 | −0.0149997 | 0.47659361 | −0.4639786 |
| −0.0380792 | −0.0468904 | 0.37975076 | −0.7120748 | −0.1078557 | 0.10635795 |
| 0.42699403 | −0.6348544 | 0.00025528 | 0.06202703 | 0.57867163 | −0.6733171 |
| −0.0381787 | 0.09532065 | 0.50065184 | −0.7413587 | −0.0193744 | −0.1180785 |
| 0.74187845 | −0.8996705 | 0.03180836 | 0.04010354 | 0.82366729 | −0.6429569 |
| 0.02410492 | −0.0632124 | 0.73732454 | −0.8188882 | 0.04538922 | −0.1471086 |
| 0.7597335 | −0.6287012 | 0.03615654 | −0.1248241 | 0.56647652 | −0.6294683 |
| 0.15992545 | −0.1780757 | 0.3820785 | −0.5642462 | −0.0609947 | −0.0350918 |
| 0.25537059 | −0.4526066 | −0.0761788 | −0.0242514 | 0.35473567 | −0.3512402 |
| −0.1888455 | 0.1974159 | 0.01620384 | −0.1306533 | −0.1468564 | 0.25235301 |
| 0.08058657 | −0.0768841 | −0.316401 | 0.09779498 | 0.08537519 | −0.0738487 |
| −0.2839164 | 0.12684187 | −0.2450078= | | | |
| −0.1147067 | −0.0084124 | −0.5239977 | −0.5021591 | 0.02636886 | 0.1470097 |
| −0.5139894 | −0.6221746 | −0.3979228 | 0.30136263 | −0.742976 | −0.4011821 |
| 0.19038832 | 0.55414283 | −1.1652025 | −0.3686967 | −0.4750175 | 0.54713631 |
| −0.9312411 | −0.410718 | −0.1498093 | 0.55332947 | −1.0870041 | −0.4378341 |
| −0.5433689 | 0.92539561 | −0.9013531 | −0.6145319 | −0.5512772 | 1.0310978 |
| −0.9422795 | −0.6914638 | −0.7839714 | 1.4393494 | −0.7092296 | −0.894987 |
| −0.6896155 | 1.1251011 | −0.8161536 | −0.8204682 | −0.8957642 | 1.3315079 |
| −1.0231192 | −0.5556009 | −0.7499282 | 1.281976 | −0.9347371 | −0.6562014 |
| −0.6568274 | 1.1967098 | −1.150661 | −0.5503616 | −0.6640182 | 0.84698498 |
| −0.7811472 | −0.5740913 | −0.4527726 | 0.64911705 | −0.6970047 | −0.5759697 |
| −0.4704399 | 0.51728982 | −0.545236 | −0.8311051 | −0.4240301 | 0.37167478 |
| −0.7735854 | −0.3031097 | −0.4083092 | −0.0152683 | −0.2330878 | −0.5839304 |
| −0.1544528 | 0.2042688 | −0.8989772 | −0.3088974 | −0.2014994 | 0.11505035 |
| −0.4815812 | −0.5319371 | −1.3798244= | | | |
| 0.07143499 | −0.1589592 | 0.04816094 | −0.0301291 | 0.15144217 | −0.3037405 |
| 0.1549352 | −0.0608833 | 0.21059546 | −0.4705076 | 0.16360784 | −0.0684895 |
| 0.44703272 | −0.6194252 | 0.19459446 | −0.0523894 | 0.31194624 | −0.8030509 |
| 0.2595928 | −0.119705 | 0.4913742 | −0.8455008 | 0.15694356 | −0.0023983 |
| 0.53066176 | −0.9705743 | 0.1324198 | 0.08982921 | 0.43900672 | −0.8588745 |
| 0.1702383 | 0.02221953 | 0.44412452 | −0.7700244 | 0.10496679 | 0.14137991 |
| 0.5403164 | −0.5077381 | 0.00849557 | 0.1611405 | 0.31764683 | −0.5240273 |
| −0.092208 | 0.21902563 | 0.25788471 | −0.3861519 | −0.2022993 | 0.13711917 |
| 0.22238699 | −0.156256 | −0.2092034 | 0.16458821 | 0.20111787 | −0.1418906 |
| −0.180493 | 0.17164391 | 0.15690604 | −0.0254563 | −0.1990184 | 0.10211211 |
| 0.17421109 | −0.0730809 | −0.3717274 | 0.1436436 | −0.0215865 | −0.2363243 |
| −0.1982318 | 0.06996673 | 0.19735655 | 0.05625506 | −0.241524 | 0.12768924 |
| 0.05979542 | −0.0623277 | −0.2521037 | 0.0944353 | −0.0492548 | 0.05238663 |
| −0.1978694 | 0.05119598 | −0.2067173= | | | |
| 0.06230025 | −0.0752745 | 0.32974288 | 0.00985043 | 0.07881941 | −0.0835249 |
| 0.1073643 | −0.090154 | −0.0938452 | 0.00704324 | 0.2569764 | 0.08700065 |
| −0.0272076 | −0.1014201 | 0.19723812 | −0.0935401 | 0.0913924 | −0.0728388 |
| 0.33091745 | −0.0610701 | 0.01335303 | 0.02156818 | 0.21619918 | −0.0909865 |
| 0.01069087 | 0.02569587 | 0.11676744 | −0.0213131 | 0.1322203 | 0.11848255 |
| 0.11231339 | −0.0392407 | 0.06117272 | −0.0234323 | 0.14693312 | 0.13509636 |
| −0.0213237 | −0.0261696 | 0.09474246 | −0.0100756 | 0.10580003 | −0.0147534 |
| 0.12980145 | −0.038394 | 0.08167668 | −0.0105376 | 0.02142166 | −0.0161705 |
| 0.15833771 | 0.01835199 | 0.04420554 | 0.02605363 | 0.27427858 | 0.05774866 |
| −0.0696303 | 0.03802699 | 0.0806741 | 0.03993953 | −0.0121658 | 0.07568218 |
| 0.05538817 | 0.01067943 | 0.04131892 | −0.0267609 | 0.14418064 | 0.0897231 |
| −0.0677462 | −0.0772208 | 0.16641215 | 0.09142463 | 0.02115551 | −0.0876383 |
| 0.14652038 | 0.06084725 | −0.1150111 | −0.0687876 | 0.10878915 | 0.32776353 |
| −0.1929855 | 0.00694158 | 0.26604816= | | | |
| −0.0786668 | 0.05454836 | −0.0834711 | 0.07707115 | 0.05659099 | −0.0285798 |
| −0.0029815 | −0.0837616 | 0.02468397 | 0.03531792 | −0.1437671 | 0.10122854 |
| −0.1259448 | −0.0845026 | 0.10171869 | −0.0541042 | 0.05257236 | 0.04065102 |

TABLE 3-continued

Neural net weights (81 × 20 matrix) (weights_1).

| | | | | | |
|---|---|---|---|---|---|
| −0.1091328 | 0.0090488 | 0.06142418 | −0.167912 | −0.098868 | 0.02574896 |
| 0.00333312 | −0.2812204 | 0.02039073 | −0.052828 | −0.0439769 | −0.0458286 |
| 0.14768517 | 0.02989549 | 0.09454407 | −0.1860176 | −0.0505908 | 0.088718 |
| 0.0611263 | −0.1895157 | 0.08583955 | 0.09382812 | −0.0001466 | −0.4065202 |
| 0.09951859 | 0.14843601 | 0.12351749 | −0.1327625 | 0.10949049 | 0.07129322 |
| 0.05554885 | −0.3743193 | −0.0205463 | 0.12675567 | 0.0775801 | −0.1869074 |
| 0.01806534 | 0.09599103 | −0.0570596 | −0.15233B1 | 0.08384241 | 0.00704122 |
| 0.10942505 | −0.0473638 | 0.01151769 | 0.09737793 | 0.07082167 | −0.2184597 |
| −0.0365961 | −0.0962418 | 0.01007566 | −0.0049753 | 0.01404589 | −0.0406134 |
| 0.01934035 | −0.0073082 | −0.0489736 | 0.10457312 | −0.0520154 | −0.0454775 |
| −0.0525739 | 0.06086259 | −0.1788069= | | | |
| 0.19904579 | −0.2001437 | 0.04977471 | 0.26628217 | 0.19910193 | 0.15184447 |
| 0.01703933 | 0.06875326 | 0.09066898 | −0.2003548 | 0.26507998 | 0.0629771 |
| 0.39202845 | −0.6033413 | 0.57940209 | −0.0460919 | 0.53419203 | −0.7680838 |
| 0.65535748 | 0.32430753 | 0.64831889 | −1.0950515 | 0.80829531 | 0.05049393 |
| 0.95144385 | −1.2075449 | 0.94851351 | −0.0852669 | 0.94320357 | −1.680338 |
| 0.99852085 | 0.48870567 | 1.7470727 | −1.7586045 | 0.56886804 | 0.66196042 |
| 1.2572207 | −1.5854638 | 0.89351815 | 0.39586932 | 1.586942 | −1.6365775 |
| 0.73526824 | 0.31977594 | 1.2270083 | −1.2818555 | 0.71813524 | 0.37488377 |
| 0.95438999 | −1.2543333 | 0.55854511 | 0.1672449 | 0.56084049 | −0.7980669 |
| 0.45917389 | 0.27823627 | 0.26923344 | −0.9804664 | 0.62299174 | 0.53984308 |
| 0.33946255 | −0.5412283 | 0.1085042 | 0.44658452 | 0.39120093 | −0.5676367 |
| 0.19083619 | 0.37056214 | 0.24114503 | −0.3020035 | 0.39015424 | 0.09788869 |
| 0.30190364 | −0.3655235 | 0.33355939 | 0.44246852 | 0.17172456 | −0.3479928 |
| 0.18584418 | 0.34009755 | 4.5490937= | | | |
| 0.13698889 | −0.0798945 | 0.3366704 | 0.17313539 | 0.01228174 | −0.2679709 |
| 0.31540671 | 0.08274947 | 0.11212139 | −0.428847 | 0.57447821 | −0.0305296 |
| 0.00119518 | −0.1978176 | 0.59532708 | −0.0309942 | −0.0107875 | −0.7312108 |
| 0.74023747 | 0.38564634 | 0.03748908 | −0.6475483 | 0.87958473 | 0.05327692 |
| 0.06987014 | −0.5168169 | 1.0081589 | −0.0517421 | 0.08651814 | −0.761238 |
| 0.7840901 | 0.4372991 | 0.13783893 | −0.8574924 | 0.90612286 | 0.06334394 |
| 0.05702339 | −0.5161278 | 0.66693234 | −0.0496743 | 0.07689167 | −0.5775976 |
| 0.70519674 | 0.15731441 | 0.08724558 | −0.7325026 | 0.65517086 | 0.29064488 |
| 0.11747536 | −0.612968 | 0.98160452 | 0.02407174 | 0.02613025 | −0.677594 |
| 0.81293154 | 0.18651071 | 0.03182137 | −0.7051651 | 0.89682412 | 0.181806 |
| 0.24770954 | −0.4320194 | 0.72470272 | 0.12951751 | 0.14626819 | −0.3964331 |
| 0.54755467 | 0.08819038 | 0.22105552 | −0.3489864 | 0.4620938 | 0.06516677 |
| 0.03049339 | −0.1913544 | 0.4782092 | −0.098419 | −0.0160188 | 0.07177288 |
| 0.1008145 | 0.01412579 | 0.42727205= | | | |
| −0.0048454 | 0.1204864 | 0.15507312 | 0.25648347 | 0.03982652 | 0.14641231 |
| −0.0273505 | 0.10494121 | 0.1988914 | 0.09454013 | −0.0560908 | 0.07466536 |
| 0.1325469 | 0.15324508 | −0.01398 | 0.08281901 | 0.07909692 | 0.36858437 |
| −0.0007111 | 0.13285491 | −0.1658676 | 0.25348473 | 0.08835109 | 0.16466415 |
| −0.118853 | 0.26435438 | −0.0775707 | 0.09143513 | −0.1019902 | 0.29236633 |
| 0.07947435 | 0.07329605 | −0.0903666 | 0.10754076 | 0.04456592 | 0.18368921 |
| −0.162177 | 0.18712705 | 0.03216886 | 0.04698242 | −0.0385783 | 0.2276271 |
| 0.04106503 | 0.08498254 | −0.0325038 | 0.29328787 | 0.01249749 | 0.10016124 |
| −0.0012895 | 0.2371086 | 0.14713244 | −0.053306 | −0.0808243 | 0.28909287 |
| 0.13412228 | 0.10756335 | −0.0486093 | 0.05799349 | 0.21323961 | −0.0118695 |
| −0.142963 | 0.09792294 | 0.06907349 | 0.05942665 | −0.143813 | 0.21673524 |
| 0.19903891 | 0.02989559 | 0.15750381 | −0.0373194 | 0.12471988 | 0.10462648 |
| −0.0027455 | 0.16604523 | 0.06245366 | −0.0775013 | −0.0160873 | 0.21550164 |
| 0.25000233 | 0.05931267 | 0.22881882= | | | |
| 0.04679342 | 0.10153926 | −0.122116 | 0.23491009 | −0.0625733 | 0.19985424 |
| −0.1704439 | 0.302394 | −0.0671487 | 0.33251444 | −0.0581705 | 0.21095584 |
| −0.215752 | 0.32740423 | −0.1597161 | 0.18950906 | −0.1232446 | 0.27883759 |
| −0.0430407 | 0.04886867 | −0.0914212 | 0.28192514 | 0.05275658 | 0.21014904 |
| −0.1322077 | 0.2981362 | 0.1254565 | 0.15627012 | 0.04116358 | 0.08507752 |
| 0.10109599 | 0.23081669 | −0.1617257 | 0.29508773 | −0.0405337 | −0.0497829 |
| −0.0808031 | 0.15750171 | 0.08072432 | 0.12990661 | −0.1935954 | 0.29120663 |
| 0.13912162 | 0.04256131 | −0.1625126 | 0.25232118 | 0.04736055 | −0.0530935 |
| −0.2270383 | 0.22945035 | 0.18167619 | 0.00080986 | −0.1253632 | 0.15695702 |
| 0.01596376 | 0.03504543 | 0.00964208 | 0.11757679 | −0.0230768 | 0.04350457 |
| −0.1284984 | 0.24145114 | 0.20540115 | 0.07580803 | −0.0932236 | 0.14288881 |
| 0.00538179 | 0.05302088 | −0.1001294 | 0.27505419 | 0.22654785 | 0.02355938 |
| −0.0861699 | 0.05814215 | 0.21307872 | 0.01372274 | 0.04515802 | −0.0269269 |
| 0.20031671 | 0.23140682 | 0.16010799= | | | |
| 0.37838998 | 0.00934576 | −0.139213 | 0.29823828 | 0.40640026 | −0.067578 |
| −0.038453 | 0.24550894 | 0.30729383 | −0.2807365 | −0.0689575 | 0.26537073 |
| 0.58336282 | −0.2145292 | −0.2378269 | 0.25939462 | 0.64761585 | −0.3581158 |
| 0.07741276 | 0.45081589 | 0.65251595 | −0.4543131 | −0.0671543 | 0.48592216 |
| 0.85640681 | −0.6068144 | −0.1187844 | 0.35959438 | 0.71842372 | −0.7140775 |
| −0.0642752 | 0.37914035 | 0.71409059 | −0.7180941 | 0.21169594 | 0.27888221 |
| 0.79736245 | −0.7102081 | 0.14268413 | 0.41374633 | 0.75569016 | −0.7394939 |
| 0.02592243 | 0.37013471 | 0.82774776 | −0.8136597 | 0.24068722 | 0.45081198 |
| 0.88004726 | −0.6990998 | 0.23456772 | 0.24596012 | 0.67229778 | −0.8148533 |
| 0.30492786 | 0.39735735 | 0.55497372 | −0.6593497 | 0.20656242 | 0.3752968 |

TABLE 3-continued

Neural net weights (81 × 20 matrix) (weights_1).

| | | | | | |
|---|---|---|---|---|---|
| 0.54989374 | −0.5660355 | 0.1205707 | 0.22377795 | 0.46045718 | −0.519361 |
| 0.17151839 | 0.39539635 | 0.50465524 | −0.3791285 | 0.07184427 | 0.36315975 |
| 0.51068121 | −0.3502096 | −0.2094818 | 0.31471297 | 0.18174268 | −0.1241962 |
| −0.1255455 | 0.35898197 | 0.79502285= | | | |
| 0.02952595 | −0.0751979 | −0.2556099 | −0.3040917 | −0.0942183 | −0.0541431 |
| −0.6262,965 | −0.1423945 | −0.0537339 | 0.11189342 | −0.3791296 | −0.3382006 |
| 0.02978903 | 0.20563391 | −0.5457558 | −0.3666513 | −0.1922515 | 0.29512301 |
| −0.7473708 | −0.0415357 | 0.18283925 | 0.28153449 | −0.7847292 | −0.2313099 |
| 0.00290797 | 0.6284017 | −0.6397845 | −0.5606785 | −0.1479581 | 0.57049137 |
| −1.0829539 | −0.1822221 | −0.1832336 | 0.49371469 | −0.6362705 | −0.2790937 |
| 0.06966544 | 0.75524592 | −0.9053063 | −0.5826979 | −0.114608 | 0.90401584 |
| −0.8823278 | −0.3404879 | −0.0334436 | 0.50130409 | −0.57275 | −0.3842527 |
| 0.0915129 | 0.44590429 | −0.7808504 | −0.4399623 | −0.1189605 | 0.59226018 |
| −0.499517 | −0.4873153 | −0.2889721 | 0.47303999 | −0.4015501 | −0.2875251 |
| −0.1106236 | 0.27437851 | −0.6061368 | −0.4166524 | −0.0637606 | 0.33875695 |
| −0.6255118 | −0.1046614 | −0.2710638 | 0.26425925 | −0.4123208 | −0.2157291 |
| −0.1468192 | −0.1719856 | −0.4140109 | −0.1058299 | 0.02873472 | −0.1210428 |
| −0.213571 | −0.1335077 | −0.7155944 | | | |
| 0.06424081 | −0.0978306 | −0.1169782 | 0.13909493 | −0.0838893 | −0.1300299 |
| −0.1032737 | 0.11563963 | −0.0709175 | −0.028875 | −0.1718288 | −0.026291 |
| 0.05533361 | −0.033985 | −0.049436 | 0.11520655 | −0.0279296 | −0.0170352 |
| 0.05850215 | 0.03830531 | −0.0893732 | −0.0066427 | 0.06969514 | 0.13403182 |
| −0.012636 | −0.1925185 | 0.13028348 | −0.0045112 | 0.05260766 | −0.2759708 |
| −0.0395793 | 0.03069885 | 0.07913893 | −0.1470363 | 0.09080192 | 0.19741131 |
| −0.0917266 | −0.2185763 | 0.04743406 | −0.0364127 | 0.00991712 | −0.2093729 |
| 0.23327024 | −0.0898143 | −0.0578982 | −0.2096201 | 0.09257686 | 0.00566842 |
| 0.10926479 | −0.1167006 | 0.18223672 | 0.09710353 | 0.03838636 | −0.2026017 |
| 0.12219627 | 0.05705986 | −0.0505442 | −0.1334345 | −0.0204458 | 0.01167099 |
| −0.1091286 | −0.075133 | 0.02949276 | −0.0217044 | −0.0782921 | −0.1160332 |
| −0.0210903 | 0.11607172 | −0.0943146 | −0.1014408 | 0.02903902 | 0.02963065 |
| −0.1233738 | −0.0760847 | 0.00098273 | 0.07522969 | 0.05794976 | −0.1959872 |
| 0.06584878 | −0.0323083 | −0.0581293= | | | |

TABLE 4

Second neural net weighting matrix (2 × 21) (weights_2).

| | | | | | |
|---|---|---|---|---|---|
| −0.5675537 | −0.6119734 | 0.20069507 | 0.26132998 | −0.5071653 | 0.2793434 |
| −0.5323685 | 0.31165671 | −0.9999997 | −0.4128213 | −1.0000007 | −0.6456627 |
| −0.209513 | 1.6362301 | −1.9999975 | −0.2563241 | 0.04389827 | 1.7597554 |
| 2.0453076 | 0.03412334 | −0.1645829= | | | |
| 0.55343837 | 0.68506379 | −1.1869608 | 0.39551663 | 0.38050765 | 0.40832204 |
| 0.12712023 | −1.7462951 | 0.0813732 | 6.111361 | 0.62210494 | 0.42921746 |
| 0.19891988 | −4.0000067 | −0.5605077 | 1.3601962 | 1.7318885 | −1.0558798 |
| 3.1242371 | 0.22860088 | 1.6726165= | | | |

E) Code for Running the Net

Code for running the neural net is provided below in Table 5 (neural_n.c) and Table 6 (lin_alg.c).

TABLE 5

Code for running the neural net (neural_n.c).

```
#define local far
#include <windows.h>
#include <alloc.h>
#include "utils.h"
#include <string.h>
#include <ctype.h>
#include <stdio.h>
#include <math.h>
#include <mem.h>
#include "des_util.h"
#include "chipwin.h"
#include "lin_alg.h"
void reportProblem( char local * message, short errorClass);
char inFileName[] = "designer. ini";
static void sigmoid( vector local * transformMe ){
    short i;
    for( i = 0; i <transformMe->size; i++)
```

TABLE 5-continued

Code for running the neural net (neural_n.c).

```
            transformMe->values[i] = 1/(1+ exp(-1 * transformMe->values[i]));
    }
    static short getNumCols(char far * buffer){
        short count = 1;
        for( ;*buffer ![32 0; buffer++)
            if( *buffer == '\t') count++;
        return count;
    }
    static short getNumRows(char far * buffer){
        char far * last, far * current;
        short count = -1;
        current = buffer;
        do{
            count++;
            last = current;
            current = strchr( last+1, 0);
        }while( current>last+1 );
        return count;
    }
    static void readMatrix( matrix local * theMat, char far * buffer ){
        short i,j;
        char far * temp;
        temp = buffer;
        for( i = 0; i <theMat->numRows; i++){
            for(j = 0; j <theMat->numCols; j++){
                while( isspace( *temp) || (*temp == && *(temp-1) != 0 ) ) = temp++;
                sscanf( temp, "%f", &theMat->values[i][j]);
                while( !isspace( *temp) && *temp != 0) temp++;
            }
        }
    }
    #define MaxNumLines (20)
    #define MaxLineSize (1024)
    short readNeuralNetWeights(matrix local *weights1, matrix local *weights2
    ){
        char far * buffer;
        int copiedLength;
    short numCols, numRows;
        buffer = farcalloc( MaxNumLines * MaxLineSize, sizeof( char));
        if(buffer == NULL ){errorHwnd( "failed to allocate file reading = buffer"); return
    FALSE; }
        copiedLength = GetPrivateProfileString("weights_1", NULL, "[0][0]", buffer,
    MaxNumLines * MaxLineSize, iniFileName);
        if( copiedLength < || 10 copiedLength >= (MaxNumLines * MaxLineSize =
    -10)){
            errorHwnd("failed to read .ini file"); return FALSE;
        }
        numCols = getNumcols( buffer);
        numRows = getNumRows( buffer);
        if( !allocateMatrix( weights1, numRows, numCols )) return FALSE;
        readMatrix( weights1, buffer);
        copiedLength = GetPrivateProfileString("weights_2", NULL, "[0][0]", buffer,
    MaxNumLines * MaxLineSize, iniFileName);
        if( copiedLength < 10 || copiedLength >= (MaxNumLines * MaxLineSize
    -10)){
            errorHwnd("failed to read ini file");
            farfree( buffer);
            return FALSE;
        }
        numCols = getNumCols( buffer);
        numRows = getNumRows( buffer);
        if( !allocateMatrix( weights2, numRows, numCols )){ farfree( buffer); return
    FALSE; }
        readMatrix( weights2, buffer);
        farfree( buffer);
    return TRUE;
    }
    short runForward( vector local *input, vector local *output,
                                    matrix local *weights 1, matrix local
    *weights2) {
        vector hiddenLayer;
        if( !allocateVector( &hiddenLayer, (short)(weights1 ->numRows +1) )) return
    FALSE;
        if( !vectorTimesMatrix( input, &hiddenLayer, weights1 ) ){
            freeVector( &hiddenLayer); return FALSE;
        }
        sigmoid( &hiddenLayer);
```

TABLE 5-continued

Code for running the neural net (neural_n.c).

```
        hiddenLayer.values[hiddenLayer.size -1] = 1;
        if( !vectorTimesMatrix( &hiddenLayer, output, weights2 ) ){
            freeVector( &hiddenLayer); return FALSE;
        }
    freeVector( &hiddenLayer);
        sigmoid( output);
        return TRUE;
    }
    static vector inputVector= {NULL, 0}, outputVector = {NULL, 0}; static matrix
    firstWeights = {NULL, 0, 0}, secondWeights = {NULL, 0, 0};
    static short beenHereDoneThis = FALSE;
    static short makeSureNetIsSetUp( void ){
        if( beenHereDoneThis) return TRUE;
        if( !readNeuralNetWeights( &firstWeights, &secondWeights )) return = FALSE;
        if( !allocateVector( &inputVector, firstWeights.numCols )) return = FALSE;
        if( !allocateVector( &outputVector, secondWeights.numRows )) return = FALSE;
        beenHereDoneThis = TRUE;
        return TRUE;
    }
    void removeNetFromMemory( void) {
        freeVector( &inputVector); freeVector( &outputVector);
        freeMatrix( &firstWeights); freeMatrix( &secondWeights);
    beenHereDoneThis = FALSE;
    }
    short nnEstimateHybAndXHyb( float local * hyb, float local * xHyb, char = local *
    probe) {
        short probeLength, i;
        if( !makeSureNetIsSetUp()) return FALSE;
        probeLength = (short)(strlen( probe));
        if( (probeLength *4 + 1) != inputVector.size ){
//          reportProblem("Neural net not set up to deal with probes of this = length", 0);
            if( probeLength *4 + 1)>inputVector.size ){
//          reportProblem( "probe being trimmed to do analysis", 1);
                probeLength = (short)(inputVector.size / 4);
            }
        }
        memset( inputVector.values, 0, inputVector.size * sizeof( float));
        inputVector.values[inputVector.size -1] = 1;
        for( i = 0; i <probeLength; i++)
            inputVector.values[i* 4 + lookupIndex( tolower(probe[i]))]= 1;
        runForward( &inputVector, &outputVector, &firstWeights, &secondWeights);
        *hyb = outputVector.values[0];
        *xHyb = outputVector.values[1];
        return TRUE;
    }
```

TABLE 6

Code for running the neural net (lin_alg.c).

```
lin_alg.c
#include "utils.h"
#include "lin_alg.h"
#include <alloc.h>
short allocateMatrix( matrix local * theMat, short rows, short columns){
    short i;
    theMat->values = calloc( rows, sizeof( float local *));
    if( theMat->values == NULL ) { errorHwnd( "failed to allocate = matrix"); return
FALSE;}
    for( i = 0; i <rows; i++){
        theMat->values[i] = calloc( columns, sizeof(float));
        if( theMat->values[i] = NULL ){
            errorHwnd ("failed to allocate matrix");
            for( --i;i >= 0;i--)
                free( theMat->values[i] );
            return FALSE;
        }
    }
    theMat->numRows = rows; theMat->numCols = columns;
    return TRUE;
} short allocateVector( vector local * theVec, short columns){
    theVec->values = calloc( columns, sizeof ( float));
    if( theVec->values = NULL) { errorHwnd("faile to allocate = vector"); return
FALSE;}
```

TABLE 6-continued

Code for running the neural net (lin_alg.c).

```
        theVec->size = columns;
        return TRUE;
}
void freeVector( vector local * theVec ){
    free( theVec->values);
    theVec->values = NULL;
    theVec->size = 0;
}
void freeMatrix( matrix local * theMat){
        short i;
        for( i = 0; i <theMat->numRows; i++)
        free( theMat->values[i] );
            free( theMat->values);
        theMat->values = NULL;
        theMat->numRows = theMat->numCols = 0;
}
float vDot( float local * input1, float local * input2, short size ){
    float returnValue = 0;
    short i;
    for(i = 0; i<size; i++)
        returnValue += input1 [i] * input2[i];
    return returnValue;
}
short vectorTimesMatrix( vector local *input, vector local *output,
                            matrix local *mat){
    short i;
    if( (input->size != mat->numCols) || (output->size <mat->numRows) ){
        errorHwnd( "illegal multiply");
        return FALSE;
    }
    for(i = 0;i<mat->numRows; i++)
        output->values[i] = vDot( input->values, mat->values[i], input->size =
);
    return TRUE;
}
```

Example 7

Generic Difference Screening

High density arrays comprising arbitrary (haphazard) probe oligonucleotides for generic difference screening were produced by shuffling (randomizing) the masks used in light-directed polymer synthesis. The resulting arrays contained more than 34,000 pairs 25 mer arbitrary probe oligonucleotides. The oligonucleotides in each pair differed by a single nucleotide at position 13.

After hybridization, washing, staining, and scanning as described above, data files (containing information regarding probe identity and hybridization intensity) were created.

Differences in intensity between the two oligonucleotides comprising each probe pair K (where K ranges from 1 to 34,320) were calculated. More specifically, the intensity differences between the oligonucleotides of pair K for replicate j of sample i was calculated as:

$$X_{ijk1} - X_{ijk2}$$

where X is the hybridization intensity, i indicates which sample (in this case sample 1 or 2), and j indicates which replicate (in this case replicate 1 or two for each sample), and K is the probe pair (in this case 1 . . . 34,320), and 1 indicates one member of the probe pair, while 2 indicates the other member of the probe pair.

Figure 15A:
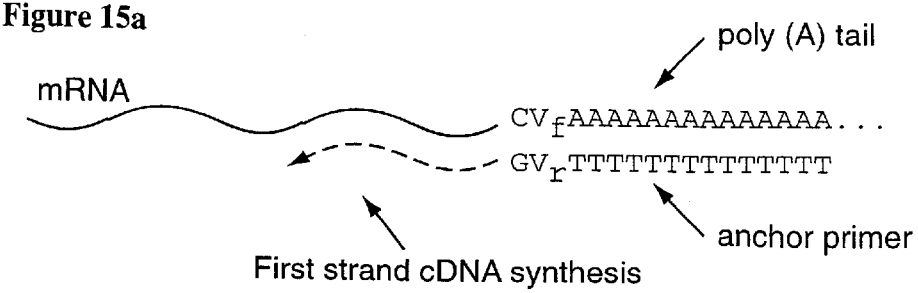
FIGS. 15a, 15b, 15c, 15d, and 15e illustrate the analysis of differential diaplay DNA fragments on a generic difference screenign array.
Figure 15B:
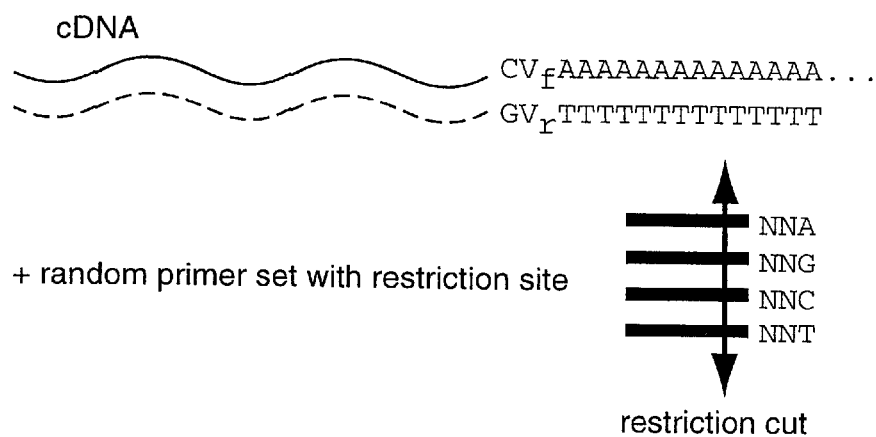
Figure 15C:
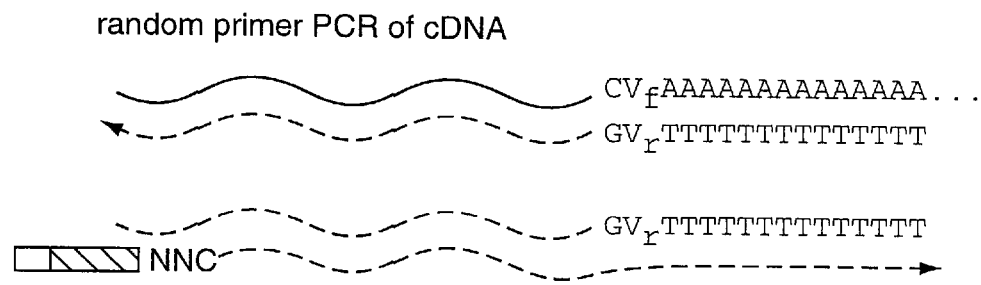
Figure 15D:
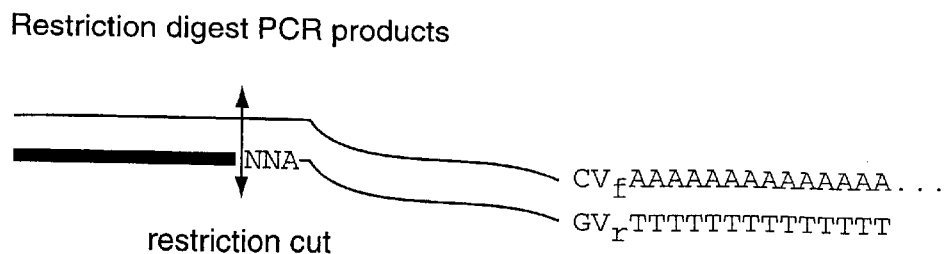
Figure 15E:
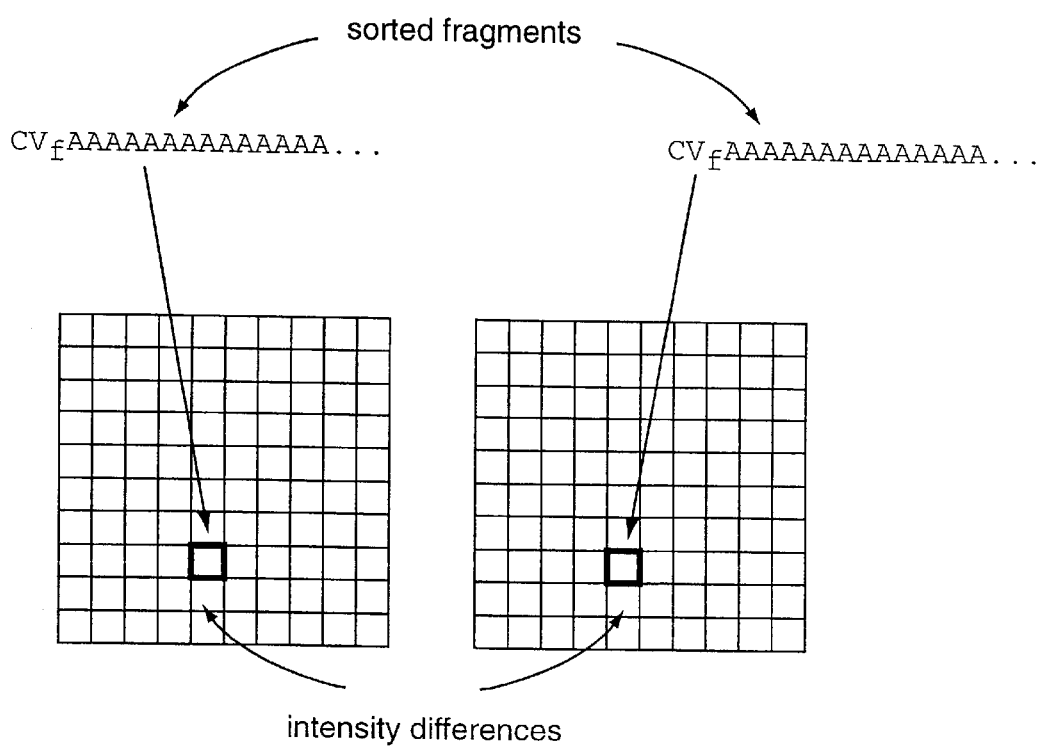

FIGS. 16a and 16b and 16c illustrate the differences between replicate 1 and 2 of sample 1 (FIG. 16a, the normal cell line) and between replicate 1 and replicate 2 of sample 2 (FIG. 16b, the tumor cell line) for each probe. Thus, FIG. 16a plots the value of $(X_{11k1}-X_{11k2})-(X_{12k1}-X_{12k2})$ for k–1 to 34,320 on the vertical axis and K on the horizontal axis. The two replicates were normalized based on the average ratio of $(X_{11k1}-X_{11k2})/(X_{12k1}-X_{12k2})$ for all probe pairs (i.e., after normalization, the average ratio should approximate 1). Similarly, FIG. 15b plots the value of $(X_{21k1}-X_{21k2})-(X_{22k1}-X_{22k2})$ after normalization between the two replicates based on the average ratio of $(X_{21k1}-X_{21k2})/(X_{22k1}-X_{22k2})$. FIG. 16c plots the differences between sample 1 and 2 averaged over the two replicates. This value is calculates as $((X_{21k1}+X_{22k2})/2)-((X_{11k1}+X_{12k2})/2)$ after normalization between the two samples based on the average ratio of $[(X_{21k1}+X_{22k2})/2]/[(X_{11k1}+X_{12k2})/2]$.

Figure 17B:
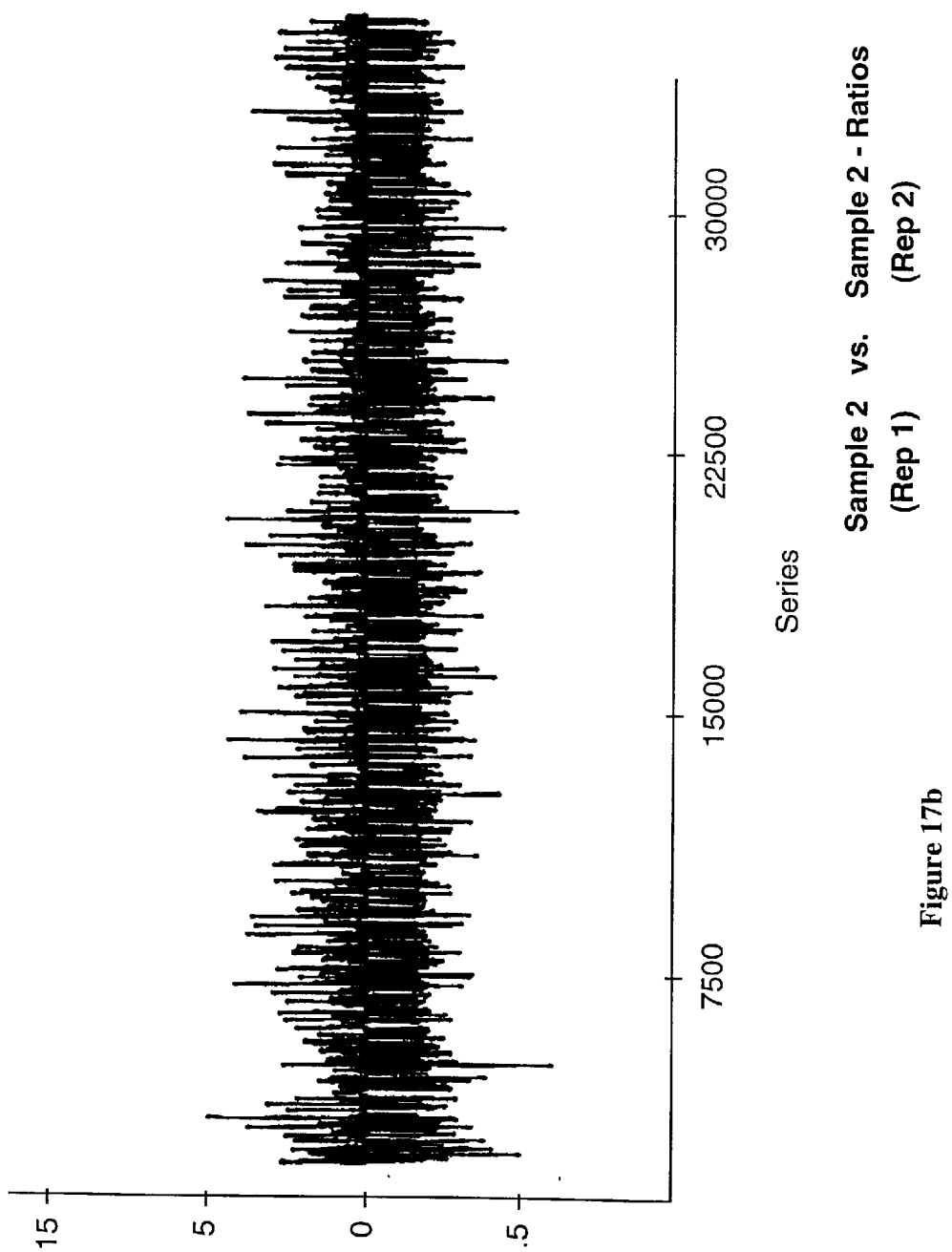
Figure 17C:
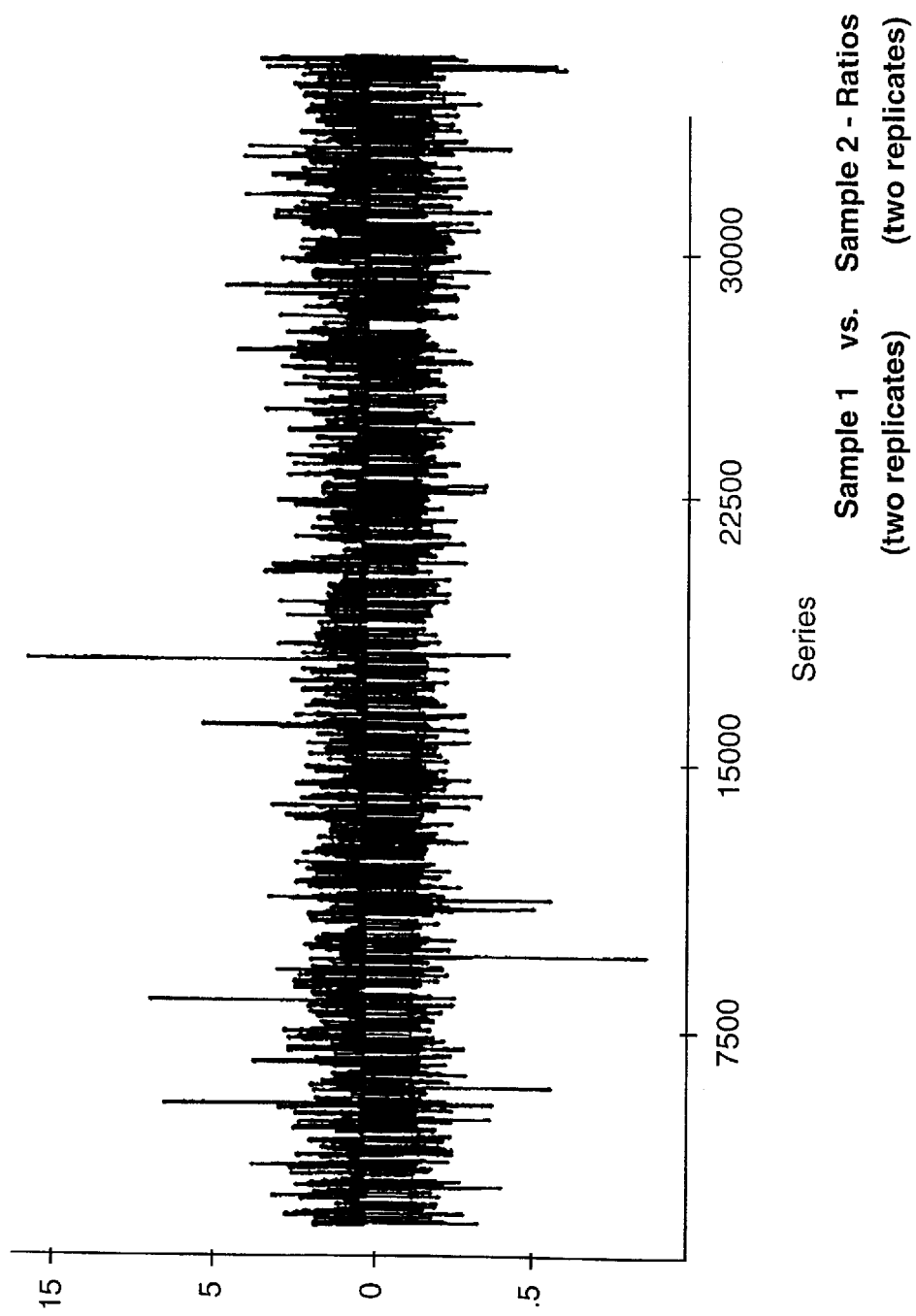

FIGS. 17a, 17b, and 17c show the data filtered. FIG. 16a shows the relative change in hybridization intensities of replicate 1 and 2 of sample 1 for the difference of each oligonucleotide pair. After normalization between replicates (see above), the ratio is calculated as follows: If the absolute value of $(X_{11k1}-X_{11k2})/(X_{12k1}-X_{12k2})>1$, then the ratio= $(X_{11k1}-X_{11k2})/(X_{12k1}-X_{12k2})$ else the ratio=$(X_{12k1}-X_{12k2})/(X_{11k1}-X_{11k2})$ (the inverse). The ratio of replicate 1 and 2 of sample 2 for the difference of each oligonucleotide pair, normalized, filtered, and plotted the same way as in FIG. 17a is shown in FIG. 17b. The ratio is calculated as in FIG. 17a, but based on the absolute value of $(X_{21k1}-X_{21k2})/(X_{22k1}-X_{22k2})$ and $(X_{22k1}-X_{22k2})/(X_{21k1}-X_{21k2})$. FIG. 17c shows the ratio of sample 1 and sample 2 averaged over two replicates for the difference of each oligonucleotide pair. The ratio is calculated as in FIG. 17a, but based on the absolute value of $[(X_{21k1}+X_{22k2})/2]/[(X_{11k1}+X_{12k2})/2]$ and $[(X_{11k1}+X_{12k2})/2]/[(X_{21k1}+X_{22k2})/2]$ after normalization as in FIG. 16c.

The oligonucleotide pairs that show the greatest differential hybridization between the two samples can be identified by sorting the observed hybridization ratio and difference values. The oligonucleotides that show the largest change (increase or decrease) can be readily seen from the ratio plot of samples 1 and 2 (FIG. 17c). These differences do not appear to be in the background noise. Based on the identified oligonucleotide pair sequences, a gene or EST with the suspected sequence tag can be searched for in the sequence databases, such as GENBANK, to determine whether the gene has been cloned and characterized. If the search is negative, appropriate primers can be made to obtain the cDNA or part of the cDNA directly from mRNA, cDNA, or from a cDNA library.

From FIGS. 16a and 16b, it is observed that several oligonucleotide pairs show large differences between two replicates for the same sample. It is believed that this results from differential expression in a given tissue. These oligonucleotide pairs detect genes that are likely highly expressed, so the deviation of replicates for these pairs are larger than those oligonucleotide pairs that bind to nucleotides expressed at low levels (i.e., the standard deviation of the mean is proportional to the mean). That is also why the relative change between two samples is a better indicator to detect the differential expression between two samples (see FIG. 17c). In order to determine which oligonucleotide pairs are of greatest interest, the absolute and relative difference measures could be combined into a scoring function.

Increasing the number of related oligonucleotide pairs (increased redundancy) and employment of two-color hybridization/detection schemes is expected to help reduce the background variation. This allows more sensitive detection of small differences and decreases the noise and occurrence of false positives. The 25 mer array used in this example is a small subset of all possible 25 mers, thus, increasing the total number of oligonucleotide pairs will greatly increase the ability to detect changes in genes of unknown sequences by allowing more complete coverage of the available sequence space.

Example 8

Nucleic Acid End Labeling

Several RNA transcripts as well as a full mRNA sample from mouse cells were fragmented by heat in the presence of $Mg^{2+}$. A riboA$_6$ (deoxyribonucleic acid 6 mer poly A) labeled with either fluorescein or biotin at the 5' end was then ligated to the fragmented RNA using RNA ligase under standard conditions.

The labeling appeared to be efficient and the hybridization pattern obtained using the labeled RNA as a probe was similar to one obtained using RNA that was labeled during an in vitro transcription step.

Example 9

Quantification of Labeling Efficiency

Quantification of the labeling efficiency is accomplished by spiking experiments in which specific full-length unfragmented RNA species are spiked into the total mRNA pool at different concentrations prior to the end-labeling procedure. The relative concentrations of the spiked RNA in the pool can then be measured by hybridization to a high density array of target oligonucleotides prepared as described above. This permits evaluation of the ability to detect particular RNA species at low concentration in the mRNA pool.

Example 10

PCR Labeling of Nucleic Acids
Polymerase Chain Reaction (PCR)

20 μl PCR reactions substituted with 10% biotin-dUTP were conducted and the quantity of each PCR product was estimated with gel analysis. Approximately 250 fmoles of each PCR product was pooled. A Pharmacia S300 sephacryl column (cat #27-5130-01) was prepared with a 1 minute prespin at 3000×g followed with a 200 μl H$_2$O wash and spin at 3000×g for 1 more minute. The pooled PCR product was loaded and spun for 2 minutes at 3000×g.

The column was discarded and the eluate was speed vacuumed to dryness.
DNase Fragmentation The dried down PCR pool in was resuspended in 13 μl H$_2$O from NEN DuPont End Labeling Kit (cat #NEL824). 2.5 μl CoCl$_2$ and 12.5 μl TdT buffer were added. Gibco BRL DNase 1 was diluted to 0.25 U/μl using 10 mM Tris pH 8. 1 μl of diluted DNase was added to PCR product pool and incubated for 6 minutes at 37° C., denatured for 10 minutes at 99° C., and cooled to 4° C. The total volume was 29 μl.
Terminal Transferase (TdT) Labeling To the fragmented PCR pool, 2 μl of TdT enzyme (from NEN kit 2 U/μl stock) was added and 4 μl NEN kit biotin-ddATP was then added. The final volume was 35 μl, and was incubated at 37° C. for 1.5 hr.
Hybridization The 35 μl labeled target was split into two 17.5 μl aliquots, one for a coding chip (GeneChip containing sense-strand sequences and permutations thereof) and one for the non-coding (antisense) chip. 182.5 μl of 2.5 M TMACl (Sigma 5 M stock diluted 1:2 using 10 mM Tris pH 8) was added. Triton X-100 was added to a final concentration of 0.001%. In certain experiments, 4 μl of 100 nM control oligonucleotide was added to the solution rather than at the stain step.

The mixture was denatured at 95° C. for 5 minutes, added directly to the chip cartridge and hybridized with mixing at 37° C. for 60 minutes.
Staining and Washing The hybridization solution was removed from the flow cell used in the GeneChip system (Affymetrix, Inc., Santa Clara, Calif.) and the chamber was manually rinsed with 3× with 6×SSPE /0.001% Triton X-100 to remove TMACl.

A phycoerythrin stain solution was prepared as follows: 190 μl 6×SSPE/0.001% Triton X-100+10 μl of 20 mg/ml acetylated BSA+0.4 μl stock phycoerythrin (Molecular Probes Cat #S866)+4 μl fluorescein control oligo 100 nM stock.

The staining solution was added to the flow cell with mixing at room temperature for 5 minutes. The staining solution was removed from the flow cell and manually rinsed 3× with washing buffer.

The chip was washed on hybridization station (the Gene-Chip system, Affymetrix, Inc.) using 6×SSPE/0.001% Triton X-100 at 35° C. 9 fill/drain changes of fresh wash solution were used and scanning took place in this buffer. Target sequences were accurately identified in this experiment.

Example 11

End Labeling PCR Product

PCR product was fragmented and end labeled using TdT from Boehringer Mannheim: After the PCR amplification, 5 µl of a 50 µl PCR reaction was run on a 1% agarose gel to estimate total yield of the amplification reaction. To fragment the DNA, the remaining 45 µl of solution was combined with DNAse I (diluted in H2O to a final concentration of 5 U DNAse I/µg DNA) and reacted for 15 minutes at 31° C. The DNAse was then heat killed for 10 minutes at 95° C. The fragmented DNA solution was then held at 4° C. until ready for the terminal transferase reaction.

The terminal transferace reaction mixture consisted of the fragmented PCR sample, 20 µL 5×terminal transferase reaction buffer, 6 µl 25 mM $CoCl_2$ (final concentration 1.5 mM), 1 µl of fluorescent dideoxynucleotide triphosphates (ddNTP final concentration 10 µM) and 2 µL of Boehringer Mannheim terminal transferase (TdT, final concentration 50 U/reaction), and $H_2O$ up to 100 µl volume.

The reaction was incubated for 30 minutes at 37° C. The whole reaction volume was then transferred to a 1.7 ml tube, brought up to 500 µl with 5×SSPE, 0.05% Triton hyb and scanned normally.

Protocols for the 50 µL PCR reaction are found in the instructional materials accompanying the GeneChip™ HIV PRT Assay (Affymetrix, Sunnyvale, Calif.).

Example 12

CAIP Improves Base Calling

In certain fragment end labeling experiments, the accuracy of base calling in a GeneChip system was improved when calf intestinal alkaline phosphatase (CAIP) was used during fragmentation with DNAse. See FIG. 18.

CIAP is useful in degrading any nucleotides that were not incorporated in any previous amplification, transcription, and polymerase other polymerase reactions. Such degredation prevents the incorporation of those nucleotides in subsequent reactions, such as tailing and labeling reactions for example.

Example 13

Post-Hybridization End Labeling

Figure 19:
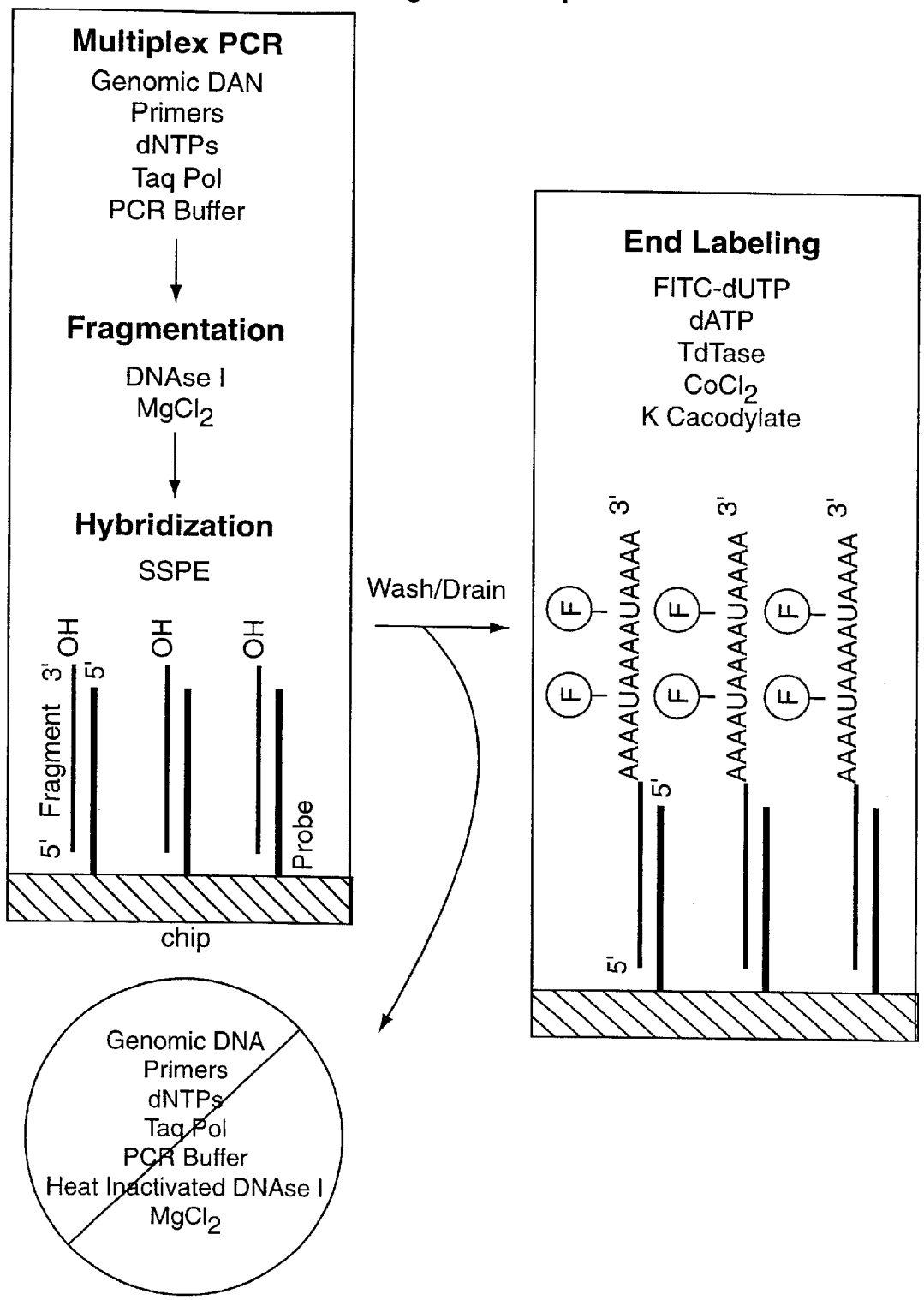
FIG. 19 provides a schematic illustration of pos-hybidrization end labeling (SEQ ID NO:9) on a high density oligonucleotide array.

Post-hybridization end labeling experiments were performed. After hybridization of a target to a probe array in the GeneChip system, the targets were labeled using terminal transferase (shown as TdTase) as shown in FIG. 19.

Figure 20:
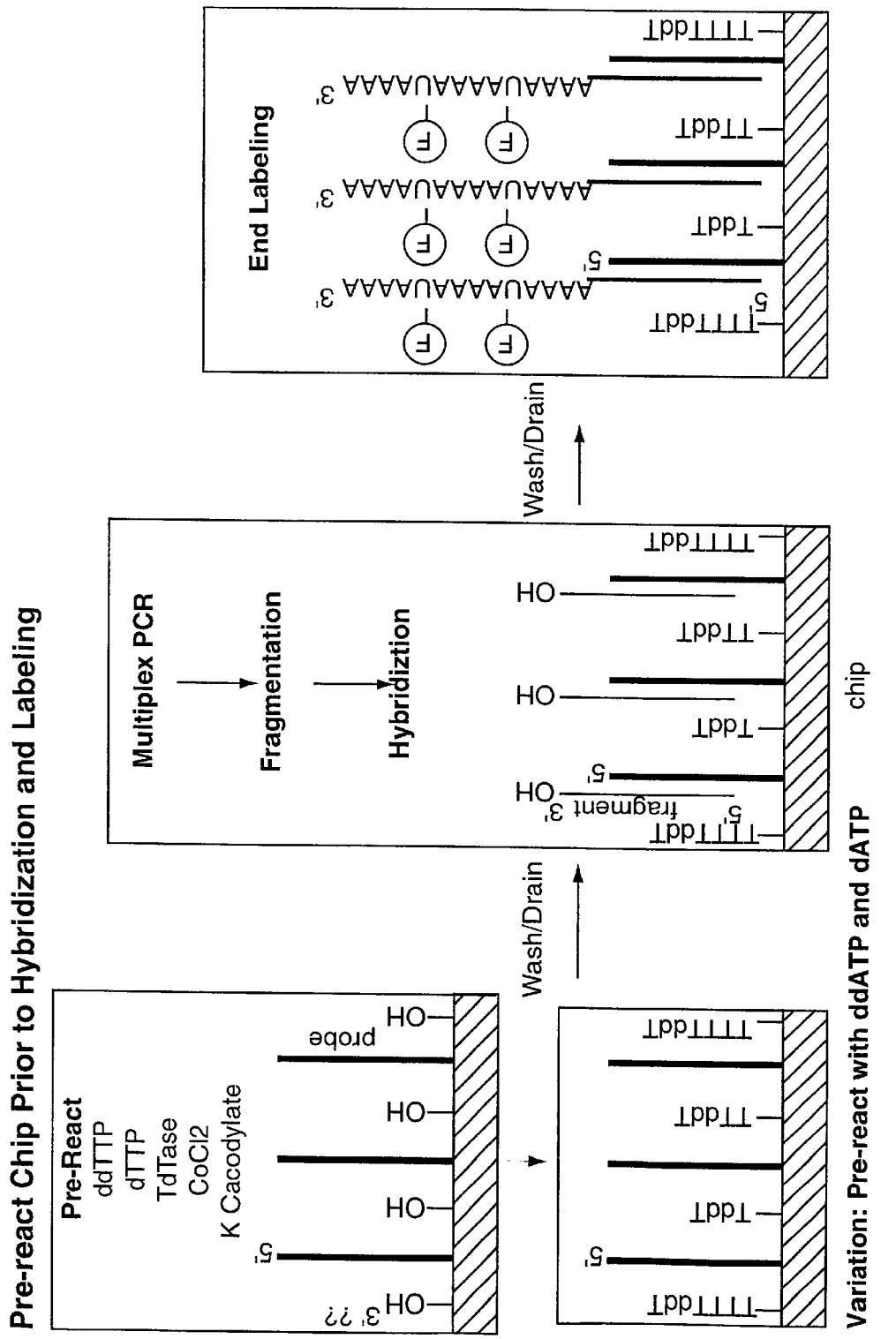
FIG. 20 provides a schematic illustration end-labeling utilizing pre-reaction of a high density array prior to hybridization and end labeling.
Figure 21:
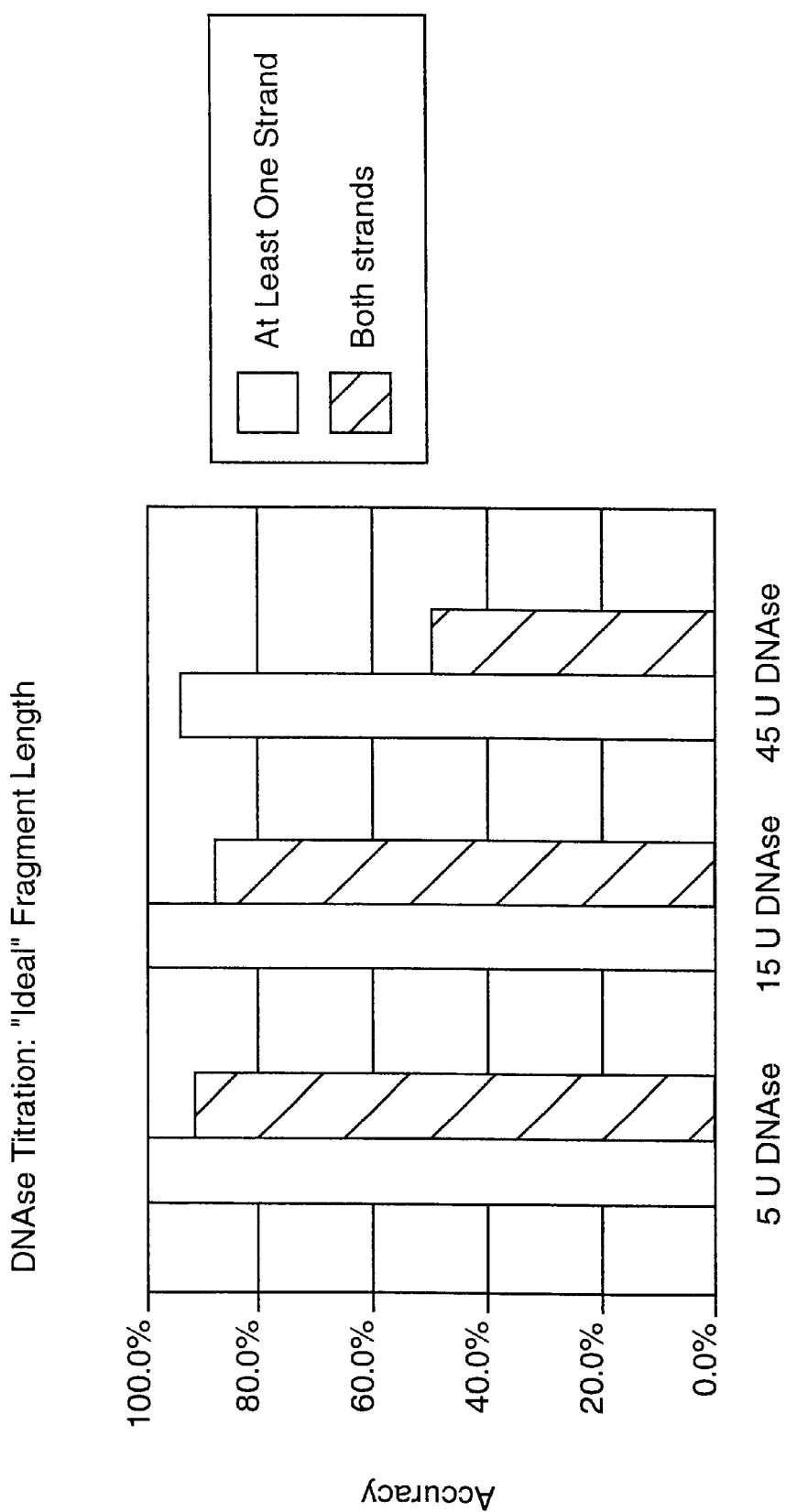
FIG. 21 illustrates the results of a measure of post-hybridization Td Tase end labeling call accuracy.

Post-hybridization labeling was shown to yield better results when the probe array (Chip) was pre-reacted as shown in FIGS. 20 and 21.

FIG. 21 also shows the results of a DNAse titrations experiment. The various titration experiments are shown below in Table 7.

TABLE 7

Hybridization TdTase end labeling call accuracy. Accuracy is based on Ratio = 1.2 of maximum to next highest calculated intensities. Calculated intensities = minimum of A, C, G, or T in tile set subtracted from adjusted intensity. Adjusted intensity = raw intensity of PCR - raw intensity of no PCR.

| Experiment | Pre-react | Labeling | Accuracy |
|---|---|---|---|
| HM207<br>5 U DNAse | ddTTP = 1.8 mM<br>dTTP =<br>TdTase = 50 U<br>Temp = room T<br>Time = 1 hr | FITC-dUTP = 5 nmol<br>dATP = 50 nmol<br>TdTase = 50 U<br>Temp = room T<br>Time = 1 hr | At least one strand = 100.0%<br>Both strands = 91.3%<br>GeneSeq Composite = NA |
| HM217<br>5 U DNAse | ddTTP = 1.0 mM<br>dTTP =3.0 mM<br>TdTase = 12.5 U<br>Temp = room T<br>Time = overnight | FITC-dUTP = 0.5 nmol<br>dATP = 5 nmol<br>TdTase = 5 U<br>Temp = room T<br>Time = 15 min | At least one strand = 98.8%<br>Both strands = 89.6%<br>GeneSeq Composite = 99.2% |
| HM220<br>5 U DNAse | ddTTP = 1.8 mM<br>dTTP =3.0 mM<br>TdTase = 12.5 U<br>Temp = 37° C.<br>Time = overnight | FITC-dUTP = 0.5 nmol<br>dATP = 5 nmol<br>TdTase = 5 U<br>Temp = 37° C.<br>Time = 15 min | At least one strand = 100.0%<br>Both strands = 91.1%<br>GeneSeq Composite = 99.1% |

These results show that base calling accuracy can impacted by the length of the target fragments. Such results further demonstrate the utility of the methods disclosed herein.

Other experiments have shown that 1U of DNAse is particularly useful in obtaining ideal fragment lengths.

Example 14

End-Labeling (Tailing) with Poly T

The nucleic acids tailed with poly-A or poly-A analogs (labeled or unlabeled) using methods similar to those set forth in Example 13 can be labeled using labeled poly-T, as shown in FIG. 22.

Example 15

Synthesis of Fluorescent Triphosphate Labels

To 0.5 µmoles (50 µL of a 10 mM solution) of the amino-derivatized nucleotide triphosphate, 3'amino-3'deoxythymidinetriphosphate (1) or 2'-amino-2'-deoxyuridine triphosphate (2), in a 0.5 ml ependorf tube was added 25 µL of 1 1 M aqueous solution of sodium borate, pH 7, 87 μL of methanol, and 88 μL (10 μmol, 20 wquiv) of a 100 mM solution of 5-carboxyfluorescein-X-NHS ester in methanol. The mixture was vortexed briefly and allowed to stand at room temperature in the dark for 15 hours. The sample was then purified by ion-exchange HPLC to afford the fluoresceinated derivatives Formula 3 or Formula 4, below, in about 78–84% yield.

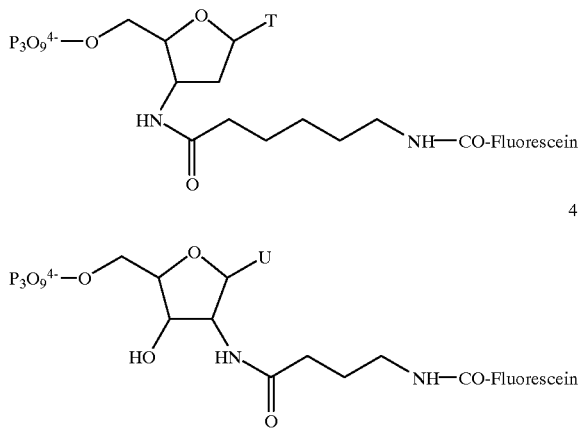

Experiments suggest that these molecules are not substrates for terminal transferase (TdT). It is believed, however, that these molecules would be substrates for a polymerase, such as klenow fragment.

Example 10

Synthesis of as-Triazine-3,5[2H,4H]-diones

Figure 23A:
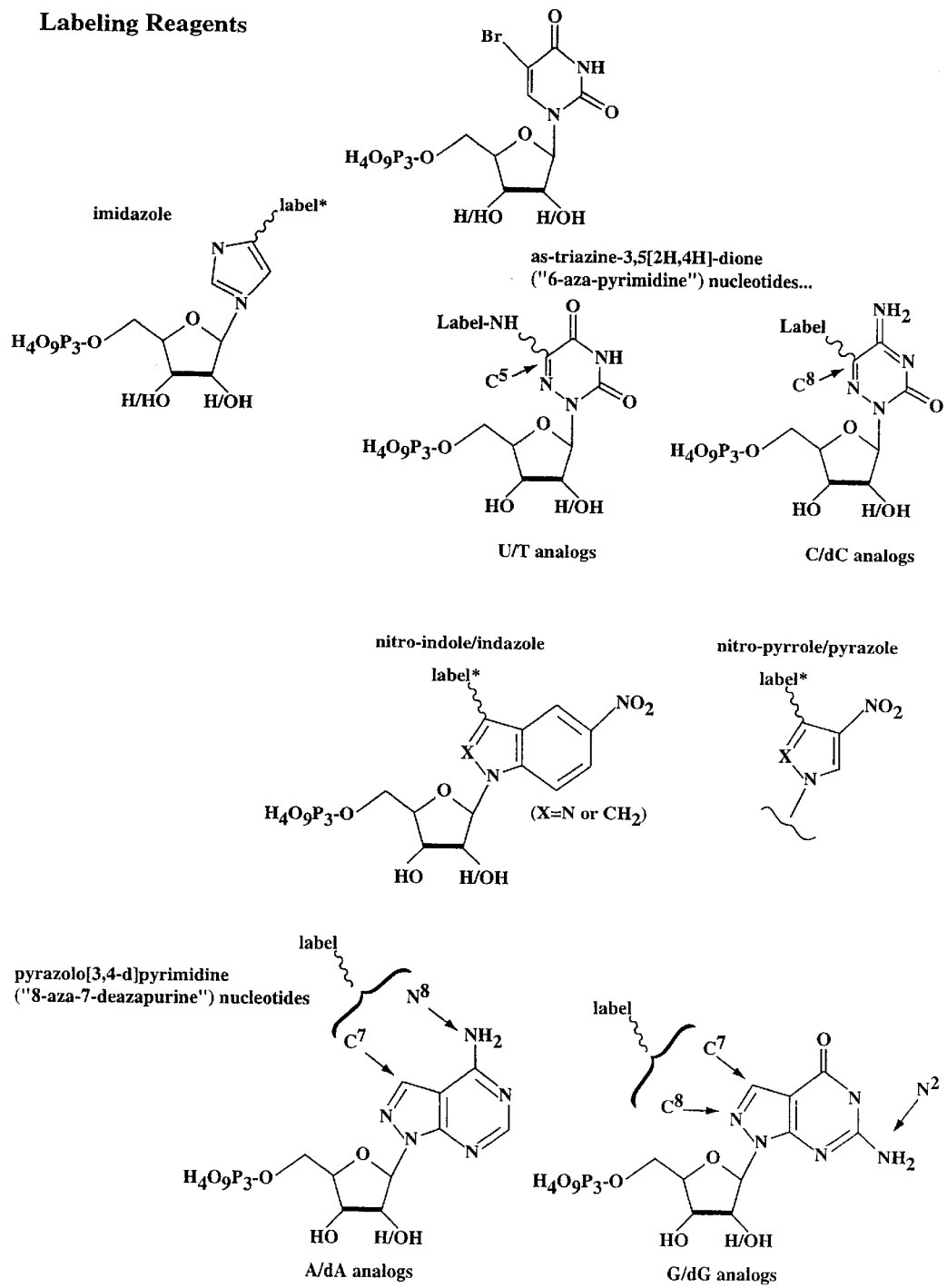
FIG. 23a shows various labeling reagents.

The analogs as-triazine-3,5[2H,4H]-dione ("6-aza-pyrimidine") nucleotides (see, FIG. 23a) are synthesized by methods similar to those used by Petrie, et al., Bioconj. Chem. 2: 441 (199 1).

Figure 23B:
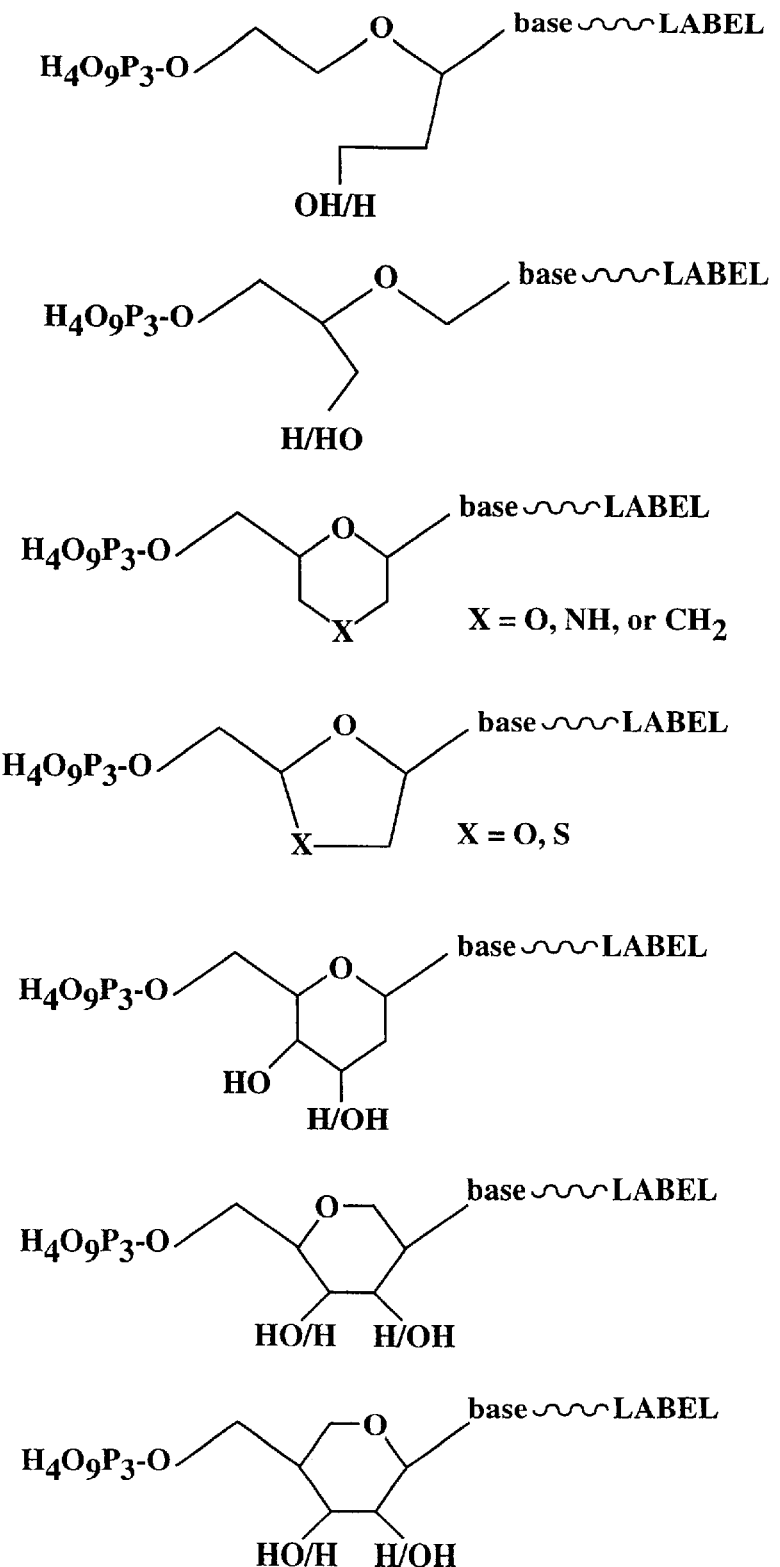
FIG. 23b shows still other labeling reagents.

Other useful labeling reagents are synthesized including 5-bromo-U/dUTO or ddUTP. See for example Lopez-Canovas, L. Et al., Arch. Med Res 25: 189–192 (1994); Li, X., et al., Cytometry 20: 172–180 (1995); Boultwood, J. Et al., J. Pathol. 148: 61 ff. (1986); Traincard, et al., Ann. Immunol. 1340: 399–405 (1983); and FIGS. 23a, and 23b set forth herein.

Details of the synthesis of nucleoside analogs corresponding to all of the above structures (in particular those of FIG. 23b) have been described in the literature Known procedures can be applied in order to attach a linker to the base. The linker modified nucleosides can then be converted to a triphosphate amine for final attachment of the dye or hapten which can be carried out using commercially available activated derivatives.

Figure 23C:
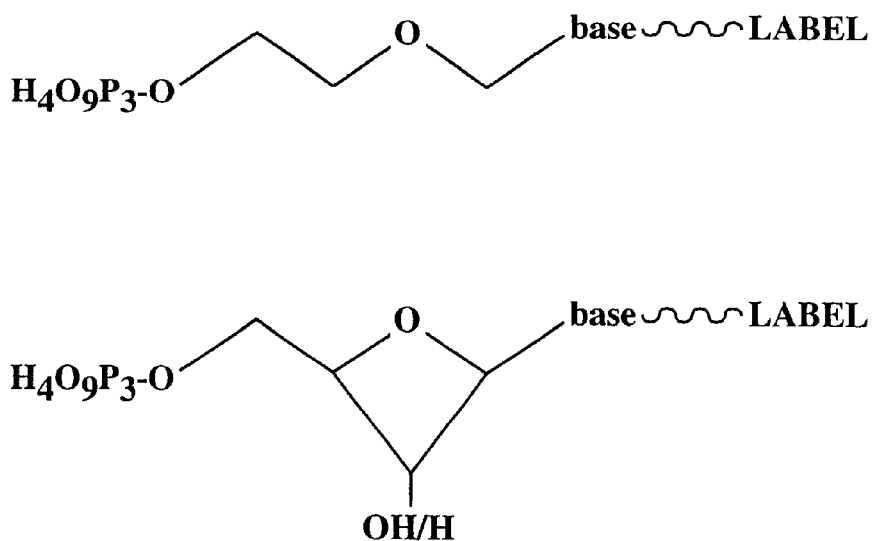
FIG. 23c shows non-ribose or non-2'-deoxyribose-containing labels.
Figure 23D:
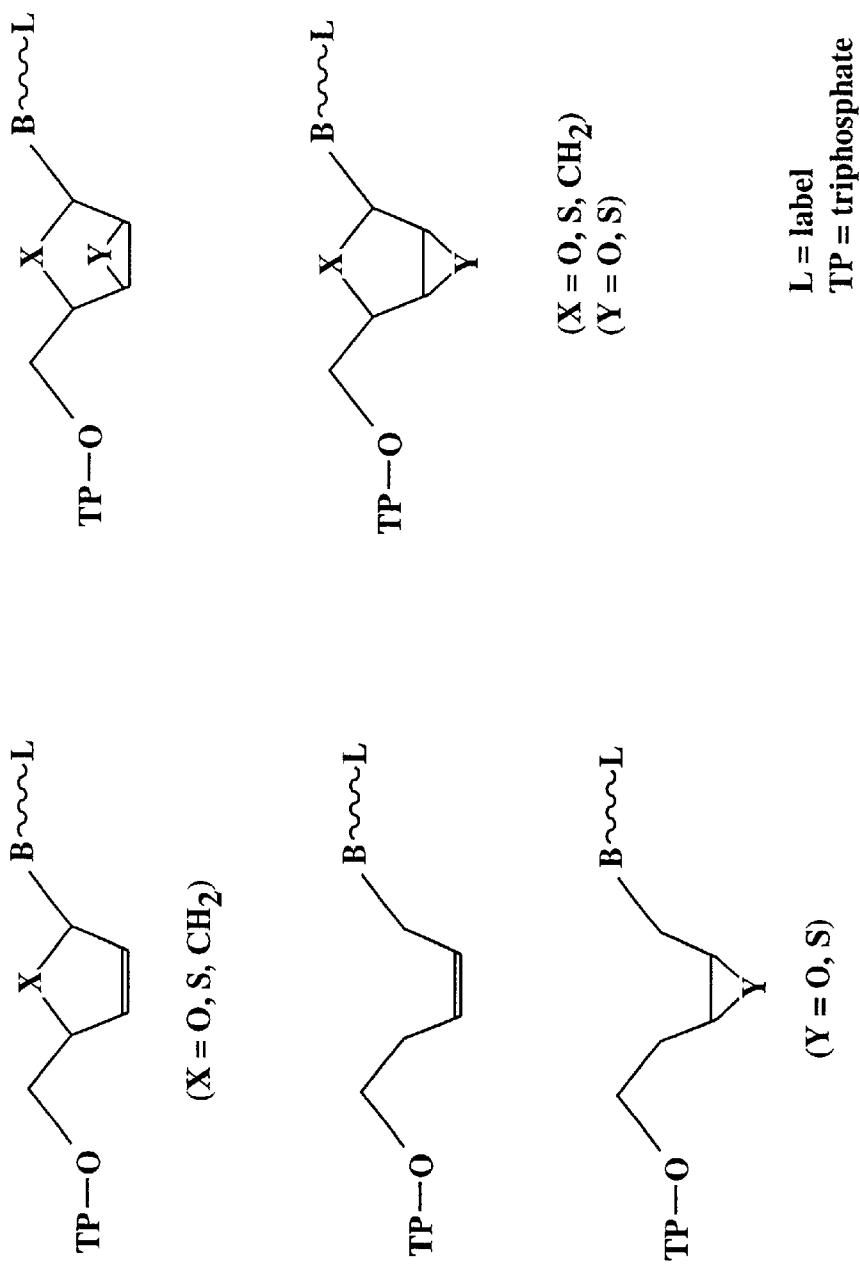
FIG. 23d shows sugar-modified nucleotide analogue labels 23d.

Other suitable labels include non-ribose or non-2'-deoxyribose-containing structures some of which are illustrated in FIG. 23c and sugar-modified nucleotide analogues such as are illustrated in FIG. 23d.

Using the guidance provided herein, the methods for the synthesis of reagents and methods (enzymatic or otherwise) of label incorporation useful in practicing the invention will be apparent to those skilled in the art. See, for example, Chemistry of Nucleosides and Nucleotides 3, Townsend, L. B. ed., Plenum Press, New York, at chpt. 4, Gordon, S. The Synthesis and Chemistry of Imidazole and Benzamidizole Nucleosides and Nucleotides (1994); Gen Chem. Chemistry of Nucleosides and Nucleotides 3, Townsend, L. B. ed., Plenum Press, New York (1994); can be made by methods similar to those set forth in Chemistry of Nucleosides and Nucleotides 3, Townsend, L. B. ed., Plenum Press, New York, at chpt. 4, Gordon, S. "The Synthesis and Chemistry of Imidazole and Benzamidizole Nucleosides and Nucleotides (1994); Lopez-Canovas, L. Et al., Arch. Med. Res 25: 189–192 (1994); Li, X., et al., Cytometry 20: 172–180 (1995); Boultwood, J. Et al., J. Pathol. 148: 61 ff. (1986); Traincard, et al., Ann. Immunol. 1340: 399–405 (1983).

Example 11

Biotin-chem Link (Boehringer-Mannheim)

The labeling density is suppose to be 1 biotin per 10 bases.

Coordinative, non-covalent binding of Biotin-chem-Link to N7 of adenosine and guanosine involves heating 1 ug RNA or DNA+1 ul BCL in 20 ul vol. 85° C. for 30 minutes.

RNA Labeling Experiment (4 Sets of 4 Pooled RNA Transcripts)

Very poor labeling and/or hybridization (cant see 5 pM at all, 20 pM is very weak). Samples may have been lost after labeling when microcon-100s was used to remove unincorporated label. RNA was fragmented after labeling. It is believed that this should not be a problem (BM tech help).

BCL Labeling of dsDNA

Low signal, background across the entire chip. No discrimination.

Fast-Tag (Vector Labs) (RNA)

Should get 1 biotin per 10–20 bases. Five reactions were run:

a) RNA1+RNA2+RNA3 (5 pmoles each, total of 5.2 ug)+25 ul Fast Tag reagent
b) RNA1+RNA2+RNA3 (9 pmoles each, total of 9.4 ug)+25 ul Fast Tag reagent
c) RNA1+RNA2+RNA3 (18 pmoles each, total of 19 ug)+40 ul Fast Tag reagent
d) RNA4+RNA5+RNA6 (10 pmoles each, total of 8.7 ug)+25 ul Fast Tag reagent
e) RNA7+RNA8+RNA9 (10 pmoles each, total of 11.4 ug)+25 ul Fast Tag reagent The heat method was used to link S-S to RNA. The result: 20×lower hybridization signal than same targets labeled by IVT method.

Example 12

RNA Ligase/Bio-a6 End Labeling

This experiment generally involved the following steps: a). RNA was fragmented; b) RNA fragments were 5' phosphorylated with polynucleotide kinase/ATP; and c) The 5' end of the RNA is ligated to the 3' end of BioA6 using RNA ligase. This is illustrated by the following formula:

Previously this technique was used to label total cellular mRNA which was hybridized to unpackaged chips (high density oligonucleotide arrays) (on 2×3 slides) in a 10 ul volume. Lack of mixing was a significant problem and resulted in low hybridization intensities. In vitro transcription (IVT) labeled RNA under these conditions gave 10×higher signal than bio-A6/RNA Ligase labeled target.

In other experiments 3 different ratios of bio-A6:RNA were used:

1) 1×bioA6=0.5 nmoles biotin-A6 per 1 ug RNA);

2) 2×bioA6; and 3) 4×Bio A6.

After labeling, the sample was spun through a microcon-EZ and microcon-3 to remove enzymes and dilute out buffer components.

Bio-A6 labeled target hybridized to chips (high density oligonucleotide arrays) gave approximately the same hyb, intensity as in vitro transcription (IVT) labeled target.

Staining was for 15 minutes with PE at normal conc. No significantly higher signal or background was seen with 4× as much bioA6 per ug RNA.

For these experiments, BioA6: (5' biotin-AAAAAA RNA) was ordered from Genset.

Example 13

Preparation of Gene-Specific Transcripts

Template DNA Preparation

Linearization of Vector

If the gene is not already cloned in a vector with T3 and T7 RNA polymerase promoter sites flanking the insert, see PCR amplification below.

The vector is linearized with an enzyme that cuts at the 3' end of the insert for sense transcripts, or at the 5' end for antisense transcripts. The insert sequence was checked to verify that the RE does not cut internally. In a preferred embodiment, a restriction enzyme was chosen that does not produce 3' protruding ends.

Following linearization, an aliquot of the sample is run on a gel (next to uncut vector) to verify complete digestion.

The sample is optionally treated with Proteinase K (100–200 ug/ml) at 50 C./20 min—1 hour to remove enzyme or residual RNases (used in plasmid miniprep protocols).

The linearized DNA is purified DNA by phenol/chloroform extraction and ethanol precipitation or 3–4 rounds of microcon- 100 concentration/redilution (see below).

PCR Amplification

Amilification is only preferred if the desired region of the gene is not already in a cloning vector with RNA polymerase promoters.

Starting with genomic DNA (or cDNA), amplify the ORF of interest (or region of the gene represented on the chip) using PCR primers with 5' T3/T7 RNA polymerase promoter sequences and 3' gene-specific sequences.

The following 5' sequence (SEQ ID NO:5) has worked well (with 19–21 gene-specific bases added to the 3' end).
5'-GAATTGTAATACGACTCACTATAGGGAGG-[+ 19–21 gene-specific bases]-3'
The 5' end consists of:

a) six 5' flanking bases of your choice—not part of the promoter sequence, but necessary for maximum IVT efficiency.

b) 17 bases of the core T7 RNA polymerase promoter sequence c) 1st 6 bases transcribed (sequence of +1 to +6 can affect efficiency)

The other PCR primer would then contain the T3 RNA polymerase promoter sequence at the 5' end. The following sequence (SEQ ID NO:6) has worked well:
5'-AGATGCAATTAACCCTCACTAAAGGGAGA-(+ 19–21 gene-specific bases)-3'
The 5' end consists of:

a) six 5' flanking bases (sequence can vary from this example)

b) 17 bases of core T3 RNA Polymerase promoter sequence c) +1 to +6 transcribed bases Amplify the desired sequence using standard PCR conditions with 1st 5 cycles at the annealing temp, best suited for the gene specific part of the primers alone (typically 55–58° C.), followed by 25 cycles with annealing at 70° C. Check PCR products on an agarose gel (3–5 ul of a 100 μl rxn). It is not necessary to quantify at this stage.

Optional Proteinase K Treatment

Add 1 ul of Proteinase K (20 mg/ml) (Ambion) to the remainder of the PCR reaction and incubate 20 min to 1 h at 50–60° C. This is usually not necessary, but if the in vitro transcription (IVT) products appear degraded while the control IVT product included in the kit (described later) is full length, then this step may be added prior to the microcon-100 and IVT.

Microcon 50/100 Purification

Other purification methods are being tested. Ethanol precipitation can be substituted for micron-50 purification. CAUTION: Microcons may leak. Save all flow-through portions.

Add 380 μl RNase-free water to the PCR product and concentrate using a microcon-100 or microcon-50 as suggested in instructions (Amicon). Repeat the dilution and concentration 2–3 times. The final concentrated sample should be 5–100 μl.

In Vitro Transcription Labeling with Biotin

For maximum yield use Ambion's T3 (#1338) or T7 (#1334) Megascript system (their proprietary buffer allows higher nucleotide concentrations without inhibiting the polymerase). (Read Ambion instructions and suggestions in kit book!).

Perform IVT as suggested, but with (1:3) biotinylated:unlabeled CTP and UTP. Do not interchange T3 and T7 10×nucleotides that come with the Megascript kits For example, make a NTP mix for 4 IVT-labeling reactions as follows:

8 μl Ambion's T7 10×ATP [75 mM]

8 μl Ambion's T7 10×GTP [75 mM]

6 μl Ambion's T7 10×CTP [75 mM]

6 μl Ambion's T7 10×UTP [75 mM]

15 μl Bio-11-CTP [10 mM] (ENZO #42818)

15 μl Bio-16-UTP [10 mM] (ENZO #42814)

For each IVT-labeling reaction, add (at room temp.—not on ice):

14.5 ul NTP mix 2.0 ul 10×T7 transcription buffer (Ambion)

*1.5 ul purified PCR product (not more than 1 μg)

2.0 ul 10×T7 enzyme mix (Ambion)

*Do NOT add more than 1 ug of DNA to the IVT reaction. Higher concentrations of DNA actually inhibit the reaction and result in LOWER yields. Final rNTP composition:

7.5 mM ATP 7.5 mM GTP 5.625 mM cold UTP/1.875 mM bio-UTP 5.625 mM cold CTP/1.875 mM bio-CTP Incubate 4–6 hours at 37° C. Shorter incubation times may be sufficient for some transcripts or when maximum yield is not important.

Optional: DNase 1 Treatment

Add 1 μl RNase-free DNaseI (provided with Ambion kit) to each reaction and mix well. Incubate 15–20 min. at 37° C.

Optional—Proteinase K Treatment

This step may help reduce background caused by nonspecific protein binding to chip and to Streptavidin-phycoerythrin:
   Add RNase-free water to IVT reactions to a final volume of 99 ul.
   Add 1 µl of Ambion's 20 mg/ml proteinase K.
   Incubate at 50° C. 20–30 min.
Microcon Purification
   Several other purification methods have been tested—many did not sufficiently remove rNTPs or had low yields. A protocol for Carboxy bead-based purification (Archana Nair) looks very promising and will soon be used in place of microcon purification.
   Note: Set aside an aliquot of the IVT reaction before further purification. Setting aside 1% will enable trouble shooting of this step if necessary.
   1. Add 400 ul DEPC water to sample and concentrate sample with microcon 50 or 100 (as suggested by Amicon). SAVE ALL FLOW-THROUGH FRACTIONS.
   2. Repeat dilution/concentration 3–4 times. Final volume can be 10–100 µl.
See comments below.
Check IVT Product(s) on a Gel
   Usually it is sufficient to check ~0.01–1% of the reaction on a nondenaturing agarose/TBE gel. Samples are heated to 65° C. for 15 minutes prior to electrophoresis. A single band close to the expected size is usually observed. If there is enough space on the gel, run 2 or 3 different dilutions of both the unpurified and purified IVT products on a gel (~0.01%, 0.1% and 1% of each). Gels can be stained with Sybr Green II (FMC) at a 1:10,000 dilution in 1×TBE buffer (more sensitive than ethidium bromide).
   If precise determination of transcript size it desired, a denaturing gel can be run with biotinylated RNA standards (available from Ambion).
Quantify Transcript Yield by $A_{260}$
   Expect 75–150 µg RNA per 1 ug starting DNA template. For quantitation of purified transcript, about 1% of the concentrated sample diluted with water (or TE) into a final volume of 60–70 ul (for a microcuvette) should give absorbance readings within the accurate range (0.1–1 OD). For accurate pipetting volumes (>1 µl), it is usually necessary to make a serial dilution first (for example, make a 1/10 dilution of your RNA sample, then measure 10% of the dilution in 60–70 ul final vol.). Always be sure to take a blank reading in the same cuvette and using the same buffer/water that the RNA sample is diluted into.
   Since accurate quantitation of pure transcript is essential for meaningful spiking experiments, extra care should be taken to verify that excess nucleotides from the IVT reaction have been sufficiently removed and are not contributing to the $A_{260}$. The microcon flow through should be saved and checked for $A_{260}$. If significant absorbance is present in the last flow through, the RNA should be subjected to additional rounds of dilution and concentration until no significant absorbance is detected at 260 nm.
   Since microcon filtration devices occasionally leak, it is advisable to save all flow-through fractions. If the transcript RNA concentration in the retained/collected sample is much lower than predicted, the flow-through fractions can be re-concentrated using a fresh cartridge (then diluted and reconcentrated at least 4 times).

Example 14

Labeling Total mRNA from Cells/Tissues

Starting material: Good quality poly $A^+$ RNA from at least $5 \times 10^5$–$1 \times 10^6$ cells *(0.1 ug–5 ug poly A+). It is more economical to start with more poly A+ RNA (up to 5 µg), but if material is limited, as little as 0.1 µg of poly(A)+ can yield a sufficient quantity of labeled RNA target (10 µg after IVT labeling/amplification).
Double Stranded cDNA Synthesis
   This protocol is a supplement to instructions provided in Gibco BRLOs Superscript Choice System. Before proceeding read the Gibco protocol. Follow Gibco BRL's Superscript Choice System for cDNA Synthesis, except use the T7-$(T)_{24}$ sequence (below) for priming the reverse transcription-first strand cDNA synthesis instead of the oligo(dT) or random primers provided with the kit.
   T7-$(T)_{24}$ primer: 5'-GGCCAGTGAATTGT AATACGACTCACTATAGGGAGGCGG-$(T)_{24}$-3'
First Strand Synthesis
   Use 0.1 µg–5 µg Poly $(A)^+$RNA and adjust amount of $H_2O$ and enzyme as indicated in the BRL instructions. For example:
   3 µl DEPC-water
   4.5 µl (1 µg/µl) mRNA
   1 µl (100 pmol/ul) T7-$(T)_{24}$ primer
   1. Mix/Spin/Incubate at 70° C. for 10 minutes.
   2. Chill on ice.
   3. Add the following components (on ice) to the RNA/primer mix:
      4 µl of 5×1st strand cDNA buffer
      2 µl 0.1 M DTT
      1 µl [10 mM] dNTP mix
   4. Incubate at 37° C. for 2 minutes.
   5. Add 4.5 ul Superscript II reverse transcriptase/mix well. Use (1 ul SSII RT per ug RNA). For<1 ug RNA, use 1 ul RT.
   6. Incubate for 1 hour at 37° C.
Final Reaction Composition (20 µl vol.):
   50 mM Tris-HCl, pH 8.3
   75 mM KCl
   3 mM $MgCl_2$
   10 mM DTT
   500 uM each: dATP, dCTP, dGTP, dTTP
   100 pmol T7-$(T)_{24}$ primer
   4.5 ug mRNA
   900 U RT (200 U per µg mRNA)
Second Strand Synthesis
   1. Place first strand reactions on ice (quickly spin down).
   2. Add:
   95 µl DEPC-$H_2O$
   30 µl 5×Second Strand Buffer
   3 µl [10 mM] dNTP mix
   1 µl [10 U/µl] E.coli DNA Ligase
   4 µl [10 U/µl] E.coli DNA Polymerase I
   1 µl [2 U/µl] RNaseH
Final Composition (150 µl):
   25 mM Tris-HCl, pH 7.5
   100 mM KCl
   5 mM $MgCl_2$
   10 mM $(NH_4)_2SO_4$
   0.15 mM b-$NAD^+$
   250 µM each: dATP, dCTP, dGTP, dTTP
   1.2 mM DTT
   65 U/ml DNA ligase
   250 U/ml DNA Polymerase I
   13 U/ml RNase H 3. Mix/spin down/ incubate at 16° C. for 2 hours.
4. Add 2 μl [10 U] T4 DNA Polymerase.
5. Incubate 5 min. at 16° C.
6. Add 10 μl 0.5 M EDTA/store at −20° C.

Clean Up

Phenol/Chloroform Extraction

Optional:To reduce sample loss during extraction, see the PLG protocol below

1. Add an equal volume (162 ul) of (25:24:1) Phenol:chloroform:isoamyl alcohol (saturated with 10 mM Tris-HCL pH 8.0/1 mM EDTA-Sigma).
2. Vortex/spin 5 minutes @ 14000×g. Transfer aqueous phase to a fresh 1.5 ml tube.

PLG-Phenol/Chloroform Extraction

Phase Lock Gels (PLG)* form an inert sealed barrier between the aqueous and organic phases of phenol-chloroform extractions. The solid barrier allows more complete recovery of the sample (aqueous phase) and minimizes interface contamination of the sample. PLGOs are sold as premeasured aliquots in 1.5 ml tubes, to which the user directly adds sample and phenol-chloroform.

1. Pellet the Phase Lock Gel (1.5 ml tube with PLG I-light.) in a microcentrifuge for 20–30 seconds [PLG I-heavy should also work, but we haven't specifically tested it for this application].
2. Transfer the entire (162 μl) cDNA sample to the PLG tube.
3. Add an equal volume (162 μl) of (25:24:1) Phenol:chloroform: isoamyl alcohol (saturated with 10 mM Tris-HCL ph 8.0/1 mMEDTA-Sigma).
4. Mix by inverting (DO NOT VORTEX). PLG will not become part of the suspension. Microcentrifuge at full speed (12,000×g or greater) for 2 min.
5. Transfer the aqueous upper phase to a fresh 1.5 ml tube. PLG I IS available from 5 Prime→3 Prime, Inc., cat. #pl-175850 for 50 or #pl-188233 for 200

Microcon-50 Purification

Other purification methods are being tested. Ethanol precipitation can be substituted for micron-50 purification. CAUTION: Microcons may leak. Save all flow-through portions.

1. Add 300 ul of 5 mM Tris pH 7.5 to sample.
2. Concentrate by spinning through a Microcon-50 column (Microcon-50 columns, Amicon part #42416) following directions supplied by Amicon.
3. Repeat dilution/concentration 3–4 times collect and set aside flow through in case of column failure.

Concentrate to a final volume of 5–10 ul if possible, taking care not to allow the cartridge to spin to dryness. Collect upper volume.

In Vitro Transcription Labeling with Biotin

For maximum yield use Ambion's T3 (#1338) or T7 (#1334) Megascript System (their proprietary buffer allows higher nucleotide concentrations without inhibiting the polymerase).

Perform IVT as suggested, but with (1:3) biotinylated:unlabeled CTP and UTP. Do not interchange T3 and T7 10×nucleotides that come with the Megascript System. Read the Ambion detailed instructions and suggestions before proceeding.

NTP Labeling Mix

To make NTP labeling mix for 4 IVT-labeling reactions combine:

8 μl Ambion's T7 10×ATP [75 mM]
8 μl Ambion's T7 10×GTP [75 mM]
6 μl Ambion's T7 10×CTP [75 mM]
6 μl Ambion's T7 10×UTP [75 mM]
15 μl Bio-11 -CTP [10 mM] (ENZO #42818)
15 μl Bio-16-UTP [10 mM] (ENZO #42814)

IVT Reaction

1. For each reaction, combine the following at room temperature, not on ice 14.5 μl NTP labeling mix
2.0 μl 10×T7 transcription buffer (Ambion)
*1.5 μl ds cDNA (0.1–1 ug is optimal: see note below!)
2.0 μl 10×T7 enzyme mix (Ambion)

*Do NOT add more than 1 μg of ds cDNA to the IVT reaction. Higher concentrations of DNA actually inhibit the reaction and result in LOWER yields.

Final rNTP Composition:
7.5 mM ATP
7.5 mM GTP
5.625 mM cold UTP/1.875 mM bio-UTP
5.625 mM cold CTP/1.875 mM bio-CTP 2. Incubate 4–6 hours at 37° C. (Shorter incubation times may be sufficient for some transcripts or when maximum yield is not important).
3. Store unused NTP labeling mix at −20° C.

Clean Up

Optional DNAse 1 Treatment

1. Add 1 ul RNase-free DNaseI (provided with Ambion kit) to each reaction and mix well.
2. Incubate 15–20 min. at 37° C.

Optional Proteinase K Treatment

This treatment may help reduce background caused by nonspecific protein binding to chip and to Streptavidin-phycoerythrin.

1. Add RNase-free water to IVT reactions to a final volume of 99 μl.
2. Add 1 μl of Ambion's 20 mg/ml Proteinase K.
3. Incubate at 50° C. 20–30 minutes.

Microcon Purification

Several other purification methods have been tested—many did not sufficiently remove rNTPs or had low yields. A protocol for Carboxy bead-based purification (Archana Nair) looks very promising and will soon be used in place of microcon purification. Set aside an aliquot of the IVT reaction before further purification. Setting aside 1% will enable trouble shooting of this step if necessary.

1. Add 400 ul DEPC water to sample and concentrate sample with microcon 50 or 100 (as suggested by Amicon). SAVE ALL FLOW-THROUGH FRACTIONS.
2. Repeat dilution/concentration 3–4 times. Final volume can be 10–100 ul.
3. Since microcon filtration devices occasionally leak, it is advisable to save all flow-through fractions. If transcript RNA concentration in the retained/collected sample is much lower than predicted, the flow-through fractions can be re-concentrated using a fresh column then diluted and reconcentrated at least 4 times.

Notes on Yield

1. Starting with 4–5 ug poly (A)$^+$ for the ds cDNA synthesis and using 20% of the purified ds cDNA sample for the IVT, expect ~75–125 ug labeled RNA per IVT reaction.
2. Reading ~1% of the concentrated sample diluted with water (or TE) into a final volume of 60–70 ul (for a microcuvette) should give absorbance data within the accurate range (0.1–1 OD). For accurate pipetting volumes (>1 ul), it is usually necessary to make a serial dilution first. For example, make a 1/10 dilution of your RNA sample, then measure 10% of the dilution in 60–70 ul final volume. Be sure to take blank readings in the same cuvette and use the same buffer/water that was used for diluting the RNA sample.

3. For accurate quantitation of labeled RNA, extra care should be taken to verify that excess nucleotides from the IVT reaction have been sufficiently removed and are not contributing to the $A_{260}$.

The microcon flow-through should be saved and checked for $A_{260}$. If significant absorbance is present in the last flow through, the RNA should be subjected to additional rounds of dilution and concentration until no significant absorbance is detected at 260 nm.

Check Unfragmented Samples on Gel

Electrophorese the labeled RNA before fragmentation to observe the size distribution of labeled transcripts. Samples can be heated to 65° C. for 15 minutes and electrophoresed on agarose/TBE gels to get an approximate idea of the transcript size range. If there is enough space on the gel, run 2 or 3 different dilutions of both the unpurified and purified IVT products on a gel (~0.01%, 0.1% and 1% of each). Gels can be stained with Sybr Green II (FMC) at a 1:10,000 dilution in 1×TBE buffer (more sensitive than ethidium bromide).

Alternatively, for more accurate estimations of the size distribution of the RNA population pre and post fragmentation, electrophorese samples through a denaturing gel using biotinylated RNA molecular weight markers (Ambion).

Example 15

Direct Labeling of DNA with Psoralen-Biotin

The psoralen-biotin reagent comes lyophilized and can be bought separately or as part of "Rad-Free Universal Oligo Labeling and Hybridization Kit" (Schleicher & Schuell). It is actually cheaper (per nmole) when bought with the kit so you might as well get the extra kit components and save money. The Rad-Free Universal Oligo Labeling and Hybridization kit: catalog #483122 (contains 20 nmoles of Psoralen-biotin). The same kit with UV Long wave 365 nm lamp: #483124.

1. Spin down then resuspend the lyophilized psoralen-biotin reagent in either:
    a) 14 ul of DMF if you may label fragmented DNA/RNA or oligonucleotides with some of the reagent (it needs to be more concentrated) OR
    b) 56 ul of DMF if you will definitely be labeling before fragmentation. Labeling has been performed both before and after fragmenting with similar results, but it is easier to do before fragmentation because it can't be labeled in high salt (>20 mM).

2. Adjust the RNA/DNA concentration to 0.5 ug/10 ul (200 ul for 10 ug of DNA), less than 20 mM salt. pH does not matter (pH 2.5–10) so you can just use sterile or DEPCed water to resuspend or dilute the RNA/DNA into. Plasmid DNA needs to be linearized. If RNA/DNA is in high salt, it can be diluted and concentrated using the appropriate size of microcon (even microcon 3 works for fragmented material but takes ~70 min per cycle).

3. Boil sample 10 min./quick chill on ice (store on ice 5 min-3hrs) [important—ds DNA will become cross-linked by reagent if strands are not separated before labeling]

4. In dim light add 1 ul of psoralen-biotin reagent per 20 ul of DNA/RNA solution (1 ul psoralen-biotin that was resuspended in 56 ul DMF per ug DNA/RNA). *if Psoralen-biotin was resuspended in 14 ul, dilute the amount you will need for labeling 1:3 in DMF (1 ul conc. psoralen-biotin +3 ul DMF)

5. Transfer solution to into a well of a 96-microwell plate on ice (up to 150 ul/well).

6. Place 365 nm UV lamp directly on top of plate so that light source is about 2 cm from the sample. Irradiate samples for one hour.

7. Transfer samples to microcentrifuge tubes and add 2 volumes of $H_2O$-saturated n-butanol to extract unincorporated psoralen biotin. vortex/centrifuge 1 min.

8. Discard butanol (top layer). Repeat extraction.

9. Fragment as you would normally. Denature as normal before hybridization (10 min 99–1 00° C.).

*longer UV irradiation does not improve results.

*adding more psoralen-biotin per ug DNA/RNA does not seem to improve results.

Example 16

Psoralen-Biotin Labeling Experiments

Labeling RNA by Standard Protocol

Pool of 4 diff. fragmented RNA transcripts labeled with psoralen-biotin Results of hybridization to chip (5 pM each). PB labeled targets showed approximately ~5×lower intensities than IVT(bio-U+C) labeled targets Labeling Before vs. After Fragmentation No significant difference in hybridization intensities Ratio of Psoralen-biotin to RNA Labeling with a 4×higher ratio of PB:RNA does not significantly affect hybridization intensities on chips.

Time of Labeling Reaction/UV Lamp Intensity

No significant difference between 1 vs. 3 hr. labeling or 15–20 mW/cm2 (Affy lamp) vs. 5–7 mW/cm2 (S&S lamp) intensity at 365 nm.

Psoralen-biotin

Psoralens: planar, tricyclic compounds

Psoralen-biotin: psoralen conjugated to biotin via 14-atom linker arm.

High affinity for nucleic acids

Intercalates into DNA/RNA

Becomes covalently attached when irradiated with long wave UV light.

Example 17

Terminal Transferase End-Labeling Protocol

This protocol is tested and optimized thoroughly with only PRT 440S chips.)

DNAse Fragmentation

This will have enough for 4 labeling reactions:

| | |
|---|---|
| 4 pmol of HIV PCR target (3.17 ug of 1.2 kb insert) | X ul |
| DNAse (BRL) | X ul (1 U/ug) |
| Calf Alkaline Phosphatase, 1 U/ul (BRL) | 2.5 ul (2.5 U/rx) |
| Dilution CAP Buffer (BRL) | 2.5 ul |
| $MgCl_2$ | X ul (1.25 mM) |

Bring up with H2O to 100 ul

37° C. for 15 min.

95° C. for 10 min.

4° C. on hold.

TdT Labeling

F-N6-ddATP, F-ddATP, F-ddCTP, and F-ddUTP are comparable labeled in the reaction. We decided to use F-N6-ddATP.

| | | |
|---|---|---|
| Fragment DNA sample | 25 ul | (1 pmol) |
| 5× TdT Buffer (Boehringer) | 20 ul | (1 X) |
| 25 mM CoCl2 (Boehringer) | 10 ul | (2.5 mM) |
| F-N6-ddATP (1 mM) | 1 ul | (10 uM) |
| TdT (25 U/ul) (Boehringer) | 1 ul | (25 U/rx) |
| $H_2O$ | 43 ul | |

37° C. for 30 min.
95° C. for 5 min.
4° C. on hold.
PRT 440S Hybridization (Rela Station)

| | |
|---|---|
| Labeled sample | 100 ul |
| 10× SSPE; 0.1% Triton X-100 | 300 ul |
| Control (100 nM) 213 Oligos | 5 ul |
| $H_2O$ | 195 ul |

45° C. Hyb for 30 min.
20° C. Wash with 6×SSPE, 0.005% Triton X-100; 4 cycles/10 drain-fill.
Scan chip at 530 nm, 11.25 um pixel size.

Example 18

Alternate Labeling Procedures

Ligation Assay

RNA can be directly labeled by ligating an A6 RNA oligonucleotide with biotin at the 5' end with RNA ligase. Cre, a bacterial gene, was transcribed with T7 RNA polymerase to generate an antisense RNA. The RNA was fragmented and kinased with olynucleootide kinase to generate 5' phosphorylated ends. The Biotin A6 RNA was then ligated using T4 RNA ligase. 5pm of ligated RNA was tested on gene expression chips along with the labeled Cre.

Direct Labeling of 3' RNA using Poly A Polymerase

Poly A polymerse has been used to catalyze poly A tail on to the free 3' hydroxyl terminus of RNA utilizing ATP as a precursor. Recently, it was reported by Joomyeong Kim et al. (1995) *Nucl. Acids Res.*, 23(12): 2245–2251, that they successfully used poly A polymerase to tail 3' RNA with CTP. This method can be used to label fragmented RNA with biotin CTP to generate a labeled target.

The advantage of this method is that sense RNA (mRNA) can be directly labeled by biotin CTP. Antisense RNA can also be labeled after fragmentation. The consumption of CTP can be cut down by ⅕th compared to an IVT reaction.

Example 19

Direct Labeling Protocol

Reagents for Direct Labeling mRNA
1) 100 μM rATP 200 μl
   198 μL DEPC $H_2O$
   2 μL (10 rM) rATP
2) 100 μg/ml BSA
   NEB Acelylated BSA
3) 30 mMDTT
4) 10 U/μL polynucleotide kinase
   Boehringer Mannheim 3' phosphatase free cat #83829
5) 1 nmole/μL BioA6
   Genetics Institute
6) 5U/μL T4 RNA Ligase+10×T4 RNA Ligase Buffer Epicentre Technologies, catalogue #LR5025
7) 5×RNA Fragmentation Buffer
   200 mM Tris-Acetate, pH 8.1
   500 mM KOAc
   150 mM MgOAc
Direct Labeling Protocol
Fragmentation
Add to a 1.5 ml sterile tube
8 μL poly (A)⁺ RNA in DEPC-$H_2O$ (1 μg)
2 μL 5×RNA Fragmentation Buffer
Heat to 94° C. for 35 minutes.
Kinase Reaction
Add to the 10 μL fragmented RNA:
2.4 μL rATP (100 μM)
2 μL BSA (100 μg/ml)
2 μL DTT (30 mM)
1.6 μL DEPC-H2O
2 μL polynucleotide kinase (10 U/μL)
Incubate at 37° C. for 2.5 hours. Heat to 94° C. for 2 minutes (heat kill enzyme).
T4 RNA Ligase Reaction
Add to the 20 μL kinased RNA:
0.5 μL BioA6 (1 nmole/μL in DEPC-$H_2O$)
3 μL rATP (19 mM)
3 μL 10×T4 RNA Ligase buffer
0.5 μL DEPC-$H_2O$
17° C. overnight—2 days. 94° C. for 2 minutes.

Example 20

Computer Algorithms to Perform Basecalling on a Target DNA Sample Hybridized or Ligated to Generic DNA Arrays Resequencing a DNA Target by Generating a Set of n Electronic Tiling Arrays on an n-mer Generic DNA Array This method of resequencing the target is similar to the method used with customized resequencing GeneChips except that unlike the custom GeneChips which physically place a single series of tiling probes on the chip, with a generic GeneChip a computer electronically reconstructs a set of n tiling arrays by fetching the appropriate probe information from the generic array (a generic array contains a possible n-mer sequences). In general, to resequence a target DNA, the target is decomposed into an n-mer complement word spectrum of tiling probes. For each tiling probe, there exists a set of "first order nearest-neighbor" tiling probes (probes containing a single base substitution) on the generic chip (generic chips also contain higher order nearest neighbors). This process is termed tiling through the target sequence with n-mer words (FIG. 24). To make a basecall at a given position within the target, the intensity of the tiling probe at that position is compared to the intensities of its "nearest-neighbors" at that position. There are n sets of such "nearest-neighbors" because the single base substitution can occur at n different positions within the probe. The base substitution at a particular position within the probe that yields the highest intensity is the base called for that position within the probe (FIG. 25). The advantage of using a generic DNA array vs. The standard custom GeneChips is the high degree of redundancy achieved for each basecall of the target. An n-mer generic arrays makes n base calls for each base within the target whereas the custom resequencing GeneChips make only a single base call.

The final basecall of a target base is decided upon by an electronic vote of the base calls from the n different electronic tilings at each target position (FIG. 26).

Figure 27:
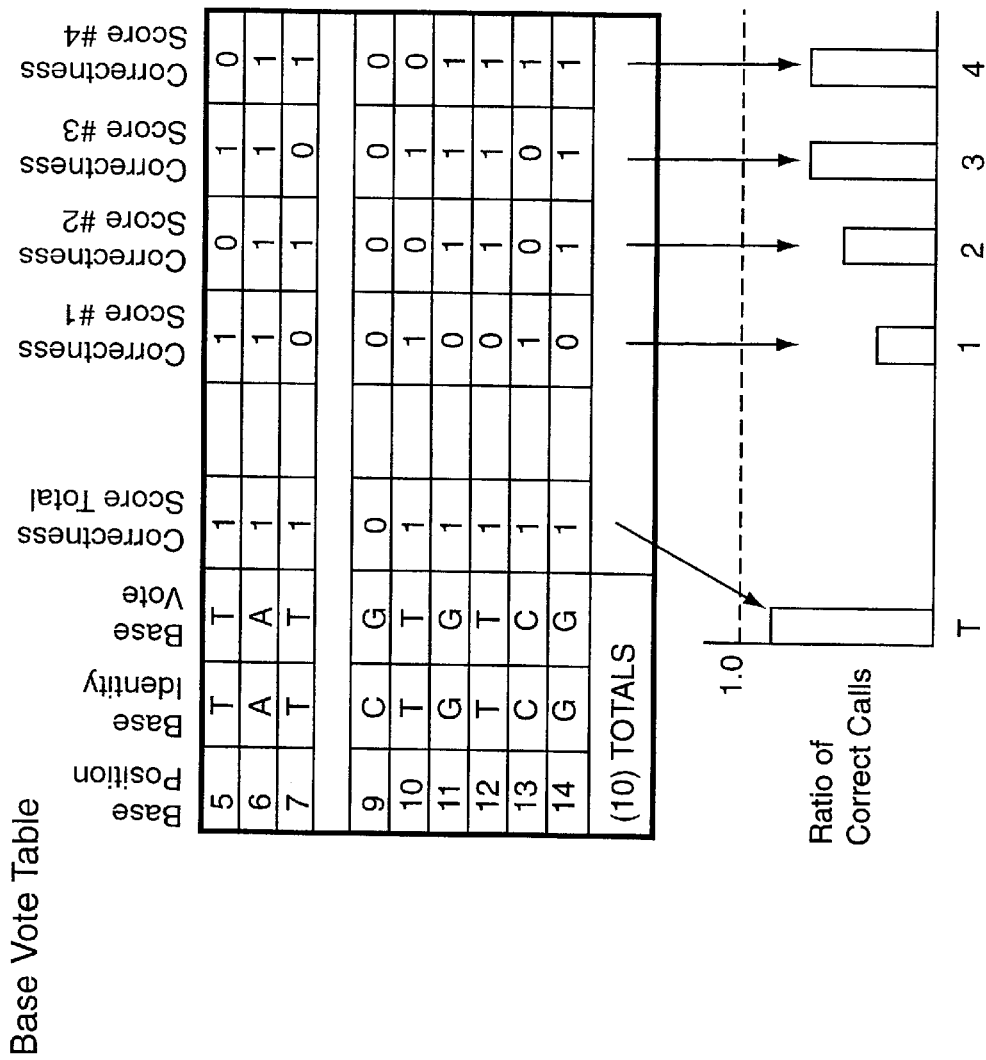
FIG. 27 illustrates a base vote table.

Emperically Using the Accuracy of the Basecalls Derived From the n Electronic Tiling Arrays to Filter Out Inaccurate Electronic Tilings A given reference DNA sample is hybridized/ligated to a generic DNA array. A set of n electronic tilings are generated and the corresponding basecalls made. A correctness score table is constructed by giving a score of 1 if a given tiling substitution series makes a correct basecall or a score of 0 if the basecall is incorrect (FIG. 27). A confidence level for a given basecall can also be attached to each scoring according to the ratio of the intensities of the base substitutions for any given basecall.

Figure 28:
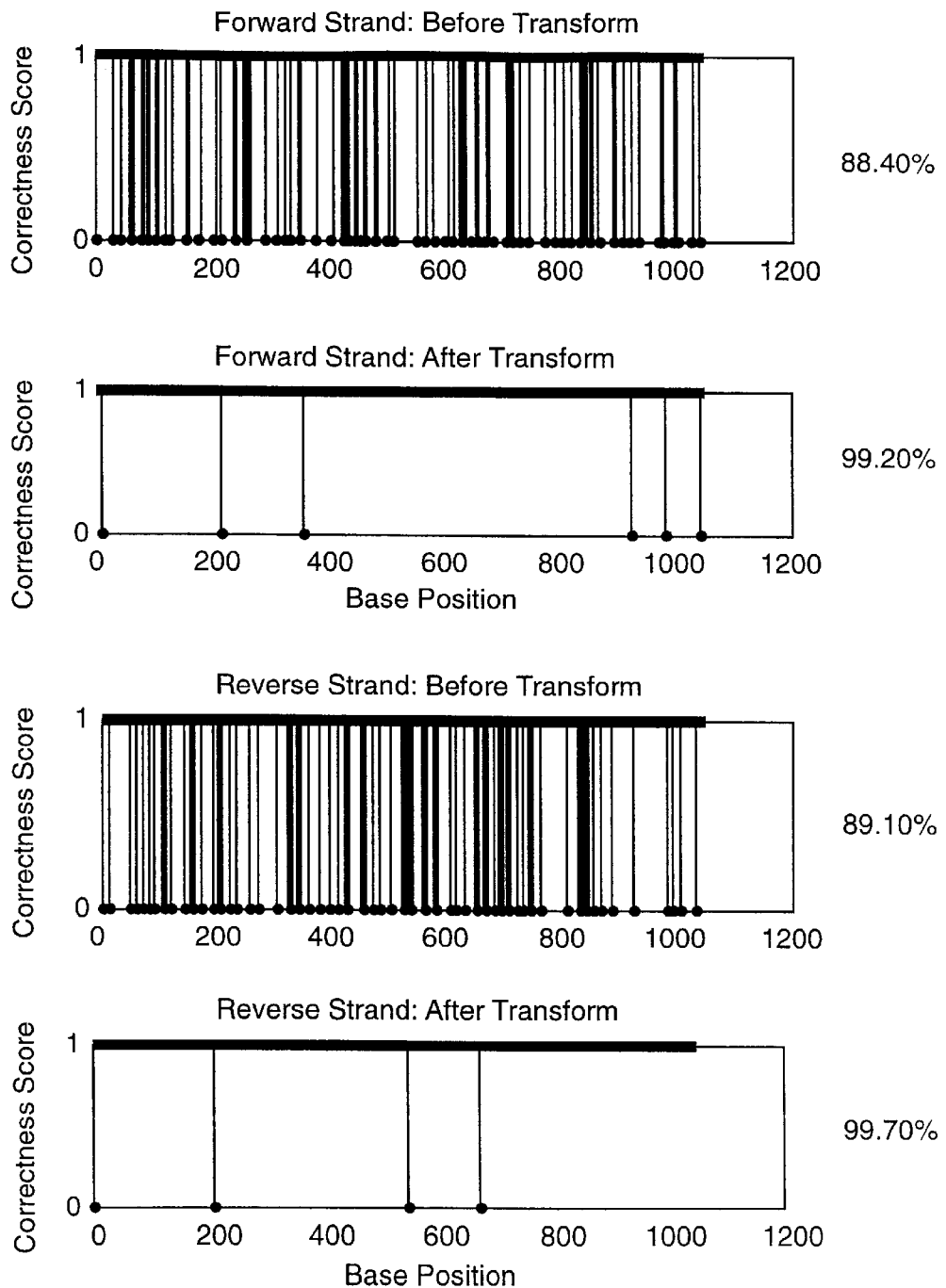
FIG. 28 illustrates the effect of applying correctness score transform to HIV data.

A variant DNA sample is then hybridized/ligated to a second generic DNA array. Again a set of n electronic tilings are generated, except this time all tilings are discarded which have a 0 correctness score, and only those tilings which have a correctness score of 1 are included in the overall base voting procedure (FIG. 28). The result is to dramatically improve the overall percentage of correct basecalls.

Comparing "Locally" Normalized Tiling Probe Intensities Between a Reference Sample and a Variant is a Sensitive Method of Detecting a Mutation For a given n-mer generic array, the ability to correctly resequence a target decreases as the complexity of the target increases. As the target complexity increases, the number of n-mer tiling probes which repeat themselves within the target increases, the cross-talk between nearest neighbors at different positions increases, and the overall cross hybridization increases. All these factors contribute to miscalls of the bases within the target. The comparison of a sample target against a reference target provides a powerful way to "filter out" all the non-specific noise via difference detection.

Figure 29:
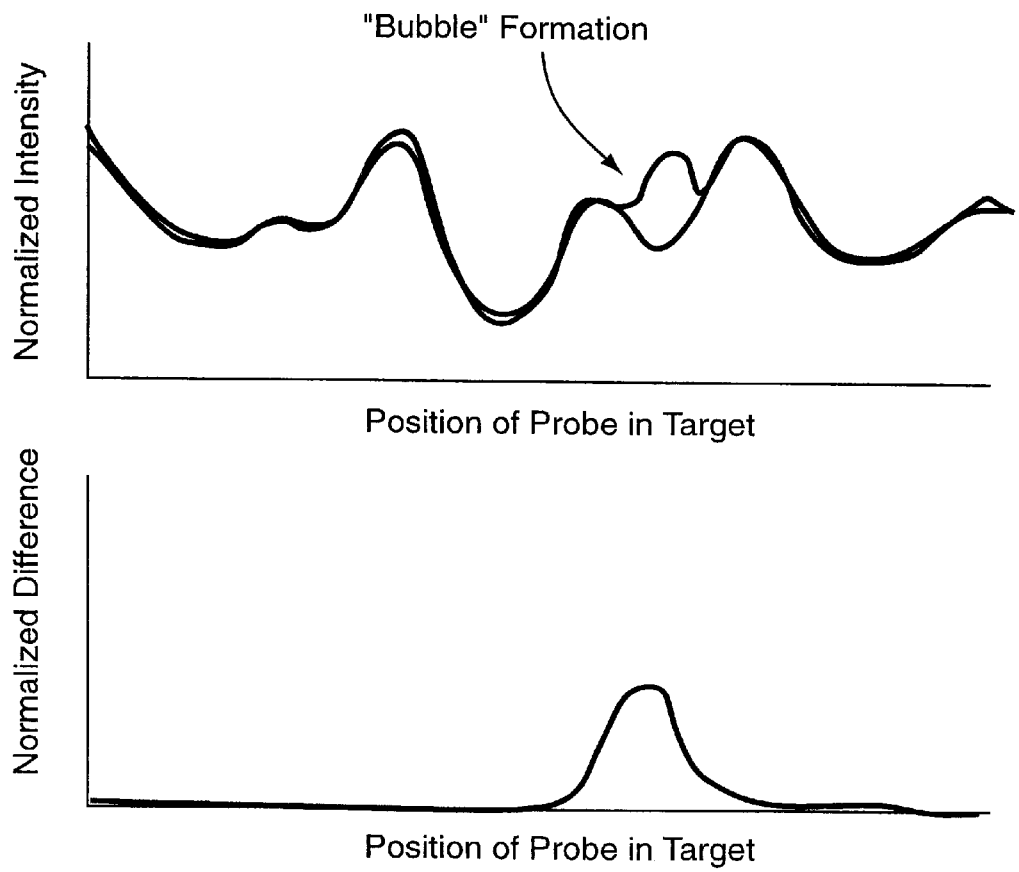
FIG. 29 illustrates mutation detection by intensity comparisons.

One method of comparison between the reference and sample is to compare the intensities of the tiling probes themselves. However, before a direct comparison can be made, the intensities have to be normalized in some matter to account for both chip to chip and sample to sample variation. I employed a "local" normalization process to normalize the signals. By "local" normalization, I simply divide the intensity of the tiling probe by the sum of the intensities of its nearest neighbors (FIG. 29). This method of normalization creates good signal tracking between samples and is quite sensitive to the presence of a mutation indicated by the formation of a "bubble" (FIG. 30). This "local" normalization tiling probe comparison can be further transformed by difference analysis and smoothing to a format where the presence of a mutation is more easily visualized.

Induced Difference Method for Detecting Mutations

Figure 33:
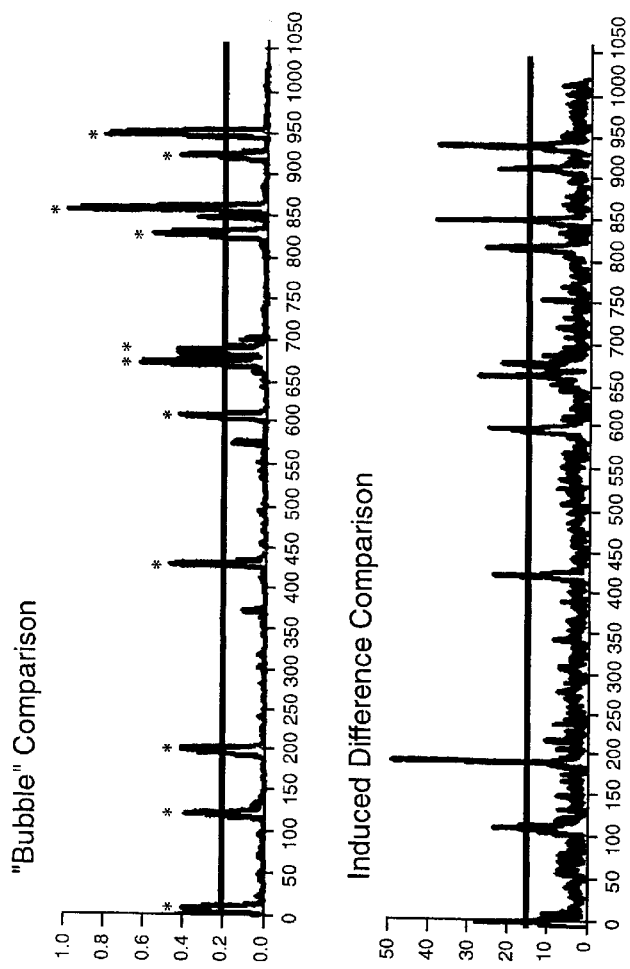
FIG. 33 illustrates mutation detection using comparisons between a reference target and a sample target.

Another method for using comparisons between a reference and a sample to detect mutations is via mutational "induced differences" between tilings probes and their nearest neighbors. Application of this method to a first order nearest neighbor tiling analysis involves comparing "locally normalized" probes in the reference target to the corresponding probe in the sample target. Tilings that where uninformative in part II, because they miscalled the base, may now be informative because certain probe members within that tiling can be induced (caused to increase or decrease in intensity) between the reference and the sample indicating the presence of a mutation (FIG. 31.) These inductions are summed over all the tilings on both the forward and reverse strand for a given target position, and the resultant number is a measure of whether a mutation is present or not (FIG. 32, FIG. 33).

Example 21

Use of Inosine on the 5' Ends of the MenPoc Synthesized Probes to Increase Duplex Stability and Increase the Resultant Ligation Signal on Generic Ligation GeneChips We investigated the use of adding degenerate bases, such as inosine (pairs with all other bases), to the end of the MenPoc synthesized probes to increase duplex stability. We found that indeed, the addition of 1–6 inosines onto the end of the probes did in fact increase the signal intensity in both hybridization and ligation reactions on a Generic Ligation GeneChip and allowed us to ligate at higher temperatures.

Inosines (0–6) are placed at the 5' end of the probe during manufacturing, and the effects of these terminal inosines are assayed by ligating a DNAaseI digested, TdT labeled 788 bp DNA fragment to the chips. The increased brightness with 2–6 inosines indicated an enhancement of duplex stability. With 6 inosines there is a slight decrease in intensity compared to 2–4 inosines because the terminal inosines are probably starting to form quartet-like secondary structures.

Example 22

Comparison Between the Specificity of T4 Ligase and Taq Ligase when used on a Generic Ligation GeneChip We investigated whether T4 ligase or Taq ligase was more specific in ligating target to the Generic Ligation GeneChip. In order use Taq ligase, we need to perform the ligation reaction at 40 degrees C or higher. Consequently, we used an 8-mer chip with 6 Inosines at the end of the MenPoc probes to increase the thermal stability of the duplexes. This allowed us to perform the Taq ligase reaction at 44 degrees C. and compare this to a T4 ligation reaction at 37 degrees C. Our results indicated that Taq is much more specific than T4 ligase, and ligates a set of target ends that T4 ligase is unable to ligate.

Taq lights up fewer features but with a brighter intensity than T4 does indicating the specificity of Taq versus T4.

Intensity profiles of the tiling probes and nearest neighbor substitutions at given probe positions within the target illustrate that Taq is more specific than T4 and that Taq detects signal intensity at probes that T4 fails to detect signal.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of identifying differences in nucleic acid levels between two or more nucleic acid samples, each sample comprising a population of mRNA or nucleic acids derived therefrom; said method comprising the steps of:

(a) providing one or more nucleic acid probe arrays each comprising probes not chosen to hybridize to nucleic acids derived from particular preselected genes or mRNAs;

(b) hybridizing said nucleic acid samples to said one or more arrays to form hybrid duplexes between nucleic acids in said nucleic acid samples and probes in said one or more arrays that are complementary to said nucleic acids or subsequences thereof; and (c) determining a first value for a difference in hybridization between two probes differing from each other in at least one position to a first sample, and a second value for a difference in hybridization between the two probes to a second sample, a difference in hybridization values between said nucleic acid samples indicating a difference in a level of a nucleic acid between the first and second samples.

2. A method of identifying differences in nucleic acid levels between two or more nucleic acid samples, each sample comprising a population of mRNA or nucleic acids derived therefrom; said method comprising the steps of:

(a) providing one or more oligonucleotide arrays each comprising probe oligonucleotides wherein said probe oligonucleotides comprise a nucleotide sequence selected according to a process selected from the group consisting of a random selection, a haphazard selection, and a nucleotide composition biased selection;

(b) hybridizing said nucleic acid samples to said one or more arrays to form hybrid duplexes between nucleic acids in said nucleic acid samples and probe oligonucleotides in said one or more arrays that are complementary to said nucleic acids or subsequences thereof; and (c) determining differences in hybridization between said nucleic acid samples wherein said differences in hybridization indicate differences in said nucleic acid levels.

3. The method of claim 1, wherein said nucleotide sequence or nucleotide subsequences are all possible oligonucleotides of a preselected length selected from the group consisting of: all possible 6 mers, all possible 7 mers, all possible 8 mers, all possible 9 mers, all possible 10 mers, all possible 11 mers, and all possible 12 mers.

4. The method of claim 1 or 2, wherein the one or more nucleic acid probe arrays comprising probes wherein said probes comprise a constant region and a variable region.

5. A method of identifying differences in nucleic acid levels between two or more nucleic acid samples each comprising a population of nucleic acids, said method comprising the steps of:

(a) providing one or more nucleic acid probe arrays each comprising probes comprising a nucleotide sequence selected according to a process selected from the group consisting of a random selection, a haphazard selection, and a nucleotide composition biased selection;

(b) providing software describing the location and sequence of probes on said array;

(c) hybridizing said nucleic acid samples to said one or more arrays to form hybrid duplexes between nucleic acids in said nucleic acid samples and probes in said one or more arrays that are complementary to said nucleic acids or subsequences thereof;

(d) operating said software such that said hybridizing indicates differences in said nucleic acid levels.

6. The method of claim 1, wherein the determining comprises determining a plurality of first values for differences in hybridization between a plurality of paired probes, a pair of probes differing from each other in at least one position, to a first sample, and a plurality of second values for differences in hybridization between the probe pairs to the second sample, differences between corresponding values between said nucleic acid samples indicating differences in a plurality of levels of nucleic acids between said first and second samples.

7. The method of claim 1, wherein the one or more nucleic acid probe arrays each comprising probes wherein said probes comprise a nucleotide sequence or subsequences selected according to a process selected from the group consisting of a random selection, a haphazard selection, and a nucleotide composition biased selection, and all possible probes of a preselected length.

8. The method of claim 1, wherein the first and second samples each comprises an mRNA population or a nucleic acid population derived therefrom.

9. The method of claim 2, wherein the nucleic acid samples are mRNA populations or nucleic acids derived therefrom.

10. The method of claim 2, wherein probes are designed to encode preferred codons from a species from which the samples were obtained.

11. The method of claim 2, wherein at least some codons have an inosine residue in the 5' position.

12. The method of claim 2, wherein the selection comprises excluding probes having palindromic sequences from an initial probe set.

13. The method of claim 2, further comprising comparing the sequence of a probe showing differential hybridization to the two samples to sequences in a database to identify a gene showing complementarity to the probe.

14. The method of claim 2, further comprising using the sequence of a probe showing differential hybridization to the two samples to synthesize a primer, and using the synthesized primer to generate an amplification product from a genomic or cDNA library.

15. The method of claim 2, further comprising using the sequence of a probe showing differential hybridization to the two samples to synthesize a further probe, and using the further probe as to isolate a complementary nucleic acid.

16. The method of claim 2, further comprising determining the identity of genes that are differentially expressed between the samples, and synthesizing a further nucleic acid probe array comprising probes complementary to the genes.

17. The method of claim 1 or 2, wherein the probes are at least 20 nucleotides long.

18. The method of claim 4, wherein the constant region is double stranded, and the variable region is single stranded, and one of more of the probes binds to a target nucleic acid through the variable region of the probe, and the method further comprises ligating the one or more hybridized nucleic acids to the constant region of the respective probes to which the one or more target nucleic acids are hybridized.

19. The method of claim 1 or 2, wherein one or more target nucleic acids hybridize to one or more probes, and the method further comprises ligating one or more oligonucleotides to the one or more probes whereby the ligated oligonucleotides hybridizes to the one or more target nucleic acids.

20. The method of claim 19, wherein the one or more oligonucleotides are labelled.

21. The method of claim 18, further comprising ligating one or more oligonucleotides to the variable regions of the one or more probes whereby the ligated oligonucleotides hybridize to the one or more target nucleic acids.

22. A method of analyzing a nucleic acid population comprising:

converting the nucleic acid population into nucleic acid fragments;

ligating the nucleic acid fragments to a labelled nucleic acid molecule to form labelled nucleic acid fragments;

hybridizing the labelled nucleic acid fragments to an array of nucleic acid probes, and determining hybridizations signals of the probes as an indication of levels of the nucleic acids in the nucleic acid population.

23. The method of claim 22, wherein the nucleic acid population is an mRNA population or nucleic acids derived therefrom.

24. The method of claim 23, wherein the nucleic acid population is contacted with the array without prior amplification.

25. A method of analyzing a nucleic acid population, comprising:

hybridizing a population of nucleic acids targets to an array of nucleic acid probes, whereby one or more of the nucleic acids hybridizes to probes in the array;

contacting the array with a labelled nucleotide and terminal deoxytransferase, whereby the labelled nucleotide is added to hybridized target molecules;

detecting label hybridized to probes as an indication of which nucleic acids are present in the nucleic acid population.

26. The method of claim 25, wherein the population of nucleic acids is an mRNA population or nucleic acids derived therefrom.

27. A method of analyzing a nucleic acid population, comprising:

hybridizing a population of nucleic acid targets to an array of nucleic acid probes, whereby a plurality of nucleic acid targets hybridize to complementary probes in the array;

forming a common tail on the hybridized nucleic acid targets or their complementary probes;

contacting the array with a labelled moiety having specific affinity for the tail, whereby the moiety binds to the tails;

detecting label hybridized to probes as an indication of the levels of the nucleic acids in the nucleic acid population.

28. The method of claim 27, wherein the population of nucleic acids is an mRNA population or nucleic acids derived therefrom.

* * * * *